United States Patent
de Frammond et al.

(10) Patent No.: US 12,428,650 B2
(45) Date of Patent: *Sep. 30, 2025

(54) CORN EVENT 5307

(71) Applicant: Syngenta Participations AG, Basel (CH)

(72) Inventors: Annick Jeanne de Frammond, Research Triangle Park, NC (US); Moez Rajabali Meghji, St. Louis, MO (US); Stephen L. New, Roseville, CA (US); Anna Underwood Prairie, Research Triangle Park, NC (US)

(73) Assignee: Syngenta Crop Protection AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/175,869

(22) Filed: Feb. 28, 2023

(65) Prior Publication Data

US 2023/0323386 A1 Oct. 12, 2023

Related U.S. Application Data

(60) Continuation of application No. 16/988,681, filed on Aug. 9, 2020, now abandoned, which is a division of application No. 16/126,171, filed on Sep. 10, 2018, now Pat. No. 10,844,400, which is a division of application No. 14/815,345, filed on Jul. 31, 2015, now Pat. No. 10,100,371, which is a division of application No. 13/140,429, filed as application No. PCT/US2009/067873 on Dec. 14, 2009, now Pat. No. 9,133,474.

(60) Provisional application No. 61/122,885, filed on Dec. 16, 2008.

(51) Int. Cl.
*C12N 15/82* (2006.01)
*C07K 14/415* (2006.01)
*C12Q 1/6895* (2018.01)

(52) U.S. Cl.
CPC ........ *C12N 15/8286* (2013.01); *C07K 14/415* (2013.01); *C12N 15/8241* (2013.01); *C12Q 1/6895* (2013.01); *Y02A 40/146* (2018.01)

(58) Field of Classification Search
CPC .................................................. C12N 15/8286
See application file for complete search history.

(56) References Cited

U.S. PATENT DOCUMENTS

| | | | |
|---|---|---|---|
| 5,495,068 A | 2/1996 | Foley | |
| 5,736,131 A | 4/1998 | Bosch et al. | |
| 8,309,516 B2 | 11/2012 | Hart et al. | |
| 8,466,346 B2 * | 6/2013 | DeFramond | C12N 15/8286 |
| | | | 514/4.5 |
| 9,133,474 B2 * | 9/2015 | DeFramond | C12N 15/8286 |
| 10,100,371 B2 * | 10/2018 | De Framond | C12N 15/8286 |
| 10,428,393 B2 * | 10/2019 | De Framond | C12N 15/8286 |
| 2004/0214272 A1 | 10/2004 | La Rosa et al. | |
| 2006/0141495 A1 | 6/2006 | Wu et al. | |
| 2010/0017914 A1 | 1/2010 | Hart et al. | |
| 2018/0112279 A1 | 4/2018 | De Framond et al. | |

FOREIGN PATENT DOCUMENTS

| | | |
|---|---|---|
| EP | 0942985 B1 | 9/2004 |
| EP | 2373153 | 5/2017 |
| WO | 9822595 A1 | 5/1998 |
| WO | 2007142840 A2 | 12/2007 |
| WO | 2008121633 A1 | 10/2008 |
| WO | 2010077816 A1 | 7/2010 |
| WO | 2011041256 A2 | 4/2011 |

OTHER PUBLICATIONS

R.K. Wilson GenBank Accession No. AC202955.4 (version 4) National Center for Biotechnology Information National Institutes of Health, U.S.A. (Year: 2013).*
Fu et al Proceedings of the National Academy of Science USA vol. 99, No. 14, pp. 9573-9578 (Year: 2002).*
Grimanelli et al., "Timing of the Maternal-to-Zygotic Transition during Early Seed Development in Maize," The Plant Cell, vol. 17, 1061-1072, Apr. 2005, Supplementary Table 1.
Corresponding to GenBank/EMBL Accession No. T14727 [Retrieved from the internet Oct. 18, 2013:<URL:http://ftp.gramene.org/archives/release26/data/maps/ibm2n04.tab] in entirety, 59 pp.
Song et al., Gene expression of a gene family in maize based on noncollinear haplotypes, Proceedings of the National Academy of Sciences of the United States of America (PNAS), Jul. 22, 2003, vol. 100, No. 15, pp. 9055-9060, ISSN: 0027-8424.
Genbank AC125584.2. Rattus norvegicus clone CH230-1F2. Oct. 9, 2002. [Retrieved from the internet Oct. 5, 2011:<URL://www.ncbi.nlm.nih.gov/nuccore/2326310>] in entirety.
Genbank AC202540.4. Zea mays chromosome 3 clone ZMMBBb-133C10; ZMMBBb0133c10, * Sequencing in Progress * , 4 unordered pieces. Jun. 27, 2008. [Retrieved from the internet Oct. 5, 2011:<URL://www.ncbi.nlm.nih.gov/nuccore/160688634>] in entirety.

(Continued)

*Primary Examiner* — David H Kruse
(74) *Attorney, Agent, or Firm* — Katherine Seguin

(57) ABSTRACT

A novel transgenic corn event designated 5307, is disclosed. The invention relates to DNA sequences of the recombinant constructs inserted into the corn genome and of genomic sequences flanking the insertion site that resulted in the 5307 event. The invention further relates to assays for detecting the presence of the DNA sequences of event 5307, to corn plants and corn seeds comprising the genotype of and to methods for producing a corn plant by crossing a corn plant comprising the event 5307 genotype with itself or another corn variety.

4 Claims, 2 Drawing Sheets

Specification includes a Sequence Listing.

(56) References Cited

OTHER PUBLICATIONS

Genbank AC208695.3. *Zea mays* chromosome 4 clone ZMMBBb-318B2; ZMMBBb0318B02, * Sequencing in Progress *, 4 unordered pieces. Jun. 27, 2008 [Retrieved from the internet Oct. 5 2011:<URL://www.ncbi.nlm.nih.gov/nuccore/189908068>] in entirety.
Fu et al., 2002, Proceedings of the National Academy of Science, USA, 99, 14, 9573-9578.
R.K. Wilson, Sep. 2013, GenBank Accession No. AC202955.4 (version 4), National Center for Biotechnology Information, National Institutes of Health, U.S.A.
International Search Report and Written Opinion for International Application No. PCT/US2009/067873, mailed Apr. 23, 2010, 9 Pages.

\* cited by examiner

Insert map of Event 5307.

```
                           SEQUENCE LISTING

Sequence total quantity: 111
SEQ ID NO: 1            moltype = DNA  length = 20
FEATURE                 Location/Qualifiers
misc_feature            1..20
                        note = 5' genome-insert juction
source                  1..20
                        mol_type = other DNA
                        organism = synthetic construct
SEQUENCE: 1
caactcacga actgatagtt                                             20

SEQ ID NO: 2            moltype = DNA  length = 20
FEATURE                 Location/Qualifiers
misc_feature            1..20
                        note = 3' insert-genome junction
source                  1..20
                        mol_type = other DNA
                        organism = synthetic construct
SEQUENCE: 2
ccacaatata ccctcttccc                                             20

SEQ ID NO: 3            moltype = DNA  length = 200
FEATURE                 Location/Qualifiers
misc_feature            1..200
                        note = 5' genome + insert sequence
source                  1..200
                        mol_type = other DNA
                        organism = synthetic construct
SEQUENCE: 3
gtcgactcaa acggctagtt ctgacagcta gccgttggac agatggcata ccggacagtc   60
cgatacgctg tccggtgtgc ctctaaaatt caactcacga actgatagtt taaactgaag  120
gcgggaaacg acaatctgat catgagcgga gaattaaggg agtcacgtta tgacccccgc  180
cgatgacgcg ggacaagccg                                              200

SEQ ID NO: 4            moltype = DNA  length = 200
FEATURE                 Location/Qualifiers
misc_feature            1..200
                        note = 3' insert + genome sequence
source                  1..200
                        mol_type = other DNA
                        organism = synthetic construct
SEQUENCE: 4
gccctgcagg aaatttaccg gtgcccgggc ggccagcatg gccgtatccg caatgtgtta   60
ttaagttgtc taagcgtcaa tttgtttaca ccacaatata ccctcttccc tgggccaggc  120
tgggcccact ggcaaagggt gcaccggaca gtccggtgcc ccaaagccag aaaccctagc  180
ttctgttttg tgctgttttt                                              200

SEQ ID NO: 5            moltype = DNA  length = 1548
FEATURE                 Location/Qualifiers
misc_feature            1..1548
                        note = 5' genome + insert sequence
source                  1..1548
                        mol_type = other DNA
                        organism = synthetic construct
SEQUENCE: 5
tacaagaata ttgagacgtg agtacatagc attggcattt tcattagcaa gcatttcaaa   60
agaatttaat tttctcatag caatgtgata tctctcctca cgctcaattc tagttccttc  120
atgtagagca catatgtcca tccacaaatc atgcaatttt ttatggtttc taactctatt  180
aaacacatct ttgcaaaggc ctctaaaaag ggtgttttg gccttagcat tccatttctc  240
```

-continued

```
atagttcaac tcttcaccta caagatttgt gggatctcta ggttcgggga atctttgtgt    300
ggcggctttg tagacaccaa tgtctatagc ctctaaatat gcttccatac gaattttcca    360
atatggaaaa tcgtcaccat aaaaaacggg agaaggtcca tccccaccgg acatcgttac    420
tctagcggtt aagctaatct aagagcaaca aggctcttat accaattgaa aggatcacga    480
tgcccaagag gggggttga attgggcttt tctaaaaatc aacactaact aaaatctaag    540
caagagccca acttcacccc gacaactagc actaagagaa taatactaga aatacaacaa    600
tgctaagata atacttcaaa tacttgctaa acaaatacac aatgtaaaat acttgaatta    660
agtgcggaat gtaaagcaag gtttagaaga ctcctccaat ttttctagag gtatcaaaga    720
gtcggcactc tccccagtc ctcgttggag cacctgcgta agggtatcgc tctcccttgg    780
tcatcgcaag aaccaagtgc tcacaacgag atgatcctt gccactccgg cgcggtggat    840
ccctcacgac cgcttacaaa cttgagtcgg gtcaccaaca agatcccac ggtgatcacc    900
gagctcccaa cgccaccaag ccgtctaggt gatgccgatc accaagagta ataagccata    960
gactttcact tgaccaagag aagcctaatg catgcggtgt gtgctctagg tggctctcgc   1020
tagcgttaat gaggtccaaa tgcgggatta agattccaa gtcacctcac taggctttgt   1080
ggtgcttgca atgctctacc aatgtgtagg agtaaatgtg ggcagcaaga ccatcaatat   1140
ggtaggtgga tggggtataa atagccctca cccaccaact agccattacc aggaatctgc   1200
tgcgcatggg cgcaccggac agtccggtgt gccaccggtg cgccaacggt cgactcaaac   1260
ggctagttct gacagctagc cgttggacag atggcatacc ggacagtccg atacgctgtc   1320
cggtgtgcct ctaaaattca actcacgaac tgatagttta aactgaaggc gggaaacgac   1380
aatctgatca tgagcggaga attaagggag tcacgttatg accccgccg atgacgcggg   1440
acaagccgtt ttacgtttgg aactgacaga accgcaacgc tgcaggaatt ggccgcagct   1500
gccatttaaa tcaattgggc gcgccgaatt cgagctcggt acaagctt                1548

SEQ ID NO: 6            moltype = DNA  length = 1093
FEATURE                 Location/Qualifiers
source                  1..1093
                        mol_type = genomic DNA
                        organism = Zea mays
SEQUENCE: 6
ccctcttccc tgggccaggc tgggcccact ggcaaagggt gcaccggaca gtccggtgcc     60
ccaaagccag aaaccctagc ttctgttttg tgctgttttt tcaatttggt ttttgttcta    120
acttgtgagt atgttctaga gttcaccta gcactatatg tgagtgtgaa tatgcaccaa    180
cactacacta gaactctttt ggtcaaacta cttatcgaca cccctcttt atagtacggc    240
taaaacaaaa taaaagacct aactatatca cgagtgtccg caactccttg acactcggaa    300
tacgaagacc ttcacttttt gtttcgtcgc tttagccgtt gcttcaagtt tttatctccg    360
ggattgtttt caccattgta gtacatctac ctgtaatgcg acctaactta ccatttgcct    420
ctgcaaaaca catgttagtc acatataaaa ttacgttgtc attaatcact aaaaccaacc    480
aggggcctag atgctttcta gtttaaatcc caacaagtc aaaattcttt ctatttttt    540
ttgcaagttc caattgacat ctgaaaggtt gtaaggtaca cgtttggctc tcattgataa    600
cgggggaaag atacagtgca aaccaccata taatgaccca cttctaatcg aatgaacctg    660
taacgacgaa atacccgtgt agaactatgg ttcactcatg ttaattcatt gaaattgttg    720
tagtgaattg acatggttgg gagcctgctt agagagtata gattgtcact tttttttgga    780
ccgcaactta tttttaaaag atattgcgat cgcttgtta gtagctgttt caggcccccaa    840
tgcagttcct atcgtgatcc atttaagtca ctcaacattc tcatacttct cattttgcat    900
taattcattc caatctccac tactataaa tactagcttc gatggtcgtc atacgccatg    960
cacgaagcat gtagatcaat ccgcatacca gtgggcatct atagataggc tgtgaaaacc   1020
acccaaatcc ctactagtgg acattttatc tatagatgga ccgtgagaaa ccacacaagt   1080
ctaacacgac agg                                                       1093

SEQ ID NO: 7            moltype = DNA  length = 6206
FEATURE                 Location/Qualifiers
misc_feature            1..6206
                        note = Vector insert
source                  1..6206
                        mol_type = other DNA
                        organism = synthetic construct
SEQUENCE: 7
ctggcagaca aagtggcaga catactgtcc cacaaatgaa gatggaatct gtaaaagaaa     60
acgcgtgaaa taatgcgtct gacaaaggtt aggtcggctg cctttaatca ataccaaagt    120
ggtccctacc acgatggaaa aactgctcag tcggtttggc ttttttctgac gaacaaataa    180
gattcgtggc cgacaggtgg gggtccacca tgtgaaggca tcttcagact ccaataatgg    240
agcaatgacg taagggctta cgaaataagt aagggtagtt tgggaaatgt ccactcaccc    300
gtcagtctat aaatacttag ccctcctc attgttaagg gagcaaggat ccaccatgac    360
tagtaacggc cgccagtgtg ctggtattcg ccctatgac gccgacaac aacaccgagg    420
cctggacagc agcaccacca aggacgtgat ccagaagggc atcagcgtgg tgggcgacct    480
gctgggcgtg gtgggcttcc ccttcggcgg cgccctggtg agcttctaca ccaacttcct    540
gaacaccatc tggcccagcg aggacccctg aaggcttc atggagcagg tggaggccct    600
gatggaccag aagatcgccg actacgccaa gaacaaggca ctggccgagc tacgggcct    660
ccagaacgac gtggaggact atgtgagcgc cctgagcgc tggcagaaga accccgctgc    720
accgttccgc aacccccaca gccagggcgc catccgcgag ctgttcagcc aggccgagag    780
ccacttccgc aacagcatgc ccagcttcgc catcagcggc tacgaggtgc tgttcctgac    840
cacctacgcc caggccgcca cacccacct gttcctgctg aaggacgccc aaatctacgg    900
agaggagtgg ggctacgaga aggaggacat cgccgagttc tacaagcgcc agctgaagct    960
gaccgcggag tacaccgacc actgcgtgaa gtggtacaac gtgggtctag acaagctccg   1020
cggcagcagc tacgagagct gggtgaactt caaccgctac cgccgcgaga tgaccctgac   1080
cgtgctggac ctgatcgccc tgttccccct gtacgacgtg cgcctgtacc ccaaggaggt   1140
gaagaccgag ctgacccgcg acgtgctgac cgacccatc gtgggcgtga caacctgcg   1200
cggctacggc accaccttca gcaacatcga gaactacatc gcaagcccc acctgttcga   1260
ctacctgcac cgcatccagt tccacacgcg tttccagccc ggctactacg gcaacgacag   1320
```

```
cttcaactac tggagcggca actacgtgag cacccgcccc agcatcggca gcaacgacat  1380
catcaccagc cccttctacg gcaacaagag cagcgagccc gtgcagaacc ttgagttcaa  1440
cggcgagaag gtgtaccgcg ccgtggctaa caccaacctg gccgtgtggc cctctgcagt  1500
gtacagcggc gtgaccaagg tggagttcag ccagtacaac gaccagaccg acgaggccag  1560
cacccagacc tacgacagca agcgcaacgt gggcgccgtg agctgggaca gcatcgacca  1620
gctgccccccc gagaccaccg acgagcccct ggagaagggc tacagccacc agctgaacta  1680
cgtgatgtgc ttcctgatgc agggcagccg cggcaccatc cccgtgctga cctggaccca  1740
caagagcgtc gacttcttca acatgatcga cagcaagaag atcacccagc tgcccctgac  1800
caagagcacc aacctgggca gcggcaaccag cgtggtgaag ggccccggct tcaccggcgg  1860
cgacatcctg cgccgcacca gcccccggca gatcagcacc ctgcgcgtga acatcaccgc  1920
cccccctgagc cagcgctacc gcgtccgcat ccgctacgcc agcaccacca acctgcagtt  1980
ccacaccagc atcgacggcc gccccatcaa ccagggcaac ttcagcgcca ccatgagcag  2040
cggcagcaac ctgcagagcg gcagcttccg caccgtgggc ttcaacaccc ccttcaactt  2100
cagcaacggc agcagcgtgt tcaccctgag cgccacgtg ttcaacgcg gcaacgaggt  2160
gtacatcgac cgcatcgagt tcgtgcccgc cgaggtgacc ttcgaggccg agtacgacct  2220
ggagagggct cagaaggccg tgaacgagct gttcaccagc agcaaccaga tcggcctgaa  2280
gaccgacgtg accgactacc acatcgatca ggtgtaggaa ctgagctcta gatccccgaa  2340
ttttccccgat cgttcaaaca tttggcaata aagtttctta agattgaatc ctgttgccgg  2400
tcttgcgatg attatcatat aatttctgtt gaattacgtt aagcatgtaa taattaacat  2460
gtaatgcatg acgttattta tgagatgggt ttttatgatt agagtcccgc aattatacat  2520
ttaatacgcg atagaaaaca aaatatagcg cgcaaactag gataaattat cgcgcgcggt  2580
gtcatctatg ttactagatc gggaattggg taccagcttg catgcctgca gtgcagcgtg  2640
acccggtcgt gcccctctct agagataatg agcattgcat gtctaagtta taaaaaatta  2700
ccacatattt ttttttgtcac acttgtttga agtgcagttt atctatcttt atacatatat  2760
ttaaacttta ctctacgaat aatataatct atagtactac aataatatca gtgttttaga  2820
gaatcatata aatgaacagt tagacatggt ctaaaggaca attgagtatt ttgacaacag  2880
gactctacag ttttatcttt ttagtgtgca tgtgttctcc ttttttttttg caaatagctt  2940
cacctatata atacttcatc catttttatta gtacatccat ttagggttta gggttaatgg  3000
ttttttataga ctaatttttt tagtacatct atttttattct attttagcct ctaaattaag  3060
aaaactaaaa ctctatttta gttttttttat ttaataattt agatataaaa tagaataaaa  3120
taaagtgact aaaaattaaa caaatacccct ttaagaaatt aaaaaaaacta aggaaacatt  3180
tttcttgttt cgagtagata atgccagcct gttaaacgcc gtcgacgagt ctaacggaca  3240
ccaaccagca aaccagcagc gtcgcgtcgg gccaagcgaa gcagacggca cggcatctct  3300
gtcgctgcct ctgaccccct ctcgagagtt ccgctccacc gttggacttg ctccgctctt  3360
ggcatccaga aattgcgtgg cggagcggca gacgtgagcc ggcacggcag ggcggcctcct  3420
cctcctctca cggcaccggc agctacgggg gattccttc ccaccgctcc ttcgctttcc  3480
cttcctcgcc cgccgtaata aatagacacc ccctccacac cctcttttccc caacctcgtg  3540
ttgttcgag cgcacacaca cacaaccaga tctccccccaa atccaccccgt cggcaccttcc  3600
gcttcaaggt acgccgctcg tcctccccccc ccccccctct ctaccttctc tagatcggcg  3660
ttccggtcca tggttagggc ccggtagttc tacttctgtt catgtttgtg ttagatccgt  3720
gtttgtgtta gatccgtgct gctagccttc gtacacggat gcgacctgta cgtcagacac  3780
gttctgattg ctaacttgcc agtgtttctc tttgggggaat cctgggatgg ctctagccgt  3840
tccgcagacg ggatcgattt catgatttttt tttgtttcgt tgcatagggt ttggtttgcc  3900
cttttccttt atttcaatat atgccgtgca cttgtttgtc gggtcatctt ttcatgcttt  3960
ttttttgtctt ggttgtgatg atgtggtctg gttgggcggt cgttctagat cggagtagaa  4020
ttctgtttca aactacctgg tggatttatt aattttggat ctgtatgtgt gtgccataca  4080
tattcatagt tacgaattga agatgatgaa tggaaatatc gatctaggat aggtatacat  4140
gttgatgcgg gttttactga tgcatataca gagatgcttt ttgttcgctt ggttgtgatg  4200
atgtggtgtg gttgggcggt cgttcattcg ttctagatcg gagtagaata ctgtttcaaa  4260
ctacctggtg tatttattaa ttttggaact gtatgtgtgt gtcatacatc ttcatagtta  4320
cgagtttaag atggatggaa atatcgatct aggatggta tacatgttga tgtgggttt  4380
actgatgcat atacatgatg gcatatgcag catctattca tatgctctaa ccttgagtac  4440
ctatctatta taataaacaa gtatgtttta taattatttt gatcttgata tacttggatg  4500
atggcatatg cagcagctat atgtggattt ttttagccct gccttcatac gctatttatt  4560
tgcttggtac tgtttcttt gtcgatgctc accctgttgt ttggtgttac ttctgcaggg  4620
atccccgatc atgcaaaaac tcattaactc agtgcaaaac tatgcctggg gcagcaaaac  4680
ggcgttgact gaactttatg gtatggaaaa tccgtccagc cagccgatgg ccgagctgtg  4740
gatgggcgca catccgaaaa gcagttcacg agtgcagaat gccgcggag atatcgtttc  4800
actgcgtgat gtgattgaga gtgataaatc gactctgctc ggagaggccg ttgccaaacg  4860
ctttggcgaa ctgcctttcc tgttcaaagt attatgcgca gcacagccac tctccattca  4920
ggttcatcca aacaaacaca attctgaaat cggttttgcc aaagaaaatg ccgcaggtat  4980
cccgatggat gccgccgagc gtaactataa agatcctaac cacaagcgg agctggtttt  5040
tgcgctgacg ccttttccttg cgatgaacgc gtttcgtgaa ttttccgaga ttgtctccct  5100
actccagccg gtcgcaggtg cacatccggc gattgctcac tttttacaac agcctgatgc  5160
cgaacgttta agcgaactgt tcgcagcct gttgaatatg cagggtgaag aaaaatcccg  5220
cgcgctggca attttaaaat cggccctcga tagccagcag ggtgaaccgt ggcaaacgat  5280
tcgtttaatt tctgaatttt accggaagaa cagcggtctg ttctcccccgc tattgctgaa  5340
tgtggtgaaa ttgaaccctg gcgaagcgat gttcctgttc gctgcatcac cgcacgctta  5400
cctgcaaggc gtggcgctgg aagtgatggc aaactgctgc gtgcgggtct  5460
gacgcctaaa tacattgata ttccggaact ggttgccaat gtgaaattcg aagccaaacc  5520
ggctaaccag ttgttgaccc agccggtgaa acaaggtgca gaactggact cccgattcc  5580
agtggatgat tttgccttct cgctgcatga ccttagtgat aaagaaacca ccattagcca  5640
gcagagtgcc gccattttgt tctgcgtcga aggcgatgca acgttgtgga aggttctca  5700
gcagttacag cttaaaccgg gtgaatcagc gtttattgcc gcaacgaat caccggtgc  5760
tgtcaaaggc cacggccgtt tagcgcgtgt ttacaacaag ctgtaagagc ttactgaaaa  5820
aattaacatc tcttgctaag ctgggagctc gatccgtcga cctgcagatc gttcaaacat  5880
ttggcaataa agtttcttaa gattgaatcc tgttgccgt cttgcgatga ttatcatata  5940
atttctgttg aattacgtta agcatgtaat aattaacatg taatgcatga cgttatttat  6000
gagatgggtt tttatgatta gagtcccgca attatacatt taatacgcga tagaaaacaa  6060
```

```
aatatagcgc gcaaactagg ataaattatc gcgcgcggtg tcatctatgt tactagatct   6120
gctagccctg caggaaattt accggtgccc gggcggccag catggccgta tccgcaatgt   6180
gttattaagt tgtctaagcg tcaatt                                         6206

SEQ ID NO: 8           moltype = DNA   length = 28
FEATURE                Location/Qualifiers
misc_feature           1..28
                       note = Primer
source                 1..28
                       mol_type = other DNA
                       organism = synthetic construct
SEQUENCE: 8
cacgaccgct tacaaacttg agttgggt                                         28

SEQ ID NO: 9           moltype = DNA   length = 21
FEATURE                Location/Qualifiers
misc_feature           1..21
                       note = Primer
source                 1..21
                       mol_type = other DNA
                       organism = synthetic construct
SEQUENCE: 9
ctcccaacgc caccaagccg t                                                21

SEQ ID NO: 10          moltype = DNA   length = 25
FEATURE                Location/Qualifiers
misc_feature           1..25
                       note = Primer
source                 1..25
                       mol_type = other DNA
                       organism = synthetic construct
SEQUENCE: 10
cctcactagg ctttgtggtg cttgc                                            25

SEQ ID NO: 11          moltype = DNA   length = 24
FEATURE                Location/Qualifiers
misc_feature           1..24
                       note = Primer
source                 1..24
                       mol_type = other DNA
                       organism = synthetic construct
SEQUENCE: 11
gagtaaatgt gggcagcaag acca                                             24

SEQ ID NO: 12          moltype = DNA   length = 24
FEATURE                Location/Qualifiers
misc_feature           1..24
                       note = Primer
source                 1..24
                       mol_type = other DNA
                       organism = synthetic construct
SEQUENCE: 12
cccaccaact agccattacc agga                                             24

SEQ ID NO: 13          moltype = DNA   length = 23
FEATURE                Location/Qualifiers
misc_feature           1..23
                       note = Primer
source                 1..23
                       mol_type = other DNA
                       organism = synthetic construct
SEQUENCE: 13
aaacggctag ttctgacagc tag                                              23

SEQ ID NO: 14          moltype = DNA   length = 21
FEATURE                Location/Qualifiers
misc_feature           1..21
                       note = Primer
source                 1..21
                       mol_type = other DNA
                       organism = synthetic construct
SEQUENCE: 14
atacgctgtc cggtgtgcct c                                                21

SEQ ID NO: 15          moltype = DNA   length = 18
FEATURE                Location/Qualifiers
misc_feature           1..18
                       note = Primer
source                 1..18
```

-continued

```
                          mol_type = other DNA
                          organism = synthetic construct
SEQUENCE: 15
ggtagtttgg gaaatgtc                                                    18

SEQ ID NO: 16             moltype = DNA  length = 18
FEATURE                   Location/Qualifiers
misc_feature              1..18
                          note = Primer
source                    1..18
                          mol_type = other DNA
                          organism = synthetic construct
SEQUENCE: 16
atacttagcc cctccctc                                                    18

SEQ ID NO: 17             moltype = DNA  length = 17
FEATURE                   Location/Qualifiers
misc_feature              1..17
                          note = Primer
source                    1..17
                          mol_type = other DNA
                          organism = synthetic construct
SEQUENCE: 17
atgactagta acggccg                                                     17

SEQ ID NO: 18             moltype = DNA  length = 18
FEATURE                   Location/Qualifiers
misc_feature              1..18
                          note = Primer
source                    1..18
                          mol_type = other DNA
                          organism = synthetic construct
SEQUENCE: 18
gccgacaaca acaccgag                                                    18

SEQ ID NO: 19             moltype = DNA  length = 17
FEATURE                   Location/Qualifiers
misc_feature              1..17
                          note = Primer
source                    1..17
                          mol_type = other DNA
                          organism = synthetic construct
SEQUENCE: 19
ctacgccaag aacaagg                                                     17

SEQ ID NO: 20             moltype = DNA  length = 17
FEATURE                   Location/Qualifiers
misc_feature              1..17
                          note = Primer
source                    1..17
                          mol_type = other DNA
                          organism = synthetic construct
SEQUENCE: 20
gagaggagtg gggctac                                                     17

SEQ ID NO: 21             moltype = DNA  length = 17
FEATURE                   Location/Qualifiers
misc_feature              1..17
                          note = Primer
source                    1..17
                          mol_type = other DNA
                          organism = synthetic construct
SEQUENCE: 21
ccaccttcag caacatc                                                     17

SEQ ID NO: 22             moltype = DNA  length = 18
FEATURE                   Location/Qualifiers
misc_feature              1..18
                          note = Primer
source                    1..18
                          mol_type = other DNA
                          organism = synthetic construct
SEQUENCE: 22
agttcagcca gtacaacg                                                    18

SEQ ID NO: 23             moltype = DNA  length = 17
FEATURE                   Location/Qualifiers
misc_feature              1..17
                          note = Primer
```

```
source                      1..17
                            mol_type = other DNA
                            organism = synthetic construct
SEQUENCE: 23
agaagatcac ccagctg                                                17

SEQ ID NO: 24               moltype = DNA   length = 17
FEATURE                     Location/Qualifiers
misc_feature                1..17
                            note = Primer
source                      1..17
                            mol_type = other DNA
                            organism = synthetic construct
SEQUENCE: 24
ccttcaactt cagcaac                                                17

SEQ ID NO: 25               moltype = DNA   length = 17
FEATURE                     Location/Qualifiers
misc_feature                1..17
                            note = Primer
source                      1..17
                            mol_type = other DNA
                            organism = synthetic construct
SEQUENCE: 25
aggtgtagga gctgagc                                                17

SEQ ID NO: 26               moltype = DNA   length = 18
FEATURE                     Location/Qualifiers
misc_feature                1..18
                            note = Primer
source                      1..18
                            mol_type = other DNA
                            organism = synthetic construct
SEQUENCE: 26
tctagatccc cgaatttc                                               18

SEQ ID NO: 27               moltype = DNA   length = 19
FEATURE                     Location/Qualifiers
misc_feature                1..19
                            note = Primer
source                      1..19
                            mol_type = other DNA
                            organism = synthetic construct
SEQUENCE: 27
cccctctcta gagataatg                                              19

SEQ ID NO: 28               moltype = DNA   length = 18
FEATURE                     Location/Qualifiers
misc_feature                1..18
                            note = Primer
source                      1..18
                            mol_type = other DNA
                            organism = synthetic construct
SEQUENCE: 28
tttgcaaata gcttcacc                                               18

SEQ ID NO: 29               moltype = DNA   length = 17
FEATURE                     Location/Qualifiers
misc_feature                1..17
                            note = Primer
source                      1..17
                            mol_type = other DNA
                            organism = synthetic construct
SEQUENCE: 29
atgccagcct gttaaac                                                17

SEQ ID NO: 30               moltype = DNA   length = 17
FEATURE                     Location/Qualifiers
misc_feature                1..17
                            note = Primer
source                      1..17
                            mol_type = other DNA
                            organism = synthetic construct
SEQUENCE: 30
cctcctcctc ctctcac                                                17

SEQ ID NO: 31               moltype = DNA   length = 20
FEATURE                     Location/Qualifiers
misc_feature                1..20
```

```
                        note = Primer
source                  1..20
                        mol_type = other DNA
                        organism = synthetic construct
SEQUENCE: 31
tctgttcatg tttgtgttag                                              20

SEQ ID NO: 32           moltype = DNA  length = 18
FEATURE                 Location/Qualifiers
misc_feature            1..18
                        note = Primer
source                  1..18
                        mol_type = other DNA
                        organism = synthetic construct
SEQUENCE: 32
gatgatgtgg tctggttg                                                18

SEQ ID NO: 33           moltype = DNA  length = 20
FEATURE                 Location/Qualifiers
misc_feature            1..20
                        note = Primer
source                  1..20
                        mol_type = other DNA
                        organism = synthetic construct
SEQUENCE: 33
tgtttcaaac tacctggtgt                                              20

SEQ ID NO: 34           moltype = DNA  length = 17
FEATURE                 Location/Qualifiers
misc_feature            1..17
                        note = Primer
source                  1..17
                        mol_type = other DNA
                        organism = synthetic construct
SEQUENCE: 34
tagccctgcc ttcatac                                                 17

SEQ ID NO: 35           moltype = DNA  length = 20
FEATURE                 Location/Qualifiers
misc_feature            1..20
                        note = Primer
source                  1..20
                        mol_type = other DNA
                        organism = synthetic construct
SEQUENCE: 35
tcattaactc agtgcaaaac                                              20

SEQ ID NO: 36           moltype = DNA  length = 18
FEATURE                 Location/Qualifiers
misc_feature            1..18
                        note = Primer
source                  1..18
                        mol_type = other DNA
                        organism = synthetic construct
SEQUENCE: 36
tccgaaaagc agttcacg                                                18

SEQ ID NO: 37           moltype = DNA  length = 20
FEATURE                 Location/Qualifiers
misc_feature            1..20
                        note = Primer
source                  1..20
                        mol_type = other DNA
                        organism = synthetic construct
SEQUENCE: 37
aaacacaatt ctgaaatcgg                                              20

SEQ ID NO: 38           moltype = DNA  length = 17
FEATURE                 Location/Qualifiers
misc_feature            1..17
                        note = Primer
source                  1..17
                        mol_type = other DNA
                        organism = synthetic construct
SEQUENCE: 38
aatcggccct cgatagc                                                 17

SEQ ID NO: 39           moltype = DNA  length = 20
FEATURE                 Location/Qualifiers
```

```
misc_feature            1..20
                        note = Primer
source                  1..20
                        mol_type = other DNA
                        organism = synthetic construct
SEQUENCE: 39
tggttgccaa tgtgaaattc                                               20

SEQ ID NO: 40           moltype = DNA   length = 19
FEATURE                 Location/Qualifiers
misc_feature            1..19
                        note = Primer
source                  1..19
                        mol_type = other DNA
                        organism = synthetic construct
SEQUENCE: 40
aacgaatcac cggtgactg                                                19

SEQ ID NO: 41           moltype = DNA   length = 17
FEATURE                 Location/Qualifiers
misc_feature            1..17
                        note = Primer
source                  1..17
                        mol_type = other DNA
                        organism = synthetic construct
SEQUENCE: 41
gtcataaggg cgaatac                                                  17

SEQ ID NO: 42           moltype = DNA   length = 19
FEATURE                 Location/Qualifiers
misc_feature            1..19
                        note = Primer
source                  1..19
                        mol_type = other DNA
                        organism = synthetic construct
SEQUENCE: 42
acgctgatgc ccttctgga                                                19

SEQ ID NO: 43           moltype = DNA   length = 17
FEATURE                 Location/Qualifiers
misc_feature            1..17
                        note = Primer
source                  1..17
                        mol_type = other DNA
                        organism = synthetic construct
SEQUENCE: 43
ccttgttctt ggcgtag                                                  17

SEQ ID NO: 44           moltype = DNA   length = 17
FEATURE                 Location/Qualifiers
misc_feature            1..17
                        note = Primer
source                  1..17
                        mol_type = other DNA
                        organism = synthetic construct
SEQUENCE: 44
tagaactcgg cgatgtc                                                  17

SEQ ID NO: 45           moltype = DNA   length = 17
FEATURE                 Location/Qualifiers
misc_feature            1..17
                        note = Primer
source                  1..17
                        mol_type = other DNA
                        organism = synthetic construct
SEQUENCE: 45
gatgttgctg aaggtgg                                                  17

SEQ ID NO: 46           moltype = DNA   length = 17
FEATURE                 Location/Qualifiers
misc_feature            1..17
                        note = Primer
source                  1..17
                        mol_type = other DNA
                        organism = synthetic construct
SEQUENCE: 46
ctgtacactg cagaggg                                                  17

SEQ ID NO: 47           moltype = DNA   length = 17
```

```
FEATURE                 Location/Qualifiers
misc_feature            1..17
                        note = Primer
source                  1..17
                        mol_type = other DNA
                        organism = synthetic construct
SEQUENCE: 47
gctgggtgat cttcttg                                                  17

SEQ ID NO: 48           moltype = DNA  length = 17
FEATURE                 Location/Qualifiers
misc_feature            1..17
                        note = Primer
source                  1..17
                        mol_type = other DNA
                        organism = synthetic construct
SEQUENCE: 48
ttgctgaagt tgaaggg                                                  17

SEQ ID NO: 49           moltype = DNA  length = 17
FEATURE                 Location/Qualifiers
misc_feature            1..17
                        note = Primer
source                  1..17
                        mol_type = other DNA
                        organism = synthetic construct
SEQUENCE: 49
gtcacgtcgg tcttcag                                                  17

SEQ ID NO: 50           moltype = DNA  length = 20
FEATURE                 Location/Qualifiers
misc_feature            1..20
                        note = Primer
source                  1..20
                        mol_type = other DNA
                        organism = synthetic construct
SEQUENCE: 50
gccaaatgtt tgaacgatcg                                               20

SEQ ID NO: 51           moltype = DNA  length = 21
FEATURE                 Location/Qualifiers
misc_feature            1..21
                        note = Primer
source                  1..21
                        mol_type = other DNA
                        organism = synthetic construct
SEQUENCE: 51
caatgctcat tatctctaga g                                             21

SEQ ID NO: 52           moltype = DNA  length = 20
FEATURE                 Location/Qualifiers
misc_feature            1..20
                        note = Primer
source                  1..20
                        mol_type = other DNA
                        organism = synthetic construct
SEQUENCE: 52
gtgacaaaaa aaatatgtgg                                               20

SEQ ID NO: 53           moltype = DNA  length = 18
FEATURE                 Location/Qualifiers
misc_feature            1..18
                        note = Primer
source                  1..18
                        mol_type = other DNA
                        organism = synthetic construct
SEQUENCE: 53
ctgcacttca aacaagtg                                                 18

SEQ ID NO: 54           moltype = DNA  length = 22
FEATURE                 Location/Qualifiers
misc_feature            1..22
                        note = Primer
source                  1..22
                        mol_type = other DNA
                        organism = synthetic construct
SEQUENCE: 54
tgaagtatta taggtgaa gc                                              22
```

-continued

```
SEQ ID NO: 55          moltype = DNA   length = 19
FEATURE                Location/Qualifiers
misc_feature           1..19
                       note = Primer
source                 1..19
                       mol_type = other DNA
                       organism = synthetic construct
SEQUENCE: 55
acaggctggc attatctac                                              19

SEQ ID NO: 56          moltype = DNA   length = 17
FEATURE                Location/Qualifiers
misc_feature           1..17
                       note = Primer
source                 1..17
                       mol_type = other DNA
                       organism = synthetic construct
SEQUENCE: 56
gttagactcg tcgacgg                                                17

SEQ ID NO: 57          moltype = DNA   length = 17
FEATURE                Location/Qualifiers
misc_feature           1..17
                       note = Primer
source                 1..17
                       mol_type = other DNA
                       organism = synthetic construct
SEQUENCE: 57
ctatttatta cggcggg                                                17

SEQ ID NO: 58          moltype = DNA   length = 17
FEATURE                Location/Qualifiers
misc_feature           1..17
                       note = Primer
source                 1..17
                       mol_type = other DNA
                       organism = synthetic construct
SEQUENCE: 58
gacgtacagg tcgcatc                                                17

SEQ ID NO: 59          moltype = DNA   length = 20
FEATURE                Location/Qualifiers
misc_feature           1..20
                       note = Primer
source                 1..20
                       mol_type = other DNA
                       organism = synthetic construct
SEQUENCE: 59
ggtagtttga aacagaattc                                             20

SEQ ID NO: 60          moltype = DNA   length = 23
FEATURE                Location/Qualifiers
misc_feature           1..23
                       note = Primer
source                 1..23
                       mol_type = other DNA
                       organism = synthetic construct
SEQUENCE: 60
gtaactatga agatgtatga cac                                         23

SEQ ID NO: 61          moltype = DNA   length = 17
FEATURE                Location/Qualifiers
misc_feature           1..17
                       note = Primer
source                 1..17
                       mol_type = other DNA
                       organism = synthetic construct
SEQUENCE: 61
acaacagggt gagcatc                                                17

SEQ ID NO: 62          moltype = DNA   length = 17
FEATURE                Location/Qualifiers
misc_feature           1..17
                       note = Primer
source                 1..17
                       mol_type = other DNA
                       organism = synthetic construct
SEQUENCE: 62
agtcaacgcc gttttgc                                                17
```

```
SEQ ID NO: 63           moltype = DNA   length = 17
FEATURE                 Location/Qualifiers
misc_feature            1..17
                        note = Primer
source                  1..17
                        mol_type = other DNA
                        organism = synthetic construct
SEQUENCE: 63
aggaaaggca gttcgcc                                                        17

SEQ ID NO: 64           moltype = DNA   length = 17
FEATURE                 Location/Qualifiers
misc_feature            1..17
                        note = Primer
source                  1..17
                        mol_type = other DNA
                        organism = synthetic construct
SEQUENCE: 64
aggctggcga acagttc                                                        17

SEQ ID NO: 65           moltype = DNA   length = 20
FEATURE                 Location/Qualifiers
misc_feature            1..20
                        note = Primer
source                  1..20
                        mol_type = other DNA
                        organism = synthetic construct
SEQUENCE: 65
gcaaccagtt ccggaatatc                                                     20

SEQ ID NO: 66           moltype = DNA   length = 19
FEATURE                 Location/Qualifiers
misc_feature            1..19
                        note = Primer
source                  1..19
                        mol_type = other DNA
                        organism = synthetic construct
SEQUENCE: 66
agcttgttgt aaacacgcg                                                      19

SEQ ID NO: 67           moltype = DNA   length = 18
FEATURE                 Location/Qualifiers
misc_feature            1..18
                        note = Primer
source                  1..18
                        mol_type = other DNA
                        organism = synthetic construct
SEQUENCE: 67
ccagcttagc aagagatg                                                       18

SEQ ID NO: 68           moltype = DNA   length = 17
FEATURE                 Location/Qualifiers
misc_feature            1..17
                        note = Primer
source                  1..17
                        mol_type = other DNA
                        organism = synthetic construct
SEQUENCE: 68
taacacattg cggatac                                                        17

SEQ ID NO: 69           moltype = DNA   length = 21
FEATURE                 Location/Qualifiers
misc_feature            1..21
                        note = Primer
source                  1..21
                        mol_type = other DNA
                        organism = synthetic construct
SEQUENCE: 69
gcctggccca gggaagaggg t                                                   21

SEQ ID NO: 70           moltype = DNA   length = 25
FEATURE                 Location/Qualifiers
misc_feature            1..25
                        note = Primer
source                  1..25
                        mol_type = other DNA
                        organism = synthetic construct
SEQUENCE: 70
```
cagcacaaaa cagaagctag ggttt                                           25

SEQ ID NO: 71            moltype = DNA   length = 26
FEATURE                  Location/Qualifiers
misc_feature             1..26
                         note = Primer
source                   1..26
                         mol_type = other DNA
                         organism = synthetic construct
SEQUENCE: 71
ccgagtgtca aggagttgcg gacact                                          26

SEQ ID NO: 72            moltype = DNA   length = 26
FEATURE                  Location/Qualifiers
misc_feature             1..26
                         note = Primer
source                   1..26
                         mol_type = other DNA
                         organism = synthetic construct
SEQUENCE: 72
cttgaagcaa cggctaaagc gacgaa                                          26

SEQ ID NO: 73            moltype = DNA   length = 22
FEATURE                  Location/Qualifiers
misc_feature             1..22
                         note = Primer
source                   1..22
                         mol_type = other DNA
                         organism = synthetic construct
SEQUENCE: 73
tacgagagct gggtgaactt ca                                              22

SEQ ID NO: 74            moltype = DNA   length = 18
FEATURE                  Location/Qualifiers
misc_feature             1..18
                         note = Primer
source                   1..18
                         mol_type = other DNA
                         organism = synthetic construct
SEQUENCE: 74
cgatcaggtc cagcacgg                                                   18

SEQ ID NO: 75            moltype = DNA   length = 20
FEATURE                  Location/Qualifiers
misc_feature             1..20
                         note = Probe
source                   1..20
                         mol_type = other DNA
                         organism = synthetic construct
SEQUENCE: 75
ccgctaccgc cgcgagatga                                                 20

SEQ ID NO: 76            moltype = DNA   length = 18
FEATURE                  Location/Qualifiers
misc_feature             1..18
                         note = Primer
source                   1..18
                         mol_type = other DNA
                         organism = synthetic construct
SEQUENCE: 76
ccgggtgaat cagcgttt                                                   18

SEQ ID NO: 77            moltype = DNA   length = 18
FEATURE                  Location/Qualifiers
misc_feature             1..18
                         note = Primer
source                   1..18
                         mol_type = other DNA
                         organism = synthetic construct
SEQUENCE: 77
gccgtggcct ttgacagt                                                   18

SEQ ID NO: 78            moltype = DNA   length = 20
FEATURE                  Location/Qualifiers
misc_feature             1..20
                         note = Probe
source                   1..20
                         mol_type = other DNA
                         organism = synthetic construct

```
SEQUENCE: 78
tgccgccaac gaatcaccgg                                                    20

SEQ ID NO: 79           moltype = DNA   length = 21
FEATURE                 Location/Qualifiers
misc_feature            1..21
                        note = Primer
source                  1..21
                        mol_type = other DNA
                        organism = synthetic construct
SEQUENCE: 79
gaacgtgtgt tgggtttgca t                                                  21

SEQ ID NO: 80           moltype = DNA   length = 24
FEATURE                 Location/Qualifiers
misc_feature            1..24
                        note = Primer
source                  1..24
                        mol_type = other DNA
                        organism = synthetic construct
SEQUENCE: 80
tgcagcctaa ccatgcgcag ggta                                               24

SEQ ID NO: 81           moltype = DNA   length = 20
FEATURE                 Location/Qualifiers
misc_feature            1..20
                        note = Probe
source                  1..20
                        mol_type = other DNA
                        organism = synthetic construct
SEQUENCE: 81
tccagcaatc cttgcacctt                                                    20

SEQ ID NO: 82           moltype = DNA   length = 20
FEATURE                 Location/Qualifiers
misc_feature            1..20
                        note = Primer
source                  1..20
                        mol_type = other DNA
                        organism = synthetic construct
SEQUENCE: 82
gccgtatccg caatgtgtta                                                    20

SEQ ID NO: 83           moltype = DNA   length = 21
FEATURE                 Location/Qualifiers
misc_feature            1..21
                        note = Primer
source                  1..21
                        mol_type = other DNA
                        organism = synthetic construct
SEQUENCE: 83
ggcccaggga agagggtata t                                                  21

SEQ ID NO: 84           moltype = DNA   length = 19
FEATURE                 Location/Qualifiers
misc_feature            1..19
                        note = Probe
source                  1..19
                        mol_type = other DNA
                        organism = synthetic construct
SEQUENCE: 84
aagttgtcta agcgtcaat                                                     19

SEQ ID NO: 85           moltype = DNA   length = 26
FEATURE                 Location/Qualifiers
misc_feature            1..26
                        note = Primer
source                  1..26
                        mol_type = other DNA
                        organism = synthetic construct
SEQUENCE: 85
tgtctaagcg tcaatttgtt tacacc                                             26

SEQ ID NO: 86           moltype = DNA   length = 16
FEATURE                 Location/Qualifiers
misc_feature            1..16
                        note = Primer
source                  1..16
                        mol_type = other DNA
```

```
                               organism = synthetic construct
SEQUENCE: 86
tttgccagtg ggccca                                                        16

SEQ ID NO: 87          moltype = DNA  length = 27
FEATURE                Location/Qualifiers
misc_feature           1..27
                       note = Probe
source                 1..27
                       mol_type = other DNA
                       organism = synthetic construct
SEQUENCE: 87
acaatatacc ctcttccctg ggccagg                                            27

SEQ ID NO: 88          moltype = DNA  length = 20
FEATURE                Location/Qualifiers
misc_feature           1..20
                       note = Primer
source                 1..20
                       mol_type = other DNA
                       organism = synthetic construct
SEQUENCE: 88
gccgtatccg caatgtgtta                                                    20

SEQ ID NO: 89          moltype = DNA  length = 19
FEATURE                Location/Qualifiers
misc_feature           1..19
                       note = Primer
source                 1..19
                       mol_type = other DNA
                       organism = synthetic construct
SEQUENCE: 89
aagttgtcta agcgtcaat                                                     19

SEQ ID NO: 90          moltype = DNA  length = 21
FEATURE                Location/Qualifiers
misc_feature           1..21
                       note = Probe
source                 1..21
                       mol_type = other DNA
                       organism = synthetic construct
SEQUENCE: 90
ggcccaggga agagggtata t                                                  21

SEQ ID NO: 91          moltype = DNA  length = 25
FEATURE                Location/Qualifiers
misc_feature           1..25
                       note = Primer
source                 1..25
                       mol_type = other DNA
                       organism = synthetic construct
SEQUENCE: 91
ccccacgatt aaatgtcaaa ctgat                                              25

SEQ ID NO: 92          moltype = DNA  length = 25
FEATURE                Location/Qualifiers
misc_feature           1..25
                       note = Primer
source                 1..25
                       mol_type = other DNA
                       organism = synthetic construct
SEQUENCE: 92
gctcagcctt gttttttgtac attca                                             25

SEQ ID NO: 93          moltype = DNA  length = 20
FEATURE                Location/Qualifiers
misc_feature           1..20
                       note = Probe
source                 1..20
                       mol_type = other DNA
                       organism = synthetic construct
SEQUENCE: 93
aattttcata gcttttgtg                                                     20

SEQ ID NO: 94          moltype = DNA  length = 27
FEATURE                Location/Qualifiers
misc_feature           1..27
                       note = Primer
source                 1..27
```

```
                              mol_type = other DNA
                              organism = synthetic construct
SEQUENCE: 94
cgctcttaag tctgctgttt gtttact                                        27

SEQ ID NO: 95             moltype = DNA   length = 24
FEATURE                   Location/Qualifiers
misc_feature              1..24
                          note = Primer
source                    1..24
                          mol_type = other DNA
                          organism = synthetic construct
SEQUENCE: 95
cacacgccac ttcttgtctt ctat                                           24

SEQ ID NO: 96             moltype = DNA   length = 13
FEATURE                   Location/Qualifiers
misc_feature              1..13
                          note = Probe
source                    1..13
                          mol_type = other DNA
                          organism = synthetic construct
SEQUENCE: 96
cgcgagctca tgc                                                       13

SEQ ID NO: 97             moltype = DNA   length = 25
FEATURE                   Location/Qualifiers
misc_feature              1..25
                          note = Primer
source                    1..25
                          mol_type = other DNA
                          organism = synthetic construct
SEQUENCE: 97
gctgcagctc acttgaaggt ataat                                          25

SEQ ID NO: 98             moltype = DNA   length = 20
FEATURE                   Location/Qualifiers
misc_feature              1..20
                          note = Primer
source                    1..20
                          mol_type = other DNA
                          organism = synthetic construct
SEQUENCE: 98
ggcaccaccc tgtaaaagca                                                20

SEQ ID NO: 99             moltype = DNA   length = 17
FEATURE                   Location/Qualifiers
misc_feature              1..17
                          note = Probe
source                    1..17
                          mol_type = other DNA
                          organism = synthetic construct
SEQUENCE: 99
aaccattaga tgcttcc                                                   17

SEQ ID NO: 100            moltype = DNA   length = 16
FEATURE                   Location/Qualifiers
misc_feature              1..16
                          note = Primer
source                    1..16
                          mol_type = other DNA
                          organism = synthetic construct
SEQUENCE: 100
ccgtcgacga ggcgaa                                                    16

SEQ ID NO: 101            moltype = DNA   length = 16
FEATURE                   Location/Qualifiers
misc_feature              1..16
                          note = Primer
source                    1..16
                          mol_type = other DNA
                          organism = synthetic construct
SEQUENCE: 101
gcggcgagct gttcag                                                    16

SEQ ID NO: 102            moltype = DNA   length = 16
FEATURE                   Location/Qualifiers
misc_feature              1..16
                          note = Probe
```

```
source                  1..16
                        mol_type = other DNA
                        organism = synthetic construct
SEQUENCE: 102
tctgagcttc ggatac                                                           16

SEQ ID NO: 103          moltype = DNA   length = 161748
FEATURE                 Location/Qualifiers
variation               2151..2250
                        note = n is a, c, g, or t
variation               6108..6207
                        note = n is a, c, g, or t
variation               9770..9869
                        note = n is a, c, g, or t
variation               18125..18224
                        note = n is a, c, g, or t
variation               33520..33619
                        note = n is a, c, g, or t
variation               44173..44272
                        note = n is a, c, g, or t
variation               91565..91664
                        note = n is a, c, g, or t
variation               136173..136272
                        note = n is a, c, g, or t
variation               148532..148631
                        note = n is a, c, g, or t
variation               154026..154125
                        note = n is a, c, g, or t
variation               158039..158138
                        note = n is a, c, g, or t
source                  1..161748
                        mol_type = genomic DNA
                        organism = Zea mays
variation               67063..67162
                        note = n is a, c, g, or t
SEQUENCE: 103
cccggccgct gatgaatcag cttgattcgt tctgttatca cgggtggtca ctcaacgagc            60
aggtccaaag gaaaggtact caggaaaata gcctgagtct cctaaagtgc cataagaaca           120
tcatcgtaat cataataaca acatcatatc ataaatattc gcatcatgtt tgttgattaa           180
agtggagcaa tagcttgaag cttaccataa taacccaaaa ggtaaacaag gacaagataa           240
atacagacta gtcaaacctt aggtttcaat taagtaaagg gggacagtga attatgaagt           300
aagtaggaca taataggtca gaggacactt gccttcacca ggttgttgcc caggaagatc           360
ttcggcaaca cactcaggaa ccatagactg cttgttgtct acgcaaagcg atcatgcatt           420
caacacattt cgataatgat aaagaaacaa tacaccaaaa atatacaatc aagtgaacac           480
taattcaaaa gaaagtaaca aactcaagcg aagcctaggg tctagggtgg accaatacac           540
atataggttt gtggttctct aagtattact tatctcaata gattacataa cttaatttca           600
tttatcttaa tgagacaaaa gaattatacc agggatagtt tcatatatta catattatta           660
acccacaaag ttaaacatct aactaccatt atggttttcc ttttatcctt cttattaata           720
aataagccat cagttacact aacctatagt ctaggcataa aattagcaca tgcagacagt           780
aaaaggttat aatttaaaca ggtagagaat aaccttacaa acattttgca atttgaatca           840
ctcaatttgg agttcatatg caaaagatat gaaataacaa agttttggaa ttcaaaatac           900
aaaactaggt ctaattatgt gataacctaa aagattaggg gcctttctgc aaaagtacag           960
gggcatgcgt gcgaaaacca gggacgatgg gttgattctc agaaagccga gggccttttt          1020
aacaaaacta ccacgcaaag gggtatcagc tgatctcgac tgcatgatca cagatcaacg          1080
gccaggatta gatttgagcg cgagcacgag cacgagctaa caggtgggcg aggatagtca          1140
gcgacctagg ggcgaggcgg actgtctggc cgggcctagc tgcaggggcg gggtgaggtg          1200
gcggatccga gtggccagat ctccatcgga cagctgggat cagatcgagt ttaattgaag          1260
ccaggtcgtt agatctcaga tggatgcctg aaatctgatg gcaagctcgg gcggggttgc          1320
taggctgctc atggcgccgc cgcccaattt cgcggcgtgg cgcggcctcc atgggtct          1380
gggcgctggg aaaaggctca ggcgagctca gggtgacacg gcgggctcag ccatggagcc          1440
gacaccggcg tagaggcacc agagagcacg gtccgaggca aagcagcccc acggcggcgc          1500
agcttaactc tggcgagcga ttgcatggac aacagggcag taaatggaa attaagggca          1560
tgggtgggtt ggttacgtcg agagatgact ctagagcgct tgagcaacgg cgaggacacc          1620
gcgagggccc tggtggacgg tggcggagac tcggctgaca ggtgataggt ccggtgagcg          1680
aaccaaggga aatagagggg ctggggaaaa ccagagggtg tctcgtgttg ctggcgagga          1740
ggcgaagatc agtagggcaa tggacgcgac aggaactcga cgacggccac ggaacggacg          1800
gtggactacg gcagtgctcc acggctgtgc gctcggtgcg agagagaggt gcgagggggt          1860
cggctgtggg acgctactga gcgaggggag tgagcgagtg agtgtgggcg ccaaaaaagt          1920
caggcggtg ggggagttgg ccgaaaaaca cgcgacatgt gtgcatccac ggcggggttg          1980
gcgagcgggt ggttagggaa aggggaggtg gctgacaggt ggggtccgct tgccagcgag          2040
ggtgaatacg cgaacgagcg gttctgcgct gacaggccga cccaccgagg caaaaaggag          2100
cgggcgtgtt gcgtgaaaga aaccggcacc gacaaaccgg cctccgcgcg nnnnnnnnnn          2160
nnnnnnnnnn nnnnnnnnnn nnnnnnnnnn nnnnnnnnnn nnnnnnnnnn nnnnnnnnnn          2220
nnnnnnnnnn nnnnnnnnnn nnnnnnnnnn ctgcgggtac cacgttctac aaggtttgat          2280
gatagtgagg aaggaagaat ttctggcact gaagcaaggg ccctgtctg tcagtgagta           2340
catggacaaa ttcctgcaac tatctcacaa tgcacccgag gatgtcaaca ttgatgctaa          2400
gaggtactac aggtttccga gagggttggt tgacccctgc actactagtt gatgaaccac          2460
acattcccta ccttccaaca tctgattgat agggcaataa tgactgagag gaagcgccag          2520
gagatggaag accaaaagcg caagattggt ggaccctagg ccaggagcag cagtcgtctc          2580
```

-continued

```
ccgtttctgg caatccaccc tagcagttca agtagatcca ccctcaggga taccaacacc     2640
agaaccaatg ttcgcaccag tagcaattcc agaggcagtt ccctcaacag cagcatgtca     2700
cacccgggtt ttaggggtcc aaaacccagg cgcgaaattc accaagtgct gggatcgagt     2760
ctcacacata tgatgactca tggtatagaa acaaatgtca catctttact atataataga     2820
agttcgcac aaaataacta aataattaca tcatacgatg acgacgatcc atcaacccaa      2880
agtttactgt gagacgacgg cctagacctc tcatgaactc atcgcgacat ccttcatgct     2940
cctcatcttg cggtacctgt tcttgaccag ggggatttga gtacagcaag ggtgagctca     3000
catacgttca tcgctcaaca agttgtgggg aataatgtgt atgaactcac caaaggtggg     3060
agctcatgtg aagtgtaagg cttaccaaag gagatgggta aagtgagca tgactttaa       3120
agttggtcaa aatttatta gcagttacta agtataagta gataccgacc caaataata      3180
agagattaaa ttaataacaa cacccacaat gcaatgcata tgacaattta agtttagttc    3240
cataatttac tcatgtgagg gtccgagctg ctcatgaccg tgagcacggc tgatataaca    3300
gttttacagt ctgcacaggt tgcacatctt tacccacaag tcatgttacc tatttgccaa    3360
gggatcgcga cttctcattc atctctaccg agaagacaag gtaggttacc actacgaggc    3420
ctttacaaac ttccactagc ttccgaaaac ccgctacggt ttctaagaag gaaaatatag    3480
gaatccctcg tccaaaaagc catcgcagca tgatcgactc gagaacctcc ctatacgcat    3540
gctcctctac cgcccttgcc ccttctcgggt aaggtagtct tccactagct ttcttaatta   3600
gtcagccaag ggcgtcccat accacccttg tggtagcact gtttccctgg gtggttgctc    3660
catgttccaa ttaacatagc aatcttatca tgaacaataa ttaaaataac aaaagaattg    3720
taacatgatc ataatgtaac attaatttcc caaaaccagg tagagcaata gcaatactac    3780
ccaatagtgc tttttgtttgc aaggtagggg ataaacaata ctaggaaaac ctattgggtc   3840
ccatcaaatt aacctgagca tgtcacagtg attaatagga acattattag gtaaagaaaa    3900
gtgatcaagg gcacaacttg gctgagactc aagattccta ggtaccagct tggtcttcaa    3960
gattctcgta acctcgctgc taatcatagc aatacaaaca acatggtat aggcaaaatt     4020
aacatcacac caaacataaa gaacaaactg cataataatg atctacgcac cacaacgaga    4080
tcctaggttc gagaaccact aaaattcgga g ttacggttaa caagatgtgg ttttcggaag  4140
acctatgtga ttaaatatga gactaggtct ttatgttgat tttataaatt atgtgataaa    4200
gatattaaag aaataacttt aatctacatc atactagagt agacataata ttttagttac    4260
cttataatca tagacaaact aactttgatt agtaggaata atctactaag catatattaa    4320
atgaattttt attttttgga aacatgctat ttgctaaaat aattttacag aagcgtaggc    4380
aaaattatta cgaagctaac gcaacatgaa tacattaaat cagagttaaa atgaaagaaa    4440
tatgtatta ttaagtttta ggatttaatt ctataattat taaatatttc tggattgggg     4500
acactattct ataaaagatc aggggctcc atataatatt taggacttat ccgcaatgat     4560
ttctacctat acccggactg cgggctgatt tgcaagaagt ctgggtgtctc ttttataagt   4620
tagtcacggt gaaggggtac acgtgactaa ttccttggat catcagccaa gcgcccagag    4680
tagaagattt gcccgccgaa ccggtacgca tcctagatcg tcgatctac gataaacggc     4740
ccacgcttaa aataatagag atcgatcctc atatgcaaga tccagatcag acgaccgga     4800
tcgattcgga tgaaacgtta cgtgtgatct aatcacagcc gatacctccc agatccacgg    4860
ttcacgcgag gcccagccat gccctgatcg tgatcgctca cccatgatct aacggctgct    4920
gcatttcctt ccacctcacg acggaaagca gagcactgtt gcgggcacgc cgcggccatg    4980
ccccaccaca ccaccagtga tatcccgccc ggctccccat ttcctagtat cgagcgtggg    5040
tacgtgaatc acgagagga ggaggctcca agtatgctag ggctgttctt accaaggatc     5100
acggtgtttc aagtgttgac cccaccacgc agttgctccg tggcgccgcg ggtcaccagc    5160
gaagcatgca ctggtcgttg ttctcgcacg aggtgccttc tagaatcctg cacgcgtccc    5220
acggatgacc caacccgacg ccgagaccgc aataccggcg tgcccgggaa ccccgtcgg     5280
tggcaattca cccctgtgt tctccttctc ccttacgacg atggtgatgg cgccttctct    5340
cccgatcggc agaccgagcg tagcccacga tgctgaagga gaggaaacta gagctgcacc    5400
catggccgag gttggagcgt ccgttatata tggccagggg tacggctagc agtgggcggg    5460
tgcaccatgg cacgaaggtc gttgcacagt ttacaggagg cgagcttgca gcggacgagc    5520
aggatcgcca tggggaggat agacttgacg gccatggccc acatgccaga cgcggctgca    5580
ggcgcaggag tgggcaggag cgggctgcgc cggagcaggg aaatagagtt gggcccgcta    5640
acgaaggaaa gaaactgggc cgagaagcca gagatccggc ccatagcgca gaaagcttcc    5700
ccttttctt tattctttaa tgattttctg tttttatcttc cctttcatat ttctttccct    5760
tatttaaac tctaatctaa atgctcaatc caaaactccg gcatgatatg caataattac     5820
atatatctgt ttagttttgt ttattttatc caaatatttt aagtatgcaa tgcacacaca    5880
tagagtaaaa attacttctt tgaatgtata gtccatttaa aattatgttc ataattttta   5940
agatagagga ttttttttgtg tgtatagtat ttattaaggt tttttaagct taattctttt   6000
ggagaatatc tctaatcatg ttattcaaca agggttggtt taaattatat gagggtcttt    6060
tatttaatct ctcattataa aagacttcta tttaaatctt ggaattcnnn nnnnnnnnn    6120
nnnnnnnnnn nnnnnnnnnn nnnnnnnnnn nnnnnnnnnn nnnnnnnnnn nnnnnnnnnn    6180
nnnnnnnnnn nnnnnnnnnn nnnnnnnggg ggttttcctt tatctcgtgc gtggttatcc    6240
atctaatcac gtgggagttt gttggctatc tcttaggaaa aggtccagac ctcctccct    6300
ataaatataa aggggtacgg ccgattgaga acccccgaac acattccaat cgaaccaatt    6360
accttattta cttttcctgc cctaggagta gatgtagcat agttctagtt gtagtcttcc    6420
acatatccac ctccaccct attcaactct acgtcgtcta gatccgtctt gggtggcctg    6480
ccgatcccaa gacgaccta ggatctcacc cctccgggg ggcaagatct agttgtccat     6540
ccaagacttc ttcctcgatt tgatctctta attcctaggc gactccacgt cgtctggga    6600
cgccccgggt gacctgtcga cccggagcac cttaagatct ttcccccag gggacgagat    6660
ctagattcca gcaaggagta ggaagacgac cctgtcgcca ggtccggac cgtccggcg    6720
agagctgcgg accgtccggt gtgacgcagg aagacaccg ctcctgcgcc caggtcgcgg    6780
accgtccggc caaggctgc ggaccgtccg gccaaggct gcggaccgtc cgcgcctgac     6840
cagagggcac cgcacggtt cttgttgagt gtttggcgct ccaaaaggc gtcaacatac     6900
ttttggcga ctccgctggg aagaagttg cagatctaca aaatcaggct tacatggccg     6960
aagaa tctcaacagt gcttctccaa acagcaacac aaggctgact aatttatccg         7020
ccgctgagca taaaaaatta gaagatgaca tgaagaaat agacgaggag gccaccgac     7080
aaaaggatca ggtgctcaag gtggcggaca agtggtaccct ctcgcacttc aaggtagact 7140
gccaccagaa gaccgtccaa gagagggaga taaacgccga gtatatgtta gccgtgctgc   7200
aacagctccc cacaataggt gatgccaggt cagccgatga tattccatct attaaaattt   7260
cttttgataa tcggattaaa agtatcacgg aggatataga gaggatgaca catgcattag   7320
```

```
gaaaaactca catgcctaat tttttatcac ataaattagg cgatgaaaca attgcgccaa    7380
acacatcggc ggcaaatggg tttcccagc catattctgg tatgccgatg gactcatatc     7440
taggacgacc gtcatcacca tctttgctaa atggtgagtc aaccctgggc acagccggac    7500
cgtccgcaca caattgcgga ccgtccggcc ctctgtcgga ccgtccggca ccctacgccg    7560
gacagtctgg agttacacag agcccaccac aagggtcaca ggtgttgcct gacgtgaccg    7620
gactgtccga ggatagtacc ggaccgtccg atccacccgc agaccgtccg actgtgcaag    7680
tcggaccgtc cggggcacca gaagtcacct gtgatccacc tagtgcggaa ggccgacata    7740
aatataatcg gccacccaag ccccaagaac taaaaaagtc acatgtccct gagcttgttt    7800
ggcccactaa ggccaaacct tctgttcgct cttacccgca ctcgaaacaa aaggaaaagg    7860
ttaagttcac atttaatatt actaaatgtg ataaaatatt tgatgagttg cttaaacatg    7920
gtaatattaa attgtcacat gtaattcctc cggttgaaca attaaaaggg cgtgtttatt    7980
gcaaatggca tggctccttt ctccataaca ccaatgattg tgccgtcttc cgtcggcaaa    8040
tacaatcggc tataaacgaa ggccggttga ggtttcaaaa agaggtgaaa attgacaggc    8100
cacctgttcc tgtcaccaca ttagagccca tggccataatt cggccttgta                8160
cggccgataa aagtaaaaat aaaaatatcg tcattggtga tcctcgcaca ccaaatatgt    8220
cacgcagaat ggttactctg aaggctccgg acaaagaaa gaccgagcc accgggggc          8280
aagcacgatc ggacacccga tcacggtcgc ctgtcatgcg tacgccggac gatccgggta    8340
ctaaggccga acagtccgag acaggccgga acagtccggc tatgatggcc ggacggtccg    8400
cagatggtca gaagcagcaa cctcagacca tcggaccaca acgttccaac acaagtgtta    8460
ggaaacaaaa cactactaag acgtctggac gactcagtag agtcggccct acttttggtc    8520
agttgcttgc caaatatatg aagaaggccg ttccacacaa ccgccaaata aaacaaacaa    8580
agtcaatagg gcgatctgtg cgaaagcaaa agccgactaa acgaacccaa agggtagcac    8640
aaccaatatc gccttatcat cctcctccag ggatagcatg gtgcgtccca ttctatccat    8700
cgccgatgtg ttgtcctact catgtgtggg gtggtacggc gatgaatttg tattactggc    8760
ccaatccgtt tgcttatttg ggctgggggg caccacaagt ttttgcctat tgacaggttg    8820
atcagataga catggctgaa gaggatgcga tccgaaacgg cctctgtgca ttaaagtcct    8880
atcaagtatt tatattatct gatcgcaaga gccgatgact tgcatcgagc tgagtcctta    8940
cttcggaaaa aaaaacctca tgaggtcaat tgtttccgaa gttttcgcta atgcttttgg    9000
ttcgccatgc tccaccaaaa ggcagggggg catatgttgg acaccaaaat gagcggacgg    9060
tccggcccat gggcccggac ggtccgcgtg tcccgagatt agattaactc ggatgtttat    9120
ccttatctcg tgcgtggtta tccatctaat cacgtgggag tttgttggct atctcttagg    9180
aaaaggtcca gacctcctcc cctataaata taaggggta cggccgattg agaaccccg      9240
aacacattct aatcgaacca attaccttat ttactttcc tgcccctagga gtagatgtag    9300
catagtctcta gttgtagtct tccacatatc cacctccacc cctattcaac tctacgtcgt    9360
ctagatccgt cttgggtggc ctgccgatcc caagacgacc ctaggatctc accccctccgg   9420
ggggcaagat ctagtgtcc atccaagact tcttcctcga tttgatctct taattcctag    9480
gcgactccac gtcgtctggg gacgccccgg gtgacctgtc gacccggagc accttaagat    9540
ctttccccca ggggacgaga tctagattcc agcaaggagt aggaagacga ccctgtcgcc    9600
aggtcgggca cgtccggccc agagctgcgg acgtccggtg tgacgcaggg aagacaccgc    9660
tcctcgccca ggtcgcggac cgtccgaccc aaggctcgga cgtccgccca aggctgggac    9720
cgtccgcgcc tgaccagagc acgccacggt ctgtgaggtt gcaagatgcn nnnnnnnnn      9780
nnnnnnnnn nnnnnnnnn nnnnnnnnn nnnnnnnnn nnnnnnnnn nnnnnnnnn               9840
nnnnnnnnn nnnnnnnnn nnnnnnnnt aatctataca gacgatctga gattcgtctc          9900
attttgagcc cgtctcaaga atccctttaa tgtctcttgg gttagagatt tttcctgtaa    9960
aaagaatacc caagtgaagc gagaataatc atccacaata actagacagt acttactccc    10020
gccgatactt atgtaagcga tcgggccgaa taaatccatg tggaggagct ccagtggcct    10080
gtcacttgtc attatgttct tgtgtgggatg atgagtgcca acttgcttcc cggcttggca    10140
tgcgctacaa atcctgtctt tctcaaaatg aacatttgtt aatcctaaaa tgtgttctcc    10200
ctttagaagc ttatgaagat tcttcatccc aacatgggct agtcggcggt gccagagcca    10260
acccatgtta gtcttggcaa ttaagcatgt gtcgagttca gctctatcaa aatctactaa    10320
gtatagctga ccctctaaca cacccttaaa tgctattgaa tcgtcacttc ttctaaagac    10380
agtgacacct acatcagtaa aaagacagtt gtagcccatt tgacacaatt gggaaacaga    10440
aagcaagttg taatcaatg aatcaacaag aaaaacattg gaaatagtat ggtcaggtga    10500
tatagcaatt ttacccaatc ctttgaccaa acctcgattt ccatcccccga atgtgatagc    10560
tcgttgggga tcttggtttt tctcatatga ggagaacatc ctttctccc cggtcatgtg    10620
ggtttgtgca cccgctgtcg agtatccaac ttgagccccc ggatgcataa acctacaaaa    10680
acaaatttag ttcttgactt taggtaccca aatggttttg ggtcctttgg cattagacac    10740
aataactttg ggtacccaaa cacaagtctt tgacccctg tgcttgcccc caacatattt      10800
ggcaactact ttgccggatt tgttttgtaag cacataagaa gcatcaaaag tttttaaatga   10860
aatagcatga tcatttgatg caataggagt tttctttcta ggcaacttgg cacgggttga    10920
ttgcctagag ctagatgtct caccccttata cataaaagca tgattagggc cagagtgaga    10980
cttcctagaa tgaattttcc taattttgct ctcgggataa ccggcagggt acaaaatgta    11040
accctcgtta tcctgaggca tgggagcctt gcccttaaca aagttagaca agttttaag    11100
aggggcatta agtttgacat tgtctcccct ttggaagcca atgccatcct taatgtcagg    11160
gcgtctccca ttataaagca tgctacgagc aaatttaaat ttctcattct ctaggttgtg    11220
ctcggcaatt ttagcatcta attttgctat atgatcattt tgttgtttaa ttaaagccat    11280
atgatcaaga atagcattaa catcaacatc tctacatcta gtacaaatag atacatgctc    11340
atcaatagat gtgagggtt tgcaagaatt aagttcaaca atcttagct gaagaaatatc     11400
attcttatct ctaagatcgg aaattgtaac tttgcaaaca tcaaaatctt tagccttagc    11460
aatcaaattt tcattctcta atctaaggct agcaagagaa atgttcaatt cttcaatcct    11520
agcaagcaac tcatcattat tatctctagg attgggaatt gaaacattac aaatatgaga    11580
atcaaccttta gcatttaaac tagcattttc atttctaagg ttgtcaatca tctcacggca    11640
agtgcttagc tcactagaca ttttcaca tttctcaact tctagagcat aagcctttct      11700
aaccttaaca tgtttcttgt ttcctttaat tagacaatctt cttgggaat caaaaggtc     11760
atccttttca tgaatagcac tgactaattc atttaatttt tccttttgag ctatgttaag    11820
gttggcaaag aggatacgca aattttcctc ctcatcacta gcattatcat cactagacga    11880
ttcatatta gtggaggagt tggatttaac cttcttcttt tgccgtcct tgccatgag      11940
gcacttgtg ccgacgttgg ggaagagaag tccttggtg acggcgatgt tggcggcatc      12000
ctcgtcgtcg gaggagtcgc ttgagctctc gtcggagtcc catttgcgac aaacatgggc    12060
```

```
atcgccgccc ttcttcttgt aatacctctt cttctccttt cttctcccct tcttgtcgtc   12120
gcctcggtca ctgtcactag atattggaca tttagcaata aaatgaccgg gcttaccaca   12180
tttgtagcaa accttcttgg agcgggactt gtagtctttc cccctccttt gtttgaggat   12240
ttggcggaag ctcttaatga cgagcgccat ctcctcattg tcaagcttgg aggcgtctat   12300
tggttgtcga cttggtgtag actcctcctt cttctcctcc gttgccttga atgcaacggg   12360
ttgggcttcg gatgagtcgc caagctcgtt gattttcctc gagccttcta tcatgcactc   12420
aaaacttaca aaatgcccga taacttcctc gggggtcatt ttagtatatc taggattacc   12480
acgaatcaat tgaacttgag tgggattaag aaaaatgaga gatcttaaaa taacatttac   12540
cacttcgtga tcgtcccact tcttgctccc gaggttgcgc acttggttca ccaaagtctt   12600
gagccggttg tacatgtgtt gtggctcctc tcctttgtga agccggaacc gaccgagctc   12660
cccctcgatc gtttcccgct tggtgatctt ggtgagctcg tctccctcgt gcgcggtttt   12720
gagtacatcc caaatctcct tggcgctctt caacccttgt actttgttat actcctctct   12780
acttagagag gcgaggagta ttgttgttgc ttgagagttg aagtgctcga tttgggccac   12840
ctcatcctca tcatagtcct catccccctac ggatagtacc tgcgcgccaa actcaacaac   12900
atcccatatg cttttgtgga gcgaggttag atgaaatcgc attaaatcgc tccacctagc   12960
gtaatcttca ccatcaaaag ttggtggttt gcctaatggg acggaaagta aaggtgtatg   13020
tttgaaaatg cgagggtagc gtaggggat cttactatac ttcttgcgct cttggcgctt   13080
agaagtgacg gagggcgcat cggagtcgga ggtcgatgtt gatgaagtgt cggtctcgta   13140
gtagaccacc ttcctcatcc ttttgtgctt gtcgcctttc cgatgcgct tgtgggaaga   13200
agatttttcc ttcttctctt tgtggtgaga agaagatttc ttctccttcc ctttgttgga   13260
ggagctcttc ttcttctccc tccttttggt gcgagactct tccgatgaag tgctcccgtg   13320
gcttgtagtg ggccttttcgc cggtctccat ctccttcttg gcgtgatctc ccgacatcac   13380
ttcgagcggt taggctctaa tgaagcaccg ggctccgata ccaattgata gtcgcctaga   13440
gggggggtgaa tagggcgaaa ctgaaatttg caaatataaaa cacaactaca agccggggtt   13500
agcgttagta ataaggaatg agtccgcaag agagggcgca aaacaaatcc caagcgaatg   13560
agcaagtgag acacggagat ttgttttacc gaggttcggt tcttgcaaac ctactccccg   13620
ttgaggaggc cacaaaggcc gggtctcttt caacccttcc ctctctcaaa ccgatccacg   13680
atcgagtgag cttctcttct caaatcaaag ccgggaacaa aacttccccg caagggccac   13740
cacacaattg gtgcctcttg ccttgattac aatggagttt tgatctcaag aacaagtgag   13800
aaagaaaaga agcaatccaa gcgcaagagc tcaaatgaac agcacaaatc actctcacta   13860
gtcactaggg ctttgtgatg aattggagag gatttgatct cttttgtatgt gtctagaatt   13920
gaatgcctag ctcttgtagt agttgggaag tggaaaactt ggatgctatg aatggtgggg   13980
tggttggggt atttatagcc ccaaccacca aacttgaccg ttggctggag gcgtctgctc   14040
gatgcgcac cggacagtcc ggtgcacacc ggacagtccg gtgccctgc cacgtcatca   14100
ctgccgttgg attctagccg ttgaagcttc cgacttgtgg gcccgcctgg cgtgtccggtg   14160
cacaccggac atgtactgtt tgatgtccgg tgcaccggta tgggcgtgcc tggcgtctgc   14220
gcgcgctgcg cgcgcattaa atgcaccgca gggagccgtt ggcgccgcag ggagccgttg   14280
ctccgctggc acaccggaca gtccggtgca caccggacag tccggtgaat tttagcggag   14340
cggctgccgc gcgaaccga ggctagcgag ttcctgaccg cacctccct tggcgcaccg   14400
gacactgtcc ggtgtacacc ggacagtccg gtgaattata gccgagtcgc cttagaaatt   14460
cccgaaggtg gcgagtttga gtctgagtcc cctggtgcac cggacaggta ctgttcactg   14520
tccggtggca caccggacag tccggtgcgc cagaccaggg gtgccttcgg ttgccccttt   14580
gctcttttgt tgaatccaaa acttggtctt tttattggct gagtgtgaac cttttactcc   14640
tgtatacact atacacttgg gcaaacaagt tagtccaaaa gatttgtgtt gggcaattca   14700
accaccaaaa ttatttagga actaggtgta agcctaattc cctttcaatc tcccccttt   14760
tggtgattga tgccaacaca aaccaaagca aatatagaag tgcataattg aactagtttg   14820
cataatgtaa gtgtaaaggt tgcttggaat tgagccaata taactactta caagatatgc   14880
atggaatgtt tctttctttta tttagcatttt tggaccacgt ttgcaccaca tgtttttgttt   14940
ttgcaaattc ttttgtaagt ccatttcaaa gatcttttgc aaatagtcaa aggtgaatga   15000
ataagatttt tgcaaagcat tttcaagatt ttgaagtttt ctcccctgt ttcaaatgct   15060
tttcctttga ctaaacaaaa ctcccctaa attaaatcct cctcttagtg ttcaagaggg   15120
ttttgatata tcatttttga aatactactt tctcccccctt ttgaacacga taggatgcca   15180
attgataaat atttcttgga aaacactaag ttttttgaaat tggtggtggt gcggtccttt   15240
tgctttgggc tcctttctcc ccctttttgg catgaatcgc caaaaacgga atcattagag   15300
ccctcgaagt aatttcttct ccctttggtca taagtaaatg agttaagatt ataccaaaga   15360
cgaagtcctt ttctttgatg ctcatttctc ccccaaagaa tagagaatg gttggagtga   15420
tggcgaagga tgagttacgg agtggaagcc tttgtcttcg ccgaagactc caattccctt   15480
ccaatatacc tatgacttgg tttgaaatag acttgaaaac acattagtca tagcatataa   15540
aagagatatg tcaaggta ttcaaatgag ctatgtgtgtg aagctagcaa aagaaatttc   15600
tagaatcaag aatattgagc tcatgcctaa gtctggtaaa agattgttca tcaagtggct   15660
tggtaaagat atcggctaat tgatcttag tattaatgta agaaatctcg atatcccccct   15720
tttgttggtg atccctaaga aaatgatacc gaatggctat gtgcttagtg cggctatgct   15780
cgacgggatt gtcggccatt tgattgcac tctcattatc acatagcaaa gggacttggg   15840
ttaatttgta accatagtcc cgcagggttt gcctcatcca gagcaattgc gcgcaacaat   15900
gtcctgcggc aatgtactcg gcttcggcgg tggaaaagagc gaccgagttt tgcttctttg   15960
aagcccaaga caccaaggat cttcccaaga actggcaagt cccgatgtg ctcttcctat   16020
taattttgca ccccgcccaa tcggcatccg aataaccaat caaatcaaac gtggatcccc   16080
gagggtacca aagcccaaac ttaggtgtat aagcaaata tctcaagatt cgttttacgg   16140
ccgtaaggtg ggattcctta gggtcggatt ggaatcttgc acacatgcaa acggagagca   16200
taatgtccgg tcgagatgca cataaataaa gcaatgaacc aatcatcgac cggtatacct   16260
tttgatccac ggacttacct cccgtgtcga ggtcgagatg cccattggtt cccatgggtg   16320
ttttgatggg cttggcatcc ttcattccaa acttgcttag gatgtcttga gtgtactttg   16380
tttggctaat gaaagtgccc tcttggagtt gcttacttg aaatcttaag aaatacttca   16440
actccccat catagacatc tcgaatttct gtgtcataat cctactaaga tcttcacatg   16500
tagactcgtt agtagaccca aatataatat catcaacata aatttggcat acaaacaagt   16560
cattttcaag agtttagta aagagtgtag gatcggcctt gccgactttg aagctattag   16620
aaataaggaa atctcttagg cattcatacc atgctcttgg ggcttgcttg agcccataaa   16680
gcgccttaga gagcctatag acatggttag ggtactcact gtcttcaaag ccgggaggtt   16740
gctcaacata gacctcttcc ttgattggtc cattgaggaa ggcactttc acgtccattt   16800
```

-continued

```
gataaagctt aaagccatgg taagtagcat atgccaataa aatgcgaatt gactcaagcc 16860
tagctacggg tgcataggtt tcaccgaaat ccaaaccttc gacttgggag tatcccttgg 16920
ccacaagtcg agctttgttc cttgtcacca caccatgctc atcttgcttg ttgcggaaga 16980
cccatttggt tcctacaaca ttttggttag gacgtggaac caaatgccat acctcattcc 17040
ttgtgaagtt gttgagctcc tcttgcattg ccaccaccca atccgaatct tgtagtgctt 17100
cctctaccct gtgtggctca atagaggaaa caaacgagta atgttcacaa aaatgtgcaa 17160
tacgagatct agttgttacc cccttatgaa tgtcgccgag gatggtgtcg acgggggtgat 17220
ctcgttgtat tgcttggtgg actcttgggt gtggcgccct tggttcttgc tcatcctcct 17280
tttcttgatt atttgcatct ccccccttgat cattgccatc atcttgaggt ggctcatttg 17340
attgatcttc ttcttcatcg acttgagctt cttcctcatc ttgagttggt ggagatgctt 17400
gcatggagga ggatggttga tcttgtgcat ttggaggctc ttcggattcc ttaggacaca 17460
catccccaat ggacatgttc cttaatgcga tgcatggagc ctcttcatca cctatctcat 17520
caagatcaac ttgctctact tgagagccgt tagtttcatc aaacacaacg tcacatgaga 17580
cttcaactag tccagtggac ttgttaaaga ccctatatgc ccttgtgttt gagtcataac 17640
caagtaaaaa accttctaca gttttaggag caaatttaga ttttctacct cttttaacaa 17700
gaataaagca tttgctacca aaaactctaa agtatgaaat gttgggcttt ttaccggtta 17760
ggagttcata tgatgtcttc ttgaggattc ggtgtagata caatcggttg atggcgtagc 17820
aggcggtgtt gaccgcctcg gcccaaaacc gatccgaagt tttgtactca tcgagcatgg 17880
tccttgccat gtccaataga gttcgattct tcctctccac tacaccattt tgttgagggg 17940
tgtagggaga agagaactca tgcttgattc cctcttcctc aagaaagctt tcaatttgag 18000
agttcttgaa ctccgttccg ttgtcgcttc ttattttctt gacccttaag ccgaactcat 18060
tttgagcccg tctcaagaat cccttaatg tctcttgggt ttgaggacga attttctaag 18120
aattnnnnnn nnnnnnnnnn nnnnnnnnnn nnnnnnnnnn nnnnnnnnnn nnnnnnnnnn 18180
nnnnnnnnnn nnnnnnnnnn nnnnnnnnnn nnnnnnnnnn nnnnttttca actctgagaa 18240
tcagcttgat tcgttcttct ggcatggctt ctactggcca actgctctct aggagggagc 18300
cgagttggtg aagtcctgcg aagcatgtca gtttcatgca aagcagacac acacacacac 18360
cagctcaggc tctgcaaatg attccaccct cttggccatt cgccgtatgg ggggtgggata 18420
tcctgggacc atttcctagg gctgtcggcg ggtaccgttt tctctttgtc gccatctaca 18480
aattcataaa gtggtcggag gccacccta tggtcagtat cacccaaggt gctgctgttg 18540
ccttcctcaa ttcgattgta tgcagatttg gggtcccaag ccatatcatt acggacaatg 18600
ggacccagtt caaaagtcga ctcttccaag agtattgcga gggcattggc acccagctct 18660
gctttacatc tgtgtctcat cccaggagca acgaccaggc tgagagggca aacacagaaa 18720
tccttagggg actcaaggca cacacctacg actgcttaaa aaagcatggt gccaattggg 18780
ccaatgagct tccgtccgta ctatggggga accggaccac acccagccga gctaccgggg 18840
agacccgtt cttcttggtc tacggggccg aagcctgcct tctcccggaa atcattatgg 18900
gctcccatg agtccagtct ttcgatgagt ctatgcagga atagctacga cgtgaggaca 18960
tggacttcat cgacgaacgc agatggcaag cggtgatccg aaatgcacgg tacaaccaag 19020
cgctcaggcg ctaccaccaa cggtttgtgc atagtaggga gctcagggtc ggggacctag 19080
tcctaggcca agtactgaac cgagaagggc tccacaaact ctccccccagt tgggaaggac 19140
ccttcaaggt gacagaaata tgccgaccat ggtgtgtccg ccttgccaca acagaaggag 19200
tgcctcttcc caatccctgg aatatagagc atctctgtaa gttctatcca taatagcaaa 19260
actgggggt tgagttttct tccttgtaa ctaggttacg catatgtgta tgtcaattcg 19320
gtgaggcccg ccctcgtaag cccatctgtt ggtctacacc catgtatatc gagttataag 19380
gaaaggattt accccctaga tgtgattttg tgatggtttt attctacttc ggtttacatg 19440
cattatttt tatctaaccc acccatatag tttcccaccc ttgttggtat gatgacatcc 19500
gaattgagta gacaggcttg cagttcaaga ccccttact gctacagggg gtccggcaaa 19560
ctgcgaacca gttctagaga atgggcgcta gcctcctgga ggggtccgga gttgtgtagc 19620
cgcttagcat ggttccgtac cctaagcctg catgctccac cactctataa cgggtgccct 19680
agtatttgga actgtgatcc tatgggtcca ggcatacggc ttggcttccc aggctaaatc 19740
ctgcaggtcc tgttgcataa atcaaaggat ggcagatacc agacgatgga tcctatggtg 19800
tgctcctaac acttttaaagc cgaagctgtg tacaagtcca ggtcccagtc cagtagtagg 19860
tagtctcaaa ctgtagagac tacctcctag gggccggacc accaatttta tctttggtat 19920
actggtatcc agcctcgaca cgtcgagcct acctcccagg gggccaagta ccaaggggaa 19980
gttgatgaca ctacacataa caaggacaaa taacatacaa ataagtttaa gttccaatgc 20040
tacctcatta gcggttctta taatatctta caaaatcaaa agttattaca accgcttccc 20100
agtggaaccc ttgctttgtc tctataggtc gtcagcagga tcgtgctgga agcgctcggc 20160
caccagctcc acggcgtctt gtacactctc ccaggcggcg tcttcatatgg cggctaccgg 20220
accagcgatc actagcgcca aggatatggt ggggtcgtga ctccggaagc atgttaggac 20280
ttattcaacc actgcccgac agagcttgct gccctctgcc tctagcgggg ccccgaggat 20340
ctgatccagg cgacggaggc gatcggcggt agagtccagc accggggagcg catcagagat 20400
cgacgctggt agctccgaca ttgggatggg gctcatccct agtggcacta gtgccgtgct 20460
tgcctcgccg gcccacgcga caatacactg gacctcgacg cggtgctccg cttggagatc 20520
ttcaagggcc ttcctggtgg cctccatcgc ttggggaccc ggtgccgcct gcgctgcatt 20580
gaactagcgg atctgctcct ccagcttcct ctctttctcc tctgcctcga gcttgtcctt 20640
ggccagcaac tcgcctcgcc gggtgagcat ttcttccctg aagctgagat ccgtctcttg 20700
cctggcgagg tccgtctccc accggtccaa ggactgctcc ttcgcttaa gattttcctc 20760
ggcgagggtg gcattgctag ccttgccctc gagctcctgc taccattttt gcagcctctc 20820
cacgaccctg acctgctggg cccgctgggc ttccagagtc tggtccaggg cactcagctg 20880
ggcctggtac tctgttgtga gggtctcccg ctgggtcacg acctcctgct tcctggtcac 20940
cttcttctcc ctccgggacg cctccagctc cctggcgcac accctctgga ggtccctctt 21000
gtactcctta tggtcctgct cgagttggga ccgctcggag atgaattgtt gggacgccgt 21060
tctggtgcgc tcctccagtt gggtgcgcca gtcacttagg cgctggtgct cagcctcaag 21120
cgcctccac tcccgcaaga ttgctgcccc agtgtcacta aggacctagt gggcacgaga 21180
cattatgcga gggaggggga ctggccgccg ttcttgctcg gcacccgacc ggagtcgccg 21240
cccaaacacc acctccatct cctccggagc aggcgggggg ttggagctgg acatgcctac 21300
tgcgtcaccc ccagtgtcga gagcgggcgc ggatccccca gctgggacct ccttcgccac 21360
tgcgacgccg cctgacgctg ccaccggacc cccggctggg gcatgagaag ccgctggtgc 21420
tgtcttggca cagctggggg gtgggccgcc ggcaccactc tcagcaggtt cctgctgttg 21480
agagccagac ccgtcggtgg gcctggtatc tggtggagga ggcatgacct tgggagcggc 21540
```

```
gaaggaagaa gccctagcga acagatgatg ggttaaaact ggtcggcatg atgattagac    21600
tcatggaaaa ggggctacgc ttacttgggg ccctagactt tctagtgacc ctggaagcgg    21660
ggcgatcacc gctcctgctg ttgctatcgc tgttgctgtt gctgttgctg ctgctggtgc    21720
ccctgggggt gaggactgac gcgcctctgc gcgccgtggg cctgggagct agcttcctcg    21780
gccccacctg cagccctctg acgcttctgg gggggcctcc gaaatgagcg acccatcagc    21840
gcgacatggc ctgcgttgcc tctcctcctc cgacccctc ggagctacct ggggcggagg     21900
cactgctcgc agccccttg cctttgtcca agggctagg ggccacggcg gggttggtgc      21960
tgggagccgc accagtgggc tgggaacctc caatcgtgc attagaaatc tggatcccac     22020
ggagggggtc ccggccaccg gtctagcgaa ccgccatgcc gctctcgtcg agggtcggca    22080
acgtggccaa gatcaccatc ctcaggcctg gatcgtcgca gagcgcaggg atgttctggg    22140
ggagtatcag ggactcaggg acaaaagttt ccccaataat ccctcccatc aggactgcta    22200
gctcgtccca ggacagaacg gtgcccggcc tgcgttggat cctatcgatg tcgtttgggc    22260
cggtgaacca acagcacata cgcggtctcc tctgcagcgg cgcgatccgg tgcttcagga    22320
gatcgccgac cacgtgcatt gatgccaggc cgcccgtagc caagcccttg attctgtcca    22380
atacaggcag gaactctagc aagagggacg gcttagtcct ccactgcttg cggtcgagcg    22440
ctggcccatc gctcggcagg acgaggcggt cgttggcctc ggcgctggca atcacccaat    22500
cgttgcgcca gttttcccac ctcgcaccgc caaaggtggg gatgtatacg acggctggat    22560
ctggcctcgt ctggaagtag taggcaccga tgtggtcct agtcttcccg aacttgacca     22620
gcacgaagaa gcagcggaag agggaagtac agggggccac acctacgaac atctcacaga    22680
ggtggacgaa gatggctgcc tggaggacgg agtggggtgt gaggtgttga agctgaagcc    22740
caaactcctc cagcagcagc aagaagaagg gcgagaatcg gcaacgccaa cccgtagaag    22800
atgtaggagg tgaacagcac gaactccccg gcggtgagat cgccatgagg gacggcgccg    22860
gcgcggaact tccggcgagc cctggcgcgc tccatccaag caggccgcgc accaggttga    22920
gcgcctcctt agactgaaag cagtcaggat gaccaagcga ggccatggcg tgtgcggcgg    22980
cgcgagcgtg aacagagga gcacgaaggc aaaggggtgc aggcgattgg gagagaatgc      23040
gaaaaggtaa ctgctgcacg cggggtgaat ccttttttcag ggaaacctga gtccttgttc    23100
agggaaaccc ttccgtgcgc ccttgaattg ccacaggaaa tctcgcccga tgcgcacata    23160
ggacccaggc agcccactct atgacacggt ggcccgggtc cacaagtcat acagattgtg    23220
tgctggattt cgagtgcgga aagagcgaat cgccatgcga actgccgcgc acgatagcgc    23280
acctcctcgg ggccgctgca gaagacaaaa ggttatgcag cgcaacgag gcgtcccacg     23340
cgtggcccga cgaaaccacc aggcatgggg ccatgggtca gtcagctgca gagacagata    23400
tggcagttga cgtgactgaa gcggattga cagcgggcgt gtctcagac gcgctaaaac       23460
ggcatgccaa tcaccgatca ggtcacgttg aagcaaagta caagctttgg ccccacatgc    23520
aggctcgcat cctccctaa ggtgggtccg ggggccactt tcggcaccct gaaacaaggg     23580
tacccctac tactgtataa atacgcagta cccacgcgac tatctttagt cgcgtggtaa      23640
aagagctgta tgtgggacca aaccatgact cgccctagcc tcgggcgact actctaggcc    23700
agcaacagca cctgacccca ccacatgggc gggtccgggg ccgccatgtg tccagagaaa    23760
gtgatgtact ccaaggcatc aatagtgagt ccggaccccc ataggagagt gccgaaccca    23820
tgccagacc ctgtatatac ggtccaggcc tccaagtttg gtcatgcgtt actctgtcag     23880
cattagttat ttacataatc tatttcttcc attatgctcc taggcccgca tgtcgaggct    23940
cagcatcctt gtatgtgcct cctgtgcacac cccagtgtca cctagggttt ctcttaaaaa    24000
gccaaaccaa ggaccattat tttatgtgaa ccaaagtaag catgagcatc aaaataactt    24060
aagtaagaaa gaattcacca agtatatgct taaaagtgtc atgatcaaga caattgagtc    24120
tcttaaagga taagaatgtg caaccctaat taagaaccct aagtgaaccc catgaacaaa    24180
attcaagaaa ataagcaaaa gggaatgaaa agtttaaaat tttgagttga gccaattata    24240
taagttaaag tatatttgat aagcaacaag atagattgag aaagcttagc caaaataatt    24300
caagaaaacc cccaaatcaa gcttctttg ttgggactca ttgggaattc tgaatttcag      24360
aattctgaaa ttcagacctt gagccaaaga tcagggatgt tcaccttgat ccctaactcg    24420
aatcctaatg gccccattga caaaattgtg tctaactaac ccctctgtct tgtgccagaa    24480
gatggcattg ggacgcgagc cctagacacg acaaaacttg ggatttgcct cgggtttggg    24540
cagggagaca gaccagattt cctggctcca tatctctgca accagtaggc aaaatcctat    24600
gacctccaca caagaatggt agcttgtagg gaggagaaga ggttttgtgc actgaccaag    24660
gcgagagcag gctcggatga gcgaccacac gcgccagagc ttgggcagaa cgcacgggca    24720
cacgtgttcg accctggtcg gcacgccaga gctcgcccaa cccgcgcgcg cgctcgcccc    24780
ggcgtccggt caagtccgcc gcgcgcccac gcctcggcc gtgcccgccc gcgcctataa     24840
agcctccccg ggcgcacctc tcttcgcccc gcactcaccc tcaccggcca gccactgttc    24900
cttagctccg gcgagctcat ttccgcccgc cattgccgcc agaactacgg ccgccgtggc    24960
cagcccactc cagccaccct ccagcccaac cagtgctcgg ctagctccgc cagtagcccg    25020
tgaagcttgc caagccctcg gacccgaccg gaacttcacc gggagccccg aagaatcaac    25080
ctcaccggac ttcggtcttc cgccgccgcg cgtggaccaa gctatccagt gagtctcccg    25140
cccgattcct ttcgctcatg tcttctctgg catcccgtgg acctcatga cctatttgat      25200
tgaactatct cgccgcgacc aggccggtct cctcgccgcc gacgagcatc cccgcctgcg    25260
cgcgtggacc gaccgactcc ggccatctcc gacggtgttc cgcacaccgt tgtgatcccc    25320
gcgacctccc cttcaccctc cggaacagt ctgccgcgg gtaagcccct                   25380
ccgcccttt cttcgccgcg gctactgttt aaggtagaag aaggacctcg ggttaggttc     25440
tgtagaaccc gaggggtttt tcgtaatgtc agcgactcat gagaatagta acctaaggac    25500
tgaattgcga ggaaaactta gaaaaccgcc agggaccccca gtgcaaagtg gatttccatt    25560
taatcaattt tgttatttct ttttaaaatg accagagaac ttagaaaatc cataacttga    25620
tgaaatctta atgaaaagct gtcaaaccaa ttttgctagc tctgaattt tatgacctat     25680
catttaaaaa tagtgaacca tatgcttct gttctaaatt ttagagttta aaattaaaaa     25740
cagaaacccc ctaaacctg ttttaattaag gaaaattagt ttttcttttg tgctgagctt     25800
aagaaaattt gtagatgctt atacccttaat tagacactgt ttaaaaatag taggagccct    25860
agcattagag attatgatgt agttattcat ttaaagccat tttgtccaaa acttagaaga    25920
aatcaaaag gccttagaa ttaatgaaca gtgattagta atattttcc tagattactt         25980
atgcagcaga gaacctagga aaaatgcaga gaccattaat ttggaccagt ttctaattaa    26040
gatgctttaa ttagcattat gtagactgaa aatcaattat tagaattgca aaactataac    26100
caaagtggtt aacaaaaatc cagtgaactt ataaccacca gagccccact acaaaaatac    26160
agagcacccc agcctaactt tttaagtagg gaaaataaat acagaatgat aataaggcat    26220
tttcccacta aatcatgagc aaccccaaat aatgtgataa tgggcaacca aaattttgct    26280
```

```
aagtccatga tgagataaac caccagagaa aaatacaaac ccatgaaaaa gaagtgaacc  26340
catgccttt  gctagtaatt tgtgaggaag gccattagc  tcaaataatg caaaccaccc  26400
cttcccttag gcaaaaggaa gccaaactcc agaatgattg ctcttgcaca aaatactagc  26460
taagaaaaat aagaactctg ttgtttgatg tttttcaagt atagtggtag tagaaagcac  26520
cccttggct  agaaacctta agaaaatctt agggaaagaa ttaaagggta ttaatgacta  26580
gaaatttgta tcaagtcatg ttataacacc taaaagccag caaaaataag ttttttgagaa 26640
ttacccacta ttaaataata gttgtagttc aaagtacccc ttctgcccta aaatttggta  26700
attttgtcca gagaaaacca ttcactttct gaacccaaa  ttttgagaca gagaaccata  26760
caccagtaac aagccactgt aattttttgca gaatttttgg aattttataa aagcaacttg  26820
tagttcaaac ctactccaaa acattaaaga gaataaaaga aaagagaaga agaaatacaac 26880
ctcatcccaa taagactaac ccaatttacc aagtatacca ctaaagggtt ttacataagt  26940
aaagttaact ggttttaaat caaaagatca tacatcttta aagttataaa ttctaaagca  27000
catatcatat catgcatata tcttacgcat tgcattcatt agattgtaat cttgccgacg  27060
gagagtacgt gctcatccct gagcaaggac ctatccagag ggaggaccag gagcaggctt  27120
cagaggctgc tattgaggat ctccccgcag ccccagcaat tgaaggcaag ccccggtttt  27180
atgcataacc atgttattat atgctacttt actacactta atgcttgtag gattgcaatg  27240
tgcacttaag tgtaggagtt gcttgaaacc tctagttgca tgaacttagg attccttttt  27300
gagatgaata ctagtatgct aggtcgagta gctgcttgct aatcaggatc tcggtagaag  27360
tcgagtgatt tttctagcac tcgcgcgagg tcaggaattg attgtattca tcttgataat  27420
ggggtatatg ttagtccgtg gacttgggtc cagggaggat gccatgtcca tgagacggga  27480
aaaatgaatt aaggattaat gtgtggatac ctgagtcaag cttttgaacg tactaagcac  27540
atgccgggaa aaatggtaac cggtaaacct agtacctgac tgaagccggg cgcggacttt  27600
atccctcatg cgacctgaga cagggtctcc catgctagct atggtgggta caagtgcggc  27660
cactgcatga cggcagtcgg ggtcagtgga gcattgtatg ccaaggcggt gaggcctgga  27720
cgcgaacggg gaatcgatgg ggacggttgt catgtgtggg gtcggagtac cctgacatgc  27780
cgtgtgttta ggtttacctt gcaaggttta aaaactcgat tcgaatcgtc tgcttctcgc  27840
agctaatgag actgcttgat tccttgtact gcatcgagta agaagtgaaa tgtggattat  27900
atgagataac ttgttgactg aactaattga ttgttaccat gtatgcttag aaggagcaaa  27960
tctagctaag ttaatgatgg tagaatttga aaagctaaaa gttgattta  gaaacagcta  28020
gtgcttttgg caaaccaaac ccctcagcca aacagctgca tagtctagag gtagaggagt  28080
agactcctca caccggttaa gtctagctga gtattagtaa actcagcctt gcttgtggca  28140
ccatttttgc aggtaccatg caggatgtag ttgatggtgt gacttggcct accaccctgc  28200
caccgggttg gacggtcgag tgggatgttg ctccggcagg agaggagcat gaggagtagt  28260
gggctaggcc ttgcccattt cctcattacc gacgacatcg attatccgct gcactttaat  28320
ttatgaactt tattcgctac tcaaaaactc cgatttatgt aataactcag tacttaattt  28380
gaggtttcct gttttattgt atttcttctg tgactcacct tcgagtgaga ttgtgggatt  28440
tgatcctggt taagtggctt catcagacta gatctgaggg actgacgggt tattccgatt  28500
taagtgtgtt acggcccctg aggcgtgact taggcactta agctggaata attcgggcgg  28560
ttctgccaca gctggtatca gagcaaattc caccacagag aggcaacaata aaccatgaat  28620
accaattttc aaaatctaaa acctgcctag aagctactac ggatcgtcag gactagaccg  28680
ctagacctag gacgaaaggc cttaggcata gagggagaaa taggtggcta actaattagg  28740
ccctgtgggc caatacttat attttaggat gccctaaaaa ggcaccctat ttccttttg   28800
agaggcaacg tttcttccg  catgcatgca ttataaaaca taaagaggaa ttaaaattga  28860
gctaacccc  ttttcttcga aatcatccgg gctctcttt  tctttttcct tccaccataa  28920
tctttatctt tgattccctt ccgcagatga attcacccac cccgccagt  ggaggagact  28980
ctcgtttcag ttctgacttc cttctctgcg atggcttccc ttccattttg tgggaagtgc  29040
ttaattccgc cggttaccct acgccccctt tgtacacggt gcagttgtat gaggagcatc  29100
gggtacctcg ttgtcgggtc tggctaactt tggaggctca tcccccttcag ccgggttggc  29160
gttctcttga ctctgagacg attggactca ggacggacga caccgttgag gcagcagcca  29220
tgaagactct gacgactttt tgtggctacc atcccctgga gatggtgatg caccccttgg  29280
gactcttccc cgctgagaag aaggatgatc ccatgtggtg taacccgctg agccatgtga  29340
aggatgtgtg ggcaatgtat cctgacttgg ttgggagggt cactgttcag tgcatgagtg  29400
cgctgtaccg ccttcaggcc cttcagagcg atgctatgac acttcttgcc aataccgctc  29460
aggcagccaa gctcaccctc gacagtcggg aagattttgt ggtcgaccta tccacagagt  29520
tggtgaaaaa ggatctgcag gtgggagaggc tgaaccagcg tattaccacc ctggagcagc  29580
aagtggagat ccgagataac actattgatg tcttggagaa ccagcttcac gacgtgcaga  29640
gggaactcga ggaagcaaat gaccacttgg acatgcacca cctggagatg gaggccaatg  29700
aagcaggaag cgagggagaa gaggctcccg aggagctagg accagcccct ggtgccaatg  29760
ggactacctc cgcgatacct ccttcacccg tatccgtagt cgcttccacc gctcagggtt  29820
aagcagtcgc tttgacattt ttaggcggat agaaacctat gcgagcttag tggtatcaca  29880
ttttggacta ggcttgtggg taccttcccc tgattaatgt aaccctgtaa acttttgata  29940
tctgtgggat ccttgtcacc atgttatctt cattcgaacc taatattatg attatggcat  30000
tttccttcca tatgagatga tatcttgtcg ttcggaaatg tgaattggga taacaatggc  30060
gacaatctct gttttcagat ggcagcgagg cagcgtcgcg ggcaaaatga gcaagctccc  30120
ccgccacctc ctccagctcc cacagtgcag gagctgatgc cccagcagaa tgagattctg  30180
cgacagctct tgcagcgcca gccccacccc tcagcatcctg gtgaaggcca gcatcagcga  30240
cctccggcta tggcaacata ccaggagttt ctgagcacgc agccgccctt gttcaccaag  30300
gcagaggatc cattggacgc cgacgtgtgg cttcgcgtcg tcgacatcaa gtttccccgc  30360
ctcacaggag actgccctga tgaggccaag gtcgctcttg ccgcacagca gcttcgccgc  30420
cctgctcgga cttggtggga tcactccgt  gctatgctcc ccggtgatcg tgaagtatct  30480
tgggaggaat tcaagactgc cttcagaggg caccacattc cagctggcat tcttgatcgg  30540
aagttgaacg aattcctggc cctcaatcaa ggaacccgca cggtactgca gtatgcgcaa  30600
gccttcaacg acttatgcca gtatgcaggg tatcatgctg attctgatga aagaagagg   30660
gatcgctcc  gcaggggtct caataccaag ctgcgggaac gactcaacac tgtccgggcc  30720
gatagcttca atgagttggt caacatggcc atctctcagg aggattgcat tgttgctcac  30780
cgggcagaga agaagagaaa ggcaccaatg gcagcaccat ccgctcaggc tcagaggttc  30840
cggattgttt ctcacaatca gagcagggt  tttcagcagc aggcaggcag atgggtgatc  30900
aggccacctc agcagcagca gcagccggca cccaaccgct atccagctcc cgccccaaga  30960
aacaatcagc ctccgcagca gcagcagttc cgccagggca atgggaacaa gtgtttcact  31020
```

```
tgtggcaatg tgggccacta tgccaagaat tgtcccagga accagcagag gcagatgcca   31080
gcaccaaatc aagacaaggg aagaaagcag aaggtacaag tcaggcaagg gaagctcaac   31140
ttcactgctc tagaggaagt gccagaagga gctcccatca tgaccggtac cttttcagtt   31200
tataatcaac ctgctttaat tctgtttgat tctggtgcat ctcatagttt cattagccaa   31260
aagttcagtg ctaattgcaa acttccattc tctcactcaa aagggtcatt catgatagtc   31320
acacctgggg gtaaaattgc aactaatcaa ttaaaccaaa gtgtgcctat tcaactggga   31380
agccacatta tcaaaaccac tcttcttgtg ttgggattgg aaaatgtgga cattattcta   31440
ggagcaaatt ggatgacctt gcaccaagtt gtgctcgacg tagccagtcg taccgtggaa   31500
gttaattctc ccttctgcgg gaatttcact ttgattctgc ctagtcaggg ttcttctcag   31560
tcatgtgctt tctctatgac ggaattaccc ctgaagagaa tcccagtggt ctgtgagtat   31620
gcagatgtct ttcctgatga attgccaaga atgccactgg accgggatat tgagttcgcc   31680
atcgagttgc aaccgggaac ggccccaatt tccaagaggc cctaccgaat gccaccgct   31740
gagttggcag agttgaagaa gcagttgcaa gagttgctgg ataagggatt tattcgccca   31800
agcacttcgc cttggggctg tccagcactg tttgtgaaga agaaggatga aagcttgagg   31860
ttgtgtatag attaccgccc tcttaatgcg gtaactatca agaacaagta tcctttgcct   31920
cgtattgatg ttctctttga ccagttggtc ggggccaagg tgtttccaa gatagacctt   31980
cgctctggct accatcagat caaaatacga gcaagtgata ttccgaagac ggcattctca   32040
accagatatg ggctatatga attcttggtg atgtcattcg ggctgacgaa tgcaccagca   32100
tatttcatgt atctgatgaa ttctgttttc atgccagaat tggacaagtt cgtggtggtt   32160
ttcatcgatg atattctggt gtactcaagg aacgaagaag aacatgccgg gcatttgcat   32220
gtagtacttc aacgtctgcg agatcaccac ctttatgcca agttatccaa atgtgatttt   32280
tggctaaagg aaatcaaatt cttgggtcac actatctctc aggctggaat agctgttgat   32340
cctgataaag tgcaagaggt gatgaactgg aggccaccaa cgactgttcg ccagattcgg   32400
agttttctgg gattggctgg ttattaccga agatttattc cggacttctc tcgaattgcg   32460
aagcctatta ctgagttgct gaagaaagaa gtcaaatttg tgtggagtca gaagtgcgaa   32520
gatgccttcc atgcattaag gcagcatctg accacagac cagtattggc gcaacccgac   32580
agcagcaagc cttttgatgt atattgtgat gcctctggca ccgggctagg ttgtgtcttg   32640
atgcaagaca accgagtcat tgcttatgcc tcaagagcac tcaggcctca tgagcaaaat   32700
tatcctactc atgaccttga gttagcagca gtggttcatg cattgaagat gtggaggcac   32760
tatctaatgg gaacccactg caacatcttc actgatcata agagccttaa gtacattttt   32820
actcaggctg atctcaacat gaggcagaga agatgctag agctgatcaa ggattatgac   32880
ctggaggtac attatcaccc agggaaagct aatgtggtag cagatgcctt gagtcggaag   32940
ttgcagtgca actgtattct gatggattct cgtgttaaca ccttgtgtga tgagttgagc   33000
aagatgcaaa ttgaagtgat tccttctggt tctttgtctc acattgctgt tgagccaggc   33060
ttgcaagacc agattatcat ggcccagctc agtgacaagg gagtgcaaat tatcaagaag   33120
aatctccatc agaaggttga gaagtataat tgtttccgcc aggatgagaa gggtgtgtta   33180
tggttcaaaa gcagattggt aattcctaag gaccaggatc tcaagaagaa aattttggat   33240
gaggctcatc tctccaaatt ctctatgcat ccgggaagca ccaagatgta ccatgatttg   33300
aagcataaca atccccaccc ttttcctata agtctcaacc ttcgcttcac cctgggagga   33360
ctctggcccg aatctcggga cgagattcct ttaagggggg aaggctgtga caccctagtg   33420
tcacctacgg tttctcttaa aaatgccaaa ccaagaacca ttattttatg tgaaccaaag   33480
taagcatgag gatcaaatta acttaggaat aaagaattcn nnnnnnnnn nnnnnnnnnn   33540
nnnnnnnnnn nnnnnnnnnn nnnnnnnnnn nnnnnnnnnn nnnnnnnnnn nnnnnnnnnn   33600
nnnnnnnnnn nnnnnnnnng gtgctaatc atgaaccagt ccagagcaac actatccgat   33660
ggccattgcg tccggtcgca cgagagacgc gtgcggaacg tcccgtagga gcggccaacc   33720
ccccattttg cagctagcag ccgtccagta gggacagccg ccgagctccc cgacatgtct   33780
ccttcgggac cgggcttcta tttcaagctg cgggacggtg ggtcaatcc atgtggacac   33840
catgcgagtt cgcgcttcac tatctgggct ggggaccac ctccatcaat ggtctgcatg   33900
acgcaggata ttccatcagc catggtgcag tggaatccgt tccagaggat ggcctctgca   33960
ccaaacgctc gccaaggtaa cagaagcaat ccaggcccat cgggcgtgat ctcccatcga   34020
tccgtatcga tcctttgaca tgaaaaggca atcacgggct cacgctttc ggagtgtaat   34080
tcaggctccc gggtgcagct tttttgcgcg cttgcggcagg gggcatctgg tggacatcaa   34140
atgatatggg cttgcttggt ccagggaacc ggcagcacct gctgtcccga gatcagttgt   34200
gatgctatgt catccgtcga tagtcggagc ttatccagct cggatcaggt gatacgcttc   34260
cctttcggag aggttttgagt ttcagacctg gtgctcagtt atgataaaaa gggtcggcag   34320
tgagagaaac cccgaaaact tgtcaatcga accaattacc ttatttactt ttcctgccct   34380
aggagtagat gtagcatagt tctagttgta gtcttccaca tatccacctc cacccctatt   34440
cgactctacg tcgtctagat ccgtcttggg tggcctgccg atcccaagac gaccctagga   34500
tctcaccccct cccgggggc aagatctagt tgtccatcca agacttcttc ctcgatttga   34560
tctcttaatt cctaggcgac tccacgtcgt ctggggacgc cccgggtgac ctgtcgaccc   34620
ggagcacctt aagatctttc cccccagggg acgagatcta gattccagca aggagtagga   34680
agacgaccct gtcgccaggt cgcggaccgt ccggcccaga gctgcggacc gtccggtgtg   34740
acgcagggaa gacaccgctc ctgcgcccag gtcgcggacc gtccgaccca aggctgcgga   34800
ccgtccggcc caaggctgcg gaccgtccgc gcctgaccag aggacaccgc cacgggtttct   34860
gttgagtgtt tggcgctcca aaaaggcgtc aacagtagcc gtcacatcat ctattgtgtg   34920
gctatgctta agtgtgcctt gatataattt agaataagtc gagtctctag aacgcggcaa   34980
tttttaaaag taaacagaag ctgaatttat tgattgctgt tttgggctgc acgcactgtt   35040
ttagttgtgc tgtttgtttg ataaaccaaa tcatgttttc tgtagaaaag tcatatagaa   35100
gagttgtaga tgacatgatt atcttgcttg tactaaaatt tgacagccat aaacctgatt   35160
gtttaggagt tgtgcttttc acaagcccag cacctgaatc tgtcaaattt ctgaacatat   35220
ttcagaaatt gcaatggttg cttaagttaa tgttgaaatt agttattggt ggtcacaaga   35280
aagttgtaga taactttatt atcgtacttg tgttaaaatt tgacaggcat aagtctaatt   35340
gtttaggagt tatgtttttt acaaattcag taactgaatc tgtccacttt ctgtacagat   35400
ttcagaagct gcattgtttg cttaagttaa tgttaagaat gcccttgta gattataaga   35460
aaagttgtag aggcttttct tatcttgctt gtgttaaaat ttcataacta taggcctgac   35520
ggtttaagag ttatgaattt tacaaactgg ttgctgtgtt ctgtccaccg tcagaacaga   35580
tttcgaaaac tgtaatattt gatttagtta aacctgaat cacttcttgg tgattatgaa   35640
agttgtgtag tacttttgct aagatttcca aaaagtctta gatcactctt tttggtggtc   35700
tgaagattaa gttacatgtg tttgaagtgt gaagactgaa tctgtccagt tttggacagc   35760
```

```
acagccttca tagtatattt taaccttgat acatgctaaa ccagcctggg atgtttataa    35820
ataatttgta gaacatttaa ttagcttttcc agaaagtcta ggatcaattt gtttggatgt   35880
ctgaatcttc agttatgaat ttttaaaatc acaagtctga atctgtccaa atctggacag    35940
agctgttgtg attgcacttt ttgaccttgc taagtgttta atcatgctgt gatgaaaata    36000
ccaaaattgt agagcacttt ctaaacttttc cagaaagttt tagtttgcta tttttttggatt   36060
aatatttgaa aagttattat taaaacaagt aactgctgtg ctgctgtcca aaaaatctgc    36120
acgtgctcaa atgaatattt agttcaccat ttttggctaaa aacgcttagt tagcacttaa    36180
cggacataga cttgtgatgg ctaaacttag gttaacatgt gttccatgat taatgtgctt    36240
gcttgctata gttgattgtg atagaggagt ccatcgacat tgatgcatcg gtcctttatt   36300
aaacttgtgt ttgtgatgct tttgtgtgat caatagaaga actaatgaaa agccgtagca    36360
actaaataaa tgcttgtaca tatgatatcg tgttgcgttg gttaattgta ggtagtgatc    36420
attgtctttc cagtggtagt gtttacgtgt gcccaatgac acataaataa ctagtgtttg    36480
cgtatagttg ttgcagtgtc ttactaatta atgtttagtt cgccactgtg tcttggtata    36540
tcttatgtta cttttattat attcatacat atgcatcttg cacctcatat aggaccgaga    36600
gatgatgatc gagccagtga tgtggtgcca accacaagat gccgttgatg gacgacctaa    36660
agaatggact taaccagtgg atgctcgcca agcgagtacc tccccagca aacactacct      36720
aagtgttaaa ttaaaggcaa gccccggttt tatgcataac tgttatatat atgctatttt    36780
actgcactta atgttttgtag gcttgtacca tgcacttaag tgtaggagtt gaatgaaacc    36840
ctagttgcat gaactcagga ttcccctttga gatggatact agtatgctag gttgagtagc    36900
tgctttgcta attagggatc tcggtagaag tcgagtgatt tttctagcac tcgcgcgagg    36960
tcaggaattg gttgtatcca ctttgataac ataatggtga tggtctgtgg acacgggtcc    37020
atggggacgc gtggtctacg agatgaaatt ggaataagta ttaacgtgcg gataacctgtg   37080
tcaagcgttt gaacgtacta aacacatgcc gagaaatatg gtaaatcggt aagcctagta    37140
cctgagtgaa cctgcccgca gattgccctc ctcaggcgac ctgagacgtg gtctcccatt   37200
ccggttatgg tgggtacaag tgcggtcact gcacgacggc agtcgggtc agtgaggcat    37260
tgtacgccaa ggcggtgagc ccctttctgt tgccaggaga tcgatgggga cggttgatgt    37320
gtgtggggac ggagtgcccc tacatgtcgt gtgtttaggt ttaccttgca aggtttaaaa    37380
acttgattcg aatcgtctgc ttctcgcagc taatgagact tcttgatcca ttgtactgca    37440
ttgagtaata agtggaaatg aggtgattgg caaaagatgt tgtttgataa aaattcttga    37500
tatcatgtat gattagctag gtacacatct agtcaaaaag gatcatacta aaacttgaaa   37560
agctaaaact tgattttaga ctcagctagt gcttttggca aaccaaaccc ctcagccaaa    37620
cagctgcatg tctagaggta gagaagtaga ctcctcacac cgggtaagtc tagttgagta    37680
atgtatactc agccttgctt gtggcataat ttttgcagat attcattagg atgattggtt    37740
gatggtgtga cttggcctcc atccctacca ccgggataga tggtcgagtg ggttactgct    37800
tccgcaagag aggaccagga ggagtagagt ggcaggctt cgccatgta ctcggttctt    37860
ctccgttagt tatttctgct gcattaaaat ttatggttat tatttctgaa actccgataa    37920
tgtaatcact aatgatactt attaaatttg tggtattatg ttttattgta tttctctgtg    37980
tctcaccttc gagtgagcta gtggtattcg atcctggata agtggcttta tcggactaga    38040
tccgagggac tgacggttta ttcctattta agtgtggtct agcctctaag gcgggacttg    38100
ggcacttaag tttgaataat tcgggcggtt ccgccacagc tggtatcgga gcgaatacca    38160
tcacagagaa gtcaataagt catgattacc aaccttttct aaaagtaaaa cttgctagaa    38220
accaatgttg gatagatgtc aggacgataa ggatagactt aggacgtgaa gccttaggaa    38280
atagatgggt agctaggtgg ctatttatat aggccataaa ggctactact actattaata    38340
aggatgctgt agaagcaacc gaaaagtag ttaggtctga gaagacgact agaatgagca      38400
tgcatcatga ttgtcgcatt ataattgtct tttgtgcacc aacatgcttc tctcaccttt    38460
attcaaataa taaaaaaaat tgtgaataat gtgctgtatt gctaggaact gcaaaaaaaa    38520
tgtcttatct tgtgtgtcat gatagtcttt actaggttat gttatgtgct tctcttgtct    38580
tgctatctag gtagtattgt aattgttcaa ccctttttgc aaaacatttt gttgcttgtt    38640
ctgttcataa aaagactcct ccaaacaacc ttgagtttag caagtgaacc cgcttttaaa    38700
aaaatgcttg tgttggcgtt ttctagccct tgtgggtttt acccttgaag ttacacctgc    38760
acagcttgta gattcccata gcttgactcc tagatcgacc aaagcttcct tgtgcactgg    38820
ttacgtcaaa aaaatttgt tgtttggtgt ctagttgcgc aaaccctatc aaggccatgt    38880
ttcttttccat aaaattccttg ccctaaaac ttcatagcat tcctgttgat catccagctg    38940
atcttgttgc ctacctctcc tttcgcatgg atctagtgat cttttttcctt gtgaatcatg    39000
ttgtgacctt atcatccgaa tctctgatct ttcatgattc tgccctatta tcttgttatc    39060
tactataacc cgttctcaag tatcgaatgt tgatctaccct aagtctctca attctggtca    39120
ttctcatact cgttctctga ggatcatgac gatgtttatc aactttatct ctaaacagtg   39180
tatccattg gttcaaggga tgttgttgtc atcttgtggt tctctcatgt ctctacaagt    39240
tcatcaacat gatctctgga gtgcttcctt ctcatatcaa atctcgtact aatcgctggc    39300
ctgctaatcc ccgtgatgat cataaaataa ctctatgagt tgaagaaaat tctccatgtga   39360
tgatcttttg ccaataatct ctgcttcaac tctgatcaca ttcttatttt ctgagccata    39420
ctctcatggg ctccaactat cagtgctatg tgaatttctt attggttgcg tttggtaatg    39480
atgtcatgac taacgactga tggtgccgcg acgaaaccga gagcctacta tggtgcacac    39540
atggttgagc tgctcggcac gcgctagtat gcgggttaat agtcgtcatc cattacgaga    39600
ctatactgat gtgctatttt tttgtggaca ctctcagaaa gatcgctgca ttttgtctcg    39660
atatgtcgcg atattctaac caaatctgtc tccagtatct tgtcagatac cctctcatga    39720
atttgcatct atcttcagtc tgggagttac atgcttctcc acccataaat atcctcattc    39780
gaatctcggg acgagattct tttaaggggg ggaaggctgt gacaccccag gtgtcagttt    39840
cgtgttacgt cgcgagattt atcctaatct cggatgctca gtaaaaattt ctatttctcg    39900
ctcgcgtatg tccctgatta tccagattat tcattcacgt ttcaccgaat tcggagttac    39960
tcagtctcac agaaggccaa tttttggagcc tgttaaaact tttatcgtcg gcacaaatgc   40020
gaactcaaaa atcattctcg aattataaac ctcatctgaa gctcattaaa tcaaactctc    40080
gacgactgtt atttgatctg tgtccgaatc caatttctcg atgttcgatc gatgtccaac    40140
tattttaatc cgagtccata ctcacaaacg aaataatcaa tttcaaaatc aacatcggca    40200
tcttactcga ctcagcttag catctctgta tccaatccga tttcaaaatc aacatcggca    40260
acgatttta tatatcacga ttcgcttttct ccgactaaaa atccaaaacc gatcaaatct    40320
caggacgatt tattttcgat ttacgcgtag ggaattattt tcaagcgaaa tctaaacaga    40380
ctctcggccg agttaatcgc gcaaccttcc gttcgtccga actcttttcg ctctgttttct   40440
cagtagcgac gaattccgca ggaacatttt tagtccggaa aatatttagc gcgacccaat    40500
```

```
ttagtgtttt gggccaaatc cagtccagcc cattcggccc ataagaaacc ctaccctaat   40560
ttctcctcta taaatatggg cttccctccc ttgcattctg aaaattttcc atttccaccc   40620
cagccgccaa caccccttctc ttcctcctct accattttcc agccgtgggc tccttcaagc   40680
acgtagagct ggagctcctt ccccagcgcg caggggcttc catggccggg cgttccttcc   40740
ctccagcgcg ccgaagctct tcccgtggcg tcctctgcct ttcttcttcc ctgcttcaca   40800
gcagcaaggc caccagcagg ctccctgctc cccgcgcccc cagccatgcc atccttcact   40860
cccctactgt ttttctccca gggcgcagca gcaaatccca tgcagcggct ccatggccga   40920
gcgccctgcc cggtgctcca gccggcctcc tctgccctg ccattttcca caggagccga   40980
gctcctacct gcagcaggcg ccccctgctc tttcctatcc gcgacaggg agcttcagct   41040
ggcgtgaaac ttcacttgcg cacggcggcc agcaccctct ccttgggctc caacagcttg   41100
gatgccgaac ccctttcttc cttccctgg ccgagctcga gcttcccatg gcgccattcc   41160
tccctctctc tgttgtacat agcgccaagc agcaactcca ttttccctgc ccgcgcccaa   41220
ggtcggcgac cagcctcccc ttccctgttc ttgctgtggc cgagccacca cttcccccagc   41280
cgtagccctc tccccctcca ttgtttcagc gcctgaaaca aacacctggc cgccatccac   41340
acttgtgctc gatgaaatgt gcagcagccc cgacggctcc gcgcgctgac ggcttgctgt   41400
tttgttgcgc agtgagcagc acgccgtgat gccgccgtgt gttcgctgtt tttgcgcagc   41460
cccaaacgtc gtcgtcgttc accccggtga gaccgcgacg ctccttgttc gattccgcat   41520
cgatgttatt ttcctatgat taattatgta tgtgtgttgc tttgttttat ttttgtggag   41580
gagagaaccc cgtgttttgc gaggagaaag caagtcgctt aacgctcgtc ggatgtttgg   41640
agcgatgcac gaatcggaat caccgtcatt cttgcaaaca tcgtttgggt ttgtttatgg   41700
tgagccgatg catgtcgctc tcgatcgact cgattaatca ttttgtatgg atgtgtgtaa   41760
aatgttcgat tatgcgcatt ggtaggatca tgtttgccag tgagaacaa gaggttaatt   41820
gatgtgcgcg atttgtagtt gtctaattat gttttggtcg atgatgtgca tgtggttata   41880
tgtgtgtaaa agtataattt tataaatgga cgcgtgtagg gaagaaaatg aaatacaaaa   41940
gaactcgagt attttttatttt tgataggaaa atatgcgatg cgttgtttga tgcgaaaact   42000
aagttacaaa atgtggattt tgttttgaaa aatgcatcga tgtgttttatg tgaaaagtgt   42060
atttgtttta agcaatgtga tgggattcgt aattttagag gggatatatt tattgatgtg   42120
acgagtagtt tagagaatgc tagttttgcgt agaggatgta tcgttaagac atgagtgtcg   42180
gagtccattt atactagtgg tcgcgccaca tggattgaag tgtctcgagt gcacgccata   42240
atatggttgt atgcgagaca gggttatgcg tacgatggt ttagtaaaaa ttccatccgt   42300
gtcagttgtg ttaagttgaa gtttatttgt gcgtataaag tagtaaggta tttaatgctt   42360
acgactctta atcgatggta gaaattgtct tgacttaaat agagaggtgg tgacatgcca   42420
gagtagtcat cgctttctct atattatag gtcaagtcat gacgatgcgt attatgcgtt   42480
cgttaaaatt atgtttcgta tatagtgtat gattgtgctc acgattcga gtagacactt   42540
caaataagtc aagtagcttt gtaatgcaag atgtgtgatg aagttagttt gttttaggat   42600
atgtgttgaa atgctccatt cctgtgatag acatgtaggg ttatttcaaa acgggtcgat   42660
gtgtgtgatg atgatattca tgatttaagt agatgtcctg aaattatgtg gcgaagctta   42720
ggttaagttg caagcgatgt ggaaatgttt tcgtaaagat atatgtggaa tgtgaacgag   42780
tcattcaatg tattcggtat gtcgtagtag ggtggtatga aaatgagtt aggaatcgat   42840
cggctaaatg ccaagttcgg ttagagttat tttgatagtt gggattgtgg ggtgaagtga   42900
tggcatgact acgtagctgt tggacaccaa aatgagcgga cggtccggcc catgggcccg   42960
gacggtccgc gtgtcccgag attagattaa ctcgatgtt tatccttatc tcgtgcgtgg   43020
ttatccatct aatcacgtgg gagtttgttg gctatctctt aggaaaaggt ccagacctcc   43080
tccccctataa atataaaggg gtacggccga ttgagaaccc ccgaacacat tccaatcgaa   43140
ccaattccct tatttacttt tcctgcccta ggagtagatg tagcatagtt ctagttgtag   43200
tcttccacat atccacctcc accccctatc gactctacgt cgtctagatc cgtcttgggt   43260
ggcctgccga tcccaagacg accctaggat ctcaccccctc ccgggggca agatctagtt   43320
gtccatccaa gacttcttcc tcgatttgat ctcttaattc ctaggcgact ccacgtcgtc   43380
tggggacgcc ccgggtgacc tgtcgacccg gagcaccta agatctttcc ccccagggga   43440
cgagatctag attccagcaa ggagtaggaa gacgaccctg tcgccaggtc gcggaccgtc   43500
cggcccagag ctgcggaccg tccggtgtga gcagggaag acaccactcc tgcgcccagg   43560
tcgcggaccg tccggcccaa ggctgcggat cgtccggccc aaggctgcag accgtccgcg   43620
cctgaccaga gggcaccgcc acggttcttg ttgagtgttt ggcgctccaa aaaggcgtca   43680
acatacttt tggcgactcc gctggggaag aagttcaga tctacaaaat caggcttaca   43740
tggccgattc taaagatctc aacagtgctt ctccaaacag caacacaagg ctgactaatt   43800
tatcggccgc tgagcataaa aaattagaag atgacatgag gaaaatagac gaggaggccc   43860
accgacaaaa ggatcaggtg ctcaaggtgg cggacaagtg gtacctctcg cacttcaagg   43920
tagactgcca ccagaagacc gtccaagaga gggagataaa cgccgagtat atgttagccg   43980
tgctgcaaca gctcccaca ataggtgatg ccaggtcagc cgatgatatt ccatctatta   44040
aaatttcttt tgataatcgg attaaaagta tcacggagga tatagagagg atgcacatg   44100
catttgttaa aactcacatg cctaattttt taaaacataa attaggcgat gagaacgatt   44160
actctagatt tcnnnnnnnn nnnnnnnnnn nnnnnnnnnn nnnnnnnnnn nnnnnnnnnn   44220
nnnnnnnnnn nnnnnnnnnn nnnnnnnnnn nnnnnnnnnn nnnnnnnnnn nngctgagca   44280
atattgccaa gagcggtagg accggtcgtc caaagagaat aaagtttatg actatgttca   44340
gaataaaga aaggatcata taaacaagcg cgattaattc acgataggag tcctcatttg   44400
ttgcagagca tgggggcagt agacacgatg agggacgccg agtgataaga aaaaggaga   44460
taagccgctc aaattcgcca ccccaatcgg tttgcatagc aatgattttt ctattgagca   44520
agcgctcaac aaggctttga aattctttga agaactgaaa cacctcagac ttatggcgaa   44580
gaagatagat ccaagtaaat ttactataat catcaatgaa gctgacataa tacctttat   44640
tacaaaaaga atcaatggcg ggtccccaga catcgaaaaa caccagatct aaaggagcag   44700
cagactgact ggtcgactta ggataaggca actgatgggc cttagcacga aggcaggcat   44760
cacaaacata ctccgaggaa tctaagcctg aacacactaa attattattt ctaatgacac   44820
gagcgacaat atcacgcgat ggatgaccta atctgcaatg ccaacgctca taggatggct   44880
ttattgcggc aaggtcgtgc ttctgggtag gtgtgcaaga gatgtcaatg gtagagcgtt   44940
acccctacat ggtccgcgca ccagcacttg cctcgtggcc tgatccttaa tcaagaaaaa   45000
gaacggatgg aactcaataa aggtgttatt atcaagattg aaacgatgaa tggaaacaag   45060
attttttatgg gtatgaggga cacgaaggac atgatttagg tgcagagggc ggaaggaagt   45120
gggcaaaaca gaataaccaa tgtgagtaat ctccatacct gcaccattag ccgcccgaat   45180
ctgatcattg ccattgtaac gatcatgctg ttagctttc cagctcgtcg gtgatgtgat   45240
```

```
cagtcacacc gaagtcaagg taccagtttg gatcagcagc agtggaggat gatgccatgg    45300
ccgcaacccg atcatcagga gtgaattctt cataaaagcg gtaccaacag atattagctc    45360
tgtgaccgac tttaaggtag acctagcagc gtggacaaga ctggccaccg gattgatctg    45420
tcggtggacc ggaactgcgc ctgaagtagt tgttgttgct gtagttgccg cgcgaagacg    45480
acgaaggata gccatggcca tttccgcgcg agcgtccgcg accgtgattt tggagaacca    45540
tcatgccagg agccaccacg gccacgagta gccgtattgg ctgatccatg agcagcgtac    45600
ctgccgccgg actgcttcgc aagccgaagc tcatagctga gcatctgcga gtataacttg    45660
gcagaggaga ttggctcgac gcaagtgacg atggacgaca caagcgggtt gtagatttct    45720
tcatcaaggt cggtgaggac ataggcgacg aactcctcat cgcccagagg ttggccggca    45780
gccgacatct catcggcata actcttcatc ttggattaga atccggccat tgtggtcgtg    45840
cctttcttcg tggtggcgag cgcaatgcgc gtgttgacag aacgcgcacg tgtgcaagat    45900
ccgtacatag ccgcgaggga gctccagacg tcggccgagg tcgtggctgt cgtgacaccc    45960
atcaagacct cacgcatcag agaggagagg atatatccca gcagcgcttg atcgtgagtc    46020
acccagttga tgtactcggg attgggcgtc tccatatagc cgtcgttagt catcacagag    46080
acagtcttaa ccagcatctt ttctttgccg atgagcagac cgtagagcg tgcagattgg     46140
atgggcggta ggatttgggc actccatagg cggtagttgg ttttggtgag tttttcggtg    46200
accgggatcg agaaggagga ggggatggtg gtggaatttg agaatctact cgccatgatg    46260
gatgtgttgt agaggacctg gctatggtac catgtagatt ggaatggttg atgtggcaga    46320
accgcccgga ttattccagt ttaagtgccc aagtcacgcc ttaaaggccg caatgcactt    46380
aaatcggaat aagccatcag tccctcagat ctagtctaat aaagccactt atccaggatc    46440
aaataccaca agctcactcg aaggtgagtc acagaagaaa tacaataaaa caggaaaacc    46500
tcaaattaaa gtactggagt tattacataa atcagagttt ttcaagtagc tgagaaaagt    46560
tcacaaaata aactgcagcg gataatcgat gtcgtcaaaa gcgaggaata gggcaaggcc    46620
tggcccacta cttctcctgc tcctctcctg ccggagcagc atcccactcg accgtccaac    46680
ccggtgcacag ggttgtaggc caagttacac cgtcaaccat atcctagagc gtacctgcaa   46740
aaattatgcc acaagcaagg ctaagtatac taatactcag ctagacttac ccggtgcaga   46800
gaatctactc ttctacctct agaccatgta gctgtttggt tgaggggttt ggtttgccaa    46860
aagcactagt tgtatctaag gtcaacttta tcttttccat ttctagtatc attattgtag    46920
ctaagtttgc tctttctaag catacatggt aacaatcatt taatacaatc aacaagttat    46980
ctcatgtaat cctcatttca cttcttactc aatgtagtac aaggggtcaa gcagtctcat    47040
tagctgcgag aagcagacga ttcaaatcga gtattaacct tgcaaggtaa acctaaacac    47100
acgacatgtc agggcactcc gtccccatcg attccccttt cgcggccagg gctcaccgcc    47160
ttggcataca atgctccact gacccgggct gccgccgtgc agtgaccgca cttgtaccca    47220
ccaaagctag cataggagac ccagtctcag gacgagtgag gagaaaagtc cgcgcccagc    47280
ttcaatcagg tactaggttt accggttacc atatttcccg acatgtgttt agtacgttca    47340
aacgcttgac tcaggtatcc acacattaat ccttaattca ttttcctgtc tcatggacaa    47400
ggcatccacc ctggatccaa gaccatagac catcatagat cccattatca agatgaatac    47460
aatcaattcc tgacctcgcg cgattgctag aaaaatcact cgacttctac cgagatccta    47520
attagtaaag cagctactcg acctagcata ctagtatcca tctcaaaaag gaatcctgag    47580
ttcatgcaac taagggtttc aagcaactcc tacacttaag tgcacattac aagcctacaa    47640
acactaagtg tagtaaagta gcatatataa attggttatg cataaaaccg gggcttgcct    47700
ccaaatgatg gggctgcggg gagatcctcg atggcagtct cgggagcttg ctcctggtct    47760
tcctcgtgga cagctccttg ctcagggatg agcacgtact ctccatcagc gaggttgcaa    47820
tctaatgaat gcaatgagta agatatatgc atggcatgat attaattta gcaattaaaa    47880
tttgatggag gatgatcaat ttaataggt agacctcatt ctcactactg gagatttttg     47940
gtggtacact caccaactta gggtcaagtt gattactgaa tggttaaccc attttttagtg   48000
ttctactgat ttctcttctt atatcttatg gatattttaa caagattctt agctgccatg   48060
ttgggtaat acttattaat ctttctaatt cctcccttct ttattccttt tatgcttta      48120
aggtgggttt gaactacaag atagcttaat aaatttccag aaattctgca acattacag    48180
tagcttctta ctggtgtata attttctgtc tcaaaatttg gggcttaaaa agtgagggt    48240
tctctctgta caaaattagc aagtgttagg gcaaagggga tgttttgaac tacaactctc   48300
ttttaacagt gggttattct ttaagactta tttttgctgg catttagatg ttataacatg   48360
attttgtaca aattttcagc cactaatatt tattagttat tttattatga ttttctaaag   48420
tttctagcca aaggggtgct ttctactacc actatacttg aaaatatca aacaacagat    48480
ttccaatttt tcctatcttc ttctttgcgc aagagcaatc attctaaaat ttggtaacct   48540
ttttcttaag ggaagggtgg taggaatttc ttgaattaaa tggcctttt catgaagtag    48600
gggcaatggg tattactttg tagtttgaat aggttttgca ttttgctctg gtgatctatt    48660
ccattaataa tctagtaaaa atttattcgc ccattgttgc acacttttg gcttgcttat    48720
gatttaattg gaatatggct caatatcaag ttttatttgt tcaaacccact taaaatgatg   48780
ggctaggtat ttatcatttt tgtagtggtg tcctagtcgt tacaagtcta ctgaattttt    48840
cttaccaatt ttgaaattgt tctcatattt ctaataattg cccttctagc tttattagtg   48900
cctaataaaa catttcacct tgaatttgct ctggactagt gttcctttta ttttttctag   48960
gttcttcatt acttaagtgg gctaggaaaa atatttgcat ccactgttca ttattttcta   49020
gtaccttct tattttccta agttttggac aattatgct tttaatagat aaccctgttt     49080
aaatcttcaa tactagggtg ctcaatattt ttaaacagtg tctaagtggg gtttgaactt   49140
ctacaaattt tcttaagttc agcacagaag cataactaat tttcttcatt ttaataaggt   49200
ttggtcagtt tctttaatta attctaaact ccaaatttta aaacgaaaag cacagggttc   49260
aatattttta tgtgatagtt cataatattt tgaatctagt aaaattggtt tgactaaatt   49320
tggttgaata tttctcaaga tacaaatttc ctaagtcctt tactgaattt aaaaagaata   49380
aacagaaatg gataaaggaa aagggttttt gcactggggt ccctggcgaa aggttttaag   49440
tgtattacag acaggtcctt ggttcactat ttatctgagt ctatgactct gcagaaaacc    49500
cctagggttt tgcgaaatcg aacccgcgat ccttccccta atggaatagt gaccgcagtg    49560
gaagaaaagg gcggagggc ttaccggcgg cgaggttgct ccggtgaggg gtcgggtgag     49620
gtccggggtc tctggcgatc acgtcgaggt gcggatccgt ggcgagtag                49680
gttggtccac gtgcacaggc ggggagctcg tcgcggcga gggatccggc ctgctcacgg     49740
cgcgatagtc caattgaaca ggttaggag cttcaccaga ggtcaaggaa gacatgcgcg    49800
cgaggaattt gagaatgaat caccggattg ctcggtctac gcgcggctgc gggtgaccga    49860
agtccagcga ggtcgatcct gggtctctgg tgaaactctg ttgggtccga ggacttgaa     49920
agcttcacgg gccactggcg aagctaaccg agtgactggt gcagcttgga agtggctgga    49980
```

```
gggagctggc cgcggtggcc gaggctcggg cggtgatggc gggcggggga gagctcgcgg    50040
agttggagtt cttgctcgag gcgtgaggcg gagtgaaggg cagaccattg tgcatccagg    50100
gtacttatag gcgccctcag gcatggctga gtgcaggcgc ggggacaga agccgaccgt    50160
gcatggcgcg cgatcagagg gcagccagtg cgcggccaag cgcttgagca cgcgatcgaa    50220
cacgtggaag tgtgattctg cccgagttca aacgcctgtt ggccgaccaa aacgtgcata    50280
tcttgccaag gatcctgtgt agcgtctctt caccgtgcca aggtcttcct gtcgtgtgtg    50340
agtcccgagt gaagatatgg cctaggtgag aagatatgat ggcctgaaga tagctctgtt    50400
agcactgtcc aaaccgagac aaaacttatg tcaagtcgtg tcaaacgatt cgggtttgat    50460
ctcaaacttc tccaaagtgt tcctagggta ttttggcgcc actttgatat ttggacttg    50520
tggattcgag ttttggaaaa cagggaacac atctgaactt tgggaaaggg tttgaaattc    50580
agttttctga atttctgaat ttccccatag ggcattggtt catgggctga tttgggatt     50640
tggaaaattc aaatggcaaa actttcttac tatattttgt tggttattta gtgcactaaa    50700
actttgttat ttggttctta ccaaaatttt gtatttccc aagtcttttc ccaaatttccc   50760
tttatgtgct taaatggtcc acttaggatt aattagggtt tgagagttct tcttaccttg    50820
aggtgcatgg catgattaag gagaaattct taagatgaaa aagactcact taaaccttgt    50880
tcttaatttt tttatgttca ttcctctttt tggttcacat gtgataatgg ttggagtcaa    50940
ctctaggaaa accctacgt gacactgggg tgtcacagtt gaagcgttct accacactag    51000
gtggccaagg attgcatgtt tatataggca caaggctggg tgcaacaact tatacaataa    51060
ggtaaccgaa tcaatctatt gttggagttt ctatctatgc acagcctaga atatatcctt    51120
tctatctata ggagattgat tcggttggct aaagattaca tgcacaagaa acttctagaa    51180
tatcgtaact tcatctaaca gttacaactc atgaacacaa tataatattc tgctatagaa    51240
atcatgattg tgtaattgtt tgttgcaata tgttatattt gatttatgt gatctgtttt    51300
tatatcagct agggggttga gctagattat ggaaatgtca ccagcaggat cacaatcaac    51360
actgatcatg gtctctcaag ttacaacaag caatatgcaa gggactcttc aaaaaagtga    51420
tgccttaact accagcttca gaggctagcc atgcttcgag aataccaaca acaaaatgtt    51480
gatgaaaatc actgaaccaa cagtgacacc acaaagcagg aatgccagga ccacttctaa    51540
ggtatattct aactcacatt tgacagtaat ttgtgaaatc actcaaacaa cagaatacag    51600
ttcgcatgtt tgactaccaa tttgattttt tgtacactca tattttatttc ttaaatctgt   51660
ggaagatgat atgaatctgc acatcatgag tgcagtttct gcaagttgct ttgcgaggtc    51720
aacagaaaca cagaaaactg atggtgatgc cctatacct aaggtaaatt tttcttctaa    51780
ctgaagcctc ttttcgcctt ggaactcatt cctttagcta atactaagag atgatgaaa    51840
ttctctcatt ccaatgtcac cagcagtatg atgctaattt ctgtcaaatg ttcttgccat    51900
attaatctta gcatttcatt gaatttacat agtacttgaa aataaaataa catgagacac    51960
catgtctaaa atatatgtg cttatcgcg ggttgtaca gatctttgat                  52020
gctagtgtga acctggggtg gttctataac cgggacacag aagagtggta taaaaaaggt    52080
aacctttgta acgcaaaaat ctacttatt gtttccataa tacatatgag atcttatcct    52140
attgttgatt gcaatctact gataggactt acccaccctt ccctgccaa aaagggcaa      52200
agaaactctt ccaagattgt gactttgaag atgttgatgg tgatgcctct gccaaagatg    52260
aggctgagct agggtactca gcctatctat ttctcaattt catcatattt ataattgtca    52320
atgcaattgg agatgataaa aatgctctat ttacataaaa aacactgatc ttgatttgga    52380
ttgtttgcta aattgtctct ttatttgatg gtcttggcta tacttgtctc tggtagattt    52440
ttgcatcaca gggtgagcga tgcttagcca ccaagaaaga aaaaaatacc actacctctc    52500
tggtttcctt ttgtattgga tattatgtc tcttgtcttt gttttttgctc caagtcttta   52560
tacattatcg ttgactgcat tttagtcctt ctcccaaaaa ttcacttgtt agtggcgagg    52620
atatcataat aattgttggg gacttgttct caaatgctat gagttaagaa caaggcaaca    52680
caaaatgtta aatgttaatg tccttcgtcc ttcgaagcat tatttccctt aggagataac    52740
gatcttcgga cgaaggttat gaaggacata cctttcataag tatgacatgt ataaacaaag    52800
gatgaagctt atgaaacata ggaagacaac ataaacaatt atataacatc ttaacataaa    52860
tatttattat taaataatca taagaacata agaataatat caaattacat ttataccttg    52920
agcttgatag aaggcaaaga taaaagtaag atgcgaaagc gtgaacagta cgagggtact    52980
gttcacctat ttataggcac agggcgcagc ctgtgtaaat ttacattcat gtcctctaca    53040
aatgattaca atcataacat agattatcat gggcccaatt cgtcatttca tcttaagtc     53100
ggtgcatctg gaaatacgct acgaagctct ctgattggta gcttcggcat cattcctgtt    53160
ctggccttcc gaaggtgttt tttctcacag gaccttcggc gacgaaacag accccaaca     53220
gtagcccctt cacggtgcca gatcatttt tgtaacgacc tcgacccgtg aaaaattctt     53280
ttaggcttcg gaatgccgaa ggtccgaaaa acaccttccc tgagctcgtt gtcgagaaac    53340
gatttaagta ttcctagtgc gaggtggtcc caccatagga cgggtacgca cgatctggtg    53400
attctccttc tcgcgccatg cggtccaccg ttcagtgaat gcgagcgact gttcggcggg    53460
tgcaggtggc ttgatgattc accttcccac ctgtagcact atataaacag acgggtaggt    53520
gtgaagttac cacagcattc attactatcg tattgttgtg ctgctgaaaa atttgaccat    53580
agccgaagct tattcttcgt attctcaatt agagcatcgt cttgttcttt agcttcgtca    53640
aaagagggag cttcggcaaa atcaaaaagt aatcaacttt gtcaaaaccg cgagaaattc    53700
agcatcaaat ggcagggtg cgttcaactg ctagagtcac acgcgacggg gaggaggccg     53760
aagctgccga gaccgcccca atctccgaag taatgagaca atcaggcttg gttgtgctag    53820
agggtgtttc tgacgaaggt gcacgtgctg ccgaaaccga gcaggctgac attgaagaag    53880
gtgaggctga tgaagaggag atagattatt tcgtcatgcc atctaaaccc agccacttgg    53940
aatttggaaa gtctaccgtc tctgaggccg atatgcccat gatgacgaag ctaggctact    54000
tcggggaagc cgagaagaag ctaattcgtt ttggcggaga ataaatcact ccgaagctag    54060
aaaatgatga ggtggtagtt ttcagaagtt tcttaaagc aggactgagg tttcctctgc      54120
atgggatgat tgtggatgtt ttggaaaatt tcgaaattta ttttcatcag ctgactccta    54180
acgctatcgt taggcttagc gtctttatct gggctcttcg aagccaagga gtggagccgc    54240
ttgccgaagc cttctaccgg gtgcacgaac ttcactatca gacgaaggct agagaagatg    54300
gactgcacga gaacttcggc tgctataatt ttgcctaccg caaagacatg aagacaccgt    54360
tggcta ccgcaccaaa tggacaaccg gttggaaaac tgaatggttt tatgttaagg         54420
ttgatgagaa gaaggagaag ctagtttaga gcccactggg cctaaccttc gggttaacta    54480
ggccccagtg tcgcatgacg ctgggatcat catgcccaga tgttgtgggt gaatttagag    54540
ttgtgtccga gcatatcgga actagggatt tggttcagga atacttagcc aatagagtat    54600
tcccaacgtt aaaggaatgg agtatgccga agcttaaagg agaagaagaaa aagaatgaac    54660
ttgttcgact gccctatcat tttaagttca agaaacactt caaagaaccc tgccaagaat    54720
```

```
ggttggatac gatcgaagtt atgtgcaatg aaatattggg caattatacg aagaaagaag  54780
atcaattgat gacggcagcc ttcggcaccc gaccgaaacg aaggctaaac cgagtaatga  54840
acactctgaa atttgaatac ccagactatg aacggttaag taaaggtgcc gaagggccaa  54900
aacaaaaaag agctgtcagt gttatgcaaa gacaagctgc cagaatgata aaagaagatg  54960
aaaatttagc aaaaaagaaa aaaaatccag ccctgagccg aaggtggccg tttcgaagaa  55020
aagaaaagct acagctccga agccaaaagc tgatttagaa gaagttccct caacaccttc  55080
tgccactgac gcagaagaaa ttttaaaggt aatgaccgaa tctctaccta ataagctaag  55140
cccgctggga ccgaactga tgaagctttt acagaagaag aagaaggaac cttcggttgc  55200
cgagaagccc gctgaaccaa aaaagcgaag gattattact atcattgagg ctattgaaga  55260
aacaccatcg tcggcctcag tgctaaaaac agcagcagcc aaagctgctc cagccgaagc  55320
ttctacttcc gaagttgcag cagccgaagc cacaaatttg gaaaacacgc ttactgacat  55380
tgatgaaata attttgaata tggctgagga agaaactgct gcagctgctg aggaaacccc  55440
ggctacagtg cctgaaaagg agaaggagct tgccgaagat gcttcggaag aagaaaatat  55500
caactttcaa aacataattg gacaagagtt gtctaaggct aaaaaagaag agctgaggga  55560
ctttgctata tcttgcgggt accagccagg ggcactgctc ttcggtggta tagacgaaga  55620
gagcttaggt tgcctttgag accggactgg ggagaaagtt gtcaggactt tatcgaaaag  55680
tgttggtttt ccgaaactcg aagccgatct cagcagatac cgacgacagc atatcgtcgg  55740
tagcctattt tattctaact ttaaggtaaa atttcttcct taactttta ttgttttgat  55800
atgaagatgt tttctgatga aggttatttt gtcagagcct actactaagc aaaaccttga  55860
ggatgcaaca agacctcgag gacaagaaaa acgaagttat aattgagggc ttagagaaca  55920
agattaaaga tcatgaagct gccctagaaa agaaagactt cataattcaa acaatggaag  55980
gttcactggc agaagctcaa gccgaatcgc ccagactgaa tgtgaactt tccatgaagt  56040
caaaaagcat tgagcaagag aagaaagatt tcgaaacaaa actcgaagct gaagttgaaa  56100
aaagttcaaa tctgcagaaa tcactcaaag atcttcaaga agcatggtct tgtacttgtt  56160
tggtgacttg tgcccgcttg atttctgctg agagccgagg caagggctga gcgcttggtc  56220
acgtacccga gccccctga caaggggtt gcccatgccg tagtggttga cacagtactg  56280
agtatggcaa aaagtcccta agtaatatgt cagctctgca gtatatggtg acgttgggcg  56340
cctttccgtt gtggatattg aggctagagt cgggctcggg cgaggcagaa gtccgcccga  56400
ggtcacgacc gagcccgctc cagtattcgc ggggagcagg taaacgaggc cgggctcagg  56460
cgaggcgaag tttgtcccga ggccgaggtc gccttcagga aggcagagtt cacgtccgag  56520
agccatcctg cactcttgtc gtattgtacg tcccatcagg ggttgacaga tggcatgtgg  56580
gaatagtggt cgcatgcgtc atcgtagttg gtgaagcttg acaggaccgc ggtcttgttg  56640
ctcctgttca cctgcaactc tacgtggggt aggtatgcat attgaatgct cctgcccccct  56700
gcagactttg gttgagtctt gcattgggt tgtcttcctt acccgagatg tgctcggcg  56760
aggcaaagac ttttgttctg ggagatggag cctcggccgg gacgagaatt ctccctagag  56820
cacaccatgt ccgagggcag gcttgagcga agccgaccta tggtgacccc tgagcggggc  56880
ctcgggcgaa gcgcggtta tgatcctttg atctcgggga atgtgtcttg aaggtggtct  56940
aagggttaag tgtgttttag gggcataatc tgggtacccc taattatgat acccgacaag  57000
tggtattgat tagaaatggc tcaacaaaag ataatggatg gttgaacaaa atgtgaatgg  57060
ctgacatcag ttttatagtg tatgtgtgta tatatgtgtg cacacataca atatctctcc  57120
tttatataac ataaacagac ataagttata gtggtagaag acgctcgctt gtatcgaaag  57180
agcatggttt gaatccccac gtcctatttt ttgtgtggtt attccacgcg cctggctggc  57240
tggttcgtga ctaggtcgga cccatgcaac tggctagcc aaatttcccc aattatttca  57300
taaccaacct ctcatttgtt ctcctttatc tttatgttat taggatcaat catttgtagt  57360
tatcaaggtg aatcacttgt acttttatca aggtcaatca ttatagttac taggatcagt  57420
cgtgtattta tcagggtcat tcattgtaat tattagggtc attttatttt ttaccagggc  57480
cagtcattgt attttatcag gatcagtcat tgtacttctt ctattagggt ctacattta  57540
tcaaggtcag ttattgtagt tatcaggatc aatcattata ttttaatcag tgtcagtcaa  57600
tgtatttatt aaggtcaatc attgtattat taggatcagt cattgtattt atatcagagt  57660
cactcattat agttatcaag gtcggtcatt gtatttttt attagggtca gtcattgtat  57720
ttagcaggat atttttatca gggttagtta ttgtattatt aggttcaatc attgtatttt  57780
atcagggtca ctcattatag ctatcaagat aagtcattgt atttttttatt agagccagtc  57840
atcgtattta ttaggaccaa tcattgtatt tattagggtc ggacattgcg attaaataaa  57900
aaattgaaaa agatatagca tgagtgtcta gttttgttcg aaaatctcat aaacacgaat  57960
ataacaaaaa aagggatttt ggttttttat gcctatatat gcgggttgca tgactgcata  58020
cacgcatact cgctgagcgt ggtgccaaat agtatccact gcgtgccctg cgctctaacc  58080
ggatgctcta tccatcacac ctcaataacc cattgagcat ccctccccc acacgcctgt  58140
gctccaatca gatgcttgtt tgactaatag caaggagatt ctccaatatc atgctaagaa  58200
tagctaggat ttcagaaga agatgtcatt cgtttgatga gaaataaaaa aggaaatcga  58260
gaattcgcgt ggctaaagct gaagcaacta ctttcgaagt aacagaaaga aaagcaacga  58320
ttggagtggg ggagtcagag tcaaaaagag aattcctcgc ttctttctct catgcaaaac  58380
cgtgcatgag actttcatct cgcacggctt ctaagtgata aaagaaagaa gtccaatcgt  58440
gataaaaata attacatcaa tttaatagaa aggaatgact taaaaacata ttatgagtct  58500
ctggatgaat aaactattgg atgacttaaa atatttgtaa gaaagttctg taacaactgt  58560
tgacaatatg aaaatatttta aataagtcat aaaatgacta aatgacatgt gatgactaga  58620
attgtaacag aatgacttaa tttaacataa tatgtactga atgacctaac gagtgaatga  58680
ctgagaaaaa aatagaatgt tttaaataat catcaaaatgt tcttaaatga ttaagaaata  58740
cttgattatc ttataaaata actagtacaa cacatgtgcg ctgcgacgac atacaatcat  58800
atttgatacc aataaaaaaa taatatcaaa tcaaaagtg aacatatggt ccatatatca  58860
gatactaaac tgataaaaac aaatattacg ctttttatctt agctaaaata tcaggaaagg  58920
tatgagttga aagaagcctg actacttttt taaagcttgc tcgatggctt gtcctccttt  58980
aggtagtgag gtggttctat gtgggagcgc tgcgctgcgt ttggcttccc tgtcgtgtta  59040
gacttgtgtg gtttctcacg gtccatctat agataaatg tccactagta gggattggg  59100
tggttttcac agccatctct tagatgccca ctggtatggg gattgatcta catgcttgtg  59160
gcatggcgta tgacgaccat cgaagctagt attttatagt agtggagatt ggaatgaatt  59220
aatgcaaaat gagaagtatg agaatgttga gtgacttaaa tggatcacga tagaaactgc  59280
attgggggcct gaaacagcta ctaaacaagc gatcgcaata tcttttaaaa ataagttgcg  59340
gtccaaaaaa aagtgacaat ctatactctc taagcaggct cccaaccatg tcaattcact  59400
acaacaattt caatgaatta acatgagtga accatagttc tcacagggta tttcgtcgtt  59460
```

```
acaggtccat tcgattagaa gtgggtcatt atatggtggt ttgcactgta tctttccccc   59520
gttatcaatg agagccaaac gtgtacctta caacctttca gatgtcaatt ggaacttgca   59580
aaaaaaaata gaaagaattt tgacttgttg gggatttaaa ctagaaagca tctaggcccc   59640
tggttggttt tagtgattaa tgacaacgta attttatatg tgactaacat gtgttttgca   59700
gaggcaaatg gtaagttagg tcgcattaca ggtagatgta ctacaatggt gaaaacaatc   59760
ccggagataa aaacttgaag caacggctaa agcgacgaaa caaaagtga aggtcttcgt     59820
attccgagtg tcaaggagtt gcggacactc gtgatatagt taggtctttt attttgtttt   59880
agccgtacta taaagagggg ttgtcgataa gtagtttgac caaaagagtt ctagtgtagt   59940
gttggtgcat attcacactc acatatagtg ctaggtgtaa ctctagaaca tactcacaag   60000
ttagaacaaa aaccaaattg aaaaaacagc acaaaacaga agctagggtt tctggctttg   60060
gggcaccgga ctgtccggtg caccctttgc cagtgggccc agcctggccc agggaagagg   60120
gttccctgcg cgcagaaacc cgagagcgcg ctgttcgtga gttgaatttt agaggcacac   60180
cggacagcgt atcggactgt ccggtatgcc atctgtccaa cggctagctg tcagaactag   60240
ccgtttgagt cgaccgttgg cgcaccggtg gcacaccgga ctgtccggtg cgccatgcg    60300
cagcagattc ctggtaatgg ctagttggtg ggtgagggct atttataccc catccaccta   60360
ccatattgat ggtcttgctg cccacattta ctcctacaca ttggtagagc attgcaagca   60420
ccacaaagcc tagtgaggtg acttgagaat cttaatcccg catttggacc tcattaacgc   60480
tagcgagagc cacctagagc acacaccgca tgcattaggc ttctcttggt caagtgaaag   60540
tctatggctt attactcttg gtgatcggca tcacctagac ggcttggtgg cgttgggagc   60600
tcggtgatca ccgtggagat cttgttggtg acccgactca agtttgtaag cggtcgtgag   60660
ggatccaccg cgccggagtg gcaaaggatc atctcgttgt gagcacttgg ttcttgcgat   60720
gaccaaggga gagcgatacc cttacgcagg tgctccaagca aggactaggg gagagtgccg   60780
actctttgat acctctagaa aaattggagg agtcttctaa accttgcttt acattccgca   60840
cttaattcaa gtattttaca ttgtgtattt gtttagcaag tatttgaagt attatcttag   60900
cattgttgta tttctagtat tattctctta gtgctagttg tcgggtgaa gttgggctct    60960
tgcttagatt ttagttagtg ttgattttta gaaaagccca attcaacccc ccctcttgag   61020
catcgtgatc ctttcaattg gtataagagc cttgttgctc ttagattagc ttaaccgcta   61080
gagtaacgat gtccggtggg gatggacctt ctcccgtttt ttatggtgac gattttccat   61140
attggaaaat tcgtatggaa gcatatttag aggctataga cattggtgtc tacaaagccg   61200
ccacacaaag attccccgaa cctagagatc ccacaaatct tgtaggtgaa gagttgaact   61260
atgagaaatg gaatgctaag gccaaaaaca ccctttttag aggcctttgc aaagatgtgt   61320
ttaatagagt tagaaaccat aaaaattgtc atgatttgtg gatggacata tgtgctctac   61380
atgaaggaac tagaattgag cgtgaggaga gatatcacat tgctatgaga aaattaaatt   61440
cttttgaaat gcttgctaat gaaaatgcca atgctgta ctcacgtctc aatattcttg   61500
tagaggaagt aaatggcttg gggcttacac aaatttcaca accggatgtt gtgaggaaga   61560
ttctcagtgt cctcccaatt gataaatatg gacacattgt cactgtgctg catcagatgg   61620
atctttcagt tgtcactcct acacaaattt tgggaaagat caatgcacat gagatgtaca   61680
tgcacatcaa tgacaaggat gagtcatctt acaagagaaa ggatttggct ctcaaagaaa   61740
atcaagaaag agaaggaaaa gctaaagtac aagttgagga ggaatcctca agtgacgatg   61800
atcttaatgc taacattgcc ttgatggtga ggaagaccac caagatatta aagaagctca   61860
acagagaagg catcaaattt gactcaagaa agaaagaatt cttttccagc aaaagaaagc   61920
ccatttctta aatggattgc tacaactgtg gagagcttgg tcatcttgct catcaatgta   61980
acaagtccaa gaagaacaag ttcaagggca agaaagaaga tgacagtgat gatgagaaaa   62040
atgaaaagag attcttcaag aggaaggatg gaaagcataa gaggttccac aaaaagaaaa   62100
atgtaaaggc atacattgtt ggtgattggc tcactgacat tgagtcgtca agtggatctt   62160
cttcaagtga agaagaaaat gatgaaaaag ttaccgccat cgctgggggac ttctcttcac   62220
caccaccatc tccatcatcg acttctcacc tatgcctcat ggctagaggt gaacgaaaag   62280
tacaaaatga taatgatatt attgatgata gtgatagtga tagtgatgaa gaatttgctt   62340
caccttccta tgatgaacta gttgacttgc ttaatgaata cactcaactc attaggaagt   62400
caaaagctaa atgtgataag ttgaaagatg aaaatgaatt tttaaatgct aaatatgaca   62460
tagttatgaa agctagtaat gaaatgaaag aagaaacaa aactatgtca tccactgtaa   62520
atgagcttac atcctcccta aaagatgcta aggataaatg tgacaagtta aatgaagcta   62580
atagggagtt gaaagataga ctagtaaaaa ataaggaaga ctatactaag attaaatttg   62640
atcatgataa tcttcttgtt gaaatgaac ttttatctt gaatacacat gaggctatta   62700
accctgttgt тааттаттgат gtaccaacct catgtgatga тттgагtсaa ggtgatcaaa   62760
ctagtctaca tgatgaattg actgaaaaag ttgaagtctt gacattagac aaccaaaaat   62820
tgaagagata cttgactgat gcaactacta gaggaaaggt tgccattgag aacaatgact   62880
tcaacaatga gttggcagtg gataaagaaa ggcttaaaat gaggtcaaga aacttaagcg   62940
tgaaaatgaa catcttgcaa caagtgtgca aaagttcaac aagggccaat acctctaaaa   63000
tgaattgctc atgaacactg tcatgaaaaa caacaagагт ggtattggat ataactcttt   63060
tgtgcaaaag aaagctacaa ctcaatacaa gccaaatcag actcataagc atatcaaatg   63120
cтттgагтgт ggaaaagaag gtcattttt ccacaactgc aaagccaaac caccaactcc   63180
cctgccaaag cactcaagac catttgcctt caatgctcat tatgttttaa gaagtagcaa   63240
atggaaaagt cgaagttaca ttcctaggtc caccaagcaa ggtagacct agcaaattt    63300
gggttgcaaa gtccttgatt gагаааgтса ctggtcctat gcaatatagg gccctcaaa    63360
cttaggcttg аттттgтстgт ggatgtaggt gaactacaag accggtggga gccattgggt  63420
tattgatagt ggatgcacat aacatatgat aggcaaccca cggatgttca cctcacttga   63480
tgataatgtt gatggacaag acaaaatcac atttgggac aattcaaagg gaaaagttca   63540
aggacttggc aaggtggcaa tttcaaatga tctatcaatt tcaaatgttc tcttggttgc   63600
acctttaaga ttcaacttat tatcagtggg tcaactctgt gттcтттggас ttcaatgctt   63660
attcactcca acagaggtta ttgtatcaaa aatggatgat gааtаааatgg tgctcaaagg   63720
atttagatac aacaatctct acttagtgga tttcacctct gaagatgcag acttaagaac   63780
ttgcctcttt accaaagcat ctcttggatg actatgcat agaaggcttg cacatgttgg    63840
aatgagcaca ctgaagaaag tattaaagaa ggactgtaa aggttat       63900
atttgaaaag gacaagcctt gtagtgctta tcagctggaa аагсааgттg ctaacacaca   63960
tcctacaaaa gctttcatgt caacatcaag gccactggaa ctacttcaca tggatctatt   64020
tggaccaaca acttatgcaa gtgctggtgg caacctctac tgtctggtga tagttgatga   64080
tttctcaaga tacacttggg tgtttttctc catgataaat ctgaagttgc atctatattc   64140
aagaagtttg ccaagaaagc tcaaaatgaa tttgattaca agatcaagaa gattagaagt   64200
```

```
gataatggaa aagaatttga caacaccaac attcatgaat actgtgatga gattgggatc   64260
aagcatgaag tatcagcaac atatacacct caacaaaatg gagttgttga aaggaaaaat   64320
aggaccttga tcacacttgc aaggacaatg attgatgagt ataacacacc ggagaggttt   64380
tgggccgaag ctatcaacac tgcatgttat gcatcaaaca ggctatttcc tcactggcta   64440
cttgcgaaga ctctctatga actgctaaat gggaaaaagc cagacgtctc attcttttgg   64500
gtgtttggat gcaaatgcta catttacaag aaacgccatc acctagggaa gtttcaaaga   64560
cgttgtgata ttggttttct tctgggttat tcattaaagt ccaaagcata tcgagtattc   64620
aatcatgcca ctggcgtggt agaataaaca tatgatgtgg agtttgatga gactaatggc   64680
tcccaaggag cacttgaaaa tcttgatgat gtaggtgatg agccacttaa ggaagccatg   64740
aagaacatgc caattggagc tatcaaacca aagaagatg aagaagaggt gcaaaacatt   64800
aataggcctt cttcatcaag tgtaccacaa gatgatgaaa aagatgagag gcatgcaaat   64860
gaagatacat ttgtctctca tgaacaagca aggatacaag ccgaagatgt tgatgctcca   64920
ggatcttctt cctaagtggt tgataggaga aactcatcac tgcttcaagc acacccacaa   64980
gatcaaatca ttggaagtcc ttcacaaggg gttattactc gatcacataa acatgcttct   65040
tttattgaac atcactcctt tgtttcttgt gttgagccta ctgtatagat gaggcgctac   65100
aggatccgga ctgggtgaat gccatgcatg aacaactaaa caacttcacc cgtaaccaag   65160
tttggaccct ggagaagcct ccacaagatg caaggatcat tggaacaaag tggttattca   65220
gaaacaaaca agatgatcaa ggcgtgattg tgaggaacaa ggcaagactt gttgcaaagg   65280
gcttctctca agttgaaggt ttagattttg gagagacctt tgcaccggtt gctcgacttg   65340
aagccatctg tatcctactc gcatatgcat catgctatga taaaaagctt tatcaaatgg   65400
atgtaaaaag tgcattttta aatggcttca taaatgaact tgtatatgtt gagcaaccac   65460
ccgggtttga agaccctaga tatcctaacc atgcttatag gttgtccaag gcgctatatg   65520
ggttaaagca agctccaagg gcttggtatg agcgtcttcg cgacttcctc atcaaaaagg   65580
gcttcaagat caagaccgtc gacacaactc tattcacaaa gaaacataac ggtgatattt   65640
tcatttgtca agtatatgtt gatgacataa tctttggctc gataaatcgc tatcattgca   65700
aggaatttgg tgagttgatg tcgaaggagt tcgagatgtc aattgattgt gagctgatgt   65760
atttcctcgg ctttcaagtg aagcaaatga aagatggtaa cttcctctca caagagaagt   65820
ataccaaaga cttgttgaaa aggttcaaca tggagatcac ttgttgaaaa gatggtaact   65880
ctctaccgtt ctatgattgg tagtttattg tatcttattg catctaggcc cgatatcatg   65940
tttagtgtat gcatgtgtgc tagatttcaa tcaaatccta agaaagctca tatttgcgct   66000
cttaaaagaa ttcttaggta tctcaagcac accccaagtg ttggcctttg gtatcccaaa   66060
ggagctactt ttgatttaat tggctattcc gattcggatt atgccggttg caaaattgat   66120
agaaaaagta cttctagggg tgtaatttgc ttgggagatc actactatta tggacatcca   66180
aaaagaaaaa tagtgttgcc ttgtcaaccg ccgaagcgga atacattgcc gctggtgctt   66240
gttgcacaca gatttatat atgaaacaaa ctcttctaga ctatggtgta gttctagaaa   66300
aggtaccttt gttgtgtgac aatgagagtc ctgttaaaat tgctaataat cttgtacaac   66360
actctcgcac caagcacatt gatattcgtc atcacttcct tagagatcat attgctaaag   66420
gagacattat tttagaagaa gtgaggtcgg aagatcaatt agaggatatt ttcactaagc   66480
ctcttgataa aacccgcttt tgcatgttga gaaatgaatt aaacatactt gatctcagaa   66540
attttatttta aagatctcaa aatagtgttg tcaagcctgc attgcatatt taaatttctt   66600
gtattgcatc tagggcttgt ctaacctagt taagataacc gccaacaaag cgagtgaaaa   66660
aagcttaact cgggctcaaa cttgacaagt cttagcttta agcttttagt acttaaattc   66720
ttatttacta tgccattgtt ggttcttgag atatgcatgt agtactacac ttaggggggg   66780
agtattcaaa actcaaatta ttcatgaaaa ccccctagttc aaagctaaaa tgcaaatctc   66840
accatttgac tatttttctct aaaaattgac tagcctatgg caaaatattt ttgaaaatta   66900
tgggaaaata tatgaggggg ccaataccta tcccaatagg tgttcttttg tatgattata   66960
agttggaatt tggtttggtt aaaatttgaa tcgaaaaatt tgaaaatttt caaaatcacc   67020
tctgcctagg ctcaccggaa agtccggtgc actgtgcact gtnnnnnnnn nnnnnnnnnn   67080
nnnnnnnnnn nnnnnnnnnn nnnnnnnnnn nnnnnnnnnn nnnnnnnnnn nnnnnnnnnn   67140
nnnnnnnnnn nnnnnnnnnn nnagctactc gacctagcat actagtatcc atctcaaagg   67200
gaatcctgag ttcatgcaac taggggtttca ttcaactcct acacttaagt gcacggtaca   67260
agcctacaaa cattaagtgc agtaaaatag catatatata atggttatgc ataaaaccgg   67320
ggcttgcctt taatttaaca cttaggtagt gtttgctggg ggaggtactc gcttggtgag   67380
catccactgg ttaagtccat tcttcaggtc gtccatcaac ggcatcttgt ggttggcacc   67440
acatcactgg ctcgatcatc atctctcggt cctatatgag gtgcaagatg catatgtatg   67500
aatataataa aagtaacata agatatacca agacacagtg gcgaactaaa cattaattag   67560
taagacactg caacaactat acgcaaacac tagttattta tgtgtcattg ggcacacgta   67620
aacactacca ctggaaagac aatgatcact acctacaatt aaccaacgca acacgatatc   67680
atatgtacaa gcatttcattt agttgctacg gcttttcatt aattcttata ttgatcacac   67740
aaaaacatca caaacacaag tttaataaaa ggaccgatgc atcaatgtcg atggactcct   67800
ctatcacaat caactacagc aagcaaacac attaattatg gaacacatgt taacctaagt   67860
ttagccatca caagtctatg tccgttaagt gcttactaaa gcgttttttag ccaaaatggt   67920
gaactaaata ttcatttgag cacgtgcaga tttttaggac agcagcacag cagctacttg   67980
ttttaatcat aacttttaaa atattaatcc aaaaatagca aataaaact ttctggaaaa   68040
tttagaaagt gctctacaat tttggtattt tcatcacagc atgattaaac acttagcaag   68100
gtcaaaaagt gcaatcacag cagctctgtc cagatttgga cagattcaga cttgtgattt   68160
taaaaattca taactgaaga ttcagacatc caaacaaatt gatcctagac tttctggaaa   68220
gctaattaaa tgttctacaa attatttata aacatcccaa gctggtttag catgtatcaa   68280
ggttaaaata tactatgaag gctgtgctgt ccaaaactgg acagattcag tcttcacact   68340
tcaaacacat gtaacttaat cttcagacca ccaaaaagag tgatctaaga cttttttgaaa   68400
agcttagcaa aagtactaca caactttat aatcaccaag aagtgattcc aggtttaact   68460
aaatcaaata ttacagtttt cgaaatctgt tctgacggtg gacagaacac agcaaccagt   68520
ttgtaaaatt cataactctt aaaccgtcag gcctatagtt atgaaatttt aacacaagca   68580
agacaagaaa agcctctaca actttcttat aattgacaag tgattttct aacattaact   68640
taagcaaaca atgcagcttt tgaaatctgt acagaaagtg gacagattca gttactgaat   68700
ttgtaaaaaa cataactcct aaacaatcag acttatgcct gtcaatttt aacacaagta   68760
cgataataaa gttatctaca acttttttgt gaccaccaat aactaattc aacattaact   68820
taagcaatca ttgcaatttc tgaaatatgt tcagaaattt gacagattca ggtgctgggc   68880
ttgtgaaaag cacaactcct aaacaatcag gtttatggct gtcaaatttt agtacaagca   68940
```

```
agataatcat gtcatctaca actcttctat atgactttc tatagaaaac atgatttggt  69000
ttatcaaaca aacagcacaa ctaaaacagt gcgtgcagcc caaaacagca atcaataaat  69060
tcagcttcta tttacttta aaaattgccg cgttctagag actcgactta ttctaaatta  69120
tatcaaggca cgcttaagca tagccacgca atagatgacg tgacggctac gtagtcatgc  69180
catcacttca ccccacaatc ccaactatca aaataactgt cggagaccat aattagggt  69240
accctcaaga ctcctaattc tcagctggta acccccacca gcataaagct gcaaaggcct  69300
gataggtgcg attaagtcag ggatcagtcc attcgagcga ctcgatcacg cctcgcccga  69360
gcctagcctc ggacaagggc agccgacccc agaggatttc cgtctcgccc gaggcccccc  69420
tctaacggcg gacacatctt cggctcgccc gaggccctcgc cttcgctaag aagcaaccct  69480
gactaaatcg ccgcaccgac cgaccaagtc gcaggagcat ttaacgcaaa ggtggcctga  69540
caccttatc ctgacgcgcg ccctccggca gagccgaagt gaccgccgtc acttcgccgc  69600
tccactgacc ggtctgacag aaggacacg ccgcctgcgc cacttcgact gcagtgccac  69660
ttgacagagt gatattgaca ggaagccagg ccctgccaaa ggcgccatag gaagctccgc  69720
ccgacccagg gctcggactc gggctcagcc cggaagacg gcgaactccg ctccgcccga  69780
cccagggctc ggactcgggc tcagcccgg aagacggcgca actccgctcc gcccgaccca  69840
gggctcggac tcgggctaag acccggaaga cggcgaactc cgctctgccc gacccagggc  69900
tcggactcgg gctaagaccc ggaagacggc gaactccgct ccgcccgacc cagggctcgg  69960
actcgggcta agacccggaa gacgacgaac tccgcttcgc ccgaccccag ggctcgggct  70020
cgagctcagc cccagaagac gacgaattcc gcttcacccg agcccagggc tcggacaccg  70080
ccctggactt tgccgacga ccttccgcct tggcccgacc cagtgggctt cggactcgac  70140
cctcggccat ggaagatcca ctccacctcg gcttcggagg agcctccacg taccccccaga  70200
ctagggcga ggccagccac gtcaacagga agcgccatca ttaccctacc ccgagctgac  70260
tcggaccgta gagaacaaga ccggtgtccc atctggctgt ctccaccaga taggcaatga  70320
tggcgcccg catgccctgt gacgacggca gctctcagct ctcttacgga agcaggagga  70380
cgtcggcaag gacacaaccg ctccgacagc tgtccctccg ccaggctccg ccgctcctcc  70440
gacggccacg acatcacact agctgggttc caagatctct ccggctgcca cattggcatg  70500
tactcagggc actagctctc cctcgctaga cacgtagcac tctgctacac ccccattgta  70560
cacatggatc ctctccttgc gtctataaaa ggaaggacca gggccctctt agagagggtt  70620
ggccgcgcgg gacgaggacg ggacaggcgc tctcttgggg ccgctcgctt ccctcacccg  70680
cgtggacact tgtaacccc tactgcaagc gcacccgacc tgggcgcggc acgaaccga  70740
aggccgcgtg attccaccct ctctcacgcc ggtctccggc cgcctcgctc ctttccccc  70800
ttcacgcttg cccacgcgct cgacccatct gggctgggc acgcggcact cactcgtcgg  70860
cctgagggac cccccggtct cgaaacgcct acagttggcg cgccaggtag gggcctgctg  70920
cgtgttgacg aacagcttcc cgtcgagctc cagatgggca gtctccaaca acctctccaa  70980
cccgggacgg tgctccgttt cgggagtctt gagttcatgt ccctcgacgg cagctacgac  71040
atgatactcc ttccaccgcc gcgcgacaac gacgatggcg gccagacagcc cgcccgccgg  71100
cggcggaatc gacgacgtct tccccgcgtg gcggaagaac aacattcgag ctcgcccgt  71160
cctctccccc gccaacggag gaggaggcgg ggcaacaaag gccaagcagg aggccgcgcc  71220
tcgtcggctg tcgagcgagt cgacgtccct agcaccccaa cgggggcgc gttgggcgtc  71280
gacctcgcgt ttgagacaaa ggcgagcgcc gtctccccgc gacacgccaa tcccgagcaa  71340
gtggacgacg ccagcgcgct tgcgaaaagc ttgcaggaca tcgccctcgt acctgaggcg  71400
acgatgcggt cagtcctcga cgtgacttca tcgccgctcg acgaccaaaa ggtaccaacc  71460
gattcccatc ctacgtcatt tgtactcagc ctcaaccgct ctagcaatct tgctttggcg  71520
ggcgcccttg tagaggcgag tacaaaccct ctggggtttc gcttgcggtc gccttgggac  71580
cggctgacgg acgtctcgac ctacgggccc tctgggtccg aggaagatga cgaccccaac  71640
atctgttggg atttctctgg atttggcaac cctagtgcca gcggaacttc atgaccgcat  71700
gtgactactg cctctccgac tgttccgacg gtagccgcag cctcgacgac gaggactgcg  71760
gcccaagccg cgaatgtttc cacgtcgatc tagggggtcc ctccgaaggc aatcatctcg  71820
gcatgccgga ggacggtgct cccccctggc cggtgcctcg cgctgacatc ccgcgggagc  71880
tagttgtggt ccctgttccg gcgggggggtt acgacccaca gctcgagcaa gtccgcgggg  71940
cgcaggccag gatcgacgag ggagcaggag cgcttgagcc gatccgccgg cacgtcgggc  72000
aggcatgggc gggccaaccc ccggccgag aaatacgtca cctgcccag ggtctccagc  72060
accgcgtcgc cgatgtcgtc agggtcaggc caccacctgc atccagtggg gtcggtcaga  72120
acctggtcgc agcagcgatg ctcctccgcg cgatgccgga gccatccacc accgagggtc  72180
ggcgaatcta gggagagctc aaaaatctcc tggaaggcgc cacggtccga cgggccgaga  72240
gcactgcctc ccgaaggcaa ggatacccct cggaacctca tgccgcgact tcccgattca  72300
tgcgggaagc ctcggtctac accgggcgca cgcgcaacac cgcgcctgcg gccccggcc  72360
acctcggcaa cgacgccat cactgcgacc gtcgagccca cctcgacgag agggtgcgct  72420
gaggctatca cccaggcgt gggggacgct acgacagcgg ggaggatcgg agtcctcgc  72480
ccgaaccacc cggtccgcag gccttcagcc gggccatccg gcgggcaccg ttcccgaccc  72540
ggttccgacc cccgactact atcacaaagt actcggggga aacgaggccg gatttgtggc  72600
tcgcggacta ccgcctggcc tgccaactgg gtggaacaga cgacgacaac ctcatcatcc  72660
gcaacctccc cctgttcctc tccgacaccg ctcgcgcctg gttggagcac ctgcctccgg  72720
gcagatcctc caactgggat gacctgttcc aagcttccgc cggaaatttc caggggacgt  72780
atgtgcgccc tgggaattcc tgggacctcc gaagctgctg acagcagccg ggagagtctc  72840
ttcgggacta catccggcga ttctcgaagc agcgcaccga gctgcccaac atcaccgact  72900
cagatgtcat cggcgcgttc cttgccggca ccacctgccg cgacctggtg agcaagttgg  72960
gtcgcaagac cccccaccagg gcgagcgagc tgatggacat cgccaccaag ttcgcctctg  73020
gccaggaggc ggtcgaggct atcttccgaa aggacaagca gccccgagcc gccgtcgg  73080
aagatgctcc cgaggcgtct actccgtgcg gcgccaagaa gaaaggcaag aagaagtcgt  73140
aagcgaaacg cgacgccgcc gacgggacc ttgtcgccgc cgccgagtac aagaaccctc  73200
gaaagccccc cggaggtgcc aacctctttg acaagatgct caaggagccg tgcccctatc  73260
atcagggggc cgtcaagcac acccttgagg agtgcgtcat gcttcggcgc cacttccaca  73320
gggccgggga acccccgacga ggtggcaggg cccgcaacga ggaagatcga  73380
aagtaggaga gttccacgag gtccgcgact gcttcatgat ctacggcggg catgtgcga  73440
atgcctcggc tcagcatcgc aagcaagagc gccggaggt ctgctcggtg aaggtggcgg  73500
cgccagccta cctagactgg tccgacaagc ccatcacctt cgaccaagct gatcaccccg  73560
accacgtgcc gagcccgggg aaatacccac tcgtcgtcga ccctgtcatc ggtgacgtca  73620
ggctcaccaa ggtcccttatg gacgggggca gcagcctcaa catcatcaac gccgagaccc  73680
```

```
tcgggctcct gcgcgtcgat ctgtcctccg tccgagcagg cgctgcgccc ttccacggga   73740
tcattcccgg gaagcgcgtc cagcccctcg gacgactcga cctccctgtc tgtttcggaa   73800
caccctccaa cttcggaagg gagactctga cgttcgaggt ggtcgggttc cgaggaacct   73860
accacgcggt gctggggagg ccatgctacg cgaagttcat ggccgtcccc aactacacct   73920
acctgaagct caagatgccg ggccccaacg gggtcatcac cgtcggcccc acgtacaaac   73980
acgcgttcga atgcgacgtg gagtgcgtgg agtacgccga ggcctcgcc gagtccgagg    74040
ccctcatcgc cgacctggag agcctctcca aagaggtgcc agacgtgaag cgtcatgccg   74100
gcaacttcga gccagtggag acggctaagg ccgtcccct cgaccccagt ggcgacgcct    74160
ccaagcagat ccggatcggt tccgggctcg agcccaaata ggaagcagtg ctcgtcgact   74220
ttctccgcgc gaacgccgac gtcttcgcgt ggagtccctc agacatgcct agcataccga   74280
gggatgtcgc cgagcactcg ctggatattc gggccggagc ccgaccggtc aagcagcctc   74340
tgcgccgatt cgacgaggag aagcgcagag cgataggcga ggagatccac aagctaatgg   74400
cagccggggtt catcaaagag gtattccatc ccgaatggct cgccaaccct gtgcttgtga   74460
gaaagaaagg ggggaaatgg cggatgtgtg tagactacac tggtctcaac aaagcatgtc   74520
cgaaggttcc ttaccctctg cctcgcatcg atcaaatcgt ggattccact gctgggtgcg   74580
aaaccctgtc tttcctcgat gcctactcag ggtatcatca aatcaggatg aaagagtccg   74640
accagctcgc gacttctttc atcacgccct tcggcatgta ctgctatgtc accatgccgt   74700
tcggttttgag gaatgcgggt gcgacgtacc agcggtgcgat gaaccatgtg ttcggcgaac   74760
acatcggtcg cacggtcgag gcctacgtcg atgacatcat agtcaagaca aggaaagctt   74820
ccgacctcct ctccgacctt gaagtgacat tccggtgtct caaggcaaaa ggcgtcaagc   74880
tcaatcccga gaagtgtgtc ttcggggtgc ccgggggcat gctcttgggg ttcatcgtct   74940
ccgagcgggg catcgaagcc aacctggaga agatcgcagc catcaccagc atgggggcca   75000
tcaaggactt aaaaggtgta cagagggtca tgggatgtct cgcggccctg agccgcttca   75060
tctcacgcct cggcgaaaga ggcctgcctc tgtaccgcct cttaaggaag gccgagtgct   75120
tcacttggac ccctgaggcc gaggaagctc tcgtagacct gaaggcgctc ctcaccaagg   75180
tgcctatctt ggtgccccca gctgatggag aaaaaagcct cttggtctac gtcgccgcca   75240
ccactcaggt ggttagcgcc gcgattgtgg tcgagaggca agaagagggg catgcattgc   75300
ccattcagag gctagtttac ttcgtcagtg aggtactgtc cgaaaccaag atccgctacc   75360
cacaagttca gaagctgctg tatgcagtga tcctgacgag gcggaagttg cgacactact   75420
ttgagtctca cccggtaact gtggtgtcat ccttccccct gggggagatc atccagtgcc   75480
gagaggcctc gggcaggatt gcgaagtggg cggtcggaaat catggcgag accatctcgt    75540
tcgcgcctcg gaaggccatc aagtcccagg tcttggcgga cttcgtagcc gaatgggtcg   75600
acacccagct accgacggct ccgatccaac cggagctctg gaccatgttt ttcgacgggt   75660
cattgatgaa gacaggagcc ggcgcgggcc tactcttcgt ctcacccctc gggaaacacc   75720
tacgctatgt gctacgcctc catttcccgg cgtcgaacac atgtggctgag tacgaagctc   75780
tgaccaacgg attgcgaatc gccatcgagc taggggtccg acgcctcgac gctcgcggcg   75840
actcgcagct cgtcatcgac caagtcatga agaaactccca ctatcgcgac tcgaagatgg   75900
aggcctattg cgatgaggtt cggcgcctgg aagacaagtt ctacgggctc gagcttaatc   75960
acatcgctcg gcgctacaac gagactgcag acgagctggc aaaaatagcc tcggggcgaa   76020
caacggttcc ccggacgtct tctcccggga tctgcattag ccctccgtca agatcgatga   76080
ccctcccgag cccgaggcgc cctcggacca gcccgaggta cgctcggcac ggcccgaggc   76140
accctcagct caacccgagg taccctcggt ctccgagggc gaggcatcgc gcatcgagga   76200
ggagcgaagt ggggccatgc ctgatcgaaa ttggcagacc ccgtacctgc aatatctccg   76260
ccaaggagag ctacccctcg accgagccga ggctcgacgg atagcgcgac gcgcaagtc    76320
gttcgtcttg ctgggcgatg agcaggagct ctaccaccgc aatccctcgg gcatcctcca   76380
gcgatgcatc tccatcgccg aaggtcagga actcctgcaa gagatacact cgggggcttg   76440
cggccatcac gcagcgcctc gagccctcgt tgggaatgct ttccggcaag gcttctactg   76500
gccaacggcg gtggctgacg ccactagaat tgtccgcacc tgcgaagggt gtcaattcta   76560
tgcaaagtag acccacctgc ccgctcaggc tctgcagaca ataccatca cctgccctt     76620
cgctgtgtgg ggtctggacc tcgtcggccc tttgcagaag gcgcccgggg gctacacgca   76680
cctgctgtc gccatcgaca aattctccaa gtgggtcgag gtccgacctc tgaacagcat   76740
caggtccgag caggcggtga cgttcttcac caacatcatc catcgcttcg gggtcctgaa   76800
ctccatcatc accgacaacg gcacccagtt caccggcaga aaattcttgg acttctgcga   76860
ggatcaccac atccgggtgg actgggccgc cgtagctcat cccatgtcga atgggcaagt   76920
agagtgtgcc agcgcgatga ttctacaagg gctcaagcct cggatttaca acgacctcaa   76980
caagttcggc aagcgatgga tgaaggaact ccccctcggtg gtctggagcc tgaggacgaa   77040
gccgagccgg gccacgggtt ttcacgccgt tcttcctggt ctacggggct gaggccgtct   77100
tgcccactga cctagaatac ggctccccga ggacgagggc ctacgacgat caaagcaacc   77160
aagctagccg agaagactcg ctggaccagc tggaagagagc tcgggacagg gccttactac   77220
actcggcgcg gtatcagcag tccctgcggc gctaccacgc cggagggggtc cgaccccgag   77280
acctccaggt gggcgacctg gtgcttcggc tgcggcaaga cgcccgaggg aggcacaagc   77340
tcacgccccc ctgggagggg ccattcgtca tcgccaaagt tctgaagccc ggaacgtaca   77400
agctggccaa cagtcaaggc gaggtctacg gcaacgcttg gaacatccaa cagctacgtc   77460
gcttctaccc ttaagatgtt ttcaggtcgt tcatatacct cgcaccacg caaagtttag    77520
tcatcaagga agggtcggcc tcgcctcggc aaagcccgac cctccctcgg gggctaaaag   77580
gggggaacc ccctctgcgt cgaaattttc ctcgaaaaaa ggtctcttct gccagaatat    77640
ctttcgtgct ttttgactac ttcgaaaagt ggatcctgaa aacgacggag tacacgtaag   77700
cagtcaaggc ggaccgagcc gagggactcc tacgcctccg ggatacggat acctcactca   77760
tcaccttctg cgataagtaa ctcgcgttcg gataaagtga ttccgccgac cgaacaagtc   77820
ttcatgttcg gaagttcttc tgccgaagca atccttcgag cctctcgac tgagtcggtg    77880
gcagggcctc atggacgagt gaaagtacgt gtaagcggca aggccgaccg agccgaggga   77940
cttccacgcc tccgggatac ggatacctca ctcatcacct tccgcgagaa gcaactccca   78000
ctcacacaaa catccctgtt accgacaaaa aagtcaagat actcgaaaca agaggaaagg   78060
agacgcagct ttacaacaca gcgagggcgt gtattctgac ctcggcggct gcagaaggca   78120
cacgctacaa gacaatctga ccctacaggc tcggtcttgg acgctcgaag ggggcagcaa   78180
cacccctcggc atcgatgaca ccttcagcga ggcccgacct agctccggac ggcgacgcgg   78240
tccgaggatc tccgctccga aggacgatgt catcaccacg cccgggcaat cgctgccagg   78300
gacttctccg gaatccggc ccgagcaggc ggctcggcc gttaccctg gggcctcggc       78360
cgaccatctc ccaagggcgc cagcccgacc tgaggcctcg gctgatcagc cccgacgtcg   78420
```

```
gtcccgccaa cggacaaccc ggctaggctc cgaccaacca ggtttcattt tcgagccaac  78480
tccgcctctg ttcacactga tatcgctacc cctggcctcg gctcgtcgaa gagcggccga  78540
ggggtccctt taactaagct agaggagcct cggacagcaa ggccgaccga gccgagggac  78600
tcctacgcct ccgggatacg gatacctcac tcgtcacctt gacacggggc gactcatgct  78660
tggtgaagcg gttcagataa tcaacagacg agtcttacgg ctcaaaaatg aggaaaaaca  78720
cggctccgtg ccggaattac atacatgttc aggcccgaa agccgcaatg aacaaaaaca  78780
ccggcattcg aagtgccatt acaaacgaa ctccggttcc ccctccgca ggtacgaaca  78840
gccccactcg ataggggtgg gcctacggag caacagaaga ctgacgagcg gctcgccgcc  78900
gcccgctctg actacgacga catgcaagca actgcaccgc cacttgcgcc accaccgcgc  78960
ctcctcgatt gcggaaccaa taccgcgact cgaggcgacc cagcgtgcga cccagcagcg  79020
ccagcctgac gcggcggtca acacggccaa aagtgggccg gcagtaatga cggtggcagg  79080
cgcgtgggag cagcggtcac gtcgtcagcc aagctcacgt cccatccggg ggcagcaaga  79140
gaacccccctc tcacgcgtg aagacaacgc gcccgtgatc cgttcctcga acggctcgcg  79200
cacgcgcaac ggctgccccg ccaactactc gcctcgtcgc attaactccg cggctggaca  79260
ggcggcgctt ctggcaggag cagcgggcga cacttcgcct tcgccgaaat aaccgcgcca  79320
aaaaaggtac gccgcgtcgt tcggtttcgt atccttttcc cttttcctc tttctctatc  79380
tcttgcgaca gggaccggga aaggggggata ccccgaaagg gatccttccc cgtgaaggaa  79440
ccaggctccg agcctcctta ctgatcagag gttcgaaggc tggcccccg aagggttcaa  79500
cagccgcctc agatcgcgtg ggccctacac ccactactgg tcagaggttc gaaggccggc  79560
cccccgaagg gttccacggt cgcctcaggc tactcgggct ccgtgcccat tactgatcag  79620
gggttcgaag gctggccccc gaagggttca cagccgcctc agacgccgag cgagggatga  79680
ccagggtac gttcgataca taaccaaggc tcgggctcg ctcctgaggt acctaggac  79740
atttccgaga ccagcgggag cgatcttgta atggaatccc atcggaggga ggcatcgagc  79800
cctcggaccc cgtcgccagg gaccgggtc cggcagatca cccgcaggta ctttgggcg  79860
tgcctctggg cccctagccg accctaacg aacggggcac ggacgtccac tcggattacc  79920
tgcttgcagc tcaccggaga caccatgttc ggcgcccatc gagggtaaca tggcgccctc  79980
ccccctagtcc tccttgcgga aaggcgacgc aggggcatat gtaaaaagc cgagtctgtc  80040
cctgatcgcc ctcttgccct gtgcagaggc tcagggcctg ctctcgcaaa cccggctccg  80100
gccaaaccgt tgacagcgtc aacataccag cccgagaact tgggcccccga ccgtacacc  80160
gggctacggc cagctcgcat gagggaacaa ccagaccagc cgaagcatta cgcaaggcat  80220
taagacctcg aaggagtgaa accactcctc cgaggcctcg ggggctacac ccggcgggtg  80280
cgctcgcgcg cacccaccgg aacaaaatgc aaccgagaaa ggctggtccc ttgcaaaaaa  80340
gtgcgacgaa agcctccaag cgagtgctaa cactcctttc gaggctcgg ggctactgtc  80400
ggggaccata attaggggta cctcaagac tcctaattct cagctggtaa ccccatcag  80460
cataaagctg caaaggcctg atgggtgcga ttaagtcagg gatcagtcca ttcgagcgac  80520
tcgatcacgc ctcgcccgag cctagcctcg gacaagggca gccgaccccg gaggatttcc  80580
gtctcgcctg aggcccccct ctaacggcgg acacatcttc ggctcgcccg aggccctgcc  80640
ttcgctaaga agcaaccctg actaaatcgc cgcaccgacc gaccaagtcg caggagcatt  80700
taacgcaaac gtgacctgac acctttatcc tgacgcgcgc cctccggcag agccgaagtg  80760
accgccgtca cttcgccgct ccactgaccg gtctgacaga aggacagcgc cgcctgcgcc  80820
acttcgactg cagtgccact tgacagagag atactgacag gaagccaggc cctgccaaag  80880
gcgccatagg aagctccgcc cgacccaggg ctcggactcg ggctcagccc cggaagacgg  80940
cgaactccgc tccgcccgac ccagggctcg gactcggact cagccccgga agacggcgaa  81000
ctccgctccg cccgacccag ggctcggact cgggctaaga cccggaagac ggcgaactcc  81060
gctccgtccg acccagggct cggactcggg ctaagacccg gaagacggcg aactccgctc  81120
caaccgaccc agggctcgga ctcggggcta gacccggaag acgacgaact ccgcttcgcc  81180
cgaccccagg gctcgggctc gggctcagcc ccagaagacg acgaactcgg ctttcccgga  81240
ccccagggct cggacaccgc cctggcctct gccgacgacc tccgcctcgc ccgacccagg  81300
ggctcggact cgtcctcggc catgaaggac agactcgacc tcggcttcgg aggagcctcc  81360
acgtcgccca acctagggcg caggccagcc acgtcaacag gaagcgccat catcacccta  81420
cccccgagctg actcgggccg tagagaacaa gaccggtgtc ccatctggct gtctccacca  81480
gataggcaat gatggcgccc cgcatgcccc gtgacgacgg cagctctcag ctctcttacg  81540
gaagcaggag gacgtcagca aggacacaac cgctccgaca gctgtccctc cgccaggctc  81600
cgccgctcct ccgacggcca cgacatcaca ctagctgggt tccaagatct cttcggctgc  81660
cacattggca tgtactcagg gcactagctc tccctgcta gacacgtagc actctgctac  81720
acccccattg tacacctgga tcctctcctt gcgtctataa aaggaaggac caggggtcctc  81780
ttagagagg ttggccgcgc gggacgagga cgggacaggc gctctcttgg ggccgctcgc  81840
ttcccctcacc cgtgtggacg cttgtaaccc cctactgcaa gcgcacccga cctgggcgcg  81900
ggacgaacac gaaggccgcg ggattccac tctctcacg cgtgtctccg gccgcctcgc  81960
tcctttcccc ccttcgcgct cgcccacgcg ctcgacccat ctgggctggc gcacgggca  82020
ctcactcgtc gacctgaggg accccccggt ctcgaaacgc cgacaataac tctaaccgaa  82080
cttggcattt agccgatcga ttcctaaccc attttcata ccaccactac atgacatacc  82140
gaatacattg aatgactcgt tcacattcca catatatctt tacgaaaaca tttccacatc  82200
gcttgcaact taacctaagc ttcgccacat aatttcagga cactactta aatcatgaat  82260
atcatcatca cacacatcga cccgttttga aataacccta catgtctatc acaggaatgg  82320
agcatttcaa cacatatcct aaaacaaact aacttcatca cacatcttgc attacaaagc  82380
tacttgactt atttgaagtg tctactcgaa atcgtgagca caatcataca ctatatacga  82440
aacataattt taacgaacgc ataatacgca tcgtcatgac ttgacctata aatatagaga  82500
aagcgatgac tactctgtgg ca tgtcaccacc tctctattta agtcaagaca atttctacca  82560
tcgattaaga gtcgtaagca ttaaatacct tactacttta tacgcacaaa taaacttcaa  82620
cttaacacaa ctgacaccga tggaattttt actaaactca tcgtacgcat aaccctgtct  82680
cgcatacaac catattatgg cgtgcactcg agacacttca atccatgtgg cgcgaccact  82740
agtataaatg gactctgaca ctcatgtctt aacgatacat cctctacgca aactagcatt  82800
ctctaaacta ctcgtcacat caataaatat atccccctca aaattatgaa tcccatacaa  82860
ttgcttaaaa caaatacact tttcacataa acacatcgat gcatttccca aaacaaaatc  82920
cacatttgt aacttagttt tcgcatcaaa caacgcatcg catattttcc tatcaaaata  82980
aaaatactcg agttctttc tatttcaatt cttccctac acgcgtccat ttataaaatt  83040
atacagttac acacatataa ccacatgcac atcatcgacc aaaacataat tagacaacta  83100
caaatcgtgc acatcaatta acctcttgtt ctccaatcgc aaacgtgatc ctaccaatgc  83160
```

```
gcataatcga acattttaca cacatccata caaaatgatt aatcgagtcg atcgagagcg    83220
acatgcatcg gctcaccata aacaaaccca aatgatgttt gcaagaatga cggtgattcc    83280
gattcgtgca tcgctccaaa catccaacga gcgttaagcg acttgctttc tcctcgcaaa    83340
acacgggggtt ctctcctcca caaaaataaa acaaagcaac acacatacat aattaatcat   83400
aggaaaataa catcgatgcg gaatcaaaca aggagcgtcg cggtctcacc ggggtgaacg    83460
acgacgacgt ttggggctgc gcaaaaacag cgaacacacg gcggcatcac ggcgtgctgc    83520
tcactacgca acaaaacagc aagccggcag cacgcggagc cgtcggggct gctgcacatt    83580
tcatcgagca caagtgtgga tggcggccag gtgtttgttt caggcgctga aacaatggag    83640
ggggagaggg ctacggctgg ggaagtggtg gctcggccac ggcaagaaca gggaagggga    83700
ggctggtcac cgaccttggg cgcggccagg gaaaatggag ttgctgcttg gcactatgta    83760
caacagagag agggaggaat ggctccatgg gaagctcgag ctcggccagg ggaaggaaga    83820
aagggggttcg gcatccaagc tgttggagcc caaggagagg gtgctggccg ccgtgcgcaa    83880
gtgaagtttc acgccagctg aagctccctg gtcgcggaca ggaaagagca gggggcgcct    83940
gctgcaggta ggagctcgac tcctatgaa aatggcaggg acagaggagg ccggctgag    84000
caccgggcag ggtgctcggc catggagccg ctgcatggat ttgctgctgc gccctggag    84060
aaaaacagta ggggagtgaa ggatgccatg gctggggggcg cggggagcag ggagcctgct    84120
ggtggccttg ctgccgtgaa gcgggaaga agaaaggcag aggacgctac gagaagagct    84180
tcgacgcgct ggagggaagg aacgcccggc catggaagcc cctgcgcgct ggggaaggag    84240
ctccagctct acgtgcttga aggagcccat ggctggaaaa tggtagagga ggaagagaag    84300
ggtgttggcg gctgggggtgg aaatggaaaa ttttcagaat gcaaggtagg gaagcccata    84360
tttatagagg agaaattagg gtagggtttc ttatgggcca aacgggctgg actggatttg    84420
gcccaaaaca ctaaattggg tcgcgctaaa taatttcggc actaaaaatg ttcctgcgga    84480
attcgtcgct actgagaaac agagcgaaaa gagttcggac gaacgaaagg ttgcgcgatt    84540
aactcagccg agagtctgtt tagattttgc ttgaaaataa ttccctacgc gtaaatcgaa    84600
aataaaccgt cctgagattt gatcggtttt ggattttttag tcgagaaag cgaatcgtga    84660
tatataaaaa tcgttgccga tgttgatttt gaaatcgaat tggatacaga gatgctaagc    84720
tgagtcgagt aagatttgat cagaggacga catattgatt atttcgtttg tgagtatgga    84780
ctcggattaa aatagttgga catcgatcga acatcgagaa attggattcg gacacagatc    84840
aaataacagc cgtcgagagt ttgatttatt gagcttcaga tgaggttat aattcgagaa    84900
tgattttttga gttcgcattt gtgccaagga taaaagttt aacaggctcc aaaattggcc    84960
ttctatgaga ctgagtaact ccgaattcgg tgaaacatga atgaataatc tggataatca    85020
gggacatacg cgagcgagaa atagaaattt ttactgagca tccgagatta ggataaatct    85080
cgcgacgtaa cacgaaactg acacctgggg tgtcacaact ccagcactgc caccctgctg    85140
gcaggcggat ccgtcgaaga aaagcatcca gtgggggctca gtgaagaccg aagcccttgg    85200
ctccgcaggt gtggtgtccg aatcgggatc tggaccccca ggagcgctcg gggaaggggt    85260
ccactccacg atgaagtcag ccaggacctg gctcttgaca gcgtggcggg gctggaactc    85320
cagttggaac tcagcaagct ccgtggccca cttggcgatg ttgcctgtgg cgtttgagtt    85380
gtggagaatg gcccttaacg ggaaggaggt caccaccaca actctgtgtg cctaaaaata    85440
gtggcgcaat ttcctggaca caacaagtat agcatagata agcttgtcg tctcaaggta    85500
cctggctttt gcctcatgga ggacctcgct gacgtagtag accggcttct ggatggttcg    85560
gaccccctgca ttcagtcccg agtcctcaaa ctcctggcct tctgtcaaca tcgtggtggt    85620
cagaccacca ccttctcccta gggaactttt atgactcccc tagggatgtt gtgtcgtact    85680
ttcgacgaac agcaccatgc tcaccgcctc tgtagccgct gcaatgtact agtataatgg    85740
ctctcctggc tctggagcta ccagtattga tagggacaca tggtgctgct tcaactcttg    85800
aaaggcttgt tctgtctctt tggtccaaga gaatgggtcg gacttccgca atagcttgaa    85860
gaagggtagt gccctctcaa ccagtcttga gatgaagcga ctaagggcgg ccagtgaccc    85920
cgtaagcttc tggacgtctt tgattcaggc cggaggcctc attgtctcta ttgctttgat    85980
cttctctggg tttgcttcaa tgccccggtg tgaaaccagg aatcctagca acttccctgc    86040
agagacacca aagacgcact tgtccgggtt cagcttcatg cgtgttgcct gcagcttgtc    86100
aaagactagg gttaagtctt ccactagggt cgaccctccc ttagtcttga ctacgatgtc    86160
atcgacgtat acctctaccc tgtccctaat caagtcacca aaagtattac tcatcgcccg    86220
tacaaatgtt ggcaaggcgt ttttcagact gtaaggcatt acaacataac agtaaagtcc    86280
atccacagtt acaaaagcgg tatgcttcct atcttgccta gacatctcga tctgatggaa    86340
actagagtaa gcatccagga aggataggag gttgcaccca gaggtagaat ccacgatttg    86400
atctattcgt ggaagtggat atgggtcctt gggacaggcc ttattgaggc tggtgtagtc    86460
gatgcacatc caaagcttcc cgttagcctt ggggacgatg actagattgg ccagccatac    86520
tgggtgatgg acctcttcga tgaaaccagc gtccagcagc ttccggacct ccttacggat    86580
gaaatcctgc cgctcgatgg actgtctttg aggcttctga ctcaccggtt tggcgtcagg    86640
gtggatcttc agatgttgct cgatccactc cctagggatc ccaggcatct gcgatagttc    86700
ccatgcgaat acattggcat ttgcctggag gaaggcgatg agcgcgattt cctatttctc    86760
ctccagatcg cccgtgatgc gagtggtctg ggaggaatcc ccgttgagcc ggatggtctt    86820
gacagggacg ccgtctgccc cagatggttg caccttaggc accttagcag gcatcttggt    86880
acaggaagtc gaggggtccc tcccctcgtc atccgggcga gcagcttctg ccgctagggc    86940
atgcaacttc tcgatagctg caagcgcagc gggacggtcg cctccatgg tgaggaccc    87000
agcagggggat ggcatcttga ggaccaagta cctgtaatgg gcaatggaca tgaaccggta    87060
cagggccggc ctgccaatga tggcattgaa agggaggtta acctccgcaa catcgaacta    87120
gacattctta tgtggaagt tatcctcagt cccgaatgta accaggagtg tgatgctccc    87180
aagggggatac accggtttag ggcccactcc agagaacgtg cgagagggtc ctagtcggga    87240
tcctgggatc tgcagctgct tgaacgcagc gtggctgagtg acgttgaccc caaccccacc    87300
atcaatcagc acatgatgca acttcatgtt ggcgatgaca ggggcagtga tgagtggtag    87360
tataccagcc cctgccatgt ttgcgggca gtcgggtgcc ccgaaggaga tagtggtgct    87420
ccgccaccgg tgatgtgggg ctgccttcgg gacccctggg gtcgcaaaaa ggacctcgcg    87480
gcgcaggac ttcacgttcc tacggaggt gagctcccaa cttccaccat acattacgta    87540
cagcttctg cagccggtcgt tgtcatcacc ggagtcgtga gcagtga gatatcctt    87600
gaggactgt cgggggcct aattctcgag gtcccattct cccgtggcca ggtcaccttc    87660
gtcgaccttc tcctttgccag gccggcgccg aggcggcgag ccatccctgg aggcatgctc    87720
gcgccgctca ctgatgcgct tcacgagctt caggatctct cgtcattctg aggcactgtg    87780
gcgactgttg gggtggacag gcatgaccc aatgtcactt ccctgttgcc gtggatgctt    87840
gccgcgctcg tcccggtccc cagccgtagc tacagcaact ggagcaccag actacggcct    87900
```

```
atcgtgacac ggtgcttctt ctttttcttg ccaccaccct gggtggcagc acctgagcca   87960
cccatttggg tgactctggt ttgcagcgtc gagtgccatg cacggccctc agtagctctg   88020
gcacatttgt cggccagagt gaagagcgta gtgacggttt ccacgtcatg cgtcgccaat   88080
ttctccaaca tcttcttatc acgcaccccc ctgttggaaa gcagtgataa tggaggcatc   88140
ggagatgcga ggtatagtcc cctgtacctt ggtgaagcgg gagatgaaag cccggagagt   88200
ctcctcgggt tcctgcctca ctgcatggag atgagcctcc acgccatgct actgataagc   88260
actggcgaag ttcattgtga accgtgcaca gagctcttcc caggagtaga tcgaccccgg   88320
ggtgaggttc atgagccagg tctgtgccgg cacattcaag gctacatgga aatagcttac   88380
cattacagca gtgttccac cagctgccgt aatggcggtg acatagacct acaggaattt   88440
cgacaggttc gatgtcccat cgtacttctc cggcaggtgt ggccgaaaca tgggtggcca   88500
agtcgccgcg cggagatgat ctgctagtgc ggcgcagccc acgccgacca atgggacacc   88560
catctggatt cgggcgtccc ttgcagtgaa gtcttggtcg aggttgcgac cctcgaagtt   88620
ttgccggcgc tcacgcgccc tctccagaga gattcgagca tcctcgcctg cacgcctgtg   88680
gttgagttct gctcgcaggt cgttagtctg tgccccctca ctgagggtga atgcacagac   88740
gttgacgcct cgcgctgatg ccggaatgat cgaggcctgg acctggccga gctaggatgg   88800
gccatgccga ggagacggtc gacatcttca cgccactgcc tcatggcccc cggggaggcc   88860
gtggaacttg tggggttacg cagcaactcc ctggctgcag acaatggccc accataggta   88920
gccctcgacg gagtcctaga ggtctgtgcg ggcgtgtgtt gctgcgcagc gtgcatagca   88980
gcagcaccag gcacagcgcg gttggagcct cgtggcatgg aagataatgc cccttcctcc   89040
atcaagaagt cctcgggaga caagccacgg tgctcgacga tctgaaccat cgtgtcgagc   89100
aagaaaacag gcaaaaacct aaagccaaag cccccctacct ggagcaccaa atgtcgaagg   89160
gaaaatcctc cggccgggtg gcgaaatgca cccgccctaa tcctaagatg aggaggggc   89220
ctaagcggtt gcctgtttgg tgaattcggg atgaacacaa gaggacacga gggattatag   89280
tggttcaggc cgccggagcg taatacacta cctccactgt gtgtatgttg tattgagtgt   89340
gtacagcgtg tcccttgtaa cgttgtgtgc cttccctttt atagtttaag ggaggcacat   89400
acaaggatgc tgagcccga catgtgggcc caggagcata atggaagaaa tacattatgt   89460
gaataactaa tgctgacaga gtaacacatg agtaatcagc gggagtcatg atggctgcag   89520
tccatgcagc attgatagac agtaacccct tccttggaaa catacgagta atggtgagtc   89580
attgccctcg atatggtaac gtgtgagtaa ctgcatggcc cacgtatcgt ggactgagca   89640
tgccgcctgt cagtggaatg gacaggcgca catcttctcc gtaatgaatg cgaaggcacg   89700
cgtagcccag aggcatcatg ccaggttcca cccgttggtt tatgccgcgc gcagtatgcc   89760
acgtggcagc atcgggtctc cgcctgagca gggagaagga gtgtatgcgg ataggtccgg   89820
atcccaccag accaggtcta gacacgtgtc ggctccggac ccccacctgg gtcctaatca   89880
aggcccgggt atgttctgtc ctagaaccct gggaccccac tatgggtggc ccagacccat   89940
acgggggtt cggatcccat cctagggtc cggtttgtac acgtggaggt cctggaccaa   90000
acttggaggc ctggaccgta tatacagggg tctggcactg gtccggcact ctcccatggg   90060
gtccggactc actgttgatg ccttggagta catcactttc tctggacaca tggcggcccc   90120
gaacccgccc atgtggtggg gtcaggtgct gttgctggcc cagagtagtc gcccgaggct   90180
agggcgagtc atggtctggt cccacataca gcttatttac cacgcgacta aagatagtcg   90240
tgtgggtact gcgtctttat acagtagtaa gggggtaccct agtttaggg tgccgacaca   90300
catcttcctc tagaacacca tgaagaaacg cgttctgcac atccagttgg cagaggctcc   90360
aaccctgaga gacagcaaga gacaaaataa ggcggacagt agcaaattta actactaggc   90420
taaaagtgtc atcatagtca atgtcgtagc gctgtttaaa acctttagcc accaatcgag   90480
ctttatgatg gtcaatagac tcatcagctt ttctcttgag tttataaacc cacttgcaat   90540
caatcaaatt tctgtcaggt gcgggaggaa ccaagtgcca tgtttattc cgcataaggg   90600
cagaaaattc taggtccatg gcagctttc cagtttgggt caaacaatgc aacagacaag   90660
ctggaggggt cttcacaaat tgccaaattt ccataacctga tcgtgccatc tgtaaacttt   90720
ctgggcttca caataccact ctgtagccga gtgcgcctag caggaagcgg aataggacac   90780
gaggctgatg gcgagggcag atggctgtca gtgagagagg gaccagccgc gccagagtcg   90840
gcacgaggca atcccgaagt ggctgctgct attgatgcgg ccgtggtggt gggaagcacc   90900
gcgttgctgg gcgcacctgt agccgcgtcg gagggggtgtg gcgtggagcc tagcaacaga   90960
tcagcaccgg gattgaggcc accagccggg acagaatttg cagcaggat cattggtggc   91020
tgcaaaagct ggttaggcca caaaatcgga gcaagcatgc tggattcagc aggagaatta   91080
gtcacaagat catctgagtt ggcccgagaa ttattaggat cgggtagaag aagcacgtca   91140
gaggtatatc gagcaccgac tgtgggatgg agagcagcaa agggaaaagc gtctcatcaa   91200
aaacaacatc atgtgaaata taaacacggc ccgttgagat gtcaagacac ttgtaaccct   91260
tgtgaaggtt gctatagact agaaaagcac accaaatgga ccgaaactag agtttatggg   91320
tgttgtatgg ccgcaaattt ggctaacatg catagccaaa gacgcgtaga ttagagtaat   91380
ctggggtagc acctaagaga cggtggagcg atgtgtcata atcaagaagc ttagtaggag   91440
ttctattgat aagatgtgtt gaggtgagga acgcttggtc ccaaaacttg agcggtattg   91500
tccattagcg agtaaagaga ggcccatctc aacaatgtgc aacgaatcaa gctgatacat   91560
aagannnnnn nnnnnnnnnn nnnnnnnnnn nnnnnnnnnn nnnnnnnnnn nnnnnnnnnn   91620
nnnnnnnnnn nnnnnnnnnn nnnnnnnnnn nnnnnnnnnn nnnncaattc tagaagatta   91680
cgtcgatctt gatggtgtcg ttggccttga tgagcggtc ggggtagcgg atggtgcggt   91740
cgtcgtaggt gtttaggcag gggatgcctt tctggccaaa ctgaacagac cttaccttgc   91800
agagcatgaa ctgcacacaa accaatagaa aagcagtgag aatttcacag gcgtactatg   91860
aaagggcatg ggaatttcca gcgatgtaaa tggatagata gacagagcaa catctattaa   91920
tagtcctaac gattgtagca catgacattt tcaatgacag actttcatgc acacaacata   91980
tatggacagt ataagcaagga taagtacat agatctacag aaaaaaaaga acaacctgaa   92040
gcattagaca aatggggaag tacagaagat tgtaggtacc aaagctagaa atatattgttt   92100
tgtcggcgtt tcgaccccgg ggggtccctg gaccgacgag taaattgtcg ctgcgtgtcc   92160
cagcccagat gggtcgacgc gagacagaac acaaggggg gaaacagca aaggggaacc   92220
cgcggccttc gtgttgtcct gcgcccaggg cggatgcgct tgcagtaggg ggttacaagc   92280
gttcgtgtgg gagagagaga gagccttgtg cgtcgcccga ttctcccgcg gcgccaaccc   92340
tctcgtacga gagccctgga ccttccttt atagacgctaa ggagagggcc caggtgtaca   92400
atgggggtg tagcaatgtg ctaacatgtc tagcagagag gagacagagc cctaagtaca   92460
tgccgtcgtg gctgtcggag aggttttggc gcccgttca tgtgatgtcg tggccgtcgg   92520
aggagcgttt gagccctgtg gaagtacaac tatcggggct gtcggatcct tgctgacgtc   92580
tccttgcttc cgtaagggc tgagagccgc cgtcgtcacg gagcacgcgg ggtgccatca   92640
```

```
ttacttgttt accggggcga gccagatggg acgccggtct tgttccccat agcctgagct  92700
agctagggt agggtaatga tggctccccc tgcgacgtgt cggtccgagc ctgaggtcgg    92760
gcgaggcgga ggctcctccg aggtcgaggt tgagcccgag ccctaggatc gggcgaggca   92820
gagtccgtct tccgaggtcg aggctaagtc caagccctgg ggtcgggcga ggcggagtcc   92880
atcgtccgag gtcgaggctg agtccgagcc ctggggtcgg gcgagccgga gtccgtcttt   92940
cgaggtcgag gttgagtccg agccctgggg tcgggcgagg cggagtccgt cgtccgacgt   93000
ccaggttgag cccgagctct ggggtcgggc gaggcggagc ttcccatggc gcccgaggct   93060
ggacttagct gctgtcagcc tcactctgtc gagtggcata gcagtcggag cagggcaggc   93120
gatgctattt tcccgtcagg tcggtcagtg gagcggcgat gtgactgcag tcacttcggc   93180
cctgtcgact gaggagcacg cgtcaggata aggtgtcagt cgatccttgc attaaatgct   93240
cctgcgatac ggttggttgg cgtggcgatc tggccaaggt tccttctccg cgaagcttgg   93300
gcctcgggcg agccgaaggt gcgtccgttg cttgagggga ccctcgggca agacgtgaat   93360
cctcctgggt cggctgcctt tgcctgaggc taggctcggg cgaggcggga tcgtgtccct   93420
tgagtggaca gagccttgac ctgaattgcg cccatccagc cctttgcagct ttgtgctgat   93480
gggggttacc agctgagatt aggagtcttg ggggtacccc taattatggt ccccgacagt   93540
agccccccgag cctcgaaggg agtgttggta ctcacttgga ggcttttgtc gcactttttt   93600
gcaagggac cggcctttct cggttgcgtt tcgttccggt gggtgcgcgc gagtgcaccc    93660
gccgggtgta gcccctgagg cctcggagga gtggtttgac tccttcgagg tcttagcacg   93720
tttcgtgatg cttcggccgg tctgttgtt ccctcatgcg aactggccgt agcccgggtg    93780
catagtcagg ttccaagttc tcgggctggt ttggttgttc cctcatgcga gagcagcccc   93840
cgagcctccg cacagagcga gaggacgcc aaggactgac tcggcttttt tcatacgccc    93900
ctgcgtcgcc tttccgcaag gaggagggg gggaaagcgc catgttgccc tcagagggcg    93960
tcgaacatgg tgtctccagt gagttgctaa cggttgatcc gagtggacgc ccgtgccccg   94020
ttcgataagg gtcggctagt ggccagagg cgcgctccaa aagtacctac aggtgatttg    94080
ccggacccgt tcccgtttga tagggtccga gggctcgatg cctccctctg atgggattcc   94140
gttacagaat cgctcctgtt ggtctcgaaa atgtcctagg atacctcggg acgctagccc   94200
gagcctcggc catgtatcgg acgtacccag agtcatccct cgctctgcgt gctctgaggc   94260
ggctggcgaa tccttcgggg gccagcctac aaaccctga tcagtagtgg gcgcagagct    94320
cgagtggctt gaggcggctg tcgaaccct ccgaggggct agccttcgaa cctctgacca    94380
gtagtgggca cggaaccgga gtgctctgag gcggctgtcg aaccctccg aggggccagc    94440
cttcgaacct ctgatcagta ggagggcgcg gagcccgagt gctctaaggc gactgtcgaa   94500
cccttccgag gggccagcct tcgaacctct gattagtagg agggctcggg gcccgcttcc   94560
ttcgcggaga aggatccctt tcggagtatc ctctttcccg gtcccatatag caagagagag  94620
aaagaggaag ggtaaaagga tacgaaatca aacgacgtgg cgcaccttttt ttgacgcggt   94680
cattaaggcg gaggtgaagc gtcacctgct tcgcctgcca aaggtgccgc ctgtcctgcc   94740
gcagagttaa tgcgacggga tgagtggttc gcggggcagc cgttgtgcgt gcgctagccg   94800
ttcgaggaac ggaacacggg cgtgtcgtct tcacgccgtg ggaggggggct ctctcgctgt   94860
cccaggaggg gacgtgagcc tacagacgac ttgaccgctg cttccgcccg cctgccgccg   94920
ccattactgc cggcccactt ttggccatat caaccatcgc ccttctccc gcggctgact    94980
gacccgtgat cgatgtgctc ggttggcact gttgggccat gcgcagggtt gcctcgagtc   95040
gcggcaccgg ttccgcagtc gagaaggcgc ggtactagca caagtggcgg tgcagtttct   95100
cgcgcgtagt aaccggcgcg ccggttacat gacgtgtggg cctgggcccc cgtgctggac   95160
ggtcggat cgaaagggtg caccccctcg tgcggttgc atgccgcctg catggcggtc      95220
cgcccttttca cccgccggtc tgggcgaaag tggaggagtg cttgtaaccg ctgggcagtt   95280
acgcactctg cgcgcgacgg tttggcttct tctgccctgg gccagcttgc atgacgcgtg   95340
ggacccagcc cccatgtcgt aggggagga ccttggagcg tgttggtgaa gactcagtcc    95400
gcgcagggtg aggacgcaag tggggagagt gccttttaaa aggaggggca cccccttgga   95460
tgcaaccat gtcttcacac tcccttcatg catcgcgccc ttccaacttc cgagcccccg    95520
gatgggagc gcccgcgttg cttttcgtctt gtcgtcgttg gaggaacgca acttcgcgga   95580
agttggtacc tttcagccat cgctcggctt caaggatttt catcaggcgg cccggctgca   95640
tccctcgct ggtggtcacc caagacggtg accaccagtt tgatggtggg gacgtgggcg    95700
agggccttgt cgcagcagcg tctgcactga ggtcatcgct gctgctgttt ggctgtccgg   95760
agcggaggtc gttgtcgctg ctgccagagc gggcctcggc gagctgtcta gggttttgtt   95820
gctgaaagtt ccctttgacc cgggaacagg atctggatgt cgcctagagg gggggtgaat   95880
aggcgaataa aacttttcac tttaaaactt aaattcttac tctactcgaa gacttagtat   95940
gcagtgggagt gagaagactc ttcaagtagg ttgcagcgga atagaagatc ctgtctcaaa   96000
atgtcctgca cttcaaataa agcttatacc acagataagt attgaagtgc agatataaag   96060
gcgagtagaa agagagtcag gatacaatac agaacagagc acacagacgc aaggatttat   96120
cctgaggttc ggccaagcct gaaatgcttg cctagtcctc gttggagtta gccacacctg   96180
ggcttggagt ctatttcaac tccttcctcc gtttgctcag atctgtcagt atgacagata   96240
gagcctttca ctattgagtg gggttacaac agaaccgcgg ctgcttacag acttcttggc   96300
agcacccgg tagagtaacg atatgctcaa gaccttgctc tagctcttag cagcactact    96360
cctctctcta aggcttatag ttgtgccttc tacacaaact atagagttac acacaagagg   96420
gagagtgaga attgattcca gtggagtcta cacttgttgg ctgcacttct attttgtggg   96480
aggcacctag gggtcccttt tatagacaca aggggcctag gagccgttgg aagcaatcca   96540
ggaaggcaaa tcttgccttc tgtcgggtgg cgcaccggac agtccggtgc acaccggaca   96600
ctgtccggtg cccgatttct ttccttctac gtcgaagccg accgttggca gtcttggagc   96660
cgttcgcgca ccggacatgt ccggtgcaca ccggacagtc cggtgcctcc atctagccgt   96720
tggctcggcc acgtgtcccg cgcagatcgc gcggccaacc gttggcccgg ccgactgcgt   96780
gctcaccgga tagtccggtg cacaccggac agtccggtga attatagccg tacgtcgccg   96840
gtgaattccc gagagtggcc agttccgcca gagttcagcct ggcgcaccgg acactgtccg   96900
gtgcaccacc ggacagtctg gtgtgccaga ctgaactaag tcttggctgt acacagccaa   96960
gcctttcaca cctcttccct tttcttcttc tttctgtttc taacacttag acaagtatat   97020
tagtcccaa aaccaatgta ctaagtctag aaacatcct tctattaatc attacatcta    97080
tagcatttca caagcttgag ctttgatgtt ggactcataa attatcaagt cagcttgact   97140
tgatctagat tgcatcgct tggctccaac atcctgtaaa ggtcacatag aacatctcca    97200
aacatagaaa caacccaaac taaagatcaa agtgaactta gctctttggg gctgcttcca   97260
gttctggttt cgacacttgt tctccttcta gtgaccttga tctcctcctt agagcttgat   97320
cttgagcctt atgacttaca ccacataact atagctgtta cctcattggc tgtaagtcac   97380
```

```
gtccttatgt agtgatcctt gatgtgccgt agctgttctc aactcgatca cccttgactt   97440
tgcaagcctt cttcttcacc cttggctttg ggttcctcag cctccttgac cttctcccat   97500
gcatttggta cctcgaagct tttcttgcct ccgtccttgg cttgatcagt tgtcttcgag   97560
ctacgcaccc gagtctcact ttgtgcaatg tccatcttac ttgtgatgtc cattatgtat   97620
ccataatcca gttcttggac catcacattt gttcacttgt gttgaaccct gtaggcttta   97680
ccttaagcac atgttcaaca cttagtatac ttgttagtcc tttaattgag ttgtcatcca   97740
aacaccaaaa ctcacaagag agctttcaat ctcccccttt ttggtgattg gtggcaacac   97800
aattaaagct tacataagaa taagatttga agcacaaatt tgaattctaa gattatagaa   97860
tgctccccct aaataagtgc ttacttcaaa aacctaattt tgaccacaaa cgtcaatttg   97920
cacatactta ggaaaattga aacatttcta caccttagca cttttttagga tgcattatgt   97980
caagaatcaa accatgatgc tataacacac aaatgcacat aatcagagtt aaacaccatt   98040
caaattagtg gatatatcac aggaatatca acctaccact attcaccatt aagataccaa   98100
cttaaactaa gatatcaatt taaagcaatc ttaaagcacc attaaccaca tgactatcta   98160
tttcactata gaagccaaat aattcatcgc agcggaaaca ctggtctagt ccatatgatc   98220
aacacgtata atactgcaag aaacatatga atataaaaca ctagtctagt ccatatgatc   98280
aacacgtata atactgcaag aaacatatga atatcacact tggcaaagct caaactaaca   98340
catcacccat taggataagc tttcctctca ggttgagata agctttaatg cacaacttct   98400
ccccctttga catcaaacac caaaaaccat actcaagcaa gaacatatga tgatgtcaag   98460
ggacagcagg gtgttaaggg gaaaaacgac tatcaaaact cccccttatt tattgaacat   98520
atgtcctatc aacatttagg taagatacat atatgcaaaa agattaatac ttcctttgt    98580
acctttacca tgatgtagtg tacttcccat cttgaaagta gttaatctct cgagagcttc   98640
tccacacttg tgcctgattc tctctcctaa cttttttcttg ttgctaagac accaaactta   98700
gaacaagtta tagtattggg cacaagaaga aacttctatt ctcatgatta tcaaaagatg   98760
tcaattgaag cgaactatta cggctaccaa ttgaaagata ccaattgcaa agttcattta   98820
ttatcatggc tccatgatat ttaagaataa gcatctatta tcaccagata ttatagagca   98880
tgagcaatct aaaaaatatgc acttactcac aacttgagat accaattttc ttgacttaca   98940
gaggtaccca agtcctgatt gctccatttc ttgcttatct tctcttttcc acctagagac   99000
tatacaagat tgctcaagaa acagttagtc tcaaaagaca caagttatgt gtgctccccc   99060
tcaagttgtg catcaagtat ttgaatgact tgcacttttgc acattctagc ttccttagaa   99120
ttagagggga tcacaacata ccttggtcaa ggcatactct accactttca tcacccaaag   99180
atgccaattt gaatatcaaa tgaaacgcca cataacacca attgaaggct aaatgaaagg   99240
ttgactaaat acaacaatgc acgcctcagt ggcacctaag ccaattgaat actcacagga   99300
agtctaacat ttacgcaact tgtacatgct tcatatttaa ctatcattgt atataccaat   99360
taaagataaa cacaatcgaa atatctaagc atgttataat taagaaggtt tcttaggtgc   99420
acaaaagaaa caacatttta aaggcataaa ttacctaagc caagatatta ccaattgaaa   99480
ggcaagaaca tagctatgat cacaatgaat ggaattttcaa gaatatttaa tgaaattgca   99540
tagctccatt ttccatacct ttgcctttat gagagcccctt gttatcgcca atttagggct   99600
ccttttgctt acgcacctca tagctcaaaa gggcacgaca tggatttgaa attcacacag   99660
taccaaacta gggtaatcat gtgaacatgg actaaacaaa atgtcataat tgcacatagc   99720
atgacttaca aaagttacag gtttatccat atacatcaag agagttatcg ttgtggatat   99780
aacaaatgaa atagctaccc atgaatgatt caaaagatat atcctttata gcaccagtca   99840
tgattaagca accatcatta tgatcaattt aacacaggca atcataaagc ataactactc   99900
taaggacagg tagcacaaca agccaactta agagcaatac taaattgcaa ttatgtactt   99960
aaaatacacg ggtaccgtcc tttggagagc aggttgtaga ttctcatcaa gatccttac   100020
ttgattcacc aataatgatt caggacctat acacctattt tctcttgaga tgaacatggg  100080
attagtgttt cacaataatt caaccttggg tcaataaaca ctaaaacaat taacagctta  100140
agcatagagt tttagataac cgtcttaatc tttcccatgg tctccagtcc atctcgaggc  100200
acctgcatgg tctagttggc acagtttggt atccatctcg ggatgggtac ataatgatca  100260
tgtaaatgtg cctttggtac ccaaattgcc tttgtgctag ttctaggtga tctcgttata  100320
gatctagcac aagtgtatga tttgggtctc ctatgcgaat aagattgaca caaattcact  100380
tgtttaggaa tcttacctttt gtaacatacc ttggatagat gaccttgctc accacacttg  100440
tagcagaagc gtcgctcaac ttgacatgac gcttgttttg tgtcatttttc cttggtgagg  100500
gtcactttgg aggatgcata tccttgattc ttcatgaccg gacatgaagt gatcatgtgg  100560
tccttattgt tgcatccaaa acaactcctt gttctttcat ccttgtcttt gtacggacaa  100620
gacgcgatga ggtggcctgt ctccttgcat ttgaagcacc tccttttcc tcttcccttt  100680
ttgtgcttga atgacatgga gagatgatca gtgcaaacaa catgactaat tgaattttta  100740
ccttttttcct tgttcatgtt gatttcttca tttatagctt tgggaacatt cttccttattg 100800
agcttaacac ttgctgcagt ttttcctttc tcaagcttct tcaccacgcg cccgtggata  100860
tcttgagaga gttgagcaat gtgtcttctc cttagttgtc tttgcttctt gttcccacag  100920
aatttcttttt gtgaccctaa aacttgttgc tcaatcaatg attggctttc ttttgagcaa  100980
cagggggttag cacatggtga tatacacttc aaatgcgcac acgtgcgaga atgaggttca  101040
catgaattta agtttgcaat tataacctca tgagcaacat taagcatgat atggtcatca  101100
actaatttat tatgagaatt tgacaacata tcatacttt tacctagagc acgttttct    101160
aagttcattg tttctacttg actcttaagc atagaatttt ccgttttaag ttgagcaata  101220
ttagataatg catcatgact atttcttttgc tcaattaaaa catattcata cctttggacc  101280
aaatcatcat gagagcgcct tagcttctca tgttctttgg tcatcttctc caggctgttg  101340
ttggttttga tgagggactc ctctagcctg agaagcgtct cgccttgttc cttgttcctt  101400
ctcaacagct taaccaagag tgcctttgtcc tctttgttga gatggatga gaaacggtga  101460
atctcctctt cctccacatc atcggtctca ttttcccgt cattaatgtc agtggaagca  101520
atataggaaa atgtaccttg tgatgatgaa gattcatcct catatttctc cttatcatgg  101580
cttttcgtctc caccgtcatt gttagcaata aacatttat cactagtgga gaacaaacct  101640
gtcgacgagg tggattcatc gtttggatgc catcgttctt gttcttctcc ctttgaatgg  101700
ttagtatcac aagtaatata gggagtagga gcatcacagt ttgccacaaa atattttct   101760
ttaatcctat tccataaatc atgagcatca acaaataagt cactatcact actcatgatg  101820
gcaaaatagg cacctctaga tagagaatca actaagatgt tgcaagcatg gtgatttaga  101880
gttagacatc ttagttcttc attggatggg tttttactaa tattggaggg aaaaatacta  101940
ctactaaaga cctgtctcaa atcaggatca acactcatga aagcactata aatagagaca  102000
gaccaagact tgtaattaga gccatcgtct aaaagaagtt ccacagttac ctcttgtgac  102060
gacatcgtca tctccggacg gctaagccca cactggagag gcctagctct gataccaatt  102120
```

```
gaaagttccc tttgacccgg gaacaggatc tggatgtcgc ctagaggggg ggggtgaat   102180
aggcgaataa aacttttcac tttaaaactt aaattcttac tctactcgaa gacttagtat   102240
gcagtggagt gagaagactc ttcaagtagg ttgcagccga atagaagatc ctgtctcaaa   102300
atgtcctgca cttcaaataa agcttatacc acagataagt attgaagtgc agatataaag   102360
gcgagtagaa agagagtcag gatacaatac agaacagagc aacagacgc aaggatttat    102420
cccgaggttc ggccaagcct gaaatgcttg cctagtcctc gttggagtta gccacacctg   102480
ggcttggagt ctatttcaac tccttcctcc gtttgctcag atctgtcagt atgacagata   102540
gagcctttca ctattgagtg gggttacaac agaaccgcgg ctgcttacag acttcttggc   102600
agcaccccgg tagagtaacg atatgctcaa gaccttgctc tagctcttag cagcactact   102660
cctctctcta aggcttatag ctgtgccttc tacacaaact atagagttac acacaagagg   102720
gagagtgaga attgattcca gtggagtcta cacttgttgg ctgcacttct attttgctgg   102780
aggcgcctag gggtcccttt tatagacaca aggggcctag aagccgttgg aagcaatcca   102840
ggaaggcaaa tcttgccttc tgtcgggtgg cgcaccggac agtccggtgc acaccggaca   102900
ctgtccggac cacaccggac actgtccggt gcccgatttc tttccttcta cgtcgaagcc   102960
gaccgttggc agtcttggag ccgttggcgc accggacatg tccggtgcac accggacaat   103020
ccggttgcctc catctagccg ttggctcggc cacgtgtccc gcgcagatcg cgcggccaac   103080
cgttggcccg gccgaccgtt ggctcaccgg acagtccggt gcaccggga cagtccggtg     103140
aattatagcc atacatcgcc tgttgaattcc cgagagcggc cagttcgcca gagttcagcc    103200
tggcgcaccg gacactgtcc ggtgcaccac cggacagtcc ggtgtgccag actgaactaa    103260
gtcttggctg tacacagcca agcctttcgc acctcttccc ttttcttctt ctttctgttt    103320
ctaacactta gacaagtata ttagtcccca aaaccaatgt actaagtcta gaaacatacc    103380
ttctattaat cattacatct atagcatttc acatgcttga gcttttgatgt tggactcata   103440
aattatcaag tcagcttgac ttgatctaga ttgacatcgc ttggctccaa catcctgtaa    103500
aggtcacata gaacatctcc aaacatagga acaacccaaa ctaaagatca aagtgaactt    103560
agctcttttg ggctgcttcc agttctggtt tcgacacttg ttctccttct agtgaccttg    103620
atctcctcct tagagcttga tcttgagcct tatgacttac accacataac tatagctgtt    103680
acctcattgg ctgtaagtca cgtccttatg tagtgatcct tgatgtgccg tagctgttct    103740
caactcgatc acccttgact ttgcaagcct tcttcttcac ccttggcttt gggttcctca    103800
gcctccttga ccttctcccg tgcatttggt acctcgaagc ttttcttgcc tccgtccttg    103860
gcttgatcag ttgtctccga gctacgcacc cgagtcctac tttgtgcaat gtccatctta    103920
cttgtgatgt ccattatgta tccataatcc agttcttgga ccatcacatt tgttcacttg    103980
tgttgaaccc tgtaggcttt accttaagca cctgttcaac acttagtaca cttgttagtc    104040
cttaattga gttgtcatcc aaacaccaaa actcacaaga gagctttcag ttgccccgca    104100
ggccctccaa tgtgggggt cgttcgtacc tgtggggcg gaaccagagt tctgtttgta     104160
atggcaccttt gagtgccggt gtcgttcat tgcggctgtc ggggcctgaa gatgtgtatt    104220
ttggctaaag ccgtattttt tcctcatttc gagcactagg actcgcctgt cggctagctg    104280
aaccgcttaa ccaagtgtga gttgcctcgt gcggaaggtg acgagtgagg tatccgtatc    104340
ccggaggcgt aggagtccct cggatcggtc ggccttgccg cccgaggctt ctcttgctta    104400
gttaaagaaa ccctcggccg ctctgcgatg agccgagctc agaggcagcg gtgtcagcgg    104460
tgtcagcgtg gacagaggcg gagttggctc aaaaagaagc ttcatcggcc ggagcctggt    104520
cgggccgtcc actggtggga ccgacgccgg agtcgggttg ccgaggccat gagccgggct    104580
gatgtcctcg ggggacagct ggctgaggct acagagcggt cggtcgagtc gtctactcgg    104640
gccggttcc tggaggacac ctcggcgatg gcccaggcgc ggtgctgaca ggttccttcg    104700
agatggagat cctccgaccg tgtcgccgtc cgaggctggg tcggactccg ccgaaggtgg   104760
agtcgacgcc gagggtgctg ctgctccccc actgatgtct gatcctgcag gaacaattta    104820
tctgtagtgt gcgtatgttt tttgcggccg ccgaggccca aacataccgt cgtcgtgttg    104880
taaagcggcg tttctttttcc cctttgtttcg agtatcggga cttgttcgtc agtaacagaa    104940
ttgcttatcc gagcaagagt tacttttcac ggaaggtgat gagtgaggta tccgtatccc    105000
gaaggtgtag gagtccctcg gctcggtcgg ccttgccgct tacgtgtact cttactcgtc    105060
cgttggattc tgttatcgat atagtcgaga aggcacaaaa aatcgtttcg gcagaaaagc    105120
tttcgaacgt taagacttgt tcggccagcg ggatcgctta tccgagcgtg agttacttat    105180
cgcagaaggt gatgagtgag gtatccgtat cccggaggcg taggagtccc tcggctcggt    105240
cgtccttgcc tgcttacgtg tactccgtcg ttttcaggat cccactttcg aagtagtcga    105300
aaagcacgaa agatgttctg gcagaaagac ttttttcgag gaaatttttg acgtagaggg    105360
ggtgcccccc ttctagcccc cgaggggaggg tcgggctttg ccgaggcaag gctgacccttt    105420
ccttgatggt tagactttgt tggcgtatgt aaacgaggtg tatgaacgac ttgaaaacat    105480
cttaagggta gaagcgacgt agctgtcgga tgttccaagc gttgatgtag acctcgcctt    105540
gactgttggc cagcttgtat gttccgggct tcttagggag gcgtgagctt gtgacaccct   105600
cgggcgtctt gacgtagccg aagcaccaag tcgcccacct gaaggtctcg gaccgaaacc    105660
ccttgggcgt ggtagcgtcg caggactggc tgataccgcg cgagtgtta taaggccatg     105720
tcccgagcct cttccagctg gtccagtgag tcttctcggt tggttcgatt gcttcggtcg    105780
tcgtacgccc tcgtccccat agactagaaa aaacagcgtg aagatggccc agtgagtctg    105840
tgggcaagat ggcctcggcc ccatagacta gaaaaaacgg cgtgaagccc gtggctcagc    105900
ttggtgtcat tctcagactc cagaccaccg agggagttc cttcatccat cgcctgctga    105960
acttgttgag gtcgttgtag atccgtggct tgagtccttg tagaatcatg tcgttggcac    106020
gctctagctg cccattcgtc atgggtgag ctacggcggc ctagtccacc cggatgtggt     106080
aatcctcgca gtaggaactt tctaccggtg aactgggtgc cgttgtcggt gatgatggag   106140
ttcgggaccc caaagcgatg gatgatgttg gtgaagaacg ccaccgcctg ttcggacctg   106200
atgctgttta gggtctgac ctcgatccac ttggagaatt tgtcgatggc gaccagcagg    106260
tgcgtgtagc ccccgggtgc cttctgcaag gggctgacaa ggtccagacc ccacacagca    106320
aacgccagg tgatgggtat tgtttgcaga gctgagcgg gcaggtgggt ctgctttgca    106380
tagaattgac accccttggca ggtgcgtaca atcctagtgg cgtcggccac gcggttggc   106440
cagtagaaac cctgtcggaa ggcatttcca acgagggctc gaggtgctgc gtggtgaccg    106500
caagccccg agtgatttc ttgtaataac tcctgacctt gagcgatgga tatgcaacgt     106560
tgtaggacgc ctgagggct gcggtggtag agctccttcc cgtcacccag caagacgaac    106620
gacttggcgc cccacgctag ttgccgagct tcggctctgt cgagggtag ctctcctcgg    106680
tggagatatt gcaggtacag ggtctgccag tttcgattag gcgtgacccc ataccgctct    106740
tcctcgacgc gcagtgcctc acctcgggg gccgagggt cctcgggcag ggccaaggct    106800
ttctcgggct cgggcgtgtc gctggtcttg actgagggtt gatgtaggtc tcgggagaag    106860
```

```
acgtccgggg gaaccgttgt ccgcgccgag gctatcttag ccagctcatc cgtagtctcg 106920
ttgtatcgtc gggcgatgtg gttgagctcg agcccataga acttgtcctc caggcgccga 106980
acctcatcgc agtaggcttc catcttcggg tcgcgacagt gggagttctt catgacttgt 107040
cgatgacaag ttgcgagtcg ccgcgagcgt cgaggcgtcg gaccccctagc tcggtggcaa 107100
ttcgcaaccc gttaaccgag cctcgtactc ggccacgttg tttggacgccg ggaaatggag 107160
gtgcaacacg tagcggaggt gcttcccgag gggcgagatg aagagcaggc ccgcgcccgc 107220
tcctgttttc atcaacgacc cgtcgaaaaa catggtccag agttccagtt ggatcggagc 107280
tgctggaagc tgggtgtcga cccattcagc cacaaagtcc gccaagactt gggacttgat 107340
ggcttccga ggggcgaatg agattgtctc gcccataatc tccactgccc actttgcaat 107400
cctacccgag gcctctcggc actgatgat ctctcccagg gggaaggatg acaccacagt 107460
caccggatga gactcgaagt agtgtcgcaa cttttcgccgc gtcagaatta ccgcgtaaag 107520
tagcttctgg aatttgcggg tagcggattt tggtctcaga cagtacttca ctgatgaagt 107580
agaccggcct ctggacgggc aatgcgtgcc cctcttctcg tctctcgacc atgatcgcgg 107640
cgctgaccac ctgagtggta gcggcgacgt agaccaagag ggcttctccg gcaacagggg 107700
gcaccaagat gggcgcgctt gtgaggagca cctttaggtt cccgagggct tcctcggcct 107760
cggggggtcca agtgaagcgc tcggtcttcc tcaagaggcg gtacagaggt aggcctcttt 107820
cgccgaggcg tgagatgaaa cggctcagag ccgcaaggca tccatgacc ctctgtactc 107880
ctttcaagtc cttgatgggg cccatgttgg tgatggccgc gattttctcc ggggttggcct 107940
cgatgccccg ctcggagacg atgaaccca agagcatgcc tcgggggact ccgaagacac 108000
acttctcggg attgagtttt acgcctttcg ccttgagaca cttgaatgtc gtttcaaggt 108060
cggagaggag gtcggaggct ttcctcgtct tgactatgat gtcatcgacg taagcctcaa 108120
ccgttcgacc aatgtgctct ccgaacacgt ggttcatgca tctttggtat ctcgcacccg 108180
cattcctcaa accgaatggc atagtaacgt agcagtacat gccaaagggt gtgatgaaag 108240
aagtcgcgag ctggtcggac tctttcatcc tgatttggtg ataccctgag taggcatcga 108300
ggaaagacag ggtttcgcac ccagcagtgg aatccatgat ttgatcgatg cgaggcagag 108360
ggagggaact ttcggacatg cttttgttta accagtgtag tctacacaca tccgccattt 108420
ccctcctttta tttctcacaa gcacaggggt gacaagccaat tcgggatgga ataacctcttt 108480
aatgaaccct gcagccatca gcttgtggat ctcctcgcct atggctctgc gcttttcttc 108540
gtcgaatcga tgtagaggct gcttcacggg tcgggctcca gctcggatat ccagcgagtg 108600
ctcggcgaca tccctcggta tgctaggcat gtccgaggga ctccatgcaa aaacctccggc 108660
gttcgcgcgg agaaagtcga cgagcactgc ttcctatttg gggtcgagct cggagccgat 108720
ccggatctgc ttggaggcgt cgttgctggg gccgagaggg acggacttaa tcgtctcagc 108780
tggctcgaag ttgccggcgt ggcgcttcgc atctggcgcc tccttggaga ggctccccag 108840
gtcggcgatg aggggcctcgg attcggcgag ggcctcggcg tactccacgc actccacgtc 108900
gcattcgtac gtgtgtcggt acgtggagcc gatggtgagtt accccgttgg ggcccgacat 108960
cttgagcttg aggtaggtgt agttgggaac ggccatgaac ttggcgtagc atggtctccc 109020
cagcactgcg tggtaggttc ctcggaaccc gaccaccctcg aacgtgaggg tttcctttcg 109080
gaagttggag ggagtccga agcagactga cagattgagt tgcccaaggg gttggacgcg 109140
tttcccgggg atgatccccgt gaaaaggcgt cgcaccggcc cggatcggag acagatcgat 109200
ctgcaggagc ccgagggtcg cggcgtagat gatgttgagg ctgctgcctc cgtccatgag 109260
gaccttggta agcctgacgt tgccgatgac ggggtcgaca atgagagggt actttcctag 109320
gctcggcacg cggtcgggt ggtcgccctg gtcgaaggtg atgggcttgt cggaccagtc 109380
taggtagact ggcgctgcca cctttactga gcagacctcc ggctgcctct gcttgcggtg 109440
ccgagtcgag gcgttcgcca cttgcccacc atagatcatg aagcagtcgt ggacctcggg 109500
gaactcctct gccttgtgat cctccttctt gtcgttgttg tgggctctgc caccctttcgc 109560
cggtggcccg gccttgtgga agtagcgtcg aagcatgacg cattcctcaa gggtgtgctt 109620
gatgggaccc tgatgatagg ggcacgactc cttgaccatc ctatcgaaca ggttggcgcc 109680
tccgggaggc ttccgagggt ttctgtgctc ggcggcggcg acaatgtctg tgtcggcgac 109740
gtcgcgtttt gcttgtgact tcttcttgcc cttcttcctc gcgccgcgct gagcggacgc 109800
cttggggacg tcttccggct gacgcccctg aggctgcttg tccttccgga agatggcctc 109860
gaccgcctcc tgaccagagg cgaacttggt ggcgatgtcc atcagctgc tcgccctagt 109920
gggagtcttg cgacccagct tgctcaccag gtcgcgacaa gtggtaccgg tgaggaacgc 109980
gccgatgaca tccgagttgg tgatgttggg cagctcggtg ccctgcttcg aaaatcgccg 110040
gatgtagtcc cagagggatt ctctcggctg ctggcggcac cttcggagat cccaggagtt 110100
cccagggcgc acgtatgtgc cctggaagtt gccgacgaaa gctttgacca ggtcgtccca 110160
gttggagatc tgcacaggag atagatgctc cagccaggct cgggcggcgt cggagaggaa 110220
caggggaagg atgcagatga tgaggttgtc atcgtccgtc ccactcagct ggcaggccag 110280
ccggtagtcc gcgagccaca gttccggctt cgactccccc gagtacttgg tgatggtagt 110340
cggggttcag aacaaggtcg ggaacggtgc ccgttgtatg gcccggctga aagcttgcgg 110400
actgggtggt tcgggcgagg ggctccgatc ctccacgctg tcgtagcgtc ccccacgcgt 110460
ggggtggtag cctcgacgca ccttctcgtc gaggtgggct tgacggtcgc ggcggtgctc 110520
gttgccgagg cgtcttgggg ccgcaggcgc tgtgtcccgc gtgcgcccgg tgtggaaccga 110580
ggcttccgc atgaatcggg aagtcgcagc gcgatgctcc ggggtaccc ctgccttcgg 110640
gaggcagagc tctcggcccg tcggaccgcg acatcctcta gagatttttt gagctctcct 110700
tggatacgcc acccctcggt ggtggatggt ttcggcatcg ctcggagtag tatcgctgct 110760
gcagccaggt tctggccgac cccactgaa gccggggca gcctcgccct ggcatcgtcg 110820
gtgatgcggt gctggacgtc ctgggccaga tgacgcgctt ctccagccgg tgctcggcct 110880
gcccactcct gcccgatatt ttgccgaagc tgcacaagtt gtcctgcttc ctcgtcgagc 110940
ctggcctgta cctcgcggat ttgctcaagc cgtgcgtctt gaccccctccc agggactggg 111000
accacagcta gctcccgaag gatgtcaacg cgaggcgcag gcctagggggg atcaccatcc 111060
tccggcatac caagatggtt gccttcgtca agaccccccta gatcgacgtg gaagcattcg 111120
caccttgggc cacagtcctc gtcgccgagg ctgtggctgc tatcggagca atcggagagg 111180
cagtagtcac atgcggtcat gaagtccgcc atgacactgg ggttatcgag cccggagaaa 111240
tcccaaccag agtcaggctc gtcatcttcc tcggaaccg gggccata ggtcgagaca 111300
gccgtcagtc ggtccaggt tgaccgcata tgataccccg gaggggtttgg acatgccttt 111360
atgaaagcgt ccaccgaagc gggatcgctt ggtgggtcac aactgaatct aaaaggcatg 111420
ggatgggaaa cggacggtac ctcttgatcg acgggtggtg acgaagtcgc gtcagggacg 111480
gactgcaccg ttgtctcagg tacgaggtta acgcccagga agtccttcgc gagcgtgctg 111540
gcgtcatccg tctgcttggg gttggcgtgt tgcggggaaa cgacgcttgt cttcgtctca 111600
```

```
gacgcgaggt caacgcccga cgtgtccccc gttggggcgt cggcgccgtc gactcgctcg   111660
acagccgacg aggtgccgcc tcctgattgg ccatgcctac cccgcctcct cctccgtcag   111720
cggggaaggt gacgggacag acccggatat cgctcttccg ccacgtgggg aagacgtcgt   111780
cgattccgcc gccgacgggc gggctgacgg ccgccattgt cgttgtcgcg cggcggagga   111840
aggagtgtca tgtcgtagct gccgtcgagg gacatgaact caagactcct gaaatggagc   111900
accgtcccgg gttggagtgg ttgctggaga ctacccatct ggaacttgac gggaagctgt   111960
tcgtcaccat gcagtaggcc cctacctggc gtgccaactg tcagcgtttc gaccccgggg   112020
ggtccctgga ccgacgagta aactgtcgct gcgtgtccca ttccagatgg gtcggcacga   112080
gacgaaacac aaagggggga aaacagcaaa ggggaacccg tggccttcgt gttgtcctgt   112140
gcccagggcg gatgcgcttg cagtaggggg ttacaagcgt tcgtgtggga gagagagaga   112200
gagagccttg tgcgtcagcc cgttctcccg cgccggccaac cctctcgtac gagagcccta   112260
gaccttcctt ttatagacgt aaggagaggg cccaggtgta caatgggggg tgtagcaatg   112320
tgctaacgtg tctagcagag aggagccaga gccctaagta catgctgtcg tggctgtcgg   112380
agaggttttg gcgccctgtt catgtgatgt cgtggccgtc ggaggagcgt ttgagccctg   112440
tggaagtaca gctgtcgggg ctgtcggatc cttgctgacg tctccttgct tccataaggg   112500
gctgagagcc gccgtcgtca cggagcacat ggggtgccat cattacttgt ttaccggggc   112560
gagccagatg ggacgtcggt cttgttcccc gtagcctgag ctagctaggg gtagggtaat   112620
gatggctccc cctgcgacgt ggtcggtccg agcccgagca cgggcgaggc ggaggctcct   112680
ccgaggtcga ggttgagccc gagccctggg atcgggcgag gcggagtccg tcttccgagg   112740
tcgaggctga gtccgagccc tggggtcggg cgaggcggag tccgtcgtcc ggcgtcgagg   112800
ttgagcccga gctctgggt cgggcgaggc ggagcttctc atgcgcccg aggctggact   112860
tagctgctgt cagcctcact ctgtcgagtg gcacagcagt cggagcaggg caggcggcgc   112920
tattttcccg tcaggtcggt cagtggagcg gcgaagtgac tgcggtcact tcggccctat   112980
cgactgagga gcgcgcgtta ggataaggtg tcagtcgatc cttgcattaa atgctcctgc   113040
gatacggttg gttggcgtgg cgatctgtcc aaggttgctt ctccgcgaag cctgggcctc   113100
gggcgagccg aaggtgcgtc cgttgcttga ggggaccctc ggggcagacg tgaatcctcc   113160
tgggtcggct gcctttgccc gaggctgggc tcgggcgagg cgggatcgtg tcccttgagt   113220
ggacggagcc ttgacctgaa tcgcgcccat caggcctttg cagcttttgt ctgatggggg   113280
ttaccagctg agattaggag tcttgggggt acccctaatt atggtccccg acatgtttac   113340
ttacaaaagc tccaccaagc ttgtcgagca tccaatgctt gggcgcattg agcctcttca   113400
agtgcttctt caatccccta gcctggattg caaaataata atgatcaaca aaagcgcaac   113460
agattccagt atggcattca taggtgactc atccagattg cattagctgt taaaagtaac   113520
agcaactaca cactacttga aaacaaaaga cccttttcat acatgtctat ctctattact   113580
tatatatgag cagtgccatc gtcagcacct cctgtatgta tacctaggac gacatcagct   113640
ggcgaggggc acggggacgc acgggcgtct tggacgggct caccctaaaa acacactaga   113700
acgactctgt tatccaaccg cccagaagag ctccttcctc aatgcaaagc gtaagaagat   113760
cagttagagt tttaccttat tggcaaggat cccagtacca caccgctaca gtgagagcgg   113820
cagtagcact ttctgccttg aaaaaaaatt gaggcccagt cttaaaacaa ctcgcagaat   113880
aataaggcat ttgaacagca gaccaaacaa ctagcagaat aaaaaagaag ctacgcaaat   113940
ttgaaggcga aggtatgctt agctgaccat cacgaatccc agtttcagcc catggagcgg   114000
gatttgttgc tcatgtctgc cttttctgtcc ttttagatag ctaatgccaa tagttcatgc   114060
aaaactatta tcaactgttc cattgtacat gtataatact tggaaataaa cacagccagt   114120
agccaccaat acccattcct tatgccaaat ttgtgacatg agatggaaat agtacatcaa   114180
taaccaaacg aggggtgagc atagaaattt aacatccaac atcaaaactt gcaaaacttg   114240
gatgtttgag tccacctctc gagcctaacg gacgtgaaat cgccatgacc tggcagcctt   114300
tgcatcaaaa aataactcca gttctatagt aaatgtaacc atgtgtgcat acgtaccttg   114360
cagttctgtg cggcctagta cttggtcacc tgcacaaggt acttgtaaca ccctcggtgt   114420
tactgcaact aaaaacttgag catagcatca taaacattgg cattgcatat gtttgacaca   114480
cctagagtgc attcactagg taaaaatttc aaacaagttg tattgtttta gtgttttgca   114540
aatagaaccc tagataggga attttaaccct aaatagggat taaaggggta agatataacc   114600
caaattgaga aaacctaaaa gctctaggga aatagtcatc aaatattctc aagaataaag   114660
ttgaaccaca tttataccccc tcggatacca aaaaccctaa ttggaaccct agaaaaccct   114720
aaatccaaac cctaggggct tatgtgcaaa attcgaccac ttttggacta aagtgcaaaa   114780
accaagttaa ataagtatct taagtcattt gggtcactca tatgtgaatt tacaagccaa   114840
accctaagtt ttggcctcat ttgcaaaaag gaccctattt gaggttttat actaagtctg   114900
aaaacagtgt tatgggctca acttttgagc cttgtaactt ttaaatcata ggttttttgc   114960
cctaggtcac cacattaaaa ttatagccca atcataggag aacaactttg cttaagagtg   115020
tgagcatagt tttaagaaaa tattggagat aattgagcct gaagttggac tgtcagactg   115080
cttgaaatct gaaattcaga ttaacagtgg gatgacatga acttagggct taattttaag   115140
caagattcag tgactttttg tgggagcaca ttgtagcaaa gttatagctg gattgtagct   115200
ctacaacttt gctgtaggtc actggatgag ttgttatttg aaattgagag aaaactgggc   115260
tccaaacttg actgtcaggc tgtctgaata taaatctcca tggtacagtg ctaccaggga   115320
gatcagacca ccagcgcggc agtctctcac cgccgatgac tgatcttcgc tgagattcac   115380
gccgccgccg ttgcgattca cgtcgccggt gaccagataa gatcgctcgg taaaggcatg   115440
cgctgacgtg cactccggtg aaccccccagt acttcccctc taccgtgcgg cttgagcaga   115500
taagcccgct ggggatcccc gtcgctcggc cttacgccac gtatccgggc acctctgtcg   115560
catcgccgtg actcccccact gttgtctcat cattgccggt gagcccgcca cggcggtgga   115620
cacgaaatcg cgaagccgat gatcttcctt atctccggcc gcccacactg tccactcaaa   115680
ttaagcgcca ccgcccctgg gatctataaa ttgaccctgc agagagcttc acaacatcat   115740
cacccaccca gccaccacgt attgctagca attgttcgcc caagctcgcg aatttttgaat   115800
tcgccccaaa tcaattctcc gccacccgaa acccaacctc actgcggcca gcttattct   115860
ggtcagttcc tctccttctc tccctcattt aagctttccc ttaagtctac gatgcttgcc   115920
gacccacaca atcgagctag gagccctttg gtcgccggga acgcgactgt cttgcgcgca   115980
tgttcacggc caccgtggcc agagcaagcc atttgggcat agatggaatt aggttagggg   116040
aaatgctcgg gctaggtcca attttgatgtc cgccgctcgg gaaccctagc cgttgccccg   116100
ttcggccggt gcaggcactc gccggagttc ggctgggcgt gaacgccgtc gaggacctcc   116160
ctctgcgaag agttagaact acaggggctt ctctgcaatc tgtcagcgac acagtgtaat   116220
agtgataaga gccagttctg attagccaaa ccccgaggac ctctgtgcaa agtcgccagg   116280
gcgcgagcgc gcgcgcgcgt tttccccctag tactgggccg gctgggctag aatcagccca   116340
```

```
acactattca atcttttttcc tttttctttt ttgtagagct ttggaaattt gttaaaaatt  116400
gtagaaaaat cctaaaattg tgaaaccaat tttcctaggc ttcttatttt ccatagaatt  116460
taataaaaat agttgtatga atttaggtt aactaaggaa ttttaaggta tttaaagtag   116520
tttaaggtag tggttctgga ttttagaaa ataaatggaa tttccaaaaa tgtccaaact   116580
ttttacataa gttctataca ttatttagag gccttggtga gaatttgggt tgatttggac  116640
cttgtttgat acttagaacc taaaacccc ctgcccttg aactcctta ctgactccgg    116700
aaaccctaag ttctcggagt tccgtgaagg aaagttgtat tcaagactta gataataaat 116760
ctttattatc ttcgcactct catgagcatt acatggcatt cattcttata tatataccta 116820
tatggttata tttagaaaat gaagaagaga ttgaagtgac caaagagaag acaccaccag 116880
ctacggattc tcaggccggc aattgtttct acttcgatat ctgcgggact gagcctgact 116940
cacctactaa cgaaggcaag ccccggtgca tttaccacct ccttgatgct tttaaaatct 117000
ttctcacttg attgctgcat taggtgatag gagttgaatg cttaaacaat tcctgcacta 117060
ccttccttga atttgattac cttccttgat cacccgtttt acaaaaggat tttgatgctt 117120
tgccttgctc tagaaaaaca aaaggatttg tttttacaaaa gatgtttggc aaaagtggga 117180
gggttatttt tgaaaataaa acttgatggt gaatctgtca aaggccttga tggattcaac 117240
atcggaaaag atgtacctct gccaggtacc aaactttggg tttgaaatga ttaagccgag 117300
accgggcggg tgacttgcac gagaaaggag tctcggtgta gtgtctccgt ctgagtcgat 117360
taaggaccgt ctcgatgtag gcctgctgac cggggacct ttaactggtc acatgcctcg  117420
tcatgggtaa gccttgcctc gggcagacta aggccagaat aagataacac gaaatgggcg 117480
tggagcggtg gcgggagtag cgtgtaccct ccgtggcaag aggctggacg gtggtgtatc 117540
tgtgctctcg gtttgtgtga acctgatctg gtcttaaaaa ccccagtggc gggttgacat 117600
atgcaagggt taagtgctac atatgtcgtg tgattggaa tcctcagctg agtataatcg  117660
attcggatcg ccgtaccttc gcggttatga agacttggtc actgacttac acgtagcatt 117720
ccactaaaga tgatggtttt gttaagaaat tggctagtgc aggacaagtg atttgaacta 117780
gggtagaaag aactctagtt acaggtaatt ctacttaatt tgacaaataa aactggattt 117840
ttaaggatcc actttagtaa gcatttctgc aaaacagatt ctttgattat tgaaaagcct 117900
taccttgact cccttaacca gcatacccctt gagagtcttt tctttagtcg ggtaagcttt 117960
gctgagtaat tccatactca gggtttatcc ctccgttgtt tttaggtgag gaagcgacaa 118020
attttttattg cttctgctcc aaggtggttc ccaaggaaga aaaacaagag tgaagccgcg 118080
ggaggacttg gtcctccata taggactttt gtttaaaaac tatcgggagg agtttttgcc 118140
tcccttggta ttgtaataat attactctgc actcctagga taactctggt ctgtaataag 118200
taacttgatc ttactttta aataaatgta agttatgtaa tcgcttctgc atttctatat   118260
cttcgatgtt ctgtaatgtc tgcaagacgg gtgaaacgtt cctggaaagg taagaaagaa 118320
gataccgaac ttgtgaagta atttaggaac atctatggg tgtctgatgt ctgttggaca   118380
aggacaactg taggtgggct taattacttg ggaggttccg tcacagctgg tatcggagcg 118440
tagcccttct ttgcagatat tatgaggcat cttcaaaaag attttctaaa agtcttacct 118500
agaaactctc ttcctttctt acctaagtat tctgaagagt ctatcttaaa gaccaggtag 118560
taagagtgca acatatagaa ggtgtgaatc aactaaggtt gattctgtaa ttatacatgc 118620
atcatgctaa gaaccatact aatcaaattt tcccccttag aaaatgccgc cgcgcacaag 118680
gagaacaacg cgcaaacata ctggaccgat tggtgtgccg agtcaccagc tgaccccaag 118740
gcatgataat agtagtagcg gaagcaatga tcctataggg gatcttgaag ctgaagtaag 118800
tcgactccaa gcgaaactcc gccgcagaac gactatctgg gtcatagatg gcgaccgcat 118860
aaatgagttg agaagagata tctgccatct gcgagatcag ctcgcggacg ggatttggc  118920
acttgactgg gttgttcaat cccgttcgct tgcatgggac aaggagcaaa aagctcaagc 118980
tcgagtagcc gagctcaact tggctgttga tgaactgcag acatattgca ataccttaca 119040
tgaagagatt catgtattat attcgcaact gcatcccagt gagcctacga atcctggtga 119100
gtcggaagcc ggaccctcgc atgttgcggg acacgcgctt ggtggtgagt tagaccttt   119160
tcagccccct ccttctatga ggctagtcga cgaatggtct cccacacccg acgacgaggc 119220
cgccaaaagc aacggaaagc aggaataatg gggtagtaga agtagaagta gtgtattgta 119280
taacaggttg ctctaatgta taatattttg tactattgca taataggttg tgctattgta 119340
taatagtaa tgtatcctgt tgtaaaaatt cgagtctgta cattactctt tttggtaatg  119400
taaaatggat ggtttttcct tggcatatca tattgttttc caaatgttgt tgccacagat 119460
gccttccaag actcgagcac aggacggagc tagtacctcc tgtgggaggg agtctacccc 119520
aaatccacct cctgttcctc ccacactggc cgaggcgatt gtggccttgg taaatgcaac 119580
cgcgataat acccgttttc ttagagagat ggcgggtcaa caattgcaac aacaaggtgg 119640
gcggggttat caacagggcc cccgtgaaac ctcttacttg gacttctcag agacgcgacc 119700
accgctgttt gtcaaagccg aagacccgtt agaagcagat gaatggcttc gtgtgattga 119760
gcaaaagttt ggactgctgc gatgttcaga aaccagaag cctttattcg cagcccagca  119820
actgcgcgga cctgccagca cttggtgggg taattttgtg gccgttcaac cggccaatca 119880
ttagataact tgggaagaat tcaaggtggc cttccgcgag cactatatac cagaaggtgt 119940
tcttcacatg aagcaagaag agtttatgaa gctgaaacaa ggaggggata ctgttaacca 120000
gtatctcaat aagttcaatc atttgtcaca atatgcaatc gatcaagtga acactgattt  120060
gaagaagaag aattgcttta tgagaggatt aaatgatcga ctgcaaagga agatggcaac 120120
ctgcatagat cttacttatg gaagagctgt cagtacagca ctggcagtag aagcgaagta 120180
tgcaggcgct ggtaaatcca aggggttgg aggtgacagg tctagtcagg gcccggtgaa  120240
caggcaacgg ttcgtcatcc ggccttctaa ccagaatcgt tctttcgctc gtccaccctc 120300
cttttccttt aagcagccag tctttattcg tcccaataat gccctactac catcaagtca 120360
gccgggtgcc ccaggcactc gattccctgc tttacccagc tcgtcgactg gatgtttcaa 120420
ttgtgcaaaa tctgggcatt ttatcaagga ttgccctat ccaaagcaga accagtcaaa  120480
taatcagcaa ggatctggga attcatctca agccaaggaa aataatatgg gcaaaaatac 120540
aaagaagacg gacgcatat attatacgca agtggccact acaccggacg tgagccggt   120600
aatgatgggt acgtttcttg tggccaatca tcccgcagtt attctctttg attctggtgc 120660
ttcgcataca ttcatcagca agaaaatttgt ggagcaacat tgcatctcat gccatgaatc 120720
aaaagagggg tttaaaaatt cactcaccag ggggacaaat atttactaga gaagtggcct 120780
atcaagtggcc cgtaaccttg gccggatggg acttttcctac taatatgatc attctgaaag 120840
gccaagatat atatgtcatt ttgggtatga attggttagc cagacataaa gcaactctca 120900
acactgatca gagaattatc aggttgagtc ataaccagga agaaattctt ttgcctatcc 120960
ccattccaac caaagctact ggcagagctt atgaagccat tataccggaa atcaaggata 121020
ttccggtggt atgcgagttt cccaatgtct ttcccgagga tttgcccgga ctgccacctg 121080
```

```
aacgggaggt agagtttgta attgagttga aacccggtac ggctccagta tctagaagat   121140
cgtaccgaat gcctcctaat gagttggcag aactgaagat ccaattacaa gatctacttg   121200
agaaaggatt tatccggcca agctcatcgc cgtggggttg tccagccata ttcgtcaaaa   121260
agaaggatca aactttacaa atgtgtgtgg attatcgacc cctgaatgag gtcaccatca   121320
aaaacaagta ccctcttcca aggattgaca ttttatttga tcaactgact ggagcaaggg   121380
tattttccaa gattgatctc agatcgggct atcaccagat ccgtattcgg cccgaagata   121440
taccaaagac cgccttcact acgcggtatg gattatttga ataccggta atgtctttcg    121500
gattgacaaa tgctcctgcc cacttcacgt atttgatgaa ctcggtattt atgcccgagt   121560
tggacaagtt tgtggtagtc ttcattgacg atattttgat atattccaag aatgaagagg   121620
agcacgccca acatttacgg atcgtgttaa cgcgcttgag agaacatcag ttatatgcca   121680
agtttagcaa atgcgtgttt tggctggacg aaattcagtt tctgggacat gtattgtctg   121740
ccaggggat tgcggtagat cccagcaaag tcaaggacat tttggagtgg aaaccccga     121800
ccactgttca tcaggtccga agtttccttg gactggctgg atattaccgc cgattcatac   121860
cagatttttc taagcttgtg aagccaatca caagtttatt gaagaatgat attaagttca   121920
attggtcttc aaagtgtgat gaagcttttg aacaattgaa agacattagta accactactc   121980
cggtattggc tcaaccggac atcaccaagc cctttgatgt atattgtgat gcatcaggca   122040
gtggactcgg ttgtgtgcta atgcaagaag gccgagtaat tgcatatgct tcaaggcagt   122100
tgcgccgaca tgaggaacat tatcctactc atgatctgga gttagctgtg gtggttcatg   122160
ccctaaagat ctggcgtcat tatttgctgg gtaatgtctg tcatatttat acagaccata   122220
aaagcttgaa atacatcttc acccagtcag aattgaatat gagacagagg cgatggctcg   122280
agctaatcaa ggattatgaa ttagaaatcc attatcaccc aggaaaagca aatgtagtgg   122340
cagatgcgct caattgcaag gcttcctgcc attgtttaac agtgaggact tctgacatta   122400
cattatgcca ggagatgag aaattaaacc tgggaatgat tcaacatggg acttcaaatc    122460
atttgaagct ggagtcaatc atcatacgaa gaataattga cgcacaaaaa gatgatgagg   122520
gtatgaagca catacgtgag aagataatgg ctggaacagc caaatgtttc aaagaagatg   122580
atcaaggtgt gatatggttc aataaccgca tagtggtgcc gaagaatgaa gaactccgcc   122640
agcaaatctt agatgaagca catcttagtc gctattctat tcatctggga agcactaaga   122700
tgtatcatga tctaaagcag cactactggt ggacgaagat gaaaattgaa attgcacgct   122760
atgtggctaa gtgtgacact tgcagacttg tcaaggccat acacatgaag atagctggtc   122820
cattacaacc tttgccgatc ccaacataga aatgggaaga tattagtatg gacttcattg   122880
tgggattacc caggactaca aaagggtatg attctatctg ggttataatt gatcggctta   122940
cgaaaattgc tcactttcta ccggtcaaga cagatcaccc ggttactgtc tatgcccatt   123000
tgtacattgc tcgtattctt agtctgcatg gtgttccgaa gacccatagt gtcggatcgt   123060
ggacctcaat ttgtagccaa gttttgggaa gcacttcaca aatccttggg tactaagttg   123120
ctccatagtt cggcctacca tcctcaaacc agtggacaga ctgagagagt aaaccaaata   123180
cttgaagata tgctgcgggc atgtgttctg gaatttccac aaaaatggga tgaatgtttg   123240
ccgttagcgg aattttcata taataatagc tatcaagaaa gcatcaagat ggcacccttt   123300
gaagctttat atggacgacg atgtcgtact ccgctaaatt ggtctgaacc tggtgaaagg   123360
tacttcttca ggcctgatat ggtgaaaag actgaagaaa gagttcaaag gataattcat   123420
aatttgaaga aagctcaagc tcgtcaaaag agttacgtag acaaacgcg aatgcccta     123480
tatttccttg aaggatacta tgtctactta aaggtttcac caatgaaggg agtatcgcgt   123540
ttcggagtta aaggaaagct tgcaccataa tatattggtc ctttctcttat cctggaaaga   123600
tggggccag tggcataccg acttcagtta cccgaaacct tgtttgctgt gcataatgtg    123660
tttcacgtgt cccaattgaa gaagtgtctt cgggttcctg atcgaaccgt tgaagtgaca   123720
gatgttgtcc ttgaaccgga cttgacatat tctgagcacc ctattcgagt cttggatcaa   123780
aaggacaggg ttacccggag aaaactctca agtttataa gatacagtgg aaccaacatt    123840
ccgaagatga ggctacatgg gaaactcaag acttttaag taagaatttc ccaggcttt    123900
tagcttcttg taaattgtaa agcctgtata gctgttgtaa taaggagtg attccaaaac   123960
caccctgcc ttgtaccaga aataaggaaa taaaagtatg tcgtgttcc ttttccatta    124020
cttaccctag gactttaat ctcgggacga gattctttta tgggggaag gatgtaacac    124080
cctggtgtt actgcaacta aaacttgagc atagcatcat aaacattggc attgcatatg   124140
tttgacacac ctagagtgca ttcactaggt aaaaatttca aacaagttgt attgttttag   124200
tgttttgcaa atagaaccta gatagggaat ttaaccctaa ataggggatta aaggggtaag   124260
atataaccca aattgagaaa acctaaaagc tctagggaaa tagtcatgaa atattcccaa   124320
gaataaagtt gaaccacatt tatacctctg ggataccaaa aaccctaatc ggaaccctag   124380
aaaaccctaa atccaaaccc taggggctta tgtgcaaaat tagtccactt ttggactaaa   124440
gtgcaaaaac caagttaaat aagtatctta agtcatttgg gtcactcata tgtgaattta   124500
caagccaaac cctaagtttt ggcctcattt gcaaaaagga ccctatttga gatttttatac   124560
taagtctgaa aaatagtgtt atgggctcaa cttttgagcc ttgtaacttt taaatcatag   124620
ggtttttccc ctaggtcacc acattaaat tatagcccaa tcataggaga acaactttc     124680
ttaagagtgt gagcatagtt gttaagaaaa tactggagat aattgagcct aaagttggac   124740
tgtcagactg cttgaaatct gaaattcaga ttaacagtgg gatgacatga acttagggct   124800
taattttaag caagatccag tgacttttgt tgggagcaca ttgtagcaaa gttatagctg   124860
gattgtagct ctacaacttt gctgcaggtc actgagtgg ttgttatttg aaattgagag    124920
aaaattgggc tccaaacttg actgtcaggc tgtctaaata taactctcca tggtacagtg   124980
ctaccaggga gatcagacag ccagcgcggt agtctctcac cgccgacgac tgatcttcgc   125040
tgagattcac gtcgccgccg ttgtgattca cgtcgccggt gaccagataa gatcgctcgg   125100
taaaggcatg cgctggacgg cactccggtg aaccccccagt acttcccctc tgccgtgcgg   125160
cttgagcaga taagcccgcc ggggatcacc gtcgcctggc cttacaccat gtatccgagc   125220
acctctgtcg catcgccgtg actcccact gttgtctcat cattgccggt gagcccgcca   125280
cggcggtgga cacgaaatcg cgaagccgat gatcttcctt atctccggcc gcccacactg   125340
tcggctcaaa ttaagcgcca ccgccctgg gatctataaa ttgaccccgc agagagcttc    125400
acaacatcat cacccaccca gccaccacgt attgctagca attgttcgcc cgagctcacg   125460
aattttgaat tcgccccaaa tcaattctcc gccaccgaa accgaaccte acctcggaca    125520
gccttattcc ggtcagttcg tctccttctc tccctcgttt aagctttccc ttaagtctat   125580
gatgcttgcc gacccacaca atcgagctag gagcccttg gtcgccggga acgcgactgt    125640
cttgccgcga tgttcacggc caccgtggcc agagcaagcc attgggccat agatggaatt   125700
aggttagggg aaatgctcgg gctaggtcca atttgatgtc cgccgctcgg gaaccctagt   125760
cgttgccccg ttcggccggt gcaggcactc gccggagttc ggctgggcgt gaacgccgtc   125820
```

```
gaggacctcc ctctgcgaag agttagaact gcaggggctt ctctgcaatc tgtcagcgac    125880
acagtgtaat agtgatagaa gccagttcta attagccaaa ccccgaggac ctctgtgcaa    125940
agtcgccagg gcgagggcgc gcgcgcgcgt tttcccctgg tactgggccg gctgggctag    126000
aatcagccca acactattca atcttttttcc tttttctttt ctatagagct ttggaaattt    126060
tttaaaaatt gtagaaaaat cctaaaattg tgaaaccaat tttcctaggc ttcttatttt    126120
ccatagaatt taataaaaat agttatatga attttaggtt aactaaggaa ttttaaggta    126180
tttaaagtag tttaaggtag tggttttgga tttttagaaa ataaatggaa tttccaaaaa    126240
tgtccaaact ttttacataa gttctatgca ttatttagag gccttgggta gaatttgggt    126300
tgatttggac cttgtttgat acttagaacc taaaacccc ctgcccttg aactcctta    126360
ctgactccgg aaaccctaag ttctcggagt tccgtgaagg aaagttgtat tcaagactta    126420
gataataaat ctttattatc ttcgcactct catgagcatt acatggcatt cattcttata    126480
tatatatata cctatatggt tatatttaga aaacgaagaa gagattgaag tgaccgaaga    126540
gaagacaccc ccaccttcgg attctcaggc cggcaattgt ttctacttcg atatctgcgg    126600
gaccgagcct aactcaccta ctaacgaagg caagccccg tgcatttgcc acctccttga    126660
tgcttttaaa atctttctca cttgattgct gcattaggtg ataggagttg aatgcttaaa    126720
caattcctgc attaccttcc ttgaatttga ttaccatcct tgatcacccg ttttacaaaa    126780
ggattttgat gcttagcctt gctctagaaa aacaaaagga tttgttttac aaaagatgtt    126840
tggcaaaagt gggagggttg ttttcaaaaa taaaacttga tggtgaatct gtcaaaggcc    126900
ttgatggatt caacatcgga aaagatgtac ctctgccagg taccaaactt tgggtttgaa    126960
atgattaagc cgagaccggg cgggtgactt gcacgagaaa ggagtctcgg tgtagtgtct    127020
ccgtctgagt cgattaagga ccgtctcgat gtaggcctgc tgatcgggga ccctttaact    127080
ggtcacatgc ctcgtcatgg gtaagcctg cctcgggcag actaaggcca gaataagata    127140
acacaaaatg ggcgtggagc ggtggcggga gtagcgtgta ccctccgtgg caagaggctg    127200
gacggtggtg tatctgtgct ctcggtttgc gtgaacctga tctggtctta agaaccccgg    127260
tggcgggttg acatatgcaa gggttaagtg ctacatatgt cgtgtgattg gagatcctca    127320
gctgagtata atcgattcgg atcgccgtac cttcgcggtt atgaagactt ggtcactgac    127380
ttacacgtag cattccacta aagatgatgg ttttgttaag aaattggcta gtgcaggaca    127440
agtgattgaa ctagggtaga aagaactcta gttacaggta attctactta atttgacaaa    127500
taaaactgga ttttttaagga tccactttag taagcatttc tgcaaaacag agtctttgat    127560
tattgaaaag ccttaccttg actccctaa ccagcatacc cttgagagtc ttttctttag    127620
tcgggtaaga cttgctgagt aattccatac tcatgggttta ttcctccgtt gtttttaggt    127680
gaggaagcga caaatttttg ttgcttctgc tccaaggtgg ttcccaagga agaaaaacaa    127740
gagtgaagcc gcgggaagac ttggtcctcc atatagaact tttgtttaaa aaccatcggg    127800
aggagtttttt gcctccctg gtattgtaat aatattactc tgcacttcta ggataactct    127860
ggtctgtaat aagtaacttg atcttacttt ttaaataaat gtaagttatg taatcgcttc    127920
tgcatttcta tatctccgat gttctgtaat gtctgcaaga tgggtgaaac gttcctggaa    127980
aggtaagaaa gaagataccg aacttgtgaa gtgatttagg aacatctata gggtgtctga    128040
tgtctgttgg acaaggacaa ctataggtgg gcctaattac ttgggaggtt ccgtcacagt    128100
actgatggta ctccggttgc gccatttaca tctcaagcaa tttttctcaa agttggattc    128160
ttgatccctg catatcgctg gtcgtgaccc gtgggcacgg cgctcggatc cggcagcagc    128220
agatcgaggc gaggccgcga gggaggagaa gagccatgat gggggggcatc agatcatcgc    128280
tcaacgacag cagtatgggc gtcctcttcc tgctggtgct cctgctggat gcgggcgtcg    128340
tcctcctagc cgtgctccta gcagtagagg tccagtagc aggagaagag gacgatgcg    128400
ggcgtcgtcc tcctgccgt gctcctactg gcggcgtgt cgtgctcctg ctggtgctcg    128460
acgactggag cctgctgctt ggtggtgctc ggcggatgag caggggatcc gatcgggtag    128520
gggatgagga tgagatgact gatcggatca gatgggcagg ggatgaggat gagtggatga    128580
ccgaccggat gagttggttt gctcggaagc tgccgctgg gggatgggga ttagatcatt    128640
agtgtttgtc ggtttgggtg tttgccactt tgggtctttg gcggaatgat gccttagtgg    128700
gcaatgggct ggcgcttggc gcctgggcac aatggacaat ggtgggctgg cgatttgttc    128760
attggtgtcc atgtgtggat cgacagtaat ggactaatgg ttaatttcgg atatccaacg    128820
aattacccgc gggtgaggtt taatatccaa atccatgtct gcttatctc ggatcgggta    128880
cgggtctaac ccgcaggtca aaaaacatat ccatatcctg atccgtcggg tcgaatatcc    128940
gacggatatc actatccacg cattaaaattg ccatccctag atgtgagact taaggcatgt    129000
ttgttcgcta cctaagttat cacactttgc ctaactttttt cgtctaaggt tagttattca    129060
attcggacga ctaaacttag gcaaagtgtg gcacatttag ccacaaacca aacatgcctt    129120
taaccctctg gtttagatcc cgtttcgttt gagctgaata tacttattaa atgtctaaag    129180
catagcctag agcctgtcat gtcatgaatc atgaaatgac aataaaacat aaacaaaagc    129240
atagcctggg agtttggagc accgcgctgg gggcactgaa gacgacggat cttgcctctc    129300
agcctcggcg atgggcgtcg gacgcaggag atggcattaa ccaccgctat attaataaaa    129360
cgtattgtat atatgtgcaa tacgtatata aagagaaata ttcgtggcat taaccaccgc    129420
ttatcaggtt gcttataccg tacaaagaga cgatatata actataaaca tactgttgat    129480
gagaaaataa aaaataatca tatttcaaac gtataatttt atttgaagaa gattcttatt    129540
taagcaagat ttttttaccta tatgatatat agaaaccgta cgaacataca gtcagctaac    129600
tagttcattt taaattccaa aaaatgttta gttcaatcta atcagaattt actattgact    129660
atgttttttc acaatatgtc ctatcaaaaa tatcgtacga gacggtttta tgtttacaag    129720
tttctagtat actcactaac atcaagaca attttgtata gtctagatga ctctaataat    129780
atcttttattt gagatggttt catatacaga agtgtctaat atactaacca aaataaaga    129840
cacttcttgt aaacttaatg cctcaaaagg tatatttatt tgagacggtt ttcaacatca    129900
aactgtatta aatcaatata agacatttcc aaccatatat ctgcctcaaa aaccttcttc    129960
attaaagacg gatatccaac aaaccgtctt accgtactca gcaccatatg ataaagacg    130020
cttctataaa atgcactgat atttgtctta agatgtatgt cttaaataag catatttcta    130080
gtagtggatg tccaagacat ccacagagtc attaacttag gtcataatca aaattttgaa    130140
cgaaacgcag tacgataagg ccttcacagg cagctaactg agggtttgcc actaatctag    130200
tctagaactc gtcgaagtcc tgaaactcct gaaagtcctc cacgttgcct tcatcttctc    130260
ctgagcacta gttgcaatgg ggacaacctg ggggtttggtg ttttttaagca atggtgagta    130320
cacctcaacg tactcaacaa atgtcctgtt tggctaaagt ggactagctg tatgtgggt    130380
taagcttaaa gcagttgctt ttagttggtt aggtatttat taccagtaga gagccatgtt    130440
ttagcaataa ccccaagtta taaacccaaa cattactccc tccaagagga aataccaaga    130500
attcataatc ataatcacca tcattaagca tcatcataaa agtatccaga gtaactctaa    130560
```

```
tcaaaggagc tcccaaggct gctcataact gtgagcatgg ctgatatact agcttctaac  130620
actctacaga ggttgcacac tttacccaca agtcgtgatc ccttttgcc tcaggtcgat    130680
caaaccctca aacactacca aggtgagtcg gcaaggtttc actacgtagc tgtaacaccc   130740
tgaattttgg ggtataaaaa tttccttgct ctatactcaa aatctaggtg ttaccctttc   130800
ctttattcac ttttctttc cctttatcaa aacagtagag agttattttg gttctatatt    130860
ggtgtgagct ctagaagtgt catgattgtt gcattcatgc tgctacatag tgtttccaag   130920
tgatgatccg aggtgaggac gagctgacca gtcgggccca gcgctagggc acagatgact   130980
gacaagtggg gcccaggggc aagggcaccc acgtgaagcg atatccagcg atctagaccg   131040
ctagatcaag gctaaacggc taggattagg cgtcaggggg gttaacagca ctgcggccgg   131100
cgctgctcca tccgcagcgg tgaagtcgcc aaagacgaga caagcgcgga ccccagggggg 131160
tctggggtcg ctggagttgg ccagaccggt gaggggacc cgacgaactc gatggcaggg    131220
ttctggccat gagaacggga ctggaggtga gtgaatggcg gaggggcgc tctgggcggg    131280
acacttattg tgatatcctg gcccctggga tgggatgtcc tggcccaagg cttaatagaa   131340
ttaatagtgt aatcatacca acaaggtgca tcttcttttt cggaagccta tctcgaaaga   131400
acctccaagt taagcgtgct tggcttgag caatttggga tgggtgaccg accgggaagt    131460
tttctcgggt gcgcatgagt gaggacaaag tgcgcacaaa agactcgtgt tggtctgtgg   131520
ggacaatata tgatcctaga cagctgccag gagtaagtac cgccggtcca gggattagac   131580
ggggtgttac aagtggtatc agagccgaca ctcgcggtt caccgggcgtg tgtgggctag   131640
ggggttcggg tatatggcgc atggcacatg tgggcccgga gtggtcacat ggcatggcat   131700
atgacggcac tagacacaca gacgtggcca agaggggagg ttcctggatt ggggttgacc   131760
gacgaggacg tcgtcttct aaggggggtg gattgtgata tcctggcccc tgggatggga   131820
tgtcctggcc caaggcttaa tagaattaat agtgtaatca taccaacaag gtgcatcttc   131880
tttttcggaa gcctatctcg aaagaacctc caagttaagc gtgcttggct tggagcaatt   131940
tgggatgggt gaccgaccgg gaagttttct cgggtgcgca tgagtgagga caaagtgcgc   132000
acaaagact cgtgttggtc tgtgggaca atatatgatc ctagacagct gccaggagta     132060
agtaccgccg gtccagggat tggacggggt gttacaagtg gtatcagagc cgacactcgc   132120
ggttacacc ccaggtgttt attttccgct caacaacgag ttcggattta agcacgcaat    132180
atcagtggat aaaacgaatt ttaaatttta atcattgtcg cttatcgcta ttttaatatc   132240
gcatcggtgt cgtttgtcgc gagtgcgaca tcgttttat ttttttatct gtccgggctc    132300
ttcctaaatt ttcgtaatgt tcggaaccta gctgttccga aaatcggtgc gtccgatgag   132360
tatttaaaat ccatcgctcg cgcgaacaca aattcggaag cccgaactca ctcgaatgat   132420
cttatttcga gcaaattaat ttgaacttga cgactaaaat gttcagggta aaataatctg   132480
aatcgcgcat tgtctgagaa agatcgtgcg cggggatatg atctaatttg ttcttagcc    132540
cgcaatgtag gataaccaaa tcaactgtgt tttggtgacg gataagtttt tatctgattt   132600
caattaaatg taacaccgat taaaacattg taactaaaat cattttaat tttagtcctc   132660
ttacatcttt ccaaattcta gtcccaatct ccagctgata attgtatttt tattcaaatt  132720
tttgagtaaa agaaaacgaa ggaagaaaat atctgcaacc gctcttctct ctgatttat   132780
ccaccgcttt tccttccat atctgaagtc actagcctgg atattttctc cacgtagttc    132840
tcctcttcct cacgtctcct tctctcttat ccattggacg ctagctcgct ggaaaatctc   132900
acgcacgtct ctcctccagc ctcgtctcca gcttgcgtcc gaccagcatt tcttccatcc   132960
atcagcatcc aaaggcagcc ggctgccggc tgtgctcgtc ggaccctccg agcacctctg   133020
tgccgacga cctgaccaag ctcgtctcca gcttgcgtcc atcctgtgct cagtttccat    133080
ccactagcac cgtgtctctg gtcctgctcg tcgtggacat cgtcggctct agttccttgc   133140
tcgagctcgc ccttttgcga gaccgcgtct ccctcacct tgccgcggtc gggctggccg    133200
tcgtcgtcag cttgtgtcca tgccgacgaa tttgtcgaac tgctcactgc atctctttaa   133260
tctcgtcgcc tgatttttct gtaccgcgcc gcgcaaccc tagaaataaa aatcacgccg    133320
ccgagcgctc ctatccttat cccgccaccg cccttggtct cctacaaatc tccagcgcgc   133380
aggtttcttc tccacgcacg ccaggcagca agccgcagcc gagcagctcc ttcccatctc   133440
ccctctgctc gctggctgaa tccccagccg ctcggctctg cttttctccc atggcgcggg   133500
gttccctgca ggctgctcgc ggtatccatc tcctctgctc ctgctcgtcc gtccctgagc   133560
tcctgtgccg cggcacctct gttcggccac gctgatcgg atttcttgtg ccgtggcttc   133620
ccctccgagc tcgcccagct ctattgccgc gcccatggcc ggcgctccct gcttggttcc   133680
gtctgtcgcg ccgtcgtctt actgctcgcc tttgcgtcgc gcgcatagcc ttctgttgtt  133740
cttgcacgcg cgaagctctt tgctcgtcaa cgcttcagcc tggatttcgc tttgtcgccc   133800
agctcggctc tacatgacta catctcccat gactgtctac tctagctcgc cgtagttcct   133860
gcgcgacgtcg agttttctct actctagctc gccgtagttc ctgcgcgcgt cgagttttcg   133920
tgtggagctc tctgctcacg cgtagctcgc tctttcttttg ttgccgcgcg cacgaatttt   133980
atctgctcgt cacagcgtgt cgagttctca caccatcatc gcttctgtcg caagctcgtt   134040
ggtcacagtt gtcttgaccg cgttaactcg cgactgtggt cgtgttcatc gaattcgcca   134100
actctttgtt gccgatttga ctgtcgtcgc ttcgcgtgtt gtcgagccgt cgtttttcc     134160
tgtcttgtgc tcgcacggtt tcctgctcgc cagcgtgccc tctcggctcg ctcggcttta   134220
atttccaatc acgtcgtcga tctcgtcgtt tgccgtcgag ttgtcaaaca cgtcatctcc   134280
ggctcgatcc ccacctcacc agcttacccc agacttcaat cgaaggtcat cgtcgctcgt   134340
gcgtcccaa gaaaacccaa gaatcgggtg aagacgaagt tagcagcgcg atattccta    134400
agcgctcgac aaattgcgta gatcgaaaaa tcactgccga tctcatggat tcgtgtcaac   134460
tgttgaaacg gtaagctgat gaattgttta gaatagttcg atcgttgaat aagttaatgt   134520
gttagtgcga ggctcattag ggtgctcgat aaattgcgta agtcacgaaa ctctcgtcga   134580
cttcgcagtt cttgcgatta tcgagccagg ttcagttata gcgagttatt tcgctattcc   134640
ggtcacttag ctgaattagt ggaccgagta gaattttagt aggcatatgt gttgataaaa   134700
tattttaatc acttataaag atgtagtata atttataagg caagggatta gttcagaatt   134760
taattaatta actgataagt tgtgattagg ctaattatat ttcttgtgta tagtttgttg   134820
ttcgtgatgt ttgcgttagg ttcgagaagc gtaatcattg cgcgtagtcg catattaata   134880
actagtgttt ccgtacaaaa ttgtacaacg cctcgccact aggtgtttaa tacgctatcg   134940
tatagcacta tttagatttg tgctattctt gtttatatgc attcatgtgc actcgtcatc   135000
tcaattaggt acgataattg atcgcggtgat gcggaagaca agccaagtgc accccaagcg   135060
cgggctaatc cgcaggatga tgctgatgga caaacctgaa aatggtcgcc aagtggacgt   135120
cgtctaacaa cactaaccta gtgttacca ggcaagccc ggtgcattg ccacctccct      135180
tgatgttttt aaaatctttc tcacttgatt gctgcattag gtgacaggag ttgattgatt   135240
aaacaattcc tgcattacct tccttgatct tgattaccct ccttgaaaac ctgtttttac   135300
aaaaaggttt tactatgctt agtattgctt agaaaaacaa
```

```
aaggatttgt tttagaaaag atgtttggca aagtgggagg gttgttttca aaaataaaac  135360
ttgatggtga atccatcatg gctatgatgg attcaacatc ggaaaagatg tacctctgct  135420
aggtaccaag ttttttggtta aaagattaag ctaaggccgg gcgggtgact tgcacgggaa  135480
aggagtctcg gtgtagtgtc tccgtctgag tcgattaagg accttgtcga tgtaggcttg  135540
atgatcgagg acccttaac tggtcacatg cctcgtcatg ggtaagcctt gcctcgggca  135600
gactaaggcc agaataagat aacacgaaat gggcgtggag cagtggcgag agtagcgtgt  135660
accctccgtg gcaagaggct ggacggtggt gtaactgtgc tctcggtttg cgtgaacctg  135720
atctggtctt aagaaccccg gtggcgggtt gacatatgca agggttaagt gctacatatg  135780
tcgtgtgatt ggagatcctc agctgagtat aatcgattcg gatcgccgta ccttcgtggt  135840
tatgaagact tggtcactgc cctacacgta gcattccact aaagatgatg ggttttttgtt  135900
aagaaattgg ctagtgcagg accagtgatt gaactagggt agaaagaact ctagttacag  135960
gtaattctac ttaacttgac aaataaaact ggattttaag gatccacatt agtaagcatt  136020
tctgcaaaac agagtctttg attattgaaa agccttacct tgactcccat ataccagca   136080
taccccttgag agtcttttct ttagtcgggt aagacttgct gagtaattcc atactcaggg  136140
ttttatccta acgaatcaag ctgatcatca acnnnnnnnn nnnnnnnnnn nnnnnnnnnn  136200
nnnnnnnnnn nnnnnnnnnn nnnnnnnnnn nnnnnnnnnn nnnnnnnnnn nnnnnnnnnn  136260
nnnnnnnnnn nnggtcagcc cagattgctt ctgcgagcgc accggctatt gggtcttcct   136320
gtgttctgct agccgctggt gcagactctg agatgcatct cacatatttg ctgggacttc   136380
tcactcttct gactaccagc ggcagatatg ttgaggagtg ggtccgtgtg ttcaatgcgt   136440
cagtatggat cgaccccgat caccagtgga tgaggttccg ctttgagcga gaggatgtta   136500
cacttcatgc tagctagatt cgccagctgt ttggattcaa tgagtcatcg acttgtcttc   136560
atagcttgtg ctatggtacc tctgatcctc ctcgtcgccc tcacgacgga gttgctccag   136620
ctacagctca catcgcggct ttgttccgac cgcccttctc agatgggtcg cgacgttctc   136680
cggcagattt cactacagta gccaagtact tatatcagct catgagacgg acgcttctgt   136740
cgtggatggg ttatagagag gctaccactc atattcagct ttggctcctc ggtgccctga   136800
tctttcattc agagtttgat gttgttgact tcctatttg tgagatcgag gacacggtat   136860
tggatggtct tcgtgctcgg cgacagctgc caaatgctca ttatctctgc cacatcttcg   136920
cacagctgat ccgaccacca tagttccagg gcacccttga ggcctcacgc ctcctatttg   136980
gctcctacca tccagcccct gaggatccag taccagtacc tgatccagtg acagacattc   137040
aggcagagga tacaagtttc catcagtttg agacttgagg cgcagcagtt cgtcgacgatg  137100
atgatgatga tgatgatgat gattttggga ttccgcctct gcctcctgtg cctccacgct   137160
cacatgacca tgaggcccgg agttctcgtg ctgccctgc tgttcctcct gccattgacc    137220
ctgctctggc tgcgatcctc cagactctta ctcagcagca ggctcatctg gcagcggtgc   137280
aacagacagat gtccgagaga atgctatcga tgttttagac tattcaggac agacaggaca  137340
ctctgcagca gcagcttttg gcagacaagg ctgagaaccg ggccttcatg actcacatac   137400
ttcagcatac cggtgctcag attcctcctg ttcagtctgc accccctcta gatcttcagg   137460
ccgctgttgt gctagcccct caggcaggac cccctctacc ttcatttggt ccttcttcct   137520
ctccgctcct gccggtcacc ctggttttct cgtcgccggt catcagctcc atcagcgctc   137580
agccgccagt gccaccagct cctgctgtta ccactgctgt tgtgcggtg tctgtgacct    137640
cttcagcttc ggtagctcct gcagcacagc ctccatccga gtcagtacta gctccagctt   137700
ctacggtaga tcctgatcc gaggctgact ctgaccctca gctggcgttt gctcttctgc    137760
cacgatcgtg atcggatgcg ccccagccac ctccttcctc ttctggtctg taggttcagg   137820
tttccttttg tgtgtttgacg ccaaagggg agagatatga gagttgggag agctaggggg   137880
agttagggag ttagtataga gtcatttga tgtaatatat gtgcttgata ctctctgtac    137940
tagatccact tttgtatgac gattttggct cacaaactct attatatgct ctcgatgctt   138000
atgttgactg tgtgtgtatt gtgttttcac cttatatgtt atcaccagtc tctagttctt   138060
gttcatcgat ttgatttcac tttatatga acaagaaact tacaatgtgt atgcactcac    138120
tcttattatt atgttacaca ctcttttctgt caaaaatttt tgagtataac taaccatctt  138180
ctctattgac agaaatttca aaacaaacta ctctcacaat cttgtaggtt gtcatcaatc   138240
accaaaaagg gggagattga aagcatctag gcccctggtt ggttttagtg attaatgaca   138300
atgtaatttt atatgtgact aacatgtgtt ttgcagaggc aaatggtaag ttaggtcgca   138360
ttacatgtag atgtactaca acggtgaaaa caatctcgga gataagaact tgaagcgacg   138420
gctaaagcga caaaacaaaa agtgaaggtc ttcgtattcc gagtgtcaag gagttgcgga   138480
cactcgtgat atagttaggt ctttttatttt gttttagtcg tactataaag aggggttgtc   138540
gatgagtagt ttgaccaaga gagttctagt gtagtgttgg tgcatattca cactcacata   138600
tagtctaggg tgccactcta gaacatactc acaagttaga acgaaaaccg aattgaaaaa   138660
acagcacaaa acagaaacta gggtttctgg ctttggggca ccggactgtc cggtgtgcac    138720
cggactgtcc ggtgcaccct ctgccagtgg ggccagcctg gcccaaggaa gagggttccc   138780
tgcgcacaga aacctgagag cgcgttgttc gcgagttgaa ttttagtgga ctgtccggtg   138840
tgccatctgc ccaacggcta gctgtcagaa ctagccattg gagtcgaccg ttggcgcacc   138900
gttggcgcac cggactgtcc ggtgcgccca tgtgcagcag attcctggta atggctagtt   138960
ggtgggtgag ggctatttat acccctcca cccactatat tgatggtctt gctacccaca   139020
tttactccta cacattggta gagcattgca agcaccaaa agcctagtga ggtatttga    139080
gaatcttaat cccgcatttg gaccttatta gcgctagcga gagccaccta gagcatcac   139140
cgcatgcatt aggcttctct tggtcaagtg aaagtctatg gcttgttact cttggtgatc  139200
gtcatcacct agacggcttg gtggcgttgg gagctcggtg atcaccgtgg agatcttgtt  139260
ggtgacccga ctcaagtttg taagcggtcg tgagggatcc actgcgctgg agtggcaaag  139320
gatcatctcg ttgtgagcac ttggttcttg cgaggaccaa gggggagtga tacccttgcg   139380
agggtgctcc aacgaggact agaggagagt gccgactctt cgatacctcg agaaaaattg   139440
gagtcttcta aaccttgctt tacattccgc acttaattaa aacatttttac attgtgtatt  139500
tgtttagcaa gtatttgaaa tattgtctta acattgttgt atttctatta ttattctctt   139560
agtgatagtt atcgggggtga agttggactc ttgcttagat tttaattagt gttgatttt    139620
agaaaagtcc aattcaccct cctcttgggc atcgtgatcc tttcaaaact cactcaattc    139680
cgtctaatcc acgtggattc aaaataaaac gaacagctcg gagagcgacgc              139740
tacaccggaa ctatcagtgg tcagcttcta ggcttcagca ttatacgtac tatgaaaata   139800
tgaatgcact tcaggtcatc atcaacaacc aaaatggata tagcaaatat tcaggctcat   139860
tatacttgaa aacaatagaa ttacattaaa aaaggccgaa accgtgaggc tggattaaca   139920
agagaaacgg taatggtaca gtaattcatg aagtgaagga ttttacatca ccaccagctg   139980
gtgctgaacc ttcccgttgg atccagctaa ctgcccttgg caggagcatc tacaaccaat    140040
```

```
acccaaagtg ggttatctta cttatctaga gccctggtat cgcaagccca atatgcctca    140100
gggtcagggc aggaccaaga aatgtggtga agttcacatt cccaaggcaa ccctacgtct    140160
caatgccacc tcgaagtatc atctagtaaa agcaaagttc aacagaaatg ctgtgccagc    140220
aagttgtctt ggaaccgacg tggtaaaatg agcatcgttt gatcactttg tttttcttct    140280
cgatgcaatc tccgctgccc atgcttttcc caagtcgtc tgaaatttgc ctgcatggga     140340
attaggtgcg gggatatggt tttgttacac aatgactcta atgctaatag cctaggctaa    140400
gtttaccatc cccatattca aattccactc tgcgaatagt gcaatctaag tgcaaaacag    140460
tgttttgggt gggtgaactg ctggacacgg tctaatacaa tgtaaaaatg agatcaaaca    140520
taagcacgtg ataaaagaaa accataaaag gcataggcat gtatcagttc atggtaaaga    140580
aaaccattat aggtggtagt gtccagtttt caattagcaa taatcattca ggcactaata    140640
tgttctgaat tgctgatgaa tgtttatatt atctcaggaa aacatttta agtgtaagac     140700
caaaaaaatg gcaacatcct tctcagctta aatgaactgt tcaaatttat gtacaggatg    140760
ctcatgaaaa ttgagaagag caagatttat gtactggatt gtcatgaaaa ttgagaagag    140820
caagatttat gtactggata ctcatgaaaa ttgagaagag cataacagaa agagaaaaat    140880
cacacctgct gttgattgga agaattcttc aaggtcccgt ccttgctctg aaaattttaa    140940
aatacatagg cgtaagtgtg atactgttaa ccccatctat caacaaggag ttcaccaggt    141000
gttaagtgat agtacattga tcatatgtat cacttctcac acccagaagg ccgtggagca    141060
aattaaataa tggtgtaagc acagatgggc agatctaggg cggaggctgc cacatgggtg    141120
gggtcttgag atgggataaa tcgagacaag cctcccctgc aaatgcagag aggctgtttc    141180
gaactggcaa catagtgact tagtgagact gccctcacca ctacaccagg cctacccaat    141240
ataagcacaa atgatgcaaa gaaaaagatg tgctgtattt gaaatgtgaa atgtgagctg    141300
attttactat atacatttat ttggttatta caacaagaat atttgatgaa tgcatttaaa    141360
tagttgtggt ttgtacttta tagctactgt gcatgggaaa tgttagttca aatattcaag    141420
caccagtatg aactcaccct tttcatactc cagagcttga agtatcatct caacctggaa    141480
atataacagt gcaacaaagg attacagcat gcaaaggaaa aggaagaagt ggagccatat    141540
gggttagggc cataaatcat aaatgattgc tacattagtt aaatatcctg ccagttatat    141600
gcattgccta ttgaatgatc acaagaacta ccatctgata gcttcagaca gacgttgcaa    141660
tcatgccacc aacttgatgg attgaaatat gaaactgtac cttgtcaaaa tctttgacaa    141720
ccttcgcttc caaagacgca ttctcctcat actccatcca aagttcacga atttcttgtg    141780
ctgcaagaca acagcatgca gataaaggca agtatttatt atatatacca tgtcaaagat    141840
cacatgaact ctttagtctc gcctgtacag agaacatcct tttatcctgc atgaaaaact    141900
gtttccaaaa ggctgctaag atactttatt tagttctaaa aggttcactt cacatgtaag    141960
ggatgctgga tctctccaat attttttaac gattaatgat atgaataatg agaacacaac    142020
cagaatacta gaattctatg ttgtgaaact cttagggaaa aatgttgga tgctatgata     142080
gccatttgag cataaataat ttacgatcca taatgcttca aggtagaaaa tcattagaga    142140
tggaataata ttatcaccat caattacaat atcatgttca aattccaaaa ctcatagtca    142200
tcaacatttg ctgaatataa actcttcggt tttggcttct acaaaaacat cccttatctt    142260
ttcaacctcc atttcaaaat gtagggcgta aggattcaaa aaagtcaatg aaactagtca    142320
aaatatttgt atatttattg cacaaagata aatctataga ttcatatttc acatgcattt    142380
tagtgagaca ttgcttttgt agtaattgat aatatattga gttcatatat tgcaagggaa    142440
attattggat aaaagcatatc tttgaatgaa attctcaaac actaatacac cttataaaaa    142500
gaaaagaga agtataaata acagtttctc tggaaataat ctgagtgatt ttaagttacc    142560
aagagtttcc ttgacaccta actaagggat gtgaatactc taagaattat ccaatactta    142620
tttaaactat gtatcaaaaa ataagaacaa aagctgcccg ctggatttct acaaaataat    142680
tgccaggtta tgatctgctt ccctgatgga agtgaaagt atcggatgga aaatgacca     142740
tctaagaaat aataataaca gatgaatagc ttttcaaggg taaaataaaa tatgtatatg    142800
acctgcaagt actatagtat tgtattcaca aaattcattg gcatccacat attgttcttt    142860
tttccttgaa actatggtac tatgcacaca taatgggatc attaagtcta gactattgag    142920
taatctagaa agatgatgcc agtgtgcaat agcaccacat tcatttcata tataactaaa    142980
tcatgaaaag acaatttgag gcataagatg cctaattaac tacagcataa aatgctaatg    143040
tatcacaatt gcaagtttca gtattcacct cttgaaccac caccaagcag ctcgcacata    143100
tggtccaatg cttctttctc cctgcggttc ttctcttcct tgggtacatt atcagaaggg    143160
gtgatgtcac caacaattgc tggagtacca aagaaaaaa caattgaaat gagtcaactg     143220
aacccacatc ctcataggca gttagttcca gaaacaggca agctggctta ggaacagcag    143280
caagagtcca tatgagcgga gggcaaaatc atgtgttcat ttctaagctg agcatgcttc    143340
tgaatgaaaa taggaaaatg tgcacatagt ttaaagtttt acactttggc tagcagaggt    143400
caaagaacca actaattggc acaagtactt gaacacacat cctacattcc tactacaggt    143460
ctccagtcca gtggtctagt taccatctac caacatctca ggtagtaata ggctcgcata    143520
ttcacaaaat tgcatccctc atctcacaca aagcccaa acttcagtga agccgtctag     143580
acggaagtct tttgagacca taccttctgc aatgtcgtgc acaatcgcca tcttgacaca    143640
cctgtaattg aagggataaa taaacagtgt atgaaacgg aaccgtaaga aggctaaata    143700
ctgccgagct agacttgaga gcgaaactgt caggatcacc tgtcgcggtt gacgccgggt    143760
agatcggccg cgacgagcgc catgacgccc atccggtaca tgtggtcggc caccgactcg    143820
ggcgcctgca ccccgcgctt cacccacccc gccctcttgg tcgtctgcaa ttacatccac    143880
aatctcatcc atcgcgtcac atttccatcc atctcaacca agccggcccg tggaaatgcg    143940
aagcgactaa acaggggcgc tcagtcgctc accttgaggc ggtagcagag cgtgaggaag    144000
tcgatgcgt tggacgccga aggggccggg gcaccgcgt ccaccgatgc ggcggggtc      144060
ggggaggaag aggaggacat ggcggcggcg aggcggtggg ggagcgcgcg gtgagccggg    144120
gcgaagggga cggggtgctg tgggggcttg gcggcggga gatggttggc gagagggag     144180
gagagggaaa gggctcggct cccaccaccc atcgttatta gctgaggccg agtaggcgg    144240
aggagcggtg ggcagcggca ggcaggctcc gcggatggcg gggtggtcgc tcgcggaacc    144300
ggcgcatgcc cgccgcgag cccgtggccc agcttgcgcg gcgggcggac cgtggatcac     144360
gtggggtact gaggttctcc taatttgggc cccagcgcac ggggatcgat cgcgctagag    144420
ggtcttt ttcctttttc attttcgct gccgggccca ttcggccaat cggattccg       144480
gagtctgcaa tgttgcggat agcccatggt tggccaagaa tgcggccgg cccgtgaggg     144540
gtccaccccc acgtggaaat aacaccagcc catcaattta tatgtctttg agtctgaatt    144600
ttaacccagc taaatctgtc gagaacttac agcaagggaa gagattaagc gctgtttgga    144660
tcaaaatatt agactcactt atccaataaa ataggtaaca cagaatttta gatgatatta    144720
tttacagagt tgcgtttaat ataggaataa aatagaggat acaataggg atcagttgga      144780
```

```
gatggcctta tactatcaaa aaatcttatg tgggctaata tcaaacgaga agctctagtc  144840
gtctatataa caaggaaata gttttttgtg cttctgcctc gacaaaaaga gaataagccc  144900
tccattgctg aggagagggt tcaaggtctg aatttggaaa ttgcaccaca gcaagtcctc  144960
ccgccttgcc taattgtctt acatgatagg cttcgtttcc gttcgctgaa taagaagca   145020
cggtatgtcg tttttgaccg ctctagacaa ttgtttagta gattttgttc aaactagatt  145080
gttttctcgc ggtcagatac atattgtaga gtgatttctt actgtcagat acatattgta  145140
gattgattta tgtatacact agcatgttaa atcctgatga tttgacctgc ttaatatatc  145200
caatctatta cttttactta aaaagccatc gatgtcctac taaccgcggg tcgtacgaat  145260
caccccgatg gcgaggctcg tgcgccagtc gcgtgcacta cacacccacc ccaccggtgg  145320
cccacacgtt gcgttcatga atagatcggt catgccggct tctagtcgta cactatgtcg  145380
gcgcccccaa ctctgcgcct tgatgtcaca ctgacccacg cacccatgcc ctgctgctgg  145440
tcacgccatc tcgagctgag atggttcacg ctgcgtcagc ccacgcgcc accccgcact   145500
gggtcgcgct tgctcggcca gctggggcgc agctcgtcgg catatgcttc agccacgcct  145560
cgtcagcacg ccctggaccg gctcccgtgg gtcatgcaat ttatctattt aaattcctat  145620
tattgataat tagcacgcct aattaaccta aagttaattt tgtgtgacgg actatggttg  145680
aagacaacag aattgattcg tggagcttgt cctcaatggc aagaactaac cgacctagac  145740
taacgactgc aagtttcacc tagaggcgat atagctagga aggagatct tctggtaggg   145800
cccgaatgac acttgcctga aacttcatga gaaagcaaaa attacgatct tcgtcgggca  145860
ccacatccat ccaggcctga agatggagta tccagaggtg aaagaccata tgatattgtg  145920
gacagagcta tgtgagtgtt tcagtgtgga gaagcatgtg atgctcccgc gggcgcaaca  145980
tgaatgggcc actctcgact tcaatgcagt tgaggcttac aacactgtca tccatcgcat  146040
tgtcgctcag ctacatttct gtggccagat agccatagac ttagagatga tcgagaaaac  146100
tctccaaacc ttctaccct ccaatatggt gctccaacag cagtactgta gcaacaagta   146160
cacaaataat gtgacctcgt caacatgttg cttggtgcta aggctcagaa tgagcttctg  146220
atgcagaact actagaagca tccattcggc acgcggtcat gcataaagca cacgccaact  146280
tctagtctta aaggaagaaa ggtccctcca gagaaagtgg tcatgggcac tgtaataatc  146340
aggggatgag aggggaatt tttacgaagc caccacaaaa tggcagtaga gtagcaatgg   146400
ctatggcaaa ggcaaaggca aaggcaaaac ctcagaaggg ctatgcaagc tcctcaaagc  146460
atgccagtga aggttgtttc aaagaaacac ttgattggca tgtatcagga gtggaagaaa  146520
cgcatagctc ataggctcac cttatttatt catgcatcta tacacgctat gattatagag  146580
cctatgtaac accctgaatt tgggggtata aaatttcttc tctaatatct accaaattca  146640
ggtgttacca cttttctcat ctccgtagat ttcctatttt cttcctttct aatagagttt  146700
tggttatata tttgggagat gtatttttt tctttactat attcaaacct aggggagaca   146760
tgaattgttg catcatgctg agcttaaact ttgttttgg ttgatgcaca tgtttgaaat   146820
attcaaattt gaatttgtgg tttcgttgga tttgaattca atagagaaaa taaaaataaa  146880
aggaactaga aattcagaat aaaaagaaaa tagaaaagca gcccagccta cgcacctgcc  146940
ctctctctcc atctgccagg tgggcccgac ctattggtgc cgctcaccct cgcgcgcacg  147000
ccccccgctct ccctctgtgc agtgggccca gcccatcagc gctgaatcat ttcctcctca  147060
cacgtgctcg tgcctctact ctgtgggccc gccttgtcag tctcatcttc cccgcaaccg  147120
ctgctgaccc gcacacgcac tcacgccgag gaagccgacc acgttgccta cccacgcccc  147180
cagctccctt ttgagcccg cctacaccg ctctccctcc ccttcctaat ttcacccact   147240
ctcaacctct ctcgcgctta gccgccgccg ctcaagctcg ccggagaagc gcgccaccgc  147300
gtcgtctgcc cggagctcc agcatcgtgt caagcatccc cgagcacact cctaaggtaa  147360
ggaaccatcc ccgtgccctt cctgcccga ttcttttccc tctacggtga atttgtgttc   147420
gctggagctc tatcgcgctg gtttgccgcg cccgctcggt gtccgaccga ttcagccccg  147480
ccccgtgccc gtgccttggc cctaggcgtc cctcacccct caccgaagct tgtgctggcc  147540
tcggtgcacc ggattccgcc tcctcacggt cgggattgct caccggagta acccccgacct  147600
gtggcagaac ctcccaagtt attaggccca catgcaccta tccttgtccc aaagacctca  147660
gaccccaaaa aacgtgcacc agataactta acaggatctg taagatctac caaaggacat  147720
cggataaacc acttacaacc agaaccgcga gaaacgaat cccaaatcac acacaccaat   147780
attgttgcag cgaacatctt actaccaaat tttacaggtt acaaaaattt tacattagtt  147840
tatcggagtg attacaaaag tataagtttg aaatatatat gctagctcaa gggatcatcc  147900
tcaataagaa gtatagaagg gttacttaga ctcataagaa ggccgagccc accggcactt  147960
aacaccatca acaacagcac aaagttagaa cctgaaaaac aacaaggaat aaaaccctga  148020
gtatggaatt actcagcaag tcttacccga ctaaagaaaa gactctcaag ggtatgctgg  148080
ttatatggga gtcaaggtaa ggcttttcaa taatcaaaga ctctgttttg cagaaatgct  148140
tactaaagtg gatccttaaa atccagtttt atttgtcaag ttaagtagaa ttacctgtaa  148200
ctagagttct ttctacccta gttcaatcac ttgtcctgca ctagccaatt tcttaacaaa  148260
aacccatcat cttttagtgga atgctacgtg taggggcagtg accaagtcgtt cataaccacg  148320
aaggtacggc gatccgaatc gattatactt agctgaggat atggaaatgct ctccaatcac acgacatatg  148380
tagcacttaa cccttgcata tgtcaacccg ccaccggggt tcttaagacc agatcaggtt  148440
cacgcaaacc gagagcacag ttacaccacc gtccagcctc ttgccacgga ggtacacgct  148500
actctcgcca ccgctccacg cccatttcgt gnnnnnnnnn nnnnnnnnn nnnnnnnnnn    148560
nnnnnnnnnn nnnnnnnnnn nnnnnnnnnn nnnnnnnnnn nnnnnnnnnn nnnnnnnnnn   148620
nnnnnnnnnn nttcagggat taaacaatgt cattttgaga aagactggat tgtagagca    148680
taccagtcgg aagcaagtgg cactcatcat ccacacacga acaaaaagac aacgaccgcc  148740
cagtgaagat cctcccccaa agcaacagtc aagcatccct gacagaactc ttaacgtaag  148800
taagtacctt caggccctc ctgccccgat tcttttccct ctacggtgaa tttgtgttcg   148860
ctggagctct atcgcggtgg tttgccgcgc ccgctcggtg tccgaccgat tcagccccga  148920
cccgtgcccg tgccttggcc ctaggcgtcc ctcacccctc accgaagctt gtgctggcct  148980
cggtgcaccg gattccgcct cctcacggtc gggattgctc accggagtaa ccccgacctg  149040
tggcagaacc tcccaagtta ttaggcccac atgcacctat ccttgtccca aagacctcag  149100
acggctgtgc atgtgcacca gataacttaa caggatgtgt ccgattgccc caaggacatc  149160
ggataaacca atttcaacca gaaccgcgag attaagtcct caacacacgg ataca          149220
aagtggtagc ggaaatatta ttgacaaatt tgacaggtta cacaaatttt tcatacctct  149280
atcggaggga atacaaaatt ctaagtctga aatataaatg ctagctcaag ggatcatcct  149340
caataagaag tatagaaggg ttacttagac tcataagaag gccgagccca ccggcactta  149400
acaccatcaa caacagcaca aagttagaac ctgaaaaaca acaaggaata aaaccctgag  149460
tatggaatta ctcagcaagt cttacccgac taaagaaaag actctcaagg gtatgctggt  149520
```

```
tatatgggag tcaaggtaag gcttttcaat aatcaaagac tctgttttgc agaaatgctt   149580
actaaagtgg atccttaaaa tccagtttta tttgtcaagt taagtagaat tacctgtaac   149640
tagagttctt tctaccctag ttcaatcact tgtcctgcac tagccaattt cttaacaaaa   149700
acccatcatc tttagtggaa tgctacgtgt agggcagtga ccaagtcttc ataaccacga   149760
aggtacggcg atccgaatcg attatactta gctgaggatc tccaatcaca cgacatatgt   149820
agcacttaac ccttgcatat gtcaaccgc caccggggtt cttaagacca gatcaggttc   149880
acgcaaaccg agagcacagt tacaccaccg tccagcctct tgccacggag ggtacacgct   149940
actctcgcca ccgctccacg cccatttcgt gttatcttat tctggcctta gtctgcccga   150000
ggcaaggctt acccatgacg aggcatgtga ccagttaaag ggtcctcgat catcaagcct   150060
acatcgacaa ggtccttaat cgactcagac ggagacacta caccgagact cctttcccgt   150120
gcaagtcacc cgcccggtct tagcttaatc ttttaaccca aaaacttggt acctggcaga   150180
ggtacatctt ttccgatgtt gaatccatca tagccatgat ggattcacca tcaagtttta   150240
ttttttgaaaa caaccctccc actttgccaa acatcttttc taaaacaaat cctttttgttt   150300
ttctaagcaa tactaagcat agtaaaacct ttttgtaaaa acgggttttc aaggagggta   150360
atcaagatca aggaaggtaa tgcaggaatt gtttaatcaa tcaactcctg tcacctaatg   150420
cagcaatcaa gtgagaaaga ttttaaaaac atcaagggag gtggcaaatg caccggggct   150480
tgcctgggta acactaggtt agtgttgtta gacgatgtcc acttggcgac cattttcagg   150540
tttgtccatc agcatcatcc tgcggattag cccgcgcttg gggtcgactt ggcttgtctt   150600
ccgcatcacg cgatcaatta tcgtacctaa ttgagatgca cgatgcacat gaatgcatat   150660
aaacaagaat agcacaaatc taaatagtgc tatacgatag cgtattaaac acctagtggc   150720
gaggcgttgt acaattttgt acagaaacac tagttattaa tatgcgacta cgcacaatga   150780
ttacgcttct cgaacctaac gcaaacatca cgaacaacaa actatacaca agaaatataa   150840
ttagcctaat cacaacttat cagttaatta attaaattct gaactaatcc cttgccttat   150900
aaattatact acatctttat aagtgattaa aatatttat caacacatat gcctactaaa   150960
attctactcg gtcactaat tcagctaagt gaccgaaata cgaaataac tcgctataac   151020
tgaacctggc tcgataatcg caagaactgc gaagtcgaca agagtttcgt gacttacgca   151080
atttatcgag caccctaatg agcctcgcac taacacatta acttattcaa cgatcgaact   151140
attctaaaca attcattagc ttaccgaact attctaaaca attcatcagc ttaccgtttc   151200
aacagctgac acgaatccgt gagatcggca gtgattttc gatccacgca atttgtcgag   151260
cgcttaggga atatcgcgct gctaacttcg tcttcacccg attcttgggt tttcttgggg   151320
acgcacgagc gacgatgacc ttcgattgaa gtctgggta agctggtgag gtggggatcg   151380
agccggagat gacgtgtttg acaactcgac ggcaaacgac gagatcgacg acgtgattgg   151440
aaattaaagc cgagcgagcc gagagggcac gctggcgagc aggaaaccgt gcgagcacaa   151500
gacaggaaaa acgacggctc gacaaacacg gaagcgacga cagtcaaatc ggcaacaaag   151560
cgttggcgaa ttcgatgaac acgaccacag tcgcgagtta acgcggtcaa gacaactgtg   151620
accaacgagc ttgcgacaga agtgatgatg gtgtgggaac tcgacacgct gtgacgagca   151680
gataaaattc gtgcgcgcgg caacaaagaa agagcgagct gcgcgtgagc agagagctcc   151740
acacgaaaac tcgacgcgcg caggaactac ggcgagctag agtagagaaa actcgacgcg   151800
cgcaggaact acggcgagct agagtagaca atcatgggag atgtagtcat gtagagccga   151860
gctgggcgac aaagcgaaat ccaggctgaa gcgttgacga gcaaagagct tcgcgcgtgc   151920
aagaacaaca gaacgctatg cgcgcgacgc aaaggcgagc agtaagacga cggcgcgaca   151980
gacggaacca agcaggagc gccggccatg ggcgcggcaa tagagctggg cgagctcgga   152040
ggggaagcca cggcacaaga aatccgatca ggcgcggccg aacagaggtg ccgcggcaca   152100
ggagctcagg gacggacgag caggagcaga ggagatggat accgcgagca gcctgcaggg   152160
aaccccgcgc catgggagaa aagcagagcc gagcggctgg ggattcagcc agcgagcaga   152220
ggggagatgg gaaggagctg ctcggctgcg gcttgctgcc gggcgtgcgt ggagaagaaa   152280
cctgcgcgct ggagatttgt aggagaccaa gggcggtggc ggataaggga taggagcgct   152340
cggcggcgtg atttttattt ctaggggttg cgcggcgcgg tacagaaaaa tcaggcgacg   152400
agattaaaga gatgcagtga gcagttcgac aaattcgtcg gcatggacac aagctgacga   152460
cgacggccaa cccgaccgcg gcaaggtgag gggagacgcg gtctgcgcaa agggcgagct   152520
cgagcaagga actagagccg acgatgtcca cgacgagcag gaccagagac acggtgctag   152580
tggatggaaa ctgagcacag gatgatgca agctggagac gagcttggtc aggtcgtcgg   152640
gcacagaggt gctcggaggg tccgacgagc acagccggct gccggctgcc tttgatgct   152700
gatggatgga agaaatgctg gtcgctgggt aaggctggag gagagacgtg cgtgagattt   152760
tccagcgcga tagcgtccaa tggataagag agaaggagac gtgaggaaga ggagaactac   152820
gtggagaaaa tatccaggct agtgacttca gatatgaag gggaaagcgg tggataaaat   152880
cagagagaag agcggttgca gatattttct tccttcgttt tcttttactc gaaaatttga   152940
ataaaaatac aattatcagc tggagattgg gactagaatt tggaaagatg taagaggact   153000
aaaattaaaa atgattttag ttacaatgtt ttaatcggtg ttacatttaa ttgaaatcag   153060
ataaaaactt atccgtcacc aaaacacagt tgatttggtt atcctacatt gcgggctaaa   153120
gaacaaatta gatcatattg aaagggaatt aggcttacac ctagttccta ataattttg   153180
gtggttgaat tgcccaacac aaatctttttg gactaacttg tttgcccaag tgtatagtgt   153240
atacaggagt aaaaggttca cactcagcca ataaaaagac caagttttgg attcaacaaa   153300
agagcaaagg ggcaaccgaa ggcaccctg gtctggccga ccggactgtc cggtgtcgca   153360
ccggacagtg aacagtacct gtccggtgca ccaggggact cagactcaaa ctcgccacct   153420
tcgggaattt ctaaggcgac tcggctataa ttcaccggac tgtccggtgt acccggaca   153480
gtgtccggtc cgcaagggga ggtcggcctc aggaactcgc tagcctcggg ttcgcgcggc   153540
agccgctccg ctaaaattca ccggactgtc cggtgtgcac cggactgtcc ggtgtgccag   153600
cggagcaagg gctccctgcg gcgccaacgg ctccctgcgg tgcatttaat gcgcgcgcag   153660
cgcgcgcaga cgccaggcac gcccataccg gtgcaccgga catcaaattc cagatgtccg   153720
cagtccgcta cacactggta ttgtgaagcc cataaaattt accgatggct cgatcccgta   153780
tggaaattg acaatttgtg aagaaccctc cagcttgtct gttgcattgt ttgacccaaa   153840
ctggaaagc tgccatggac ctagaatttt ctgcccttat cgggaataaa acatggcact   153900
tcctccc cgcacctgac agaaatttga ttgattgcaa gtgggtttat aaactcaaga   153960
gaaaagctga tgagtctatt gaccatcata aagctcgatg ggtgggctaaa tgttttaaac   154020
agcttnnnnn nnnnnnnnnn nnnnnnnnnn nnnnnnnnnn nnnnnnnnnn nnnnnnnnnn   154080
nnnnnnnnnn nnnnnnnnnn nnnnnnnnnn nnnnnnnnnn nnnntgaaa ctagagattc   154140
gtcctcagct ggtttaggcg tgagcagaag gattgtcccc tcatataagg accggtttgt   154200
catcttcact acctgtactc tttaatagta caaccactcg agactgtgtg ggcagtcact   154260
```

```
caatctgaac tcgtacggtc caaccccagg gttatgaagg ctggggagca ccgggaggat    154320
aaggaggggg aaagttttgt ccggtttgga catggtggtg gcctgactcc ttcaggataa    154380
ccattaaggt taggacatgc ggggaaagaa agagagtcgg attcgggtct cattgatcat    154440
gggatcgcag agctggacta gtgggtaaag tgtacacctc tgcgcagagt ttgaaaacct    154500
attcgaatag tctgtgtcca caggaatgga cgagtctgat atggtatggc aattaatgtt    154560
ttgttttcca aaaaaaagag atgcttttga aaagtggttt ttaaaaggtc cggcggttga    154620
gccgtgagct atggtggacg ggaagtccag tagctgtttt tgaaaatgaa aaccagtggg    154680
aaactgctga gatacctgga tggtttagtc caggggattt tgttataata ctgaaaaact    154740
tcctgctcct tttggagagg atgcactttg caaaatacaa aatgtttttc aaaacaaaca    154800
tgcataaaat attgctgttt ctgcaaatat cctgagctct acatattcca tgcattatat    154860
ctgatttccc cattccgcgg gtgaaggtgg gctgctgagt acgtttgtac tcacccttgc    154920
ttatttgttg tttttcagaa aaagagatc gggtaagagt tacgactgtt cccaaccttg    154980
cctgtggctg ttggaccgct gaattgcttc actgcgtata tcgggctgct tcagcccgac    155040
tctgatgata tgtcccgagt tgtggaccaa ctcttaaagt cgtgccac ctttataggt    155100
ttgtctcgtt taagcagatc tgaatcatct gatgtataaa tgtgtttact agcctcctgg    155160
gactagtaat tgtatcacat ttgagtccca gaggattggg gacgcttcaa gctgtggcag    155220
aacctcccaa gttattgggc ccacatgcac ctgtccttgt cccaaagacc tcagacggct    155280
gtgcatgtgc accagataac ttaacaggat ctgtccgatt gccccaagga catcggataa    155340
accacttaca accagaaccg caggattaag taacacaaat cacacacacc aatattgttg    155400
cagcggaaat cttactacca aattttacag gttacaaaaa ttttacatta gtttatcgga    155460
gtgattacaa aagtataagt ttgaaatata tatgctagct caagggatca tcctcaataa    155520
gaagtataga agggttactt agacttataa gaaggccgaa cccaccggca cttaaccaca    155580
tcaacaacag cacaaagtta gaacctgaaa aacaacaggg aataaaaccc tgagtatgga    155640
attactcagc aagtcttacc cgactaaaga aaagactctc aagggtatgc tggttatatg    155700
ggagtcaagg taaggctttt caataatcaa agactctgtt ttgcagaaat gcttactaaa    155760
gtggatcctt aaaatccagt tttatttgtc aagtaagta gaattacctg taactagagt    155820
tctttctacc ctagttcaat cactggtcct gcactagcca atttcttaac aaaaacccat    155880
catctttagt ggaatgctac gtgtagggca atgaccaagt cttcataacc gcgaaggtac    155940
ggcgatccga atcgattata ctcagctgag gatctccaat cacacgacat atgtagcact    156000
taacccttgc atatgtcaac ccgccaccgg ggttcttaag accagatcag gttcacgcaa    156060
accgagagca cagttacacc accgtccagc ctcttgccac ggagggtaca cgctactctc    156120
gccaccgctc cacgcccatt tcgtgttatc ttattctggc cttagtctgc ccgaggcaag    156180
gcttacccat gacgaggcat gtgaccagtt aaagggtcct cgatcatcaa gcctacatcg    156240
acaaggtcct taatcgactc agacggagac actacactga gactccttcc ccgtgcaagt    156300
caccccgcccg gtcttagctt aatccttttaa cccaaaaact tggtacctgg cagaggtaca    156360
tctttttccga tgttgaatcc atcatatcca tgatggattc accatcaagt tttattttg    156420
aaaacaaccc tcccactttg ccaaacatct tttctaaaac aaatccttt gttttctaa    156480
gcaatactaa gcatagtaaa acctttttgt aaaaacgggt tttcaaggag ggtaatcaag    156540
atcaaggaag gtaatgcagg aattgtttaa tcaatcaact cctgtcacct aatgcagcaa    156600
tcaagtgaga aagattttaa aaacatcaag ggaggtggca aatgcaccgg ggcttgcctg    156660
ggtaacacta ggttagtgtt gttagacgac gtccacttgg cgaccatttt caggtttgtc    156720
catcagcatc atcctgcgga ttagcccgcg cttggggtcg acttggcttg tcttccgcat    156780
cacgcgatca attatcgtac ctaattgaga tgcacgatgc acatgaatgc atataaacaa    156840
gaatagcaca aatctaaata gtgctatacg atagcgtatt aaacacctag tggcgaggcg    156900
ttgtacaatt ttgtacggaa acactagtta ttaaatgcg actacgcgct atgattacgc    156960
ttctcgaacc taacgcaaac atcacgaaca acaaactata cacaagaaat ataattagcc    157020
taatcacaac ttatcagtta attaattaaa ttctgaacta atcccttgcc ttataaatta    157080
tactacatct ttataagtga ttaaaatatt ttatcaacac atatgcctac taaaattcta    157140
ctcggtccac taattcagct aagtgaccgg aatagcgaaa taactcgcta taactgaacc    157200
tggctcgata atcgcaagaa ctgcgaagtc gacgagagtt tcgtgactta cgcaatttat    157260
cgagcaccct aatgagcctc gcactaacac attaacttat tcaacgatcg aactattcta    157320
aacaattcat cagcttacta aactattcta aacaattcat cagcttaccg tttcaacagc    157380
tgacacgaat ccgtgagatc ggcagtgatt tttcgatcca cgcaatttgt cgagcgctta    157440
gggaatattg cgctgctaac ttcgtcttca cccgattctt gggttttctt ggggacgcac    157500
gagcgacgat gaccttcgat tgaagtctgg ggtaagctgg tgaggtgggg atcgagccgg    157560
agatgacgtg tttgacaact cgacggcaaa cgacgagatc gacgacgtga ttggaaatta    157620
aagccgagcg agccgagagg gcacgctggc gagcaggaaa ccgtgcgagc aagacagg    157680
aaaaacgacg actcgacaac acgcgaagcg acgacagtca aatcggcaac aaagcgttgg    157740
cgaattcgat gaacacgacc acagtcgcga gttaacgcgg tcaagacaac tgtgaccaac    157800
gagcttgcga cagaagcgat gatggcgtgg gaactcgaca cgctgtgacg agcagataaa    157860
ttcgtgtgcg cggcacaaga tagagcgagt gctcgtgagc agagagctcc acacgaaact    157920
cgacgcgcgc tgactacgcg agctagagta gagaaactcg acgcgcgcag actacgtgag    157980
ctaagtagac agtcatggag atgtagtcat gtaaagcgag ctggcgacaa cgaatcagnn    158040
nnnnnnnnnn nnnnnnnnnn nnnnnnnnnn nnnnnnnnnn nnnnnnnnnn nnnnnnnnnn    158100
nnnnnnnnnn nnnnnnnnnn nnnnnnnnnn nnnnnnnnat ttattctaac catttcatca    158160
gctttataaa ctattctaaa caattcatca gcttaccgtt tcaacagctg acacgaatcc    158220
gtgagatcgg cagtgatttt ttcgatccac gcatttgtcg agcgcttagg gaatattgcg    158280
ctgctaactt cgtcttcacc cgattcttgg gttttcttgg ggaacgcacg agcgacgatg    158340
accttcgatt gaagtctggg gtaagctggt gaggtgggga tcgaccggga gatgacgtgt    158400
ttgacaactc gacggcaaac gacgagatcg acgacgtgat tggaaattaa gccgagcga    158460
gccgagaggg cacgctggcg agcaggaaac cgtgcgagca aagacagga aaacgacga    158520
ctcgacaaca cgcgaagcga cgacagtcaa atcggcaaca aagcgttggc gaattcgatg    158580
aacacgacca cagtcgcgag ttaacgcggt caagacaact gtgaccaacg agcttgcgac    158640
agaagcgatg atggcgtggg aactcgacac gctgtgacga gcagataaaa ttcgtgtgcg    158700
cggcaacaaa gaaagagcga gttgcgcgtg agcagagagc tccacgcgaa aactcgacgc    158760
gcgcaggaac tacggcgagc tagagtagag aaaactcgac gcgcgcagga acttcggtga    158820
gctagagtag acagtcatgg gagatgtagt catgtagagc cgagctgggc gacaaagcga    158880
aatccaggct gaagcgttga cgagcaaaga gcttcgcgcg tgcaagaaca acagaacgct    158940
atgcgcgcga cgcaaaggcg agcagtaaga cgacggcgcg acagacggaa ccaagcaggg    159000
```

```
agcgccggcc atgggagaaa agcagagccg agcggctggg gattcagcca gcgagcagag    159060
gggagatggg aaggagctgc tcggctgcgg cttgctgccg ggcgtgcgtg gagaagaaac    159120
ctgcgcgctg gagatttgta ggagaccaag ggcggtggcg ggataaggat aggagcgctc    159180
ggcggcgtga ttttattc tagggggttgc gcggcgcggt acagaaaaat caggcgacga    159240
gattaaagag atgcagtgag cagttcgaca aattcgtcgg catggacaca agctgacgac    159300
gacggccagc ccgaccgcgg caaggtgagg ggagacggcg tctgcgcaaa gggcgagctc    159360
gagcaaggaa ctagagccga cgatgtccac gacgagcagg accagagaca cggtgctagt    159420
ggatggaaac tgagcacagg atggacgcaa gctggagacg agcttggtca ggtcgtcggg    159480
cacagaggtg ctcggagggt ccgacgagca cagccggctg ccggctgcct ttggatgctg    159540
atggatggaa gaaatgctgg tcgctgggta aggctggaga agacgtgc gtgagatttt    159600
ccagcgagct agcgtccaat ggataagaga gaaggagacg tgaggaagag gagaactacg    159660
tggagaaaat atccaggcta gtgacttcag atatggaagg ggaaagcgat ggataaaatt    159720
agagagaaga gcggttgcag atattttctt ccttcgtttt cttttactcg aaaatttgaa    159780
taaaaataca attatcagct ggagattggg actagaattt ggaaagatgt aagaggacta    159840
aaattaaaaa tgattttagt tacaatgttt taatcggtgt tacatttaat tgaaatcaga    159900
taaaaactta tccgtcacca aaacacagtt gatttggtta tcctacattg cgggctaaag    159960
aacaaattag atcatatccc cgcgcacgat cttctcaga caatgcgcga ttcggattat    160020
tttaccctga acatttagt cgtcaagttc aaatttttt gctcggaata agatcattcg    160080
agtgagttcg ggcttccgaa ttcgtgttcg cgcgagcgat ggatttaaa tactcatcgg    160140
acgcaccgat tttcggaaca gctaggttcc gaacattacg aaatttagg aagagcccgg    160200
acagataaaa aaataaaaac gatgtcgcac tcgcgacaaa cgacaccgat gcgatattaa    160260
aatcgcgata agcgacgatg attaaaattt aaaatccgtt ttatccactg atattgcgtg    160320
cttaaatccg aactcgttgt tgagcggaaa ataaacacct ggggtgttac agccctcccc    160380
ccttaaaaga atctcgtccc gagattcaaa acgaaagact tctaagagta gagaagcatg    160440
taacccatgt ccatatcagc gataatcatg agacaattcc aaacaaagtc gagtgtctca    160500
aaatgtcgtt cctctagtgg acataacatg tgtcgcctta ggctaattta gaaatgtcca    160560
ccaatagaga cgatgtctgc cagaagtaca cataaggttc catgtgtgca gtttactttt    160620
tctgatgaca ctgtaaatatc tgagtctgtt gagcgagtgg tagatatgca acttacaca    160680
aacagaatca gatgcaacct cttgggtaaa acacacagaa agagatttac caacaagtgg    160740
tcacggtaag ttcatagcac acgagacgag tgtggatgtc gaataacatc acagttaact    160800
cgtgttagcc agagaatcca agtccaagaa aaatgataaa gacttgaaaa aaattaccag    160860
cagagggatc tgtaaatgct gccttcgcaa ccaatccatt ttatcaagca ctaatcatgg    160920
atctacttga tcacacatgc tggaaaagca cacgtgagac gatcgaggca tgactagagc    160980
gatgtttagg tggttactgg ccgacttaat ctcgattctt gaaagtactt ccttaggatg    161040
gtttggacca tagcgagttt agataactcg atgaaacgat ctctaaactc gaccttcgtt    161100
cacaaagcag ttacaagtta gtaaaaccaa cttgttaaac tacttttgac attgagcaag    161160
tcctctcagt accattggta atccaagggt tgagagttca catttgctaa caggaaatca    161220
tgcacttggg tagaaatcca tttggtcacg ttgttcatcc gtttcttcta tacaagatga    161280
accgacttgg ttagggaata catggattaa ataagagagc gaatgaacaa attcttgcat    161340
ttcagcagca ggggaaacaa atctccattt tgggaactaa ttggttgtct tgcaacacta    161400
aaaagctcca aggcttcacc tttacacaaa ggatgtaaag ggaacttgta tgtgtgaagt    161460
caccatcaaa gtcaagagat aagagatcac acatgaaagt ggtatgccct tttgatccac    161520
agagatgata gatgttgctt gatcacttga caaacaacat agaaaattgtt tcaagggagg    161580
actccacgga agatcacaca tcagtgtact tccacaatgg atcatgacca cagaccttga    161640
taccagcatc cgatgagtgg cacagtccta tgtgcgcatt cacaggaggc tctcagtttt    161700
cgttgcggca ccataagtca ttaatcatga ccaccactac cgaagctg               161748

SEQ ID NO: 104           moltype = DNA   length = 634
FEATURE                  Location/Qualifiers
source                   1..634
                         mol_type = genomic DNA
                         organism = Zea mays
SEQUENCE: 104
caatccaggg ccaggccagg ccaggccaac caaaccctag gcactgcgcc acgcctagcg     60
cgcgtggtat ccatgggctg accgcgtccc ggtggggagc ccggatccgg agctaggggtt   120
ccgtcctagg cggcaccacc atggagtggg acagcgagtc cgacggcgcc ggcagcgtcg   180
acgccggcta tgaggagcag gaggaggagg aggaggagcg gggaggcgag ggtggaggtg   240
gcgacgccgg gggcggcggt gggatgttca cgttcgcgat tgaaggcatg ctgcgctcct   300
ccgggccctg cgggctagtc gtcaccgacg cgctcgagcc cgattgcccc atcatctacg   360
tcaaccgcgg cttcgaggag gccacggggct accgcgccga ggaggtcctc ggcaggaact   420
gccgatttct gcagtgcaga gggccattcg ctcgaaggag gcaccccta gttgatgctg   480
cactggtttc agagattcga agatgcatag acaatgcat tgattccgt ggtgatttac    540
taaatttcag aaaagatgga tctccagtga tgaacagatt gcatctgacc cctatttatg    600
gagatgatga aaccataacc cattatatgg gcat                                634

SEQ ID NO: 105           moltype = DNA   length = 20
FEATURE                  Location/Qualifiers
misc_feature             1..20
                         note = Primer
source                   1..20
                         mol_type = other DNA
                         organism = synthetic construct
SEQUENCE: 105
accaccatgg agtgggacag                                                20

SEQ ID NO: 106           moltype = DNA   length = 21
FEATURE                  Location/Qualifiers
misc_feature             1..21
                         note = Primer
```

```
source                     1..21
                           mol_type = other DNA
                           organism = synthetic construct
SEQUENCE: 106
ttcaatcgcg aacgtgaaca t                                                  21

SEQ ID NO: 107             moltype = DNA   length = 388
FEATURE                    Location/Qualifiers
variation                  188
                           note = n is a, c, g, or t
variation                  219
                           note = n is a, c, g, or t
source                     1..388
                           mol_type = genomic DNA
                           organism = Zea mays
SEQUENCE: 107
ctgaacaaga tcgaccaaac agttcattca ccagctagaa aatgtgttca aataggagtg         60
gcagaaaaat aacacggttt accagattat actgtcacaa actgttaccg aacacttaaa        120
acaaagacta gatgttcccc aaaactgatg acaaagcaca gctcctcagt acttgatagg        180
ggcaagantc tccaactgag accccaactt ctcctcggnt gccttctcgg ccttgacacg        240
cagcttggcc aattgcttct tcctctcgta ggcaaccttg ggccttctcc ttgctctttc        300
tcctcaagtt ccctgatggt gtcatggtag ttccacccgg cctccttaga gagctcgccg        360
aggaggcagt acttgtgtcc aggctgta                                           388

SEQ ID NO: 108             moltype = DNA   length = 21
FEATURE                    Location/Qualifiers
misc_feature               1..21
                           note = Primer
source                     1..21
                           mol_type = other DNA
                           organism = synthetic construct
SEQUENCE: 108
cgaccaaaca gttcattcac c                                                  21

SEQ ID NO: 109             moltype = DNA   length = 19
FEATURE                    Location/Qualifiers
misc_feature               1..19
                           note = Primer
source                     1..19
                           mol_type = other DNA
                           organism = synthetic construct
SEQUENCE: 109
ctcctcggcg agctctcta                                                     19

SEQ ID NO: 110             moltype = DNA   length = 161748
FEATURE                    Location/Qualifiers
variation                  3611..3710
                           note = n is a, c, g, or t
variation                  7624..7723
                           note = n is a, c, g, or t
variation                  13118..13217
                           note = n is a, c, g, or t
variation                  70085..70184
                           note = n is a, c, g, or t
variation                  94587..94686
                           note = n is a, c, g, or t
variation                  117477..117576
                           note = n is a, c, g, or t
variation                  128130..128229
                           note = n is a, c, g, or t
variation                  151880..151979
                           note = n is a, c, g, or t
variation                  155542..155641
                           note = n is a, c, g, or t
variation                  159499..159598
                           note = n is a, c, g, or t
source                     1..161748
                           mol_type = genomic DNA
                           organism = Zea mays
variation                  25477..25576
                           note = n is a, c, g, or t
variation                  143525..143624
                           note = n is a, c, g, or t
SEQUENCE: 110
cagcttcggt agtggtggtc atgattaatg acttatggtg ccgcaacgaa aactgagagc         60
ctcctgtgaa tgcgcacata ggactgtgcc actcatcgga tgctggtatc aaggtctgtg        120
gtcatgatcc attgtggaag tacactgatg tgtgatcttc cgtggagtcc tcccttgaaa        180
caatttctat gttgtttgtc aagtgatcaa gcaaactctca tcatctctgt ggatcaaaag        240
ggcataccac tttcatgtgt gatctcttat ctccttgactt tgatggtgac ttcacacata        300
```

```
caagttccct ttacatcctt tgtgtaaagg tgaagccttg gagcttttta gtgttgcaag    360
acaaccaatt agttcccaaa atggagattt gtttcccctg ctgctgaaat gcaagaattt    420
gttcattcgc tctcttattt aatccatgta ttccctaacc aagtcggttc atcttgtata    480
gaagaaacga atgaacaacg tgaccaaatg gatttctacc caagtgcatg atttcctgtt    540
agcaaatgtg aactctcaac ccttggatta ccaatggtac tgagaggact tgctcaatgt    600
caaaagtagt ttaacaagtt ggttttacta acttgtaact gctttgtgaa cgaaggtcga    660
gtttagagat cgtttcatcg agttatctaa actcgctatg gtccaaacca tcctaaggaa    720
gtactttcaa gaatcgagat taagtcggcc agtaaccacc taaacatcgc tctagtcatg    780
cctcgatcgt ctcacgtgtg cttttccagc atgtgtgatc aagtagatcc atgattagtg    840
cttgataaaa tggattggtt gcgaaggcag catttacaga tccctctgct ggtaattttt    900
ttcaagtctt tatcattttt cttggacttg gattctctgg ctaacacgag ttaactgtga    960
tgttattcga catccacact cgtctcgtgt gctatgaact taccgtgacc acttgttggt   1020
aaatctcttt ctgtgtgttt tacccaagag gttgcatctg attctgtttg tgtaaagttg   1080
catatctacc actcgctcaa cagactcaga tattacagtg tcatcagaaa aagtaaactg   1140
cacacatgga accttatgtg tacttctggc agacatcgtc tctattggtg gacatttcta   1200
aattagccta aggcgacaca tgttatgtcc actagaggaa cgacattttg agacactcga   1260
ctttgtttgg aattgtctca tgattatcgc tgatatggac atgggttaca tgcttctcta   1320
ctcttagaag tctttcgttt tgaatctcgg gacgagattc ttttaagggg ggagggctgt   1380
aacaccccag gtgtttattt tccgctcaac aacgagttcg gatttaagca cgcaatatca   1440
gtggataaaa cggattttaa attttaatca tcgtcgctta tcgcgatttt aatatcgcat   1500
cggtgtcgtt tgtcgcgagt gcgacatcgt ttttattttt ttatctgtcc gggctcttcc   1560
taaattttcg taatgttcgg aacctagctg ttccgaaaat gcgtcgtcc gatgagtatt   1620
taaaatccat cgctcgcgcg aacacgaatt cggaagcccg aactcactcg aatgatctta   1680
ttccgagcaa aataatttga acttgacgac taaaatgttc agggtaaaat aatccgaatc   1740
gcgcattgtc tgagaaagat cgtgcgcggg gatatgatct aatttgttct ttagcccgca   1800
atgtaggata accaaatcaa ctgtgttttg gtgacggata agtttttatc tgatttcaat   1860
taaatgtaac accgattaaa acattgtaac taaaatcatt tttaatttta gtcctcttac   1920
atctttccaa attctagtcc caatctccag ctgataattg tatttttatt caaatttcg   1980
agtaaaagaa aacgaaggaa gaaaatatct gcaaccgctc ttctctctaa ttttatccat   2040
cgctttcccc ttccatatct gaagtcacta gcctggatat tttctccacg tagttctcct   2100
cttcctcacg tctccttctc tcttatccat tggacgctag ctcgctggaa aatctcacgc   2160
acgtctctcc tccagcctta cccagcgacc agcatttctt ccatccatca gcatccaaag   2220
gcagccggca gccggctgtg ctcgtcggac cctccgagca cctctgtgcc cgacgacctg   2280
accaagtcg tctccagctt gcgtccatcc tgtgctcagt ttccatccac tagcaccgtg   2340
tctctggtcc tgctcgtcgt ggacatcgtc ggctcagtt ccttgctcga gctcgccctt   2400
tgcgcagacc gcgtctcccc tcaccttgcc gcggtcgggc tggccgtcgt cgtcagcttg   2460
tgtccatgcc gacgaatttg tcgaactgct cactgcatct ctttaatctc gtcgcctgat   2520
ttttctgtac cgcgccgcgc aacccctaga aataaaaatc acgccgccga gcgctcctat   2580
ccttatcccg ccaccgccct tggtcctcca caaatctcca gcgccaggt ttcttctcca   2640
cgcacgcccg gcagcaagcc gcagccgagc agctccttcc catctcccct ctgctcgctg   2700
gctgaatccc cagccgctcg gctctgcttt ctcccatgg ccggcgctcc ctgcttggtt   2760
ccgtctgtcg cgccgtcgtc ttactgctcg cctttgcgtc gcgcgcatag cgttctgttg   2820
ttcttgcacg cgcgaagctc tttgctgctc aacgcttcag cctggatttc gctttgtcgc   2880
ccagctcggc tctacatgac tacatctccc atgactgtct actctagctc accgaagttc   2940
ctgcgcgcgt cgagttttct ctactctagc tcgcctagt tcctgcgcgc gtcgagtttt   3000
cgtgtggagc tctctgctca cgcgcaactc gctctttctt tgttgccgcg cacacgaatt   3060
ttatctgctc gtcacagcgt gtcgagttcc cacgccatca tcgcttctgt cgcaagctcg   3120
ttggtcacag ttgtcttgac cgcgttaact cgcgactgtg gtcgtgttca tcgaattcgc   3180
caacgctttg ttgccgattt gactgtcgtc gcttcgcgtg ttgtcgagtc gtcgtttttc   3240
ctgtcttgtg ctcgcacggt ttcctgctcg ccagcgtgcc ctctcggctc gctcggcttt   3300
aatttccaat cacgtcgtcg atctcgtcgt ttgccgtcga gttgtcaaac acgtcatctc   3360
cggctcgatc cccacctcac cagcttaccc cagacttcaa tcgaaggtca tcgtcgctcg   3420
tgcgttcccc aagaaaaccc aagaatcggg tgaagacgaa gttagcagcg caatattccc   3480
taagcgctcg acaaatgcgt ggatcgaaaa atcactgccc gatctcacgg attcgtgtca   3540
gctgttgaaa cggtaagctg atgaattgtt tagaatagtt tataaagctg atgaaatgtt   3600
tagaataaat nnnnnnnnnn nnnnnnnnnn nnnnnnnnnn nnnnnnnnnn nnnnnnnnnn   3660
nnnnnnnnnn nnnnnnnnnn nnnnnnnnnn nnnnnnnnnn nnnnnnnnnn ctgattcgtt   3720
gtcgccagct cgctttacat gactacatct ccatgactgt ctacttagct cacgtagtct   3780
gcgcgcgtcg agtttctcta ctctagctcg cgtagtcagc gcgcgtcgag tttcgtgtgg   3840
agctctctgc tcacgagcac tcgctctatc ttgtgccgcg cacacgaatt tatctgctcg   3900
tcacagcgtg tcgagttccc acgccatcat cgcttctgtc gcaagctcgt tggtcacagt   3960
tgtcttgacc gcgttaactc gcgactgtgg tcgtgttcat cgaattcgcc aacgctttgt   4020
tgccgatttg actgtcgtcg cttcgcgtgt tgtcgagtcg tcgtttttcc tgtcttgtgc   4080
tcgcacggtt tcctgctcgc cagcgtgccc tctcggctcg ctcggcttta atttccaatc   4140
acgtcgtcga tctcgtcgtt tgccgtcgag ttgtcaaaca cgtcatctcc ggctcgatcc   4200
ccacctcacc agcttacccc agacttcaat cgaaggtcat cgtcgctcgt gcgtcccaa    4260
gaaaacccaa gaatcgggtg aagacgaagt tagcagcgca atattcccta agcgctcgac   4320
aaattgcgtg gatcgaaaaa tcactgccga tctcacggat tcgtgtcagc tgttgaaacg   4380
gtaagctgat gaattgttta gaatagttta gtaagctgat gaattgttta gaatagttca   4440
atcgttgaat aagttaatgt gttagtcgaa ggctccattag ggtgctcgat aaattgcgta   4500
agtcacgaaa ctctcgtcga cttcgcagtt cttgcgatta tcgagccagg ttcagttata   4560
gcgagttatt tcgctattcc ggtcacttag ctgaattagt ggaccgagta gaattttagt   4620
aggcatatgt gttgataaaa tattttaatc acttataaag atgtagtata atttataagg   4680
caagggatta gttcagaatt taattaatta actgataagt tgtgattagg ctaattatat   4740
ttccttgtgta tagtttgttg ttcgtgatgt ttgcgttagg ttcgagaagc gtaatcatag   4800
cgcgtagtcg catattaata actagtgttt ccgtacaaaa ttgtacaacg cctcgccact   4860
aggtgtttaa tacgctatcg tatagcacta tttagatttg tgcattctt gtttatatgc   4920
attcatgtgc atcgtgcatc tcaattaggt acgataattg atcgcgtgat gcggaagaca   4980
agccaagtcg acccccaagcg cgggctaatc cgcaggatga tgctgatgga caaacctgaa   5040
```

```
aatggtcgcc aagtggacgt cgtctaacaa cactaaccta gtgttaccca ggcaagcccc    5100
ggtgcatttg ccacctccct tgatgttttt aaaatctttc tcacttgatt gctgcattag    5160
gtgacaggag ttgattgatt aaacaattcc tgcattacct tccttgatct tgattaccct    5220
ccttgaaaac ccgtttttac aaaaaggttt tactatgctt agtattgctt agaaaaacaa    5280
aaggatttgt tttagaaaag atgtttggca aagtgggagg gttgtttca aaaataaaac     5340
ttgatggtga atccatcatg gatatgatgg attcaacatc ggaaaagatg tacctctgcc    5400
aggtaccaag ttttttgggtt aaaagattaa gctaagaccg ggcgggtgac ttgcacggga   5460
aaggagtctc agtgtagtgt ctccgtctga gtcgattaag gaccttgtcg atgtaggctt    5520
gatgatcgag gacccttaa ctggtcacat gcctcgtcat gggtaagcct tgcctcgggc     5580
agactaaggc cagaataaga taacacgaaa tgggcgtgga gcggtggcga gagtagcgtg    5640
taccctccgt ggcaagaggc tggacggtgg tgtaactgtg ctctcggttt gcgtgaacct    5700
gatctggtct taagaacccc ggtggcgggt tgacatatgc aagggttaag tgctacatat    5760
gtcgtgtgat tggagatcct cagctgagta taatcgattc ggatcgccgt accttcgcgg    5820
ttatgaagac ttggtcattg ccctacacgt agcattccac taaagatgat gggtttttgt    5880
taagaaattg gctagtgcag gaccagtgat tgaactaggg tagaaagaac tctagttaca    5940
ggtaattcta cttaacttga caaataaaac tggattttaa ggatccactt tagtaagcat    6000
ttctgcaaaa cagagtcttt gattattgaa aagccttacc ttgactccca tataaccagc    6060
ataccttga gagtcttttc tttagtcggg taagacttgc tgagtaattc catactcagg     6120
gttttattcc ctgttgtttt tcaggttcta actttgtgct gttgttgatg gtgttaagtg    6180
ccggtgggct cggccttctt ataagtctaa gtaaccctcc tatacttctt attgaggatg    6240
atcccttgag ctagcatata tatttcaaac ttatactttt gtaatcactc cgataaacta    6300
atgtaaaatt tttgtaacct gtaaaatttg gtagtaagat ttccgctgca acaatattgg    6360
tgtgtgtgat ttgtgttact taatcctgcg gttctggttg taagtggttt atccgatgtc    6420
cttgggcaa tcggacagat cctgttaagt tatctggtgc acatgcacag ccgtctgagg     6480
tctttgggac aaggacaggt gcatgtgggc ccaataactt gggaggttct gccacagctt    6540
gaagcgtccc caatcctctg ggactcaaat gtgatacaat tactagtccc aggaggctag    6600
taaacacatt tatacatcag atgattcaga tctgcttaaa cgagacaaac ctataaaggt    6660
ggcgatcaac tttaagagtt ggtccacaac tcgggacata tcatcagagt ggggctgaag    6720
cagcccgata tacgcagtga agcaattcag cggtccaaca gccacaggca aggttgggaa    6780
cagtcgtaac tcttacccga tctctttttt ctgaaaaaca acaaataagc aagggtgagt    6840
acaaacgtac tcagcagccc accttcaccc gcggaatggg gaaatcagat ataatgcatg    6900
gaatatgtag agctcaggat atttgcagaa acagcaatat tttatgcagg gttgttttga    6960
aaaacatttt gtattttgca aagtgcatcc tctccaaaag gagcaggaag tttttcagta    7020
ttataacaaa atcccctgga ctaaaccatc caggtatctc agcagtttcc cactggtttt    7080
cattttcaaa aacagctact ggacttcccg tccaccatag ctcacggctc aaccgccgga    7140
cctttttaaaa accactttc aaaagcatct cttttttttg gaaaacaaaa cattaattgc     7200
cataccatac cagactcgtc cattcctgtg gacacagact attcgaatag gttttcaaac    7260
tctgcgcaga ggtgtacact ttaccccacta gtccagctct gcgatcccat gatcaatgag   7320
acccgaatcc gactctcttt cttttcccgc atgtcctaac cttaatggtt atcctgaagg    7380
agtcaggcca ccaccatgtc caaaccggac aaaaactttcc ccctccttat cctcccggtg   7440
ctccccagcc ttcataaccc tggggttgga ccgtacgagt tcagattgag tgactgccca    7500
cacagtctcg agtggttgta ctattaaaga gtacaggtag tgaagatgac aaaccggtcc    7560
ttatatgagg ggacaatcct tctgctcacg cctaaaccag ctgagacga atctctagtt     7620
tcannnnnnn nnnnnnnnnn nnnnnnnnnn nnnnnnnnnn nnnnnnnnnn nnnnnnnnnn    7680
nnnnnnnnnn nnnnnnnnnn nnnnnnnnnn nnnnnnnnnn nnnaagctgt taaaacatt     7740
tagccaccca tcgagcttta tgatggtcaa tagactcatc agcttttctc ttgagtttat    7800
aaaccactt gcaatcaatc aaatttctgt caggtgcggg aggaaccaag tgccatgttt     7860
tattccgcat aagggcagaa aattctaggt ccatgcagc ttttccagtt tgggtcaaac     7920
aatgcaacag acaagctgga gggttcttca caaattgtca aatttccata cgggatcgag    7980
ccatcggtaa attttatggg cttcacaata ccagtgtgta gcggactgcg gacatctgga    8040
atttgatgtc cggtgcaccg gtatgggcgt gcctggcgtc tgcgcgcgct gcgcgcgcat    8100
taaatgcacc gcagggagcc gttggcgccg cagggagccg ttgctccgct ggcacaccgg    8160
acagtccggt gcacaccgga cagtccggtg aattttagcg gagcggctgc cgcgcgaacc    8220
cgaggctagc gagttcctga ggccgacctc ccttggcgca ccgacactg tccggtgtac      8280
accggacagt ccggtgaatt atagccagat cgccttagaa attcccgaag gtggcgagtt    8340
tgagtctgag tcccctggtg caccggacag gtactgttca ctgtccggtg cacaccgga     8400
cagtccggtc cgccagacca gggggtgcctt cggttgcccc tttgctcttt tgttgaatcc   8460
aaaacttggt ctttttattg gctgagtgtg aaccttttac tcctgtatac actatacact    8520
tgggcaaaca agttagtcca aaagatttgt gttgggcaat tcaaccacca aaattattta    8580
ggaactaggt gtaagcctaa ttcccttttca atatgatcta atttgttctt tagcccgcaa   8640
tgtaggataa ccaaatcaac tgtgttttgg tgacggataa gttttatct gatttcaatt     8700
aaaatgtaaca ccgattaaaa cattgtaact aaaatcattt ttaattttag tcctcttaca   8760
tctttccaaa ttcagtcccc aatctccagc tgataattgt atttttattc aaattttcga    8820
gtaaaagaaa acgaaggaag aaaatatctg caaccgctct tctctctgat tttatccaac    8880
gctttcccct tccatatctg aagtcactag cctggatatt ttctccacgt agttctcctc    8940
ttcctcacgt ctccttctct cttatccatt ggacgctagc tcgctggaaa atctcacgca    9000
cgtctctcct ccagccttac ccagcgacca gcatttcttc catccatcag catccaaagg    9060
cagccggcag ccggctgtgc tcgtcggacc ctcgagcac ctctgtgccc gacgacctga     9120
ccaagctcgt ctccagcttg catccatcct gtgctcagtt tccatccact agcaccgtgt    9180
ctctggtcct gtctcgtcgtg gacatctcg gctctagttc cttgctcgag ctcgcccttt    9240
gcgcagaccg cgtctcccct caccttgccg cggtcgggct ggccgtcgtc gtcagcttgt    9300
gtccatgcca acgaatttgt cgaactgctc actgcatctc tttaatctcg tcgcctgatt    9360
tttctgtacc gcgccgcgca accccctagaa ataaaaatca cgccgccgag cgctcctatc    9420
cttatcccgc caccgccctt ggtctcctac aaatctccag gcgcaggtt tcttctccac     9480
gcacgcccgg cagcaagccg cagccgagca gctccttccc atctcccctc tgctcgctgg    9540
ctgaatcccc agccgctcgg ctctgctttt ctcccatggc gcggggtccc ctgcaggctg    9600
ctcgcggtat ccatctcctc tgctcctgct cgtccgtccc tgagctcctg tgccgcggca    9660
cctctgttcg gccgcgcctg atcggatttc ttgtgccgtg gcttccctc cgagctcgcc     9720
cagctctatt gccgcgccca tggccggcgc tccctgcttg gttccgtctg tcgcgccgtc    9780
```

```
gtcttactgc tcgcctttgc gtcgcgcgca tagcgttctg ttgttcttgc acgcgcgaag   9840
ctctttgctc gtcaacgctt cagcctggat ttcgctttgt cgcccagctc ggctctacat   9900
gactacatct cccatgactg tctactctag ctcgccgtag ttcctgcgcg cgtcgagttt   9960
tctctactct agctcgccgt agttcctgcg cgcgtcgagt tttcgtgtgg agctctctgc  10020
tcacgcgcag ctcgctcttt cttttgttgcc gcgcgcacga attttatctg ctcgtcacag  10080
cgtgtcgagt tcccacacca tcatcacttc tgtcgcaagc tcgttggtca cagttgtctt  10140
gaccgcgtta actcgcgact gtggtcgtgt tcatcgaatt cgccaacgct tgttgccga   10200
tttgactgtc gtcgcttcgc gtgttgtcga gccgtcgttt ttcctgtctt gtgctcgcac  10260
ggtttcctgc tcgccagcgt gccctctcgg ctcgctcggc tttaatttcc aatcacgtcg  10320
tcgatctcgt cgtttgccgt cgagttgtca aacacgtcat ctccggctcg atcccacct   10380
caccagctta ccccagactt caatcgaagg tcatcgtcgc tcgtgcgtcc caagaaaac   10440
ccaagaatcg ggtgaagacg aagttagcag cgcgatattc cctaagcgct cgacaaattg  10500
cgtggatcga aaaatcactg ccgatctcac ggattcgtgt cagctgttga aacggtaagc  10560
tgatgaattg tttagaatag ttcggtaagc taatgaattg tttagaatag ttcgatcgtt  10620
gaataagtta atgtgttagt gcgaggctca ttagggtgct cgataaattg cgtaagtcac  10680
gaaactctcg tcgacttcgc agttcttgcg attatcgagc caggtcagt tatagcgagt   10740
tatttcgcta tttcggtcac ttagctgaat tagtggaccg agtagaattt tagtaggcat  10800
atgtgttgat aaaatatttt aatcacttat aaagatgtag tataatttat aaggcaaggg  10860
attagttcag aatttaatta attaactgat aagttgtgat taggctaatt atatttcttg  10920
tgtatagttt gttgttcgtg atgtttcgt taggttcgag aagcgtaatc attgtgcgta   10980
gtcgcatatt aataactagt gtttctgtac aaaattgtac aacgcctcgc cactaggtgt  11040
ttaatacgct atcgtatagc actatttaga tttgtgtcat tcttgtttat atgcattcat  11100
gtgcatcgtg catctcaatt aggtacgata attgatcgcg tgatgcggaa gacaagccaa  11160
gtcgacccca agcgcgggct aatccgcagg atgatgctga tggacaaacc tgaaaatggt  11220
cgccaagtgg acatcgtcta acaacactaa cctagtgtta cccaggcaag ccccggtgca  11280
tttgccacct cccttgatgt tttttaaaatc tttctcactt gattgctgca ttaggtgaca  11340
ggagttgatt gattaaacaa ttcctgcatt accttccttg atcttgatta ccctccttga  11400
aaacccgttt ttacaaaaag gttttactat gcttagtatt gcttagaaaa acaaaaggat  11460
ttgttttaga aaagatgttt ggcaaagtgg gagggttgtt ttcaaaaata aaacttgatg  11520
gtgaatccat catggctatg atggattcaa catcggaaaa gatgtacctc tgccaggtac  11580
caagttttg ggttaaaaga ttaagctaag accgggcggg tgacttgcac gggaaaggaa   11640
tctcggtgta gtgtctccgt ctgagtcgat taaggacctt gtcgatgtag gcttgatgat  11700
cgaggaccct ttaactggtc acatgcctcg tcatgggtaa gccttgcctc gggcagacta  11760
aggccagaat aagataacac gaaatgggcg tggagcggtg gcgagagtag cgtgtacctt   11820
ccgtgcaag aggctggacg gtggtgtaac tgtgctctcg gtttgcgtga acctgatctg   11880
gtcttaagaa ccccggtggc gggttgacat atgcaagggt taagtgctac atatgtcgtg  11940
tgattggaga tcctcagcta agtataatcg attcggatcg ccgtaccttc gtggttatga  12000
agacttggtc actgccctac acgtagcatt ccactaaaga tgatgggttt ttgttaagaa  12060
attggctagt gcaggacaag tgattgaact agggtagaaa gaactctagt tacaggtaat  12120
tctacttaac ttgacaaata aaactggatt ttaaggatcc actttagtaa gcatttctgc  12180
aaaacagagt ctttgattat tgaaaagcct taccttgact cccatataac cagcataccc  12240
ttgagagtct tttctttagt cgggtaagac ttgctgagta attccatact cagggtttta  12300
ttccttgttg ttttcaggt tctaacttgt tgctgttgtt gatggtgtta agtgccggtg    12360
ggctcggcct tcttatgagt ctaagtaacc cttctatact tcttattgag gatgatccct  12420
tgagctagca tttatatttc agacttagaa ttttgtattc cctccgatag aggtatgaaa  12480
aatttgtgta acctgtcaaa tttgtcaata atatttccgc taccactttg tatccgtgtg  12540
tgagtttcaa gacttaatct cgcggttctg gttgaaattg gtttatccga tgtccttggg  12600
gcaatcggac acatcctgtt aagttatctg gtgcacatgc acagccgtct gaggtctttg  12660
ggacaaggat aggtgcatgt gggcctaata acttgggagg ttctgccaca ggtcggggtt  12720
actccgtgta gcaatcccga ccgtgaggag gcggaatccg gtgcaccgag gccagcacaa  12780
gcttcggtga ggggtgaggg acgcctaggg ccaaggcacg ggcacggggc ggggctgaat  12840
cggtcggaca ccgagcgggc gcggcaaacc accgcgatag agctccagcg aacacaaatt  12900
caccgtagag ggaaaagaat cggggcagga agggcctgaa ggtacttact tacgttaaga  12960
gttctgtcag ggatgcttga ctgttgcttt ggggaggat cttcactggg cggtcgttgt    13020
cttttgttc gtgtgtggat gatgagtgcc acttgcttcc gactggtatg ctctacaaat  13080
ccagtctttc tcaaaatgac attgtttaat ccctgaannn nnnnnnnnn nnnnnnnnnn   13140
nnnnnnnnnn nnnnnnnnnn nnnnnnnnnn nnnnnnnnnn nnnnnnnnnn nnnnnnnnnn  13200
nnnnnnnnnn nnnnnncac gaaatgggcg tggagcggtg gcgagagtag cgtgtacctc   13260
cgtggcaaga ggctggacgg tggtgtaact gtgctctcgg tttgcgtgaa cctgatctgg  13320
tcttaagaac cccggtggcg ggttgacata tgcaagggtt aagtgctaca tatgtcgtgt  13380
gattggagat cctcagctaa gtataatcga ttcggatcgc cgtaccttcg tggttatgaa  13440
gacttggtca ctgccctaca cgtagcattc cactaaagat gatgggtttt tgttaagaaa  13500
ttggctagtc aggacaagt gattgaacta gggtagaaag aactctagtt acaggtaatt   13560
ctacttaact tgacaaataa aactggattt taaggatcca ctttagtaag catttctgca  13620
aaacagagtc tttgattatt gaaaagcctt accttgactc ccatataacc agcataccct  13680
tgagagtctt ttctttagtc gggtaagact tgctgagtaa ttccatactc agggttttat  13740
tccttgttgt tttcaggtt ctaacttgt gctgttgttg atggtgttaa gtgccggtgg    13800
gctcggcctt cttatgagtc taagtaaccc ttctatactt cttattgagg atgatccctt  13860
gagctagcat atatatttca aacttatact tttgtaatca ctccgataaa ctaatgtaaa  13920
attttgtaa cctgtaaaat ttggtagtaa gatgttcgct gcaacaatat tggtgtgtgt    13980
gattggat tcgttttctc gcggttcgg ttgtaagtgg tttatccgat gtcctttggt     14040
agatcttaca gatcctgtta agttatctgg tgcacgtttt ttggggtctg aggtctttgg  14100
gacaaggata ggtgcatgtg ggcctaataa cttgggaggt tctgccacag gtcggggtta  14160
ctccggtgag caatcccgac cgtgaggagg cggaatccgg gtgcaccgag gccagcacaa  14220
cttcggtgag ggggtgaggga gccctagggc caaggcacgg gcacggggcg gggctgaatc  14280
ggtcggacac cgagcgggcg cggcaaacca ccgcgataga gctccagcga acacaaattc  14340
accgtagagg gaaaagaatc ggggcaggaa gggcacgggg atggttcctt accttaggag  14400
tgtgctcggg gatgcttgac acgatgctag gagctccggg cagacgacgc ggtggcgcgc  14460
ttctccggcg agcttgagcg gcggcggcta agcgcgagag aggttgagag tgggtgaaat  14520
```

```
taggaagggg agggagagcg ggtgtaggcg gggctcaaaa gggagctggg ggcgtgggta  14580
ggcaacgtgg tcggcttcct cggcgtgagt gcgtgtgcgg gtcagcagcg gttgcgggga  14640
agatgagact gacaaggcgg gcccacagag tagaggcacg agcacgtgtg aggaggaaat  14700
gattcagcgc tgatgggctg ggcccactgc acagagggag agcgggggcg tgcgcgcgag  14760
ggtgagcggc accaataggt cgggcccacc tggcagatgg agagagaggg caggtgcgta  14820
ggctgggctg cttttctatt ttcttttat tctgaatttc tagttccttt tatttttatt  14880
ttctctattg aattcaaatc caacgaaacc acaaattcaa atttgaatat ttcaaacatg  14940
tgcatcaacc aaaaacaaag tttaagctca gcatgatgca acaattcatg tctcccctag  15000
gtttgaatat agtaaagaaa aaaaatacat ctcccaaata tataaccaaa actctattag  15060
aaaggaagaa aataggaaat ctacggagat gagaaaagtg gtaacacctg aatttggtag  15120
atattagaga agaaattta taccccaaa ttcagggtgt tacataggct ctataatcat  15180
agcgtgtata gatgcatgaa taaataaggt gagcctatga gctatgcgtt tcttccactc  15240
ctgatacatg ccaatcaagt gtttctttga aacaacctc actggcatgc tttgaggagc  15300
ttgcatagcc cttctgaggt tttgccttg cctttgcctt tgccatagcc attgctactc  15360
tactgccatt ttgtggtggc ttcgtaaaaa ttcccctct catcccctga ttattacagt  15420
gcccatgacc cctttctctg gagggacctt tcttccttta agactagaag ttggcgtgtg  15480
ctttatgcat gaccgcgtgc cgaatggatg cttctagtag ttctgcatca gaagctcatt  15540
ctgagcctta gcaccaagca acatgttgac gaggtcacat tattgtgta cttgttgcta  15600
cagtactgct gttggagcac catattggag gggtagaagg tttggagagt tttctcgatc  15660
atctctaagt ctatgctat ctggccacag aaatgtagct gagcgacaat gcgatggatg  15720
acagtgttgt aagcctcaac tgcattgaag tcgagagtgg cccattcatg ttgcgcccgc  15780
gggagcatca catgcttctc cacactgaaa cactcacata cctctgtcca caatatcata  15840
tggtctttca cctctggata ctccatcttc aggcctggat ggatgtggtg cccgacgaag  15900
atcgtaattt ttgctttctc atgaagtttc aggcaagtgt cattcgggcc ctaccagaag  15960
atctcctttc ctagctatat cgcctctagg tgaaacttgc agtcgttagt ctaggtcggt  16020
tagttcttgc cattgaggac aagctccacg aatcaattct gttgtcttca accatagtcc  16080
gtcacacaaa attaacttta ggttaattag gcgtgctaat tatcaataat agaaattta  16140
atagataaat tgcatgaccc acgggagccg gtccagggcg tgctgacgag gcgtggctga  16200
agcatatgcc gacgagctgc gccccagctg gccgagcaag cgccgacccag tgcggggtgg  16260
cgccgtgggc tgacgcagcg tgaaccatct cagctcgaga tgacgagagg agcagcaggg  16320
catgggtgcg tgggtcagtg tgacatcaag gcgcagagtt gggggcgccg acatagtgga  16380
cgactagaag ccggcatgac cgatctattc atgaacgcaa cgtgtgggcc accggtgggg  16440
tgggtgtgta gtgcacgcga ctggcgcacg agcctcgcca tcggggtgat tcgtacgacc  16500
cgcggttagt aggacatcga tggcttttta agtaaaagta atagattgga tatattaagc  16560
aggtcaaatc atcaggattt aacatgctag tgtatacata aatcaatcta caatatgtat  16620
ctgacagtaa gaaatcactc tacaatatgt atctgaccgc gagaaaacaa tctagtttga  16680
acaaaatcta ctaacaatt gtctagagcg gtcaaaaacg acataccgtg cttctttatt  16740
cagcgaacgg aaacgaagcc tatcatgtaa gacaattagg caaggcggga ggacttgctg  16800
tggtgcaatt tccaaattca gaccttgaac cctctcctca gcaatggagg gcttattctc  16860
ttttgtcga ggcagaagca caaaaaacta tttccttgtt atatagacga ctagagcttc  16920
tcgtttgata ttagcccaca taagattttt tgatagtata aggccatctc caactgatcc  16980
cctattgtat ccctctatttt attcctatat taaacgcaac tctgtaaata atatcatcta  17040
aaattctgtg ttacctattt tatttggataa gtgagtctaa tattttgatc caaacagcgt  17100
ttaatctctt cccttgctgt aagttctcga cagatttagc tgggttaaaa ttcagactca  17160
aagacatata aattgatggg ctggtgttat tccacgtgg gggtggaccc ctcacgggcc  17220
gggccgcatt cttggccaac catgggctat ccgcaacatt gcagactccg gaatccggat  17280
tggccgaatg ggccccggcag ccgaaaatga aaaaggaaag gatcgaccct ctagcgcgat  17340
cgatccccgt gcgctgggggc ccaaattagg agaacctcag taccccacgt gatccacggt  17400
ccgcccgccg cgcaagctgg gccacgggct cgcgggcggg catgcgccgg ttccgcgagc  17460
gaccaccccg ccatcgcgg agcctgccct gcgctgccca ccgctcctcc gcctactccg  17520
gcctcagcta ataacgatgg gtggtgggag ccgagccctt tccctctcct ccctcctgcc  17580
caccaccctc gccgccgcca agccccaca gcacccgtc cccttcgccc cggctcaccg  17640
cgcgctcccc caccgcctcg ccgccgccat gtcctcctct tcctccccga ccccccgcgc  17700
atcggtggac gccggtgccc cggccccttc ggcgtccaac gccatcgact tcctcacgct  17760
ctgctaccgc ctcaaggtga gcgactgagc gcccctgttt agtcgcttcg cattccacg  17820
ggccggcttg gttgagatgg atggaaatgt gacgcgatgt atgagattgt ggatgtaatt  17880
gcagacgacc aagagggcgg ggtgggtgaa gcgcggggtg caggcgcccg agtcggtggc  17940
cgaccacatg taccggatgg gcgtcatggc gctcgtcgcg gccgatctac ccggcgtcaa  18000
ccgcgacagg tgatcctgac agtttcgctc tcaagtctag ctcggcagta tttagccttc  18060
ttacggttcc gttttcatac actgtttatt tatcccttca attacaggtg tgtcaagatg  18120
gcgattgtgc acgacattgc agaaggtatg gtctcaaaag acttccgtct agacggcttc  18180
actgaagttt tggggctttg tgtgagatga gggatgcaat tttgtgaata tgcgagccta  18240
ttactacctg agatgttggt agatggtaac tagaccactg gactggagac ctgtagtagg  18300
aattgtaggat gtgtgttcaa gtacttgtgc caattagttg gttctttgac ctctgctagc  18360
caaagtgtaa aactttaaac tatgtgcaca ttttcctatt ttcattcaga agcatgctca  18420
gcttagaaat gaacacatga ttttgccctc cgctcatatg gactcttgct gctgttccta  18480
agccagcttg cctgtttctg gaactaactg cctatgagga tgtgggttca gttgactcat  18540
ttcaattgtt ttttctttg gtactccagc aattgttggt gacatcaccc cttctgataa  18600
tgtacccaag gaagagaaga accgcaggga gaaagaagca ttggaccata tgtgcgagct  18660
gcttggtggt ggttcaagag gtgaatactg aaacttgcaa ttgtgataca ttagcatttt  18720
atgctgtagt taattaggca tcttatgcct caaattgtct tttcatgatt tagttatata  18780
tgaaatgaat gtggtgctat tgcacactgg catcatcttt ctagattact caatagtcta  18840
gacttaatga tcccattatg tgtgcatagt accatagttt caaggaaaaa agaacaatat  18900
gtggatgcca atgaattttg tgaatacaat ttgcaggtca tatacatatt 18960
ttatttacc cttgaaaagc tattcatctg ttattattat ttcttagatg gtcatttttc  19020
catccgatac ttttcacttc catcagggaa gcagatcata acctggcaat tatttttgtag  19080
aaatccagcg ggcagctttt gttcttattt tttgatacat agtttaaata agtattggat  19140
aattcttaga gtattcacat cccttagtta ggtgtcaagg aaactcttgg taacttaaaa  19200
tcactcagat tatttccaga gaaactgtta tttatacttc tcttttctt tttataaggt  19260
```

```
gtattagtgt ttgagaattt cattcaaaga tatgctttat ccaataattt cccttgcaat   19320
atatgaactc aatatattat caattactac aaaagcaatg tctcactaaa atgcatgtga   19380
aatatgaatc tatagattta tctttgtgca ataaatatac aaatattttg actagtttca   19440
ttgacttttt tgaatcctta cgccctacat tttgaaatgg aggttgaaaa gataagggat   19500
gttttgtag aagccaaaac cgaagagttt atattcagca aatgttgatg actatgagtt   19560
ttggaatttg aacatgatat tgtaattgat ggtgataata ttattccatc tctaatgatt   19620
ttctaccttg aagcattatg gatcgtaaat tatttatgct caaatggcta tcatagcatc   19680
caacattttt tccctaagag tttcacaaca tagaattcta gtattctggt tgtgttctca   19740
ttattcatat cattaatcgt taaaaaatat tggagagatc cagcatccct tacatgtgaa   19800
gtgaacctt tagaactaaa taaagtatct tagcagcctt ttggaaacag tttttcatgc   19860
aggataaaag gatgttctct gtacaggcga gactaaagag ttcatgtgat ctttgacatg   19920
gtatatataa taaatacttg cctttatctg catgctgttg tcttgcagca caagaaattc   19980
gtgaacttg atggagtat gaggagaatg cgtctttgga agcgaaggtt gtcaaagatt   20040
ttgacaaggt acagtttcat atttcaatcc atcaagttgg tggcatgatt gcaacgtctg   20100
tctgaagcta tcagatggta gttcttgtga tcattcaata ggcaatgcat ataactggca   20160
ggatatttaa ctaatgtagg caatcattat gatttatggc cctaacccat atggctccac   20220
ttcttccttt tcctttgcat gctgtaatcc tttgttgcac tgttatattt ccaggttgag   20280
atgatacttc aagctctgga gtatgaaaag ggtgagttca tactggtgct tgaatatttg   20340
aactaacatt tcccatgcac agtagctata aagtacaaac cacaactatt taaatgcatt   20400
catcaaatat tcttgttgta ataaccaaat aaatgtatat agtaaaatca gctcacattt   20460
cacatttcaa atacagcaca tcttttttctt tgcatcattt gtgcttatat tgggtaggcc   20520
tggtgtagtg gtgagggcag tctcactaag tcactatgtt gccagttcga aacagcctct   20580
ctgcatttgc agggaggct tgtctcgatt tatcccatct caagaccca ctcatgtggc   20640
agcctccgcc ctagatctgc ccatctgtgc ttaccattt atttaatttg ctccacggcc   20700
ttctgggtgt gagaagtgat acatatgatc aatgtactat cacttaacac ctggtgaact   20760
cctgttgat agatggggtt aacagtatca cacttacgcc tatgtatttt aaaattttca   20820
gagcaaggac gggaccttga agaattcttc caatcaacag caggtgtgat ttttctcttt   20880
ctgttatgct cttctcaatt ttcatgagta tccagtacat aaatcttgct cttctcaatt   20940
ttcatgacaa tccagtacat aaatcttgct cttctcaatt ttcatgagca tcctgtacat   21000
aaatttgaac agtttcattta agctgagaag gatgttgcca tttttttggt cttacactta   21060
aaaatgttttt cctgagataa tataaacatt catcagcaat tcagaacata ttagtgcctg   21120
aatgattatt gctaattgaa aactggacac taccacctat aatggttttc tttaccatga   21180
actgatacat gcctatgcct tttatggttt tcttttatca cgtgcttatg tttgatctca   21240
ttttacatt gtattagacc gtgtccagca gttcacccac ccaaaaacact gttttgcact   21300
tagattgcac tattcgcaga gtggaatttg aatatgggga tggtaaactt agcctaggct   21360
attagcatta gagtcattgt gtaacaaaac catatccccg cacctaattc ccatgcaggc   21420
aaatttcaga cagacttggg aaaagcatgg gcagcggaga ttgcatcgag aagaaaaaca   21480
aagtgatcaa acgatgctca ttttaccacg tcggttccaa gacaacttgc tggcacagca   21540
tttctgttga acttttgcttt tactagatga tacttcgagg tggcattgag acgtagggtt   21600
gccttgggaa tgtgaacttc accacatttc ttggtcctgc cctgaccctg aggcatattg   21660
ggcttgcgat accagggctc tagataagta agataaccca ctttgggtat tggttgtaga   21720
tgctcctgcc aagggcagtt agctggatcc aacgggaagg ttcagcacca gctggtggtg   21780
atgtaaaatc cttcacttca tgaattactg taccattacc gtttctcttg ttaatccagc   21840
ctcacggttt cggccttttt taatgtaatt ctattgtttt caagtataat gagcctgaat   21900
atttgctata tccattttgg ttgttgatga tgacctgaag tgcattcata ttttcatagt   21960
acgtataatg ctgaagccta gaagctgacc actgatagtt ccggtgtagc gtcggatcgc   22020
atgtattagg gtctgttcgt tttattttga atccacgtgg attagacgga attgagtgag   22080
tttgaaagg atcacgatgc ccaagaggag ggtgaattgg acttttctaa aaatcaacac   22140
taattaaaat ctaagcaaga gtccaacttc accccgataa ctatcactaa gagaataata   22200
atagaaatac aacaatgtta agacaatatt tcaaatactt gctaaacaaa tacacaatgt   22260
aaaatgtttt aattaagtgc ggaatgtaaa gcaaggttta gaagactcca attttttctcg   22320
aggtatcgaa gagtcggcac tctcctctag tcctcgttgg agcaccctcg caagggtatc   22380
actcccccttt ggtcctcgca agaaccaagt gctcacaacg agatgatcct ttgccactcc   22440
agcgcagtgg atccctcacg accgcttaca aacttgagtc gggtcaccaa caagatctcc   22500
acggtgatca ccgagctccc aacgccacca agccgtctag gtgatgacga tcaccaagag   22560
taacaagcca tagactttca cttgaccaag agaagcctaa tgcatgcggt gtatgctcta   22620
ggtggctctc gctagcgcta ataaggtcca aatgcgggat taagattctc aaataaccttc   22680
actaggcttt gtggtgcttg caatgctcta ccaatgtgta ggagtaaatg tgggtagcaa   22740
gaccatcaat atagtgggtg gaggggtat aaatagccct cacccaccaa ctagccatta   22800
ccaggaatct gctgcacatg ggcgcaccgg acagtccggt gcgccaacgg tgcgccaacg   22860
gtcgactcca atggctagtt ctgacagcta gccgttgggc agatggcaca ccggacagtc   22920
cactaaaatt caactcgcga acaacgcgct ctcaggtttc tgtgcgcagg gaaccctctt   22980
ccttgggcca ggctggcccc actggcagag ggtgcaccgg acagtccggt gcacaccgga   23040
cagtccggtg ccccaaagcc agaaaccta gtttctgttt ttgctgttt tttcaattcg   23100
gttttcgttc taacttgtga gtatgttcta gagtggcacc tagcactata tgtgagtgtg   23160
aatatgcacc aacactacac tagaactctc ttggtcaaac tactcatcga caaccctct   23220
ttatagtacg actaaacaa aataaaagac ctaactatat cacgagtgtc cgcaactcct   23280
tgcactcgg aatacgaaga ccttcacttt ttgttttgtc gctttagccg tcgcttcaag   23340
ttcttatctc cgagattgtt ttcaccgttg tagtacatct acatgtaatg cgacctaact   23400
taccatttgc ctctgcaaaa cacatgttag tcacatataa aattacattg tcattaatca   23460
ctaaaaccaa ccaggggcct agatgctttc aatctccccc ttttggtga ttgatgacaa   23520
cctacaagat tgtgagagta gtttgtttg aaatttctgt caatagagaa gatggttagt   23580
tatactcaaa aattttttgac agaaagagtg tgtaacataa taataagagt gagtgcatac   23640
acattgtaag tttcttgttc atataaaagt gaaatcaaat cgtgaacaa gaactagaga   23700
ctggtgataa catataaggt gaaaacacaa tacacacaca gtcaacataa gcatcgagag   23760
catataatag agtttgtgag ccaaaatcgt catacaaaag tggatctagt acagagtta   23820
tcaagcacat atattacatc aaaatgactc tatactaact ccctaactcc ccctagctct   23880
cacaactctc atatctctcc cccctttggcg tcaaacacca aaggaaacc tgaacctaca   23940
gaccagaaga ggaaggaggt ggctggggcg catccgatca cgatcgtggc agaagagcaa   24000
```

```
acgccagctg agggtcagag tcagcctcgg atccaggatc taccgtagaa gctggagcta    24060
gtactgactc ggatggaggc tgtgctgcag gagctaccga agctgaagag gtcacagaca    24120
ccgccacaac agcagtggta acagcaggag ctggtggcac tggcggctga gcgctgatgg    24180
agctgatgac cggcgacgag aaaaccaggg tgaccggcag gagcggagag gaagaaggac    24240
caaatgaagg tagaggggt cctgcctgaa gggctagcac aacagcggcc tgaagatcta    24300
gaggggggtgc agactgaaca ggaggaatct gagcaccggt atgctgaagt atgtgagtca    24360
tgaaggcccg gttctcagcc ttgtctgcca aaagctgctg ctgcagagtg tcctgtctgt    24420
cctgaatagt ctaaaacatc gatagcattc tctcggacat ctgctgttgc accgctgcca    24480
gatgagcctg ctgctgagta agagtctgga ggatcgcagc cagagcaggg tcaatggcag    24540
gaggaacagc aggggcagca cgagaactcc gggcctcatg gtcatgtgag cgtggaggca    24600
caggaggcag aggcggaatc ccaaaatcat catcatcatc atcatcatca tcgtcaggaa    24660
ctgctgcgcc ctaagtctca aactgatgga aacttgtatc ctctgcctga atgtctgtca    24720
ctggatcagg tactggtact ggatcctcag gggctggatg gtaggagcca aataggaggc    24780
gtgaggcctc aagggtgccc tggaactatg gtggtcggat cagctgtgcg aagatggc     24840
agagataatg agcatttggc agctgtcgcc gagcacgaag accatccaat accgtgtcct    24900
cgatctcaca aataaggaag tcaacaacat caaactctga atgaaagatc agggcaccga    24960
ggagccaaag ctgaatatga gtggtagcct ctctataacc catccacgac agaagcgtcc    25020
gtctcatgag ctgatataag tacttggcta ctgtagtgaa atctgccgga gaacgtcgcg    25080
acccatctga gaagggcggt cggaacaaag ccgcgatgtg agctgtagct ggagcaactc    25140
cgtcgtgagg gcgacgagga ggatcagagg taccatagca caagctatga agacaagtcg    25200
atgactcatt gaatccaaac agctggcgaa tctagctagc atgaagtgta acatcctctc    25260
gctcaaagcg gaacctcatc cactgctgat cggggtcgat ccatactgac gcattgaaca    25320
cacggaccca ctcctcaaca tatctgccgc tggtagtcag aagagtgaga agtcccagca    25380
aatatgtgag atgcatctca gagtctgcac cagcggctag cagaacacag gaagacccaa    25440
tagccggtgc gctcgcagaa gcaatctggg ctgaccnnnn nnnnnnnnnn nnnnnnnnnn    25500
nnnnnnnnnn nnnnnnnnnn nnnnnnnnnn nnnnnnnnnn nnnnnnnnnn nnnnnnnnnn    25560
nnnnnnnnnn nnnnnngttg atgatcagct tgattcgtta ggataaaacc ctgagtatgg    25620
aattactcag caagtcttac ccgactaaag aaaagactct caagggtatg ctgggtatat    25680
gggagtcaag gtaaggcttt tcaataatca aagactctgt tttgcagaaa tgcttactaa    25740
tgtggatcct taaaatccag tttattttgt caagttaagt agaattacct gtaactagag    25800
ttctttctac cctagttcaa tcactggtcc tgcactagcc aatttcttaa caaaaaccca    25860
tcatctttag tggaatgcta cgtgtagggc agtgaccaag tcttcataac cacgaaggta    25920
cggcgatccg aatcgattat actcagctga ggatctccaa tcacacgaca tatgtagcac    25980
ttaaccttg catatgtcaa cccgccaccg gggttcttaa gaccagatca ggttcacgca    26040
aaccgagagc acagttacac caccgtccag cctcttgcca cggagggtac acgtactctc    26100
cgccactgct ccacgcccat ttcgtgttat cttattctgg cctagtctg cccgaggcaa    26160
ggcttaccca tgacgaggca tgtgaccagt taaagggtcc tcgatcatca agcctacatc    26220
gacaaggtcc ttaatcgact cagacggaga cactacaccg agactccttt cccgtgcaag    26280
tcacccgccc ggccttagct taatctttta accaaaaact tggtacctag cagaggtaca    26340
tcttttccga tgttgaatcc atcatagcca tgatggattc accatcaagt tttattttg    26400
aaaacaaccc tcccacttg ccaaatctct tttctaaaac aaatccttt gttttctaa     26460
gcaatactaa gcatagtaaa accttttgt aaaaacaggt tttcaaggag ggtaatcaag    26520
atcaaggaag gtaatgcagg aattgtttaa tcaatcaact cctgtcacct aatgcagcaa    26580
tcaagtgaga aagatttaa aaacatcaag ggaggtggca aatgcaccgg ggcttgcctg    26640
ggtaacacta ggttagtgtt gttagacgac gtccacttgg cgaccatttt caggtttgtc    26700
catcagcatc atcctgcgga ttagcccgcg cttgggtcg acttggcttg tcttccgcat    26760
cacgcgatca attatcgtac ctaattgaga tgcacgatgc acatgaatgc atataaacaa    26820
gaatagcaca aatctaaata gtgctatacg atagcgtatt aaacacctag tggcgaggcg    26880
ttgtacaatt ttgtacggaa acactagtta ttaaatatgcg actacgcgca atgattacgc    26940
ttctcgaacc taacgcaaac atcacgaaca acaaactata cacaagaaat ataattagcc    27000
taatcacaac ttatcagtta attaattaaa ttctgaacta atcccttgcc ttataaatta    27060
tactacatct ttataagtga ttaaaatatt ttatcaacac atatgcctac taaaattcta    27120
ctcggtccac taattcagct aagtgaccgg aatagcgaaa taactcgcta taactgaacc    27180
tggctcgata atcgcaagaa ctgcgaagtc gacgagagtt tcgtgactta cgcaatttat    27240
cgagcaccct aatgagcctc gcactaacac attaacttat tcaacgatcg aactattcta    27300
aacaattcat cagcttaccg tttcaacagt tgacacgaat ccatgagatc ggcagtgatt    27360
tttcgatcca cgcaatttgt cgagcgctta gggaatatcg cgctgctaac ttcgtcttca    27420
cccgattctt gggttttctt ggggacgcac gagcgacgat gaccttcgat tgaagtctgg    27480
ggtaagctgg tgaggtgggg atcgagccgg agatgacgtg tttgacaact cgacggcaaa    27540
cgacgagatc gacgacgtga ttggaaatta aagccgagcg agcgagagg gcacgctgcg    27600
gagcaggaaa ccgtcgagc acaagacagg aaaaaacgac ggctcgacaa cacgcgaagc    27660
gacgacagtc aaatcggcaa caaagagttg gcgaattcga tgaacacgac cacagtcgcg    27720
agttaacgcg gtcaagacaa ctgtgaccaa cgagcttgcg acagaagcga tgatggtgtg    27780
agaactcgac aattctgtgc gagcagataa aattcgtgcg cgcgcaaca aagaaagagc    27840
gagctacgcg tgagcagaga gctccacacg aaaactcgac gcgcgcagga actacgcga    27900
gctagagtag agaaaactcg acgcgcgcag gaactacggc gagctagagt agacagtcat    27960
gggagatgta gtcatgtaga gccgagctgg gcgacaaagc gaaatccagg ctgaagcgtt    28020
gacgagcaaa gagcttcgcg cgtgcaagaa caacagaacg ctatcgcgc gacgcaaagg    28080
cgagcagtaa gacgacgacg cgacagacg aaccaagcag ggagcgccgg ccatgggcgg    28140
ggcaatagag ctgggcgagc tcggagggga agccacggca caagaaatcc gatcaggcgt    28200
ggccgaacag aggtgccgcg gcacaggagc tcagggacgg acgagcagga gcagaggaga    28260
tggataccgc gagcagcctg cagggaaccc cgcgccatgg gagaaaagca gagccgagcg    28320
gctgggatt cagccagcga gcagagggga gatgggaagg agctgctcgg ctgcggcttg    28380
ctgccgggcg tgcgtggaga agaaacctgc gcgctgagga tttgtaggag accaagggcg    28440
gtggcgggat aaggatagga gcgctcggcg gcgtgatttt tatttctagg ggttgcgcgg    28500
cgcggtacag aaaaatcagg cgacgagatt aaagagatgc agtgagcagt tcgacaaatt    28560
cgtcggcatg gacacaagct gacgacgacg gccagcccga ccgcggcaag gtgagggag    28620
acgcggtctg cgcaaagggc gagctcgagc aaggaactag agccgacgat gtccacgacg    28680
agcaggacca gagacacggt gctagtggat ggaaactgag cacaggatgg acgcaagctg    28740
```

```
gagacgagct tggtcaggtc gtcgggcaca gaggtgctcg gagggtccga cgagcacagc  28800
cggcagccgg ctgcctttgg atgctgatgg atggaagaaa tgctggtcgc tgggtaaggc  28860
tggaggagag acgtgcgtga gattttccag cgagctagcg tccaatggat aagagagaag  28920
gagacgtgag gaagaggaga actacgtgga gaaaatatcc aggctagtga cttcagatat  28980
ggaagggaaa agcggtggat aaaatcagag agaagagcgg ttgcagatat tttcttcctt  29040
cgttttcttt tactcaaaaa tttgaataaa aatacaatta tcagctggag attgggacta  29100
gaatttggaa agatgtaaga ggactaaaat taaaaatgat tttagttaca atgtttttaat  29160
cggtgttaca tttaattgaa atcagataaa aacttatccg tcaccaaaac acagttgatt  29220
tggttatcct acattgcggg ctaaagaaca aattagatca tatccccgcg cacgatcttt  29280
ctcagacaat gcgcgattca gattattta ccctgaacat tttagtcgtc aagttcaaat  29340
taatttgctc gaaataagat cattcgagtg agttcgggct tccgaatttg tgttcgcgcg  29400
agcgatggat tttaaatact catcggacgc accgattttc ggaacagcta ggttccgaac  29460
attacgaaaa tttaggaaga gcccggacag ataaaaaaat aaaaacgatg tcgcactcgc  29520
gacaaacgac accgatgcga tattaaaata gcgataagcg acaatgatta aaatttaaaa  29580
ttcgttttat ccactgatat tgcgtgctta aatccgaact cgttgttgag cggaaaataa  29640
acacctgggg tgttacacac cccgtccaat ccctggaccg gcggtactta ctcctggcag  29700
ctgtctagga tcatatattg tccccacaga ccaaacgacg tcttttgtgc gcactttgtc  29760
ctcactcatg cgcacccgag aaaacttccc ggtcggtcac ccatcccaaa ttgctccaag  29820
ccaagcacgc ttaacttgga ggttctttcg agataggctt ccgaaaaaga agatgccacct  29880
tgttggtatg attacactat taattctatt aagccttggg ccaggacatc ccatcccagg  29940
ggccaggata tcacaatcca cccccttag aagaccgacg tcctcgtcgg tcaacccaa  30000
tccaggaacc tcccctcttg gccacgtctg tgtgtctagt gccgtcatat gccatgccat  30060
gtgaccactc cgggcccaca tgtgccatgc gccatatacc cgaacccct agcccacaca  30120
cgcccgtgaa accgcgagtg tcggctctga taccacttgt aacacccgt ctaatccctg  30180
gaccggcggt acttactcct ggcagctgtc taggatcata tattgtcccc acagaccaac  30240
acgagtcttt tgtgcgcact ttgtcctcac tcatgcgcac ccgagaaaac ttcccggtcg  30300
gtcacccatc ccaaattgct ccaagccaag cacgcttaac ttggaggttc tttcgagata  30360
ggcttccgaa aaagaagatg caccttgttg gtatgattac actattaatt ctattaagcc  30420
ttgggccagg acatcccatc ccaggggcca ggatatcaca ataagtgtcc cgcccagagc  30480
gccccctccg ccattcactc acctccagtc ccgttctcat ggccagaacc ctgccatcga  30540
gttcgtcggg tccccctcac cggtctggcc aactccagcg accccagacc ccctggggtc  30600
cgcgcttgtc tcgtctttgg cgacttcacc gctgcggatg gagcagcgcc ggccgcagtg  30660
ctgttaaccc ccctgacgcc taatcctagc cgtttagcct tgatctagcg gtctagatcg  30720
ctggatatcg cttcacgtgg gtgcccttgc ccctggccc cacttgtcag tcatctgtgc  30780
cctagcgctg ggcccgactg gtcagctcgt cctcacctcg gatcatcact tggaaacact  30840
atgtagcagc atgaatgcaa caatcatgac acttctagag ctcacaccaa tatagaacca  30900
aaataactct ctactgtttt gataaaggga aagaaaagt gaataaagga aagggtaaca  30960
cctagatttt gagtatagag caaggaaatt tttatacccc aaaattcagg gtgttacagc  31020
tacgtagtga aaccttgccg actccaccttg gtagtgtttg aggtttgat cgacctgagg  31080
caaaaaggga tcacgacttg tgggtaaagt gtgcaacctc tgtagagtgt tagaagctag  31140
tatatcagcc atgctcacag ttatgagcag ccttgggagc tcctttgatt agagttactc  31200
tggatacttt tatgatgatg cttaatgatg gtgattatga ttatgaattc ttggtatttc  31260
ctcttggagg gagtaatgtt tgggtttata acttggggtt attgctaaaa catggctctc  31320
tactggtaat aaatacctaa ccaactaaaa gcaactgctt taagcttaac cccacataca  31380
gctagtccac tttagccaaa caggacattt gttgagtacg ttgaggtgta ctcaccattg  31440
cttaaaaaca ccaaaccccc ggttgtcccc attgcaacta gtgctcagga gaagatgaag  31500
gcaacgtgga ggactttcag gagtttcagg acttcgacga gttctagact agattagtgg  31560
caaaccctca gttagctgcc tgtgaaggcc ttatcgtact gcgtttcgtt caaaattttg  31620
attatgacct aagttaatga ctctgtggat gtcttggaca tccactacta gaaatatgct  31680
tatttaagac atacatctta agacaaatat cagtgcattt tatagaagcg tcttttatca  31740
tatggtgctg agtacggtaa gacggtttgt tggatatccg tctttaatga agaaggtttt  31800
tgaggcagat atatggttgg aaatgtctta tattgattta atacagtttg atgttgaaaa  31860
ccgtctcaaa taaatatacc ttttgaggca ttaagtttac aagaagtgtc ttttatttg  31920
gttagtatat tagacacttc tgtatatgaa accatctcaa ataaagatat tattagagtc  31980
atctagacta tacaaaattg tcttagatgt tagtgagtat actagaaact tgtaaacata  32040
aaaccgtctc gtacgatatt tttgatagga catattgtga aaaaacatag tcaatagtaa  32100
attctgatta gattgaacta aacatttttt ggaatttaaa atgaactagt tagctgactg  32160
tatgttcgta cggtttctat atatcatata ggtaaaaaat cttgcttaaa taagaatctt  32220
cttcaaataa aattatacgt ttgaaaatatg attatttttt attttctcat caacagtatg  32280
tttatagtta taatatcgtc tctttgtacg gtataagcaa cctgataagc ggtggttaat  32340
gccacgaata tttctctta tatacgtatt gcacatatat acaatacgtt ttattaatat  32400
agcggtggtt aatgccatct cctgcgtccg acgccatcg ccgaggctga gaggcaagat  32460
ccgtcgtctt cagtgccccc agcgcggtgc tccaaactcc caggctatgc ttttgtttat  32520
gttttattgt catttcatga ttcatgacat gacaggctct aggctatgct ttagacattt  32580
aataagtata ttcagctcaa acgaaacggg atctaaacca gagggttaaa ggcatgtttg  32640
gtttgtggct aaatgtgcca cacttttgcct aagttatgtc gtccgaattg aataactaac  32700
cttagacgaa aaagttaggc aaagtgtgat aacttaggta gcgaacaaac atgcttaag  32760
tctcacatct agggatggca atttatgcg tggatagtga tatccgtcgg atattcgacc  32820
cgacggatca ggatatggat atgttttttg acctgcgggt tagacccgta cccgatccga  32880
gataaagcag acatggattt ggatattaaa cctcacccgc gggtaattcg ttggatatcc  32940
gaaattaacc attagtccat tactgtcgat ccacacatgg acaccaatga acaaatcgcc  33000
agcccaccat tgtccattgt gcccaggcgc caagcgccag cccattgccc actaaggcat  33060
cattccgcca aagacccaaa gtggcaaaca cccaaaccga caaacactaa tgatctaatc  33120
cccatccccc agccggcagc ttccgagcaa accaactcat ccggtcgtc atccactcat  33180
cctcatcccc tgcccatctg atccgatcag tcatctcatc ctcatcccct acccgatcgg  33240
atccctgct catccgccga gcaccaccaa gcagcaggct ccagtcgtcg agcaccagca  33300
ggagcacgac acgccgccca gtaggagcac ggccaggagg acgacgcccg catcctgcct  33360
cttctcctgc tactggagcc tctactgcta ggagcacggc taggagacg acgcccgcat  33420
ccagcaggag caccagcagg aagaggacgc ccatactgct gtcgttgagc gatgatctga  33480
```

```
tgcccccat  catggctctt  ctcctccctc  gcggcctcgc  ctcgatctgc  tgctgccgga  33540
tccgagcgcc  gtgcccacgg  gtcacgacca  gcgatatgca  gggatcaaga  atccaacttt  33600
gagaaaaatt  gcttgagatg  taaatggcgc  caccggagta  ccatcagtac  tgtgacggaa  33660
cctcccaagt  aattaggccc  acctatagtt  gtccttgtcc  aacagacatc  agacacccta  33720
tagatgttcc  taaatcactt  cacaagttcg  gtatcttctt  tcttaccttt  ccaggaacgt  33780
ttcacccatc  ttgcagacat  tacgaaacat  cggagatata  gaaatgcaga  agcgattaca  33840
taacttacat  ttatttaaaa  agtaagatca  agttacttat  tacagaccag  agttatccta  33900
gaagtgcaga  gtaatattat  tacaatacca  agggaggcaa  aaactcctcc  cgatggtttt  33960
taaacaaaag  ttctatatgg  aggaccaagt  cttcccgcgg  cttcactctt  gtttttcttc  34020
cttgggaacc  accttggagc  agaagcaaca  aaaatttgtc  gcttcctcac  ctaaaaacaa  34080
cggaggaata  aaccatgagt  atggaattac  tcagcaagtc  ttacccgact  aaagaaaaga  34140
ctctcaaggg  tatgctggtt  aagggagtca  aggtaaggct  tttcaataat  caaagactct  34200
gttttgcaga  aatgcttact  aaagtggatc  cttaaaaatc  cagttttatt  tgtcaaatta  34260
agtagaatta  cctgtaacta  gagttctttc  taccctagtt  caatcacttg  tcctgcacta  34320
gccaatttct  taacaaaacc  atcatcttta  gtggaatgct  acgtgtaagt  cagtgaccaa  34380
gtcttcataa  ccgcgaaggt  acggcgatcc  gaatcgatta  tactcagctg  aggatctcca  34440
atcacacgac  atatgtagca  cttaaccctt  gcatatgtca  acccgccacc  ggggttctta  34500
agaccagatc  aggttcacgc  aaaccgagag  cacagataca  ccaccgtcca  gcctcttgcc  34560
acggagggta  cacgctactc  ccgccaccgc  tccacgccca  ttttgtgtta  tcttattctg  34620
gccttagtct  gcccgaggca  aggcttaccc  atgacgaggc  atgtgaccag  ttaaagggtc  34680
cccgatcagc  aggcctacat  cgagacggtc  cttaatcgac  tcagacggag  acactacacc  34740
gagactcctt  tctcgtgcaa  gtcacccgcc  cggtctcgtc  ttaatcattt  caaacccaaa  34800
gtttggtacc  tggcagaggt  acatctttc  cgatgttgaa  tccatcaagg  cctttgacag  34860
attcaccatc  aagttttatt  tttgaaaaca  accctcccac  ttttgccaaa  catcttttgt  34920
aaaacaaatc  cttttgtttt  tctagagcaa  ggctaagcat  caaaatcctt  ttgtaaaacg  34980
ggtgatcaag  gatggtaatc  aaattcaagg  aaggtaatgc  aggaatttgtt  taagcattca  35040
actcctatca  cctaatgcag  caatcaagtc  agaaagattt  taaaagcatc  aaggaggtgg  35100
caaatgcacc  ggggcttgcc  ttcgttagta  ggtgagttag  gctcggtccc  gcagatatcg  35160
aagtagaaac  aattgccggc  ctgagaatcc  gaaggtgggg  gtgtcttctc  ttcggtcact  35220
tcaatctctt  cttcgttttc  taaatataac  catatagagta  tatatatata  taagaatgaa  35280
tgccatgtaa  tgctcatgag  agtgcgaaga  taataaagat  ttattatcta  agtcttgaat  35340
acaactttcc  ttcacggaac  tccgagaact  tagggtttcc  ggagtcagta  aaggagttca  35400
aagggcaggg  gggttttagg  ttctaagtat  caaacaaggt  ccaaatcaac  ccaaattcta  35460
cccaaggcct  ctaaataatg  catagaactt  atgtaaaaag  tttggacatt  tttggaaatt  35520
ccatttatt  tctaaaaatc  caaaaccact  accttaaact  actttaaata  ccttaaaatt  35580
ccttagttaa  cctaaaattc  atataactat  ttttattaaa  ttctatggaa  aataagaagc  35640
ctaggaaaat  tggtttcaca  attttaggat  ttttctacaa  ttttttaaaaa  atttccaaag  35700
ctctatagaa  aaagaaaagg  aaaaagattg  aatagtgttg  ggctgattct  agcccagccg  35760
gcccagtacc  aggggaaaac  gcgcgcgcgc  gccctgccc  tggcgacttt  gcacagaggt  35820
cctcggggtt  tggctaatta  gaactggctt  ctatcactat  tacactgtgt  cgctgacaga  35880
ttgcagagaa  gcccctgcag  ttctaactct  tcgcagaggg  aggtcctcga  cggcgttcac  35940
gcccagccga  actccggcga  gtgcctgcac  cggccgaacg  gggcaacgac  tagggttccc  36000
gagccgcgga  catcaaattg  gacctagccc  gagcatttcc  cctaacctaa  ttccatctat  36060
ggcccaatgg  cttgctctgg  ccacggtggc  cgtgaacatc  gcggcaagac  agtcgcgttc  36120
ccggcgacca  aagggctcct  agctcgattg  tgtgggtcgg  caagcatcat  agacttaagg  36180
gaaagcttaa  acgagggaga  gaaggagacg  aactgaccgg  aataaggctg  ccgaggtga  36240
ggttcggttt  cgggtggcgg  agaattgatt  tggggcgaat  tcaaaattcg  tgagctcggg  36300
cgaacaattg  ctagcaatac  gtggtggctg  ggtgggtgat  gatgttgtga  agctctctgc  36360
ggggtcaatt  tatagatccc  aggggcgtg  gcgcttaatt  tgagccgaca  gtgtgggcgg  36420
ccggagataa  ggaagatcat  cggcttgcg  atttcgtgtc  caccgccgtg  gcgggctcac  36480
cggcaatgat  gagacaacag  tggggaagtca  cggcgatgca  acagaggtgc  tcggatacat  36540
ggtgtaaggc  cgagcgacgg  tgatcccggc  cgggcttatc  tgctcaagcc  gcacggcaga  36600
ggggaagtac  tggggggttca  ccggagtgcc  gtccagcgca  tgcctttacc  gagcgatctt  36660
atctggtcac  cggcgacgtg  aatcacaacg  gcggcgacgt  gaatctcagc  gaagatcagt  36720
cgtcggcggt  gagagactac  cgcgctggct  gtctgatctc  cctggtagca  ctgtaccatg  36780
gagagttata  tttagacagc  ctgacagtca  agtttggagc  ccaattttct  ctcaatttca  36840
aataacaact  catccagtga  cctgcagcaa  agttgtagag  ctacaatcca  gctataactt  36900
tgctacaatg  tgctcccaca  aaaagtcact  ggatcttgct  taaaattaag  ccctaagttc  36960
atgtcatccc  actgttaatc  tgaatttcag  atttcaagca  gtctgacagt  ccaactttag  37020
gctcaattat  ctccagtatt  ttcttaacaa  ctatgctcac  actcttaaga  aaagttgttc  37080
tcctatgatt  gggctataat  tttaatgtgg  tgacctaggg  aaaaaacccct  atgatttaaa  37140
agttacaagg  ctcaaaagtt  gagcccctaaa  cactatttt  cagacttagt  ataaaatctc  37200
aaatagggtc  cttttttgcaa  atgaggccaa  aacttagggt  ttggcttgta  aattcacata  37260
tgagtgaccc  aaatgactta  agatacttat  ttaacttagt  ttttgcactt  tagtccaaaa  37320
gtggactaat  tttgcacata  agccctagg  gtttggattt  agggttttct  agggttccga  37380
ttagggtttt  tggtatccca  gaggtataaa  tgtggttcaa  ctttattctt  gggaatattt  37440
catgactatt  tccctagagc  ttttaggttt  tctcaatttg  ggttatatct  tacccccttta  37500
atccctattt  agggttaaat  tccctatcta  ggttctatt  gcaaaacact  aaaacaatac  37560
aacttgtttg  aaattttttac  ctagtagaatg  cactctaggt  gtgtcaaaca  tatgcaatgc  37620
caatgtttat  gatgctatgc  tcaagttttta  gttgcagtaa  caccagggt  gttcatcct  37680
tccccccata  aaagaatctc  gtcccgagat  taaaagtcct  agggtaagta  atggaaaagg  37740
aaacacgaca  tactttttatt  tccttatttc  tggtacaagg  caggggtggt  tttgaaatca  37800
ctcctttatt  acaacagcta  tacaggcttt  acaatttaca  agaagctaaa  aagcctggga  37860
aattcttatc  taaaaagtct  tgagtttccc  atgtagccttc  attcttcggaa  tgttggttcc  37920
actgtatctt  ataaaacttg  agagtttttct  ccgggtaacc  ctgtccttttt  gatccaagac  37980
tcgaataggg  tgctcagaat  atgtcaagtc  cggttcaagg  acaacatctg  tcacttcaac  38040
ggttcgatca  ggaacccgaa  gacacttctt  caattgggac  acgtgaaaca  cattatgcac  38100
agcaaacaag  gtttcgggta  actgaagtcg  gtatgccact  ggcccatatc  tttccaggat  38160
aagaaaagga  ccaatatatt  atggtgcaag  ctttccttta  actccgaaac  gcgatactcc  38220
```

```
cttcattggt gaaacccttta agtagacata gtatccttca aggaaatata agggcattcg   38280
ccgtttgtct acgtaactct tttgacgagc ttgagctttc ttcaaattat gaattatcct   38340
ttgaactctt tcttcagtct cttttcaccat atcaggcctg aagaagtacc tttcaccagg   38400
ttcagaccaa tttagcggag tacgacatcg tcgtccatat aaagcttcaa agggtgccat   38460
cttgatgctt tcttgatagc tattattata tgaaaattcc gctaacggca aacattcatc   38520
ccattttttgt ggaaattcca gaacacatgc ccgcagcata tcttcaagta tttggtttac   38580
tctctcagtc tgtccactgg tttgaggatg gtaggccgaa ctatggagca acttagtacc   38640
caaggatttg tgaagtgctt cccaaaactt ggctacaaat tgaggtccac gatccgacac   38700
tatgggtctt cggaacacca tgcagactaa gaatacgagc aatgtacaaa tgggcataga   38760
cagtaaccgg gtgatctgtc ttgaccggta gaaagtgagc aattttcgta agccgatcaa   38820
ttataaccca gatagaatca tacccttttg tagtcctggg taatcccaca atgaagtcca   38880
tactaatatc ttcccatttc tatgttggga tcggcaaagg ttgtaatgga ccagctatct   38940
tcatgtgtat ggccttgaca agtctgcaag tgtcacactt agccacatag cgtgcaattt   39000
caattttcat cttcgtccac cagtagtgct gctttagatc atgatacatc ttagtgcttc   39060
ccagatgaat agaatagcga ctaagatgtg cttcatctaa gatttgctgg cggagttctt   39120
cattcttcgg caccactatg cggttattga accatatcac accttgatca tcttctttga   39180
aacatttggc tgttccagcc attatcttct cacgtatgtg cttcatacc tcatcatctt    39240
tttgtgcgtc aattattctt cgtatgatga ttgactccag cttcaaatga tttgaagtcc   39300
catgttgaat cattcccagg tttaatttct ccatctcctg gcataatgta atgtcagaag   39360
tcctcactgt taaacaatgg caggaagcct tgcaattgag cgcatctgcc actacatttg   39420
cttttcctgg gtgataatgg atttctaatt cataatcctt gattagctcg agccatcgcc   39480
tctgtctcat attcaattct gactgggtga agatgtattt caagcttttta ttggtctgtat 39540
aaatatgaca gacattaccc agcaaataat gacgccagat ctttagggca tgaaccacca   39600
cagctaactc cagatcatga gtaggataat gttcctcatg tcggcgcaac tgccttgaag   39660
catatgcaat tactccggcct tcttgcatta gcacacaacc gagtccactg cctgatgcat   39720
cacaatatac atcaaagggc ttggtgatgt ccggttgagc caataccgga gtagtggtta   39780
ctaatgtctt caattgttca aaagcttcat cacactttga agaccaattg aacttaatat   39840
cattcttcaa taaacttgtg attggcttca caagcttaga aaaatctggt atgaatcggc   39900
ggtaatatcc agccagtcca aggaaacttc ggacctgatg aacagtggtc gggggttcc    39960
actccaaaat gtccttgact ttgctgggat ctaccgcaat ccccctggca gacaatacat   40020
gtcccagaaa ctgaatttcg tccagccaaa acacgcattt gctaaacttg gcatataact   40080
gatgttctct caagcgcgtt aacacgatcc gtaaatgttg ggcgtgctcc tcttcattct   40140
tggaatatat caaaatatcg tcaatgaaga ctaccacaaa cttgtccaac tcgggcataa   40200
ataccgagtt catcaaatac gtgaagtggg caggagcatt tgtcaatccg aaagacatta   40260
ccaggtattc aaataatcca taccgcgtag tgaaggcggt ctttggtata tcttcgggcc   40320
gaatacggat ctggtgatag cccgatctga gatcaatctt ggaaaatacc cttgctccag   40380
tcagttgatc aaataaaatg tcaatccttg aagagggta cttgtttttg atggtgacct    40440
cattcagggg tcgataatcc acacacattt gtaaagtttg atccttcttt ttgacgaata   40500
tggctggaca acccacggc gatgagcttg gccggataaa tccttctca agtagatctt    40560
gtaattggat cttcagttct gccaactcat taggaggcat tcggtacgat cttctagata   40620
ctggagccgt accgggtttc aactcaatta caaactctac ctcccgttca ggtggcagtc   40680
cgggcaaatc ctcgggaaag acattgggaa actcgcatac caccggaata tccttgatttt 40740
ccggtataat ggcttcataa gctctgccag tagctttggt tggaatgggg ataggcaaaa   40800
gaatttcttc ctggttatga ctcaacctga taattctctg atcagtgttg agagttgctt   40860
tatgtctggc taaccaattc atacccaaaa tgacatatat atcttggcct ttcagaatga   40920
tcatattagt aggaaagtcc catccggcca aggttacggg cacttgatag gccacttctc   40980
tagtaaatat ttgtccccct ggtgagtgaa tttttaaacc cctcttttga ttcatggcat   41040
gagatgcaat gttgctccac aaatttcttg ctgatgaatg tatgcgaagc accagaatca   41100
aagagaataa ctgcgggatg attggccaca agaaacgtac ccatcattac cggctcaccg   41160
tccggtgtag tggccacttg cgtataatat atgcgtcccg tcttctttgt attttttgccc   41220
atattatttt ccttggcttg agatgaattc ccagatcctt gctgattatt tgactggttc   41280
tgctttggat aagggcaatc cttgataaaa tgcccagatt tgccacaatt gaaacatcca   41340
gtcgacgagc tgggtaaagc agggaatcga gtgcctgggg cacccggctg acttgatgta   41400
gtaggggcat tattgggacg aataaagact ggctgcttaa aaggaaagga gggtggacga   41460
gcgaaagaac gattctggtt agaaggccgg atgacgaacc gttgcctgt caccgggccc    41520
tgactagacc tgtcacctcc aaaaccttg gatttaccag cgcctgcata cttcgcttct    41580
actgccagtg ctgtactgac agctcttcca taagtaagat ctatgcaggt tgccatcttc   41640
ctttgcagtc gatcatttaa tcctctcata aagcaattct tcttcttcaa atcagtgttc   41700
acttgatcga ttgcatattg tgacaaatga ttgaacttat tgagatactg gttaacagta   41760
tccctcctt gtttcagctt cataaactct tcttgcttca tgtgaagaac accttctgga   41820
atatagtgct cgcggaaggc caccttgaat tcttcccaag ttatctaatg attggccggt   41880
tgaacggcca caaaattacc ccaccaagtg ctggcaggtc cgcgcagttg ctgggctgcg   41940
aataaaggct tctgggtttc tgaacatcgc agcagtccaa acttttgctc aatcacacga   42000
agccattcat ctgcttctaa cgggtcttcg gcttttgacaa acagcggtgg tcgcgtctct   42060
gagaagtcca agtaagaggt ttcacggggg ccctgttgat aaccccgcccc accttgttgt   42120
tgcaattgtt gacccgccat ctctctaaga aaacgggtat tatccgcggt tgcatttacc   42180
aaggccacaa tcgcctcggc cagtgtggga ggaacaggag gtggatttgg ggtagactcc   42240
ctcccacagg aggtactagc tccgtcctgt gctcgagtct tggaaggcat ctgtggcaac   42300
aacatttgga aaacaatatg atatgccaag gaaaaaccat ccattttaca ttaccaaaaa   42360
gagtaatgta cagactcgaa tttttacaac aggatacatt acctattata caatagcaca   42420
acctattatg caatagtaca aaatattata cattagagca acctgttata caatacacta   42480
cttctacttc tactaccca ttattcctgc tttccgttgc ttttggcggc ctcgtcgtcg    42540
ggtgtgggag accattcgtc gactagcctc ataaggag gggctgaaaa aggtctaac     42600
tcaccaccaa gcgcgtgtcc cgcaacatgc cagggtccgt tccgactc accaggatcc    42660
gtaggctcac tgggatgcag ttgcgaatat aatacatgaa tctcttcatg taaggtattg   42720
caatatgtct gcagttcatc aacagccaag ttgagctcgg ctactcgagc ttgagctttt   42780
tgctccttgt cccatgcaag cgaacgggat tgaacaaccc agtcaagtgc caaatcccgg   42840
tccgcgagct gatctcgcag atggcagata tctcttctca actcatttat gcggtcgcca   42900
tctatgaccc agatagtcgt tctgcggcgg agtttcgctt ggagtcgact tacttcagct   42960
```

```
tcaagatccc ctataggatc attgcttccg ctactactat tatcatgcct tggggtcagc   43020
tggtgactcg gcacaccaat cggtccagta tgtttgcgcg ttgttctcct tgtgcgcggc   43080
ggcattttct aagggggaaa atttgattag tatggttctt agcatgatgc atgtataatt   43140
acagaatcaa ccttagttga ttcacacctt ctatatgttg cactcttact acctggtctt   43200
taagatagac tcttcagaat acttaggtaa gaaaggaaga gagtttctag gtaagactttt  43260
tagaaaatct tttttgaagat gcctcataat atctgcaaag aagggctacg ctccgatacc  43320
agctgtgacg gaacctccca agtaattaag cccacctaca gttgtccttg tccaacagac   43380
atcagacacc ctatagatgt tcctaaatta cttcacaagt tcggtatctt ctttcttacc   43440
tttccaggaa cgtttcaccc gtcttgcaga cattacagaa catcgaagat atagaaatgc   43500
agaagcgatt acataactta catttattta aaaagtaaga tcaagttact tattacagac   43560
cagagttatc ctaggagtgc agagtaatat tattacaata ccaagggagg caaaaactcc   43620
tcccgatagt ttttaaacaa aagtcctata tggaggacca agtcctcccg cggcttcact   43680
cttgtttttc ttccttggga accaccttgg agcagaagca ataaaaattt gtcgcttcct   43740
cacctaaaaa caacggaggg ataaaccctg agtatggaat tactcagcaa gtcttacccg   43800
actaaagaaa agactctcaa gggtatgctg gttaagggag tcaaggtaag gcttttcaat   43860
aatcaaagac tctgttttgc agaaatgctt actaaagtgg atccttaaaa atccagtttt   43920
atttgtcaaa ttaagtagaa ttacctgtaa ctagagttct ttctacccta gttcaaatca   43980
cttgtcctgc actagccaat ttcttaacaa aaccatcatc tttagtggaa tgctacgtgt   44040
aagtcagtga ccaagtcttc ataaccgcga aggtacggcg atccgaatcg attatactca   44100
gctgaggatc tccaatcaca cgacatatgt agcacttaac ccttgcatat gtcaacccgc   44160
cactgggggtt tttaagacca gatcaggttc acacaaaccg agagcacaga tacaccaccg   44220
tccagcctct tgccacggag ggtacacgct actcccgcca ccgctccacg cccatttcgt   44280
gttatcttat tctggcctta gtctgcccga ggcaaggctt acccatgacg aggcatgtga   44340
ccagttaaag ggtcccccggt cagcaggcct acatcgagac ggtccttaat cgactcagac   44400
ggagacacta caccgagact cctttctcgt gcaagtcacc cgcccggtct cggcttaatc   44460
atttcaaacc caaagtttgg tacctggcag aggtacatct tttccgatgt tgaatccatc   44520
aaggcctttg acagattcac catcaagttt tattttcaaa aataaccctc ccactttgc    44580
caaacatctt ttgtaaaaca aatccttttg ttttttctaga gcaaggcaaa gcatcaaaat  44640
cctttttgtaa aacgggtgat caaggaaggt aatcaaattc aaggaaggta gtgcaggaat  44700
tgtttaagca ttcaactcct atcacctaat gcagcaatca agtgagaaag attttaaaag  44760
catcaaggag gtggtaaatg caccgggggct tgccttcgtt agtaggtgag tcaggctcag  44820
tcccgcagat atcgaagtag aaacaattgc cggcctgaga atccctaggt ggtggtgtct  44880
tctctttggt cacttcaatc tcttcttcat tttctaaata taaccatata ggtatatata  44940
taagaatgaa tgcatgtaa tgctcatgag agtgcgaaga taataaagat ttattatcta  45000
agtcttgaat acaactttcc ttcacggaac tccgagaact tagggtttcc ggagtcagta   45060
aaggagttca aagggcaggg gggttttagg ttctaagtat caaacaaggt ccaaatcaac   45120
ccaaattcta cccaaggcct ctaaataatg tatagaactt atgtaaaaag tttggacatt   45180
tttggaaatt ccatttattt tctaaaaatc cagaaccact accttaaact actttaaata   45240
ccttaaaatt ccttagttaa cctaaaattc atacaactat ttttattaaa ttctatggaa   45300
aataagaagc ctaggaaaat tggtttcaca atttttaggat ttttctacaa tttttaacaa  45360
atttccaaag ctctacaaaa aaagaaaagg aaaaagattg aatagtgttg ggctgattct   45420
agcccagccg gccagtact aggggaaaac gcgcgcgcgc gctcgcgccc tggcgacttt    45480
gcacagagt cctcggggtt tggctaatca gaactggctt ctatcactat tacactgtt    45540
cgctgacaga ttgcagagaa gcccctgtag ttctaactct tcgcagaggg aggtcctcga   45600
cggcgttcac gcccagccga actccggcga gtgcctgcac cggccgaacg gggcaacggc   45660
tagggttccc gagcggcgga catcaaattg gacctagccc gagcatttcc cctaacctaa   45720
ttccatctat ggcccaatgg cttgctctgg ccacggtggc gtgaacatc gcggcaagac    45780
agtcgcgttc ccggcgacca aagggctcct agctcgattg tgtgggtcgg caagcatcgt   45840
agacttaagg gaaagcttaa atgagggaga aaggagacg aactgaccag aataaggctg    45900
gccgcagtga ggttgggttt cgggtggcgg agaattgatt tggggcgaat tcaaaattcg   45960
cgagccttggg cgaacaattg ctagcaatac gtggtggctg ggtgggtgat gatgttgtga  46020
agctctctgc agggtcaatt tatagatccc aggggcggtg gcgcttaatt tgagtggaca   46080
gtgtgggcgg ccggagataa ggaagatcat cggcttcgcg atttcgtgtc caccgccgtg   46140
gcgggctcac cggcaatgat gagacaacag tggggagtca cggcgatgcg acagaggtgc   46200
ccggatacgt ggcgtaaggc cgagcgacgg ggatccccag cgggcttatc tgctcaagcc   46260
gcacggtaga ggggaagtac tgggggttca ccggagtgcc gtccagcgca tgcctttacc   46320
gagcgatctt atctggtcac cggcgacgtg aatcgcaacg gcgcggcgt gaatctcagc    46380
gaagatcagt catcggcggt gagagactgc cgcgctggtg gtctgatctc cctggtagca   46440
ctgtaccatg gagatttata ttcagacagc ctgacagtca agtttggagc ccagtttttct  46500
ctcaatttca aataacaact catccagtga cctacagcaa agttgtagag ctacaatcca   46560
gctataactt tgctacaatg tgctcccaca aaaagtcact gaatcttgct taaaattaag   46620
ccctaagttc atgtcatccc actgttaatc tgaatttcag atttcaagca gtctgacagt   46680
ccaacttcag gctcaattat ctccaatatt ttcttaaaac tatgctcaca ctcttaagca   46740
aagttgttct cctatgattg ggctatatt ttaatgtggt gacctagggc aaaaaccta    46800
tgatttaaaa gttacaaggc tcaaagttg agcccataac actgttttca gacttagtat   46860
aaaacctcaa atagggtcct ttttgcaaat gaggccaaaa cttagggttt ggcttgtaaa   46920
ttcacatatg agtgacccaa atgacttaag atacttattt aacttggttt ttgcacttta   46980
gtccaaaagt ggtcgaattt tgcacataag cccctagggt ttggatttag ggttttctag   47040
ggttccaatt agggtttttg gtatccgagg ggtataaatg tggttcaact ttattcttga   47100
gaatatttga tgactatttc cctagagctt ttaggttttc tcaatttggg ttatatctta   47160
cccctttaat ccctatttag ggttaaattc cctatctagg gttctatttg caaaacacta   47220
aaacaataca acttgtttga aattttacc tagtgaatgc actctaggtg tgtcaaacat    47280
atgcaatgcc aatgtttatg atgctatgct caagttttag ttgcagtaac accagggtgt   47340
ttacaagtac cttgtgcagg tgaccaagta ctaggccgca cagaactgca aggtacgtat   47400
gcacacatgg ttacatttac tatagaactg gagttatttt ttgatgcaaa ggctgccagg   47460
tcatggcgat ttcacgtccg ttaggctcga gaggtggact caaacatcca agttttgcaa   47520
gttttgatgt tggatgttaa atttctatgc tcacccctcg tttggttatt gatgtactat   47580
ttccatctca tgtcacaaat ttggcataag gaatgggtat tggtgctac tggctgtgtt    47640
tatttccaag tattatacat gtacaatgga acagttgata atagttttgc atgaactatt   47700
```

```
ggcattagct atctaaaagg acagaaaggc agacatgagc aacaaatccc gctccatggg   47760
ctgaaactgg gattcgtgat ggtcagctaa gcataccttc gccttcaaat ttgcgtagct   47820
tcttttttat tctgctagtt gtttggtctg ctgttcaaat gccttattat tctgcgagtt   47880
gttttaagac tgggcctcaa ttttttttca aggcagaaag tgctactgcc gctctcactg   47940
tagcggtgtg gtactgggat ccttgccaat aaggtaaaac tctaactgat cttcttacgc   48000
tttgcattga ggaaggagct cttctgggcg gttggataac agagtcgttc tagtgtgttt   48060
ttagggtgag cccgtccaag acgcccgtgc gtccccgtgc ccctcgccag ctgatgtcgt   48120
cctaggtata catacaggag gtgctgacga tggcactgct catatataag taatagagat   48180
agacatgtat gaaaagggtc tttttgttttc aagtagtgtg tagttgctgt tacttttaac   48240
agctaatgca atctggatga gtcacctatg aatgccatac tggaatctgt tgcgcttttg   48300
ttgatcatta ttattttgca atccaggcta ggggattgaa gaagcacttg aagaggctca   48360
atgcgcccaa gcattggatg ctcgacaagc ttggtggagc ttttgtaagt aaacatgtcg   48420
gggaccataa ttaggggtac ccccaagact cctaatctca gctggtaacc cccatcagca   48480
caaagctgca aaggcctgat gggcgcgatt caggtcaagg ctccgtccac tcaagggaca   48540
cgatcccgcc tcgcccgagc ccagcctcgg gcaaaggcag ccgacccagg aggattcacg   48600
tctcgcccga gggtcccctc aagcaacgga cgcaccttcg gctcgcccga ggcccaggct   48660
tcgcggagaa gcaaccttgg acagatcgcc acgccaacca accgtatcgc aggagcattt   48720
aatgcaagga tcgactgaca ccttatccta acgcgcgctc ctcagtcgat agggccgaag   48780
tgaccgcagt cacttcgccg ctccactgac cgacctgacg ggaaaatagc gccgcctgcc   48840
ctgctccgac tgctgtgcca ctcgacagag tgaggctgac agcagctaag tccagcctcg   48900
ggcgccatga gaagctccgc ctcgcccgac cccagagctc gggctcaacc tcgacgccgg   48960
acgacggact ccgcctcgcc cgaccccagg gctcggactc agcctcgacc tcggaagacg   49020
gactccgcct cgcccgatcc cagggctcgg gctcaacctc gacctcggag gagcctccgc   49080
ctcgcccgac ctcgggctcg gaccgaccac gtcgcagggg gagccatcat taccctaccc   49140
ctagctagct caggctacgg ggaacaagac cgacgtccca tctggctcgc cccggtaaac   49200
aagtaatgat ggcaccccat gtgctccgtg acgacgggcg ctctcagcgc cttatggaag   49260
caaggagacg tcagcaagga tccgacagcc ccgacagctg tacttccaca gggctcaaac   49320
gctcctccga cggccacgac atcacatgaa cagggcgcca aaacctctcc gacagccacg   49380
acagcatgta cttagggctc tggctcctct ctgctagaca cgttagcaca ttgctacacc   49440
ccccattgta cacctgggcc ctctccttac gtctataaaa ggaaggtcta gggctctcgt   49500
acgagagggt tggccgcgcg ggagaacggg ctgacgcaca aggctctctc tctctctctc   49560
ccacacgaac gcttgtaacc ccctactgca agcgcatccg ccctgggcac aggacaaacac  49620
gaaggccacg ggttcccctt tgctgttttc ccccctttgt gtttcgtctc gtgccgaccc   49680
atctggaatg ggacacgcag cgacagttta ctcgtcggtc cagggacccc cggggtcga    49740
aacgctgaca gttggcacgc caggtagggg cctactgcat ggtgacgaac agcttcccgt   49800
caagttccag atgggtagtc tccagcaacc actccaaccc gggacggtgc tccatttcag   49860
gagtcttgag ttcatgtccc tcgacggcag ctacgacatg acactccttc ctccgccgcg   49920
cgacaacgac aatggcggcc gtcagcccgc ccgtcggcgg cggaatcgac gacgtcttcc   49980
ccacgtgcgg gaagagcgat atccgggtct gtccgtcac cttcccgct gacggaggag     50040
gaggcggggt aggcatggcc aatcaggagg cggcaccctcg tcggctgtcg agcgagtcga  50100
cggcgccgac gccccaacgg gggacacgtc gggcgttgac ctcgcgtctg agacgaagac   50160
aagcgtcgtt tccccgcaac acgccaaccc caagcagacg gatgacgcca gcacgctcgc   50220
gaaggacttc ctgggcgtta acctcgtacc tgagacaacg gtgcagtccg tccctgacgg   50280
gacttcgtca ccaccgtcg atcaagaggt accgtccgtt tcccatccca tgcctttta     50340
attcagttgt gacccaccaa gcgatcccgc ttcggtggac gctttcataa aggcatgtcc   50400
aaacccctccg gggtatcata tgcggtcaac ctgggaccga ctgacggccg tctcgaccta  50460
tgggcccccg ggttccgagg aagatgacga gcctgactct ggttgggatt tctccgggct   50520
cgataacccc agtgtcatgc gggacttcat gaccgcatgt gactactgcc tctccgattg   50580
ctccgatagc agccacagcc tcggcacga ggactgtggc ccaaggtgcg aatgcttcca    50640
cgtcgatcta ggggtcttg acgaaggcaa ccatcttggt atgccggagg atggtgatcc    50700
ccctaggcct gcgcctcgcg ttgacatcct tcgggagcta gctgtggtcc cagtccctgc   50760
gggggtcaa gacgcacggc ttgagcaaat ccgcgaggta caggccaggc tcgacgagga   50820
agcaggacaa cttgtgcagc ttcggcaaaa tatcgggcag gagtgggcag gccgagcacc    50880
ggctggagaa gcgcgtcatc tggcccagga cgtccagcac cgcatcaccg acgatgccag   50940
ggcgaggctg ccccccggctt ccagtggggt cggccagaac ctggctgcag cagcgatact  51000
actccgagcg atgccgaaac catccaccac cgagggggtgg cgtatccaag gagagctcaa   51060
aaatctccta gaggatgtcg cggtccgacg ggccgagagc tctgcctccc gaaggcaggg   51120
gtaccccgg agcatcgcgc tgcgacttcc cgattcatgc gggaagcctc ggtccacacc     51180
gggcgcacgc gggacacagc gcctgcggcc ccaagacgcc tcggcaacga gcaccgccgc    51240
gaccgtcaag cccacctcga cgagaaggtg cgtcgaggct accacccccag gcgtggggga  51300
cgctacgaca gcgtggagga tcggagcccc tcgcccgaac cacccagtcc gcaagctttc    51360
agccgggcca tacaacgggc accgttcccg acctggttct gaaccccgac taccatcacc    51420
aagtactcgg gggagtcgaa gccggaactg tggctcgcgg actaccggct ggcctgccag    51480
ctgagtggga cggacgatga caacctcatc atctgcatcc ttcccctgtt cctctccgac    51540
gccgcccgag cctggctgga gcatctatct cctgtgcaga tctccaactg ggacgacctg    51600
gtcaaagctt tcgtcggcaa cttccagggc acatacgtgc gccctgggaa ctcctgggat    51660
ctccgaaggt gccgccagca gccgagagaa tccctctggg actacatccg gcgattttcg    51720
aagcagggca ccgagctgcc caacatcacc aactcggatg tcatcggcgc gttcctcagc    51780
ggtaccactt gtcgcgacct ggtgagcaag ctggggcgca agactcccac tagggcgagc    51840
gagctgatgg acatcgccac caagttcgcc tctggtcagg aggcggtcga ggccatcttc    51900
cggaaggaca agcagcctca ggggcgtcag ccggaagacg tccccaaggc gtccgctcag    51960
cgcggcgcga ggaagaaggg caagaagaag tcacaagcaa aacgcgacgt cgccgacaca    52020
gacattgtcc ccgccgccga gcacagaaac cctcggaagc ctcccggagg cgcaacctg     52080
ttcgatagga tggtcaagga gtcgtgcccc tatcatcaag agccatcaa gacacccctt     52140
gaggaatgcg tcatgcttcg acgctacttc cacaagggcg ggccaccggc gaaaggtggc    52200
agagcccaca acaacgacaa gaaggaggat cacaaggcga aggagttccc cgaggtccac    52260
gactgcttca tgatctatgg tgggcaagtg gcgaacgcct cgactcggca ccgcaagcaa    52320
gagcgtcggg aggtctgctc agtaaaggtg gcagcgccag tctacctaga ctggtccgac    52380
aagcccatca ccttcgacca gggcgaccac cccgaccgcg tgccgagcct aggaaagtac    52440
```

```
cctctcattg tcgaccccgt catcggcaac gtcaggctta ccaaggtcct catggacgga   52500
ggcagcagcc tcaacatcat ctacgccgcg accctcgggc tcctgcagat cgatctgtcc   52560
tcgatccggg ccggtgcgac gccttttcac gggatcatcc ccgggaaacg cgtccaaccc   52620
cttgggcaac tcaatctgtc agtctgcttc gggactccct ccaacttccg aaaggaaacc   52680
ctcacgttcg aggtggtcgg gttccgagga acctaccacg cagtgctggg gagaccatgc   52740
tacgccaagt tcatggccgt ccccaactac acctacctca agctcaagat gtcgggcccc   52800
aacgggtca tcaccatcgg ctccacgtac cgacacacgt acgaatgcga cgtggagtgc   52860
gtggagtacg ccgaggccct cgccgaatcc gaggccctca tcgccgacct ggggagcctc   52920
tccaaggagg cgccagatgc gaagcgccac gccggcaact tcgagccagc tgagacgatt   52980
aagtccgtcc ctctcggccc cagcaacgac gcctccaagc agatccggat cggctccgag   53040
ctcgacccca aataggaagc agtgctcgtc gactttctcc gcgcgaacgc cgaggttttt   53100
gcatggagtc cctcggacat gcctagcata ccgaggatg tcgccgagca ctcgctggat   53160
atccgagctg gagcccgacc cgtgaagcag cctctacatc gattcgacga agaaaagcgc   53220
agagccatag gcgaggagat ccacaagctg atggctgcag ggttcattaa agaggtattc   53280
catcccgaat ggcttgtcaa ccctgtgctt gtgagaaata aaggagggaa atggcggatg   53340
tgtgtagact acactggtct aaacaaagca tgtccgaaag ttccctccct ctgcctcgca   53400
tcgatcaaat catggattcc actgctgggt gcgaaacccT gtctttcctc gatgcctact   53460
cagggtatca ccaaatcagg atgaaagagt ccgaccagct cgcgacttct ttcatcacac   53520
cctttggcat gtactgctac gttactatgc cattcggttt gaggaatgcg ggtgcgacat   53580
accaaagatg catgaaccac gtgttcgag agcacattgg tcgaacggtt gaggcttacg   53640
tcgatgacat catagtcaag acgaggaaag cctccgacct cctctccgac cttgaaacga   53700
cattcaagtg tctcaaggcg aaaggcgtaa aactcaatcc cggagaagtgt gtcttcggag   53760
tcccccgagg catgctcttg gggttcatcg tctccgagcg gggcatcgag gccaacccgg   53820
agaaaatcgc ggccatcacc aacatgggcc ccatcaagga cttgaaagga gtacagaggg   53880
tcatgggatg ccttgcggct ctgagccgtt tcatctcacg cctcggcgaa agaggcctac   53940
ctctgtaccg cctcttgagg aagaccgagc gcttcacttg gccaccccga gccgaggaag   54000
ccctcgggaa cctaaaggtg ctcctcacaa gcgcgcccat cttggtgccc cctgttgccg   54060
gagaagccct cttggtctac gtcgccgcta ccactcaggt ggtcagcgcc gcgatcatgg   54120
tcgagagacg agaagagggg cacgcattgc ccgtccagag gccggtctac ttcatcagtg   54180
aagtactgtc tgagaccaaa atccgctacc cgcaaattcc agaagctact ttacgcggta   54240
attctgacgc ggcgaaagtt gcgacactac ttcgagtctc atccggtgac tgtggtgtca   54300
tccttccccc tgggagagat catccagtgc cgagaggcct cgggtaggat tgcaaagtgg   54360
gcagtggaga ttatgggcga gacaatctca ttcgcccctc ggaaggccat caagtcccaa   54420
gtcttggcgg acttttgtgg tgaatgggtc gacacccagc ttccagcagc tccgatccaa   54480
ctggaactct ggaccatgtt tttcgacggg tcgttgatga aaacaggagc ggggcgcgggc   54540
ctgctcttca tctcgcccct cgggaagcac ctccgctacg tgttgcacct ccatttcccg   54600
gcgtccaaca acgtggccga gtacgaggct cggttaacgg gttgcgaatt gccaccgagc   54660
tagggtccg acgcctcgac gctcgcggcg actcgcaact tgtcatcgac aagtcatgaa   54720
gaactccac tgtcgcgacc cgaagatgga agcctactgc gatgaggttc ggcgcctgga   54780
ggacaagttc tatgggctcg agctcaacca catcgcccga cgatacaacg agactacgga   54840
tgagctggct aagatagcct cggcgcggac aacggttccc ccggacgtct ctcccgagga   54900
cctacatcaa ccctcagtca agaccagcga cacgcccgag cccgagaaag ccttggccct   54960
gcccgaggca ccctcgggcc ccgaggggtga ggcactgcgc gtcgaggaag agcggtatgg   55020
ggtcacgcct aatcgaaact ggcagaccct gtacctgcaa tatctccacc gaggagagct   55080
accctcgac agagccgaag ctcggcaact agcgtgggc gccaagtcgt tcgtcttgct   55140
gggtgacggg aaggagctct accaccgcag cccctcaggg gtcctacaac gttgcatatc   55200
catcgccgaa ggtcaggagt tattacaaga aatacactcg ggggcttgcg gtcaccacgc   55260
agcacctcga gccctcgttg gaaatgcctt ccgacagggt ttctactggc caaccgcggt   55320
ggccgacgcc actaggattg tacgcacctg ccaagggtgt caattctatg caaagcagac   55380
ccacctgccc gctcaggctc tgcaaacaat acccatcacc tggccgtttg ctgtgtgggg   55440
tctggaccctt gtcagcccct tgcagaaggc acccggggc tacacgcacc tgctggtcgc   55500
catcgacaaa ttctccaagt ggatcgaggt cagaccccta aacagcatca ggtccgaaca   55560
ggcggtggcg ttcttcacca acatcatcca tcgctttggg gtcccgaact ccatcatcac   55620
cgacaacggc acccagttca ccggtagaaa gttcctactg cgaggattac acatccggg   55680
tggactaggc cgccgtagct caccccatga cgaatgggca gctagagcgt gccaacgaca   55740
tgattctaca aggactcaag ccacggatct acaacgacct caacaagttc agcaggcgat   55800
ggatgaagga actcccctcg gtggtctgga gtctgagaac gacaccaagc tgagccacgg   55860
gcttcacgcc gttttttcta gtctatgggg ccgaggccat cttgcccaca gactcactgg   55920
gccatcttca cgctgttttt tctagtctat ggggacgagg gcgtacgacg accgaagcaa   55980
tcgaaccaac cgagaagact cactggacca gctggaaagg gctcgggaca tggcctact   56040
acactcggcg cggtatcagc agtccctgcg acgctaccac gcccaagggg ttcggtcccg   56100
agacctccag gtgggcgact tggtgcttcg gctacgtcaa gacgcccgag ggtgtcacaa   56160
gctcacgcct cctaagaag cccggaacat acaagctggc caacagtcaa ggcgaggtct   56220
acatcaacgc ttggaacatc cgacagctac gtcgcttcta ccctttaagat gttttcaagt   56280
cgttcataca cctcgtttac atacgccaac aaagtctaac catcaaggaa gggtcagatc   56340
tgcctcggca aagcccgacc ctccctcggg ggctagaagg ggggcacccc ctctacgtca   56400
aaattttcct cgaaaaaagt ctttctgcca gaacatcttt cgtgctttc gactacttcg   56460
aaagtgggat cctgaaaacg acggagtaca cgtaagcaga caaggacgac cgagccgagg   56520
gactcctaca cctccgggat acggatacct cactcatcac cttctgcgat aagtaactca   56580
cgctcggata agcgatcccg ctggccgaac aagtcttaac gttcgaaagc ttttctgccg   56640
aaacgatttt ttgtgccttc tcgactatat cgataacaga atccaacgga cgagtaagag   56700
tacacgtaag cggcaaggcc gaccgagccg agggactcct acaccttcgg gatacggata   56760
cctcactcat caccttccgt gaaaagtaac tcttgctcga taagcaatt ctgttactga   56820
cgaacaagtc ccgatactcg aaacaagggg aaaagaaacg ccgctttaca acacgacgac   56880
ggtatgtttg ggcctcggcg gccgcaaaaa acatacgcac actacagata aattgttcct   56940
gcaggatcag acatcagtgg gggagcagca gcacccctcg gtcgactcc accttcggcg   57000
gagtccgacc cagcctcgga cggcgacacg gtcggaggat ctccatctcg aaggaacctg   57060
tcagcaccgc gcctgggcca tcgccgaggt gtcctccagg aacccggccc gagtagacga   57120
ctcgaccgac cgctctgtag cctcagccag ctgtcccccg aggacatcag cccggctcat   57180
```

```
ggcctcggca acccgactcc ggcgtcggtc ccaccagtgg acggcccgac caggctccgg    57240
ccgatgaagc ttcttttttga gccaactccg cctctgtcca cgctgacacc gctgacaccg    57300
ctgcctctag ctccggctca tcgcagagcg gccgagggtt tctttaacta agcaagagaa    57360
gcctcgggcg gcaaggccga ccgatccgag ggactcctac gcctccggga tacggatacc    57420
tcactcgtca ccttccgcac gaggcaactc acacttggtt aagcggttca gctagccgac    57480
aggcgagtcc tagtgctcga aatgaggaaa aaatacggct ttagccaaaa tacacatctt    57540
caggccccga cagccgcaat gaacagacac cggcactcaa ggtgccatta caaacagaac    57600
tctggttccg cccccacagg tacgaacgac cccccacatt ggagggcctg cggggcaact    57660
gaaagctctc ttgtgagttt tggtgtttgg atgacaactc aattaaagga ctaacaagtg    57720
tactaagtgt tgaacaggtg cttaagtaa agcctacagg gttcaacaca agtgaacaaa    57780
tgtgatggtc caagaactgg attatggata cataatggac atcacaagta agatggacat    57840
tgcacaaagt gagactcggg tgcgtagctc ggagacaact gatcaagcca aggacggagg    57900
caagaaaagc ttcgaggtac caaatgcacg ggagaaggtc aaggaggctg aggaacccaa    57960
agccaagggt gaagaagaag gcttgcaaag tcaagggtgg tcgagttgag aacagctacg    58020
gcacatcaag gatcactaca taaggacgtg acttacagcc aatgaggtaa cagctatagt    58080
tatgtggtgt aagtcataag gctcaagatc aagctctaag gaggagatca aggtcactag    58140
aaggagaaca agtgtcgaaa ccagaactgg aagcagccca aaagagctaa gttcactttg    58200
atctttagtt tgggttgttc ctatgtttgg agatgttcta tgtgacctttt acaggatgtt    58260
ggagccaagc gatgtcaatc tagatcaagt caagctgact tgataaattta tgagtccaac    58320
atcaaagctc aagcatgtga aatgctatag atgtaatgat taatagaagg tatgtttcta    58380
gacttagtac attggttttg gggactaata tacttgtcta agtgttagaa acagaaagaa    58440
gaagaaaagg gaagaggtgc gaaaggcttg gctgtgtcaa gccaagactt agttcagtct    58500
ggcacaccgg actgtccggt ggtgcaccgg acagtgtccg gtgcgccagg ctgaactctg    58560
gcgaactggc cgctctcggg aattcaccgg cgatgtatgg ctataattca ccggactgtc    58620
cggtgtgcac cggactgtcc ggtgagccaa cggtcggccg ggcaacggt tggccgcgcg    58680
atctgcgcgg gacacgtggc cgagccaacg gctagatgga ggcaccggat tgtccggtgt    58740
gcaccggaca tgtccggtgc gccaacggct ccaagactgc caacggtcgg cttcgacgta    58800
gaaggaaaga aatcgggcac cggacagtgt ccggtgtgca ccggacagtg tccggtgtgc    58860
accggactgt ccggtgcgcc acccgacaga aggcaagatt tgccttcctg gattgcttcc    58920
aacggcttct aggcccctt g tgtctataaa agggacccct aggcgcctcc agcaaaatag    58980
aagtgcagcc aacaagtgta gactccactg gaatcaattc tcactctccc tcttgtgtgt    59040
aactctatag tttgtgtaga aggcacagct ataagcctta gagagaggag tagtgctgct    59100
aagagctaga gcaaggtctt gagcatatcg ttactctacc ggggtgctgc caagaagtct    59160
gtaagcagcc gcggttctgt tgtaaccca ctcaatagtg aaaggctcta tctgtcatac    59220
tgacagatct gagcaaacgg aggaaggagt tgaaatgaac tccaagccca ggtgtggcta    59280
actccaacga ggactaggca agcatttcag gcttggccga acctcgggat aaatccttgc    59340
gtctgtgtgc tctgttctgt attgtatcct gactctcttt ctactcgcct ttatatctgc    59400
acttcaatac ttatctgtgg tataagcttt atttgaagtg caggacattt tgagacagga    59460
tcttctattc ggctgcaacc tacttgaaga gtcttctcca tccactgcat actaagtctt    59520
cgagtagagt aagaatttaa gttttaaagt gaaaagtttt attcgcctat tcacccccc    59580
ccctctaggc gacatccaga tcctgttccc gggtcaaagg gaactttcaa ttggtatcag    59640
agctaggcct ctccagtgtg ggcttagccg tccggagatg acgatgtcgt cacaagaggt    59700
aactggtgga cttcttttag acgatggctc taattacaag tcttggtctg tctctattta    59760
tagtgctttc atgagtgttg atcctgattt gagacaggtc tttagtagta gtatttttcc    59820
ctccaatatt agtaaaaacc catccaatga agaactaaga tgtctaactc taaatcacca    59880
tgcttgcaac atcttagttg attctctatc tagaggtgcc tatttttgcca tcatgagtag    59940
tgatagtgat ctattgttg atgctcatga tttatggaat aggattaaag aaaaaatatt    60000
tgtggcaaac tgtgatgctc ctactcccta tattacttgt gatactaacc attcaaaggg    60060
agaagaacaa gaacgatggc atccaaacga tgaatccacc tcgtcgacag gtttgttctc    60120
cactagtgat aaatgtttta ttgctaacaa tgacggtgga gacgaaagcc atgataagga    60180
gaaatatgag gatgaattct catcatcaca aggtacattt tcctatattg cttccactga    60240
cattaatgac agggaaaatg agaccgatga tgtggaggaa gaggagattc accgtttcta    60300
catccatctc aacaaagagg acaaggcact cttggttaag ctgttgagaa ggaacaagga    60360
acaaggcgag acgcttctca ggctagagga gtccctcatc aaaaccaaca acagcctgga    60420
gaagatgacc aaagaacatg agaagctaag gcgctctcat gatgatttgg tccaaaggta    60480
tgaatatgtt ttaattgagc aaagaaatag tcatgatgca ttatctaata ttgctcaact    60540
taaaacggaa aattctatgc ttaagagtca agtagaaaca atgaacttag aaaaacgtgc    60600
tctaggtaaa aagtatgata tgttgtcaaa ttctcataat aaaattagttg atgaccatat    60660
catgcttaat gttgctcatg aggttataat tgcaaactta aattcatgtg aacctcattc    60720
tgcacgtgt gcgcatttga agtgtatatc accatgtgct aacccctgtt gctcaaaaga    60780
aagccaatca ttgattgagc aacagttttt agggtcacaa aagaaattct gtgggaacaa    60840
gaagcaaaga caactaagga gaagacacat tgctcaactc tctcaagata tccacgggcg    60900
cgtggtgaag aagcttgaga aaggaaaaac tgcagcaagt gttaagctca ataagaagaa    60960
tgttcccaaa gctataaatg aaaaaagtaa catgaacaag aaaaggta aaaattcaat    61020
tagtcatgtt gtttgcactg atcatctctc catgtcattc aagcacaaaa agggaagagg    61080
aaaaaggagg tgcttcaaat gcaaggagac aggccacctc atcgcgtctt gtccgtacaa    61140
agacaaggat gaaagaacaa ggagttgttt tggatgcaac aataaggacc acatgatcac    61200
ttcatgtccg gtcatgaaga atcaaggata tgcatcctcc aaagtgaccc tcaccaagga    61260
aatgacaca aaacaagcgt catgtcaagt tgagcgacgc ttctgctaca agtgtggtga    61320
gcaaggtcat ctatccaagg tatgttacaa aggtaagatt cctaaacaag tgaatttgtg    61380
tcaatcttat tcgcataggaa gacccaaatc atacacttgt gctagatcta taacgagatc    61440
acctagaact agcacaaagg caatttggga accaaaggca catttacatg atcattatgt    61500
accccatcccg agatggatac caaactgtgc caactagacc atgcaggtgc ctcgagatgg    61560
actgaagtca atgggaaaga ttaagacggt tatctaaactc tctatgtcta agctgttaat    61620
tgttttagtg tttattgacc caaggttgaa ttattgtgaa acactaatcc catgttcatc    61680
tcaagagaaa taaggtgtat aggtcctgaa tcattattgg tgaatcaagt aaaggatctt    61740
gatgagaatc tacaacctgc tctccaaagg acggtacccg tgtattttaa gtacataatt    61800
gcaatttagt attgctctta agttggcttg ttgtgctacc tgtccttaga gtagttatgc    61860
tttatgattg cctgtgttaa attgatcata atgatggttg cttaatcatg actggtgcta    61920
```

```
taaaggatat atcttttgaa tcattcatgg gtagctattt catttgttat atccacaacg   61980
ataactctct tgatgtatat ggataaacct gtaacttttg taagtcatgc tatgtgcaat   62040
tatgacattt tgtttagtcc atgttcacat gattaccta gtttggtact gtgtgaattt    62100
caaatccatg tcgtgccctt ttgagctatg aggtgcgtaa gcaaaggag ccctaaattg    62160
gcgataacaa gggctctcat aaaggcaaag gtatggaaa tggagctatg caatttcatt    62220
aaatattctt gaaattccat tcattgtgat catagctatg ttcttgcctt tcaattggta   62280
atatcttggc ttaggtaatt tatgccttta aaatgttgtt tcttttgtgc acctaagaaa   62340
ccttcttaat tataacatgc ttagatattt cgattgtgtt tatctttaat tggtatatac   62400
aatgatagtt aaatatgaag catgtacaag ttgcgtaaat gttagacttc ctgtgagtat   62460
tcaattggct taggtgccac tgaggcgtgc attgttgtat ttagtcaacc tttcatttag   62520
ccttcaattg gtgttatgtg gcgtttcatt tgatattcaa attggcatct ttgggtgatg   62580
aaagtggtag agtatgcctt gaccaaggta tgttgtgatc ccctctaatt ctaaggaagc   62640
tagaatgtgc aaagtgcaag tcattcaaat acttgatgca caacttgagg gggagcacac   62700
ataacttgtg tcttttgaga ctaactgttt cttgagcaat cttgtatagt ctctaggtgg   62760
aaaagagaag ataagcaaga aatggagcaa tcaggacttg ggtacctctg taagtcaaga   62820
aaattggtat ctcaagttgt gagtaagtgc atattttttag attgctcatg ctctataata  62880
tctggtgata atagatgctt attcttaaat atcatggagc catgataata aatgaacttt   62940
gcaattggta tctttcaatt ggtagccgta atagttcgct tcaattgaca tcttttgata   63000
atcatgagaa tagaagtttc ttcttgtgcc caatactata acttgttcta agtttggtgt   63060
cttagcaaca agaaaaagtt aggagagaga atcaggcaca agtgtggaga agctctcgag   63120
agattaacta ctttcaagat gggaagtaca ctacatcatg gtaaaggtac aaaaggaagt   63180
attaatcttt ttgcatatat gtatcttacc taaatgttga taggacatat gttcaataaa   63240
taaggggggag ttttgatagt cgttttttccc cttaacaccc tgctgtccct tgacatcatc   63300
atatgttctt gcttgagtat ggttttttggt gtttgatgtc aaaggggggag aagttgtgca  63360
ttaaagctta tctcaacctg agaggaaagc ttatcctaat gggtgatgtg ttagtttgag   63420
ctttgccaag tgtgatattc atatgttttct tgcagtatta tacgtgttga tcatatggac   63480
tagactagtg ttttatattc atatgttttct tgcagtatta tacgtgttga tcatatggac   63540
tagaccagtg tttccgctgc gatgaattat ttggcttcta tagtgaaata gatagtcatg   63600
tggttaatgg tgctttaaga ttgctttaaa ttgatatctt agtttaagtt ggtatcttaa   63660
tggtgaatag tggtaggttg atattcctag tgatatatcca ctaatttgaa tggtgtttaa   63720
ctctgattat gtgcatttgt gtgttatagc atcatggttt gattcttgac ataatgcatc   63780
ctaaaaagtg ctaaggtgta gaaatgtttc aattttccta agtatgtgca aattgacgtt   63840
tgtggtcaaa attaggtttt tgaagtaagc acttatttag ggggagcatt ctataatctt   63900
agaattcaaa tttgtgcttc aaatcttatt ctttatgtaag ctttaattgt gttgccacca   63960
atcaccaaaa aggggggagat tgaaagctct cttgtgagtt ttggtgtttg gatgacaact   64020
caattaaagg actaacaagt atactaagtg ttgaacatgt gcttaaggta aagcctacag   64080
ggttcaacac aagtgaacaa atgtgatggt ccaagaactg gattatggat acataatgga   64140
catcacaagt aagatggaca ttgcacaaag tgagactcgg gtgcgtagct cgaagacaac   64200
tgatcaagcc aaggacggag gcaagaaag cttcgaggta ccaaatgcat gggagaaggt   64260
caaggaggct gaggaaccca aagccaaggg tgaagaagaa ggcttgcaaa gtcaagggtg   64320
atcgagttga gaacagctac ggcacatcaa ggatcactac ataaggacgt gacttacagc   64380
caatgaggta acagctatag ttatgtggtg taagtcataa ggctcaagat caagctctaa   64440
ggaggagatc aagtgcacta gaaggagaac aagtgtcgaa accagaactg gaagcagccc   64500
aaaagagctc agttcacttt gatctttagt ttggggttgtt cctatgtttg gagatgttct   64560
atgtgacctt tacaggatgt tggagccaag cgatgtcaat ctagatcaag tcaagctgac   64620
ttgataattt atgagtccaa catcaaagct caagcttgtg aaatgctata gatgtaatga   64680
ttaatagaag gtatgttttct agacttagta cattggtttt gggggactaat atacttgtct   64740
aagtgttaga aacagaaaga agaagaaaag ggaagaggtg tgaaaggctt ggctgtgtac   64800
agccaagact tagttcagtc tggcacacca gactgtccgg tggtgcaccg gacagtgtcc   64860
ggtgcgccag gctgaactct ggcgaactgg ccactctcgg gaattcaccg cgacgtacg    64920
gctataattc accggactgt ccggtgtgca ccggactatc cggtgagcca acggtcggcc   64980
gggccaacgg ttggccgcgc gatctgcgcg ggacacgtgg ccgagccaac ggctagatgg   65040
aggcaccgga ctgtccggtg tgcaccggac atgtccggtg cgcgaacggc tccaagactg   65100
ccaacggtcg gcttcgacgt agaaggaaag aaatcgggca ccggacagtg tccggtgtgc   65160
accggactgt ccggtgcgcc acccgacaga aggcaagatt tgccttcctg gattgcttcc   65220
aacggctcct aggcccttg tgtctataaa agggacccct aggtgcctcc agcaaaatag    65280
aagtgcagcc aacaagtgta gactccactg gaatcaattc tcactctccc tcttgtgtgt   65340
aactctatag tttgtgtaga aggcacaact ataagcctta gagagaggag tagtgctgct   65400
aagagctaga gcaaggtctt gagcatatcg ttactctacc gggtgctgc caagaagtct   65460
gtaagcagcc gcggttctgt tgtaaccca ctcaatagtg aaaggctcta tctgtcatac    65520
tgacagatct gagcaaacgg aggaaggagt tgaaatagac tccaagccca ggtgtggcta   65580
actccaacga ggactaggca agcatttcag gcttggccga acctcaggat aaatccttgc   65640
gtctgtgtgc tctgttctgt attgtatcct gactctcttt ctactcgcct ttatatctgc   65700
acttcaatac ttatctgtgg tataagcttt atttgaagtg tgagacagga   65760
tcttctattc cgctgcaacc tacttgaaga gtcttctcac tccactgcat actaagtctt   65820
cgagtagagt aagaatttaa gttttaaagt gaaaagtttt attcgcctat tcaccccccc   65880
tctaggcgac atccagatcc tgttcccggg tcaaagggaa ctttcagcaa caaaaccta    65940
gacagctcgc cgaggcccgc tctggcagca gcgacaacga cctccgctcc ggacagcaa    66000
acagcagcag cgatgaccatc agtcgacg ctgctgcgaa caggccctcg cacacgtccg    66060
caccatcaaa ctggtggtca ccgtcttggg tgaccaccag cgaggggatg cagccgggcc   66120
gcctgatgaa aatccttgaa gccgagcgat ggctgaaagg taccaacttc cgcgaagttg   66180
cgttcctcca acgacgacaa gacgaaagca acgcgggcgc tccccatccg ggggctcgga   66240
agttggaagg gcgcgatgca tgaagggagt gtgaagacat ggttgccatc caaggggtc    66300
gccctcctt taaaggcgac tctcccccact tgcgtcctca gtcgtcgcgg actgactctt   66360
caccaacacg ctccaaggtc ctcccctac gacatggggg ctgggtccca cgcgtcatgc   66420
aagctgccc agggcagaag aagccaaacc gtcgcgcgca gagtgcgtaa ctgcccagcg   66480
gttacaagca ctcctccact ttcgcccaga ccggcgggtg aaaggggcgga ccgccatgca   66540
ggcggcatgc aaccgcacca aggggggtgca cccttttcgac tccgacgcgt ccagcacggg   66600
ggcccaggcc cacacgtcat gtaaccggcg cgccggttac tacgcgcgag aaaactgcacc  66660
```

```
gccacttgtg ctagtaccgc gccttctcga ctgcggaacc ggtgccgcga ctcgaggcaa  66720
ccctgcgcat ggcccaacag tgccaaccga gcacatcgat cacgggtcag tcagccgcgg  66780
gagaaggcgc gatggttgat atggccaaaa gtgggccggc agtaatgcgc gcggcaggcg  66840
ggcggaagca gcggtcaagt cgtctgtagg ctcacgtccc ctcctgggac agcgagagag  66900
cccctcccca cggcgtgaag acgacacgcc cgtgttccgt tcctcgaacg gctagccgac  66960
gcacaacggc tgccccgcga accactcatc ccgtcgcatt aactctgcgg caggacaggc  67020
ggcacctttg gcaggcgaag caggtgacgc ttcacctccg ccttaatgac cgcgtcaaaa  67080
aaggtgcgcc acgtcgtttg atttcgtatc cttttaccct tcctctttct ctctcttgct  67140
atagggaccg ggaaagagga tactccgaaa gggatccttc tccgcgaagg aagcgggccc  67200
cgagccctcc tactaatcag aggttcgaag gctggcccct cggaagggtt cgacagtcgc  67260
cttagagcac tcgggctccg cgccctccta ctgatcagag gttcgaaggc tggcccctcg  67320
gaagggttcg acagccgcct cagagcactc gggttccgtg cccactactg gtcagaggtt  67380
cgaaggctag cccctcggag gggttcgaca gccgcctcaa gccactcgag ctctgcgccc  67440
actactgatc agggggtttgt aggctggccc ccgaaggatt cgccagccgc ctcagccgcac  67500
(sic)
gcagagcgag ggatgactct gggtacgtcc gatacatggc cgaggctcgg gctacgctcc  67560
cgaggtaccc taggacattt ccgagaccaa caggagcgat tctgtaacgg aatcccatca  67620
gagggaggca tcgagccctc ggaccctatc aaacgggacc gggtccggca aatcacctgt  67680
aggtacttttt ggagcgcgcc tctgaccgca tagccgaccg cggggcactg ggcacgggc  67740
gtccactcgg atcaaccgtt agcaactcac tggagacacc atgttcgacg ccctctgagg  67800
gcaacatggc gctttccccc ccctcctcct tgcggaaagg cgacgcaggg gcgtatgaaa  67860
aaagccgagt cagtccttgg ccgtcctctc gctctgtgcg gaggctcggg ggctgctctc  67920
gcatgaggga acaaccaaac cagcccgaga acttggaacc tgactatgca cccgggctac  67980
ggccagttcg catgagggaa caaccagacc ggccgaagca tcacgaaacg tgctaagacc  68040
tcgaaggagt caaaccactc ctccgaggcc tcagggcta cacccggcgg gtgcactcgc  68100
gcgcacccac cggaacgaaa cgcaaccgag aaagccggt cccctgcaa aaaagtgcga  68160
caaaagcctc caagtgagta ccaacactcc cttcgagagt cggggcta tgtcgggac  68220
cataattagg ggtaccccca agactcctaa tctcagctgg taaccccat cagcacaaag  68280
ctgcaaaggc ctgatgggcg caattcaggt caaggctctg tccactcaag gacacgatc  68340
ccgcctcgcc cgagcctagc ctcaggcaaa ggcagccgac ccaggaggat tcacgtcttg  68400
cccgagggtc ccctcaagca acggacgcac cttcggctcg cccgaggccc aagcttcgcg  68460
gagaaggaac cttggccaga tcgccacgcc aaccaaccgt atcgcaggag catttaatgc  68520
aaggatcgac tgcacaccttta tcctgacgcg tgctcctcag tcgacagggc cgaagtgact  68580
gcagtcacat cgccgctcca ctgaccgacc tgacgggaaa atagcatcgc ctgccctgct  68640
ccgactgcta tgccactcga cagagtgagg ctgacagcag ctaagtccag cctcgggcgc  68700
catgggaagc tccgcctcgc ccgaccccag agctcgggct caacctggac gtcggacgac  68760
ggactccgcc tcgcccgacc ccagggctcg gactcaacct cgacctcgaa agacggactc  68820
cggctcgccc gaccccaggg ctcggactca gcctcgacct cggacgatgg actccgcctc  68880
gcccgacccc agggcttgga cttagcctcg acctcggaag acggactctg cctcgcccga  68940
tcctagggct cgggctcaac ctcgacctcg gaggagcctc cgcctcgccc gacctcaggc  69000
tcggaccgac acgtcgcagg gggagccatc attaccctac ccctagctag ctcaggctat  69060
ggggaacaag accggcgtcc catctggctc gccccggtaa acaagtaatg atggcacccc  69120
gcgtgctccg tgacgacggc ggctctcagc cccttacgag agcaaggaga cgtcagcaag  69180
gatccgacag ccccgatagt tgtacttcca cagggctcag acgctcctcc gacggccacg  69240
acatcacatg aacagggcgc caaaacctct ccgacagcca cgacggcatg tacttagggc  69300
tctgtctcct ctctgctaga catgttagca cattgctaca ccccccattg tacacctggg  69360
ccctctcctt acgtctataa aaggaaggtc cagggctctc gtacgagagg gttggccgcg  69420
cgggagaacg ggctgacgca caaggctctc tctctctcca acacgaaccgc ttgtaaccco  69480
ctactgcaag cgcatccgcc ctgggcgcag gacaacacga aggccgcggg ttccccttttg  69540
ctgtttttccc cccttttgtgt tctgtctcgc gtcgacccat ctgggctggg acacgcagcg  69600
acaattttact cgtcggtcca gggacccccc ggggtcgaaa cgccgacaaa acaatatttt  69660
ctagctttgg tacctacaat cttctgtact tccccatttg tctaatgctt caggttgttc  69720
tttttttttct gtagatctat gtaccttatc cttgctatac tgtccatata tgttgtgtgc  69780
atgaaagtct tgcattgaaa atgtcatgtg ctacaatcgt taggactatt aatagatgtt  69840
gctctgtcta tctatccatt tacatcgctg gaaattccca tgcccttttca tagtacgcct  69900
gtgaaattct cactgcttttt ctattggttt gtgtgcagtt catgctctgc aaggtaaggt  69960
ctgttcagtt tggccagaaa ggcatccct gcctaaacac ctacgacgac cgcaccatcc  70020
gctaccccga cccgctcatc aaggccaacg acaccatcaa gatcgacgaa atcttctaga  70080
attgnnnnnn nnnnnnnnnn nnnnnnnnnn nnnnnnnnnn nnnnnnnnnn nnnnnnnnnn  70140
nnnnnnnnnn nnnnnnnnnn nnnnnnnnnn nnnnnnnnnn nnnntcttat gtatcagctt  70200
gattcgttgc acattgttga gatgggcctc tctttactcg ctaatggaca ataccgctca  70260
agttttggga ccaagcgttc ctcacctcaa cacatcttat caatagaact cctactaagc  70320
ttcttgatta tgcacatcg ctccaccgtc tcttaggtgc tacccagat tactctaatc  70380
tacgcgtctt tggctatgca tgttagcaa atttgcggcc atacaacacc cataaactct  70440
agtttcggtc catttggtgt gcttttctag tctatagcaa cccttcacaag ggttacaagt  70500
gtcttgacat ctcaacgggc cgtgtttata tttcacatga tgttgtttttt gatgagacgc  70560
ttttcccttt gctgctctcc atcccacagt cggtgctcga tatacctctg acgtgcttct  70620
tctacccgat cctaataatt tcggggccaa tcagatgat cttgtgacta attcctctgc  70680
tgaatccagc atgcttgctc cgattttgtg gcctaaccag ctttttgcagc caccaatgat  70740
ccctgctgca aattctgtcc cggctggtgg cctcaatccc ggtgtgatc tgttgctagg  70800
ctccacgcca cacccctccg acgcggctac aggtgcgccc agcaacgcgg tgcttcccac  70860
caccacggcc gcatcaatag cagcagccac ttcgggattg cctcgtgccg actctggcgc  70920
ggctggtccc tctctcactg acagccatct gccctcgcca tcagcctcgt gtcctattcc  70980
gcttcctgct aggcgcactc ggctacagag tggtattgtg aagcccagaa agtttacaga  71040
tggcacgatc aggtatggaa atttggcaat tgtgaagaa cctctccagt tgtctgttgc  71100
attgtttgac ccaaactgga aaagctgcca tggacctaga attttctgcc cttatgcgga  71160
ataaaacatg gcacttggtt cctccgcac ctgacagaaa tttgattgat tgcaagtggg  71220
tttataaact caagagaaaa gctgatgagt ctattgacca tcataaagct cgattggtgg  71280
ctaaaggttt taaacagcgc tacgacattg actatgatga cactttttagc ctagtagtta  71340
aatttgctac tgtccgcctt attttgtctc ttgctgtctc tcagggttgg agcctctgcc  71400
```

```
aactggatgt gcagaacgcg tttcttcatg gtgttctaga ggaagatgtg tgtcggcacc   71460
ctaaaactag ggtacccctt actactgtat aaagacgcag tacccacacg actatctta    71520
gtcgcgtggt aaataagctg tatgtgggac cagaccatga ctcgccctag cctcgggcga   71580
ctactctggg ccagcaacag cacctgaccc caccacatgg gcgggttcgg ggccgccatg   71640
tgtccagaga aagtgatgta ctccaaggca tcaacagtga gtccggaccc catgggagag   71700
tgccggacca gtgccagacc cctgtatata cggtccaggc ctccaagttt ggtccaggac   71760
ctccacgtgt acaaaccgga cccctaggat gggatccgaa cccccgtat gggtctgggc    71820
cacccatagt ggggtcccag ggttctagga cagaacatac ccgggccttg attaggaccc   71880
aggtggggt ccggagccga cacgtgtcta gacctggtct ggtgggatcc ggacctatcc    71940
gcatacactc cttctccctg ctcaggcgga gacccgatgc tgccacgtgg catactgcgc   72000
gcggcataaa ccaacgggtg gaacctggca tgatgcctct gggctacgcg tgccttcgca   72060
ttcattacgg agaagatgtg cgcctgtcca ttccactgac aggcggcatg ctcagtccac   72120
gatacgtggg ccatgcagtt actcacacgt taccataatcg agggcaatga ctccaccatta  72180
ctcgtatgtt tccaagaaaa gggttactgt ctatcaatgc tgcatggact gcagccatca   72240
tgactcccgc tgattactca tgtgttactc tgtcagcatt agttattcac ataatgtatt   72300
tcttccatta tgctcctggg cccacatgtc ggggctcagc atccttgtat gtgcctccct   72360
taaactataa aagggaaggc acacaacgtt acaagggaca cgctgtacac actcaataca   72420
acatacacac agtggaagta gtgtattacg ctccggccgg ctgaaccact ataatccctc   72480
gtgtcctctt gtgttcatcc cgaattcacc aaacaggcaa ccgcttaggc cccctcctca   72540
tcttaggatt agggcgggtg cattccgcca cccggccgga ggattttccc ttcgacattt   72600
ggtgctccag gtaggggct ttggctttag gttttttgcct gttttcttgc tcgacacgat    72660
ggttcagatc gtcgagcacc gtggcttgtc tcccgaagca ttcttgatgg aggaagggc    72720
attatcttcc atgccacgag gctccaaccg cgctgtgcct ggtgctgctg ctatgcacgc   72780
tgcgcagcaa cacacgcccg cacagacctc taggactccg tcgagggcta cctatggtgg   72840
gccattgtct gcagccaggg agttgctgcg taacccacca agttccacgg cctcccccggg 72900
ggccatgagg cagtggcgtg aagatgtcga ccgtctcctg ggcatggccc atcctagctc   72960
ggccaggtcc aggcctcgat cattccggca tcagcgcgag gcgtcaacgt ctgtgcattc   73020
accctcagtg aggggcaca gactaacgac ctgcgagcag aactcaacca caggcgtgca    73080
ggcgaggatg ctcgaatctc tctggagagg gcgcgtgagc gccggcaaaa cttcgagggt   73140
cgcaacctcg accaagactt cactgcaagg gacgcccgaa tccagatggg tgtcccattg   73200
gtcggcgtgg gctgcgccgc actagcagat catctccgcg cggcgacttg gccacccatg   73260
ttccggccac acctgccgga gaagtacgat gggacatcga acctgtcgaa attcctgtag   73320
gtctatgtca ccgccattac ggcagctggt gggaacactg ctgtaatggt aagctatttc   73380
catgtagcct tgaatgtgcc ggcacagacc tggctcatga acctcacccc ggggtcagtg   73440
tactcctggg aagagctctg tgcacggttc acaatgaact tcgccagtgc ttatcagtag   73500
catggcgtgg aggctcatct ccatgcagtg aggcaggaac ccgaggagac tctccgggct   73560
ttcatctccc gcttcaccaa ggtacagggg actataacctc gcatctccga tgcctccatt   73620
atcactgctt tccaacaggg gggtgcgtga taagaagatg ttggagaaat tggcgacgca   73680
tgacgtggaa accgtcacta cgctcttcac tctggccgac aaatgtgcca gagctactga   73740
gggccgtgca tggcactcga cgctgcaaac cagagtcacc caaatgggtg gctcaggtgc   73800
tgccacccag ggtggtggca agaaaaagaa gaagcaccgt gtcacgatag gccgtagtct   73860
ggtgctccag ttgctgtagc tacggctggg gaccgggacg agcgcggcaa gcatccacgg   73920
caacagggaa gtgacattgg gtcatgccct gtccacccca acagtcgcca cagtgcctca   73980
gaatgacgag agatcctgaa gctcgtgaag cgcatcagtg agcggcgcga gcatgcctcc   74040
agggatggct cgccgcctcg gcgccggcct ggcaaggaga aggtcgacga aggtgacctg   74100
gccacgggag aatgggacct cgagaattag gcccccgagc aagtcctcaa ggatatcctc   74160
actggagct ccgactccgg tgatgacaac gaccgccgca agaagctgta cgtaatgtat    74220
ggtggaagct gggagctcac ctcccgtagg aacgtgaagt ccctgcgccg cgaggtcctt   74280
ttggcgaccc caggggtccc gaaggcagcc ccacatcagc ggtggcggag caccactatc   74340
tccttcgggg cacccgactg ccccgaaaac atggcagggg ctggtatact accactcatc   74400
actgcccctg tcatcgccaa catgaagttg catcatgtgc tgattgatgg tggggttgag   74460
ctcaacgtca tcagccacgc tgcgttcaag cagctgcaga tcccaggatc ccgactagga   74520
ccctctcgca cgttctctgg agtgggccct aaaccggtgt atcccttgg gagcatcaca    74580
ctcctggtta cattcgggac tgaggataac ttccacacta agaatgtcta gttcgatgtt   74640
gcggaggtta acctcccttt caatgccatc atttggcaggc cggccctgta ccggttcatg   74700
tccattgccc attacaggta cttggtcctc aagatgccat cccctgctgg ggtcctcacc   74760
atgcggggcg accgtcccgc tgcgcttgca gctatcgaga agttcatgc cctagcggca    74820
gaagctgctc gcccggatga cgaggggagg gacccctcga cttcctgtac caagatgcct   74880
gctaaggtgc ctaaggtgca accatctggg gcagacggcc tccctgtcaa gaccatccgg   74940
ctcaacggga attcctccca gaccactcga atcacgggcg atctggagga gaaataggaa   75000
atcgcgctca tcgccttcct ccaggcaaat gccaatgtat tcgcatggga actatcgcag   75060
atgcctggga tccctaggga ggtgatcgag caacatctga agatccaccc tgacgccaaa   75120
ccggtgagtc agaagcctca aagacagtcc atcgagcggc aggatttcat ccgtaaggag   75180
gtccggaagc tgctggacgc tggtttcatc gaagaggtcc atcacccagt atggctgacc   75240
aatctagtca tcgtcccaa ggctaacggg aagcttggga tgtgcatcga ctacaccagc     75300
ctcaataagg cctgtcccaa ggacccatat ccacttccac gaatagatca aatcgtggat   75360
tctacctctg ggtgcaacct cctatccttc ctggatgctt actctagttt ccatcagatc   75420
gagatgtcta ggcaagatag gaagcatacc gcttttgtaa ctgtggatgg actttactgt   75480
tatgttgtaa tgccttacag tctgaaaaac gccttgccaa catttgtacg ggcgatgagt   75540
aatacttttg gtgacttgat tagggacagg gtagaggtaa acgtcgatga catcgtagtc   75600
aagactaagg gagggtcgac cctagtgaaa gacttaaccc tagtctttga caagctgcag   75660
gcaacacgca tgaagctgaa cccggacaag tgcgtctttg gtgtctctgc agggaagttg   75720
ctaggattcc tggtttcaca ccggggcatt gaagcaaacc cagagaagat caaagcaata   75780
gagacaatga ggctccggc ctgaatcaaa gacgtccaga agcttacggg gtcactggcc     75840
gcccttagtc gcttcatctc aagactggtt gagagggcac tacccttctt caagctattg   75900
cggaagtccg acccattctc ttggaccaaa gagacagaac aagcctttca agagttgaag   75960
cagcaccatg tgtccctatc aatactggta gctccagagc caggagagcc attatactag   76020
tacattgcag cggctacaga ggcggtgagc atggtgctgg tcgtcgaaag tacgacacaa   76080
catccctagg ggagtcataa agttccccta ggagaaggtg tggtctgac caccacgatg     76140
```

```
ttgacagaag gccaggagtt tgaggactcg ggactgaatg caggggtccg aaccatccag   76200
aagccggtct actacgtcag cgaggtcctc catgaggcaa aagccaggta ccttgagacg   76260
cacaagctta tctatgctat acttgttgtg tccaggaaat tgcgccacta ttttaggca    76320
cacagagttg tggtggtgac ctccttcccg ttaagggcca ttctccacaa ctcaaacgcc   76380
acaggcaaca tcgccaagtg ggccacggag cttgctgagt tccaactgga gttccagccc   76440
cgccacgctg tcaagagcca ggtcctggct gacttcatcg tggagtggac cccttcccg    76500
agcgctcctg ggggtccaga tcccgattcg gacaccacac ctgcggagcc aagggcttcg   76560
gtcttcactg agccccactg gatgcttttc ttcgacggat ccgcctgcca gcagggtggc   76620
agtgctggag ttgtgacacc ccaggtgtca gtttcgtgtt acgtcgcgag atttatccta   76680
atctcggatg ctcagtaaaa atttctattt ctcgctcgcg tatgtccctg attatccaga   76740
ttattcattc atgtttcacc gaattcggag ttactcagtc tcatagaagg ccaattttgg   76800
agcctgttaa aactttatc cttggcacaa atgcgaactc aaaatcatt ctcgaattat     76860
aaacctcatc tgaagctcaa taaatcaaac tctcgacggc tgttattga tctgtgtccg    76920
aatccaattt ctcgatgttc gatcgatgtc caactatttt aatccgagtc catactcaca   76980
aacgaaataa tcaatatgtc gtcctctgat caaatcttac tcgactcagc ttagcatctc   77040
tgtatccaat ccgatttcaa aatcaacatc ggcaacgatt tttatatatc acgattcgct   77100
ttctccgact aaaaatccaa aaccgatcaa atctcaggac ggttttatttt cgatttacgc   77160
gtagggaatt attttcaagc aaaatctaaa cagactctcg gctgagttaa tcgcgcaacc   77220
ttccgttcgt ccgaactctt ttcgctctgt ttctcagtag cgacgaattc cgcaggaaca   77280
tttttagtcc ggaaattatt tagcgcgacc caatttagtg ttttgggcca aatccagtcc   77340
agcccgtttg gcccataaga aacccctaccc taatttctcc tctataaata tgggcttccc   77400
taccttgcat tctgaaaatt ttccatttcc acccccaggcc ccaacaccct tctcttcctc   77460
ctctaccatt ttccagccat gggctccttc aagcacgtag agctggagct ccttccccag   77520
cgcgcagggg cttccatggc cgggcgttcc ttccctccag cgcgtcgaag ctcttctcgt    77580
agcgtcctct gcctttcttc ttccccgctt cacggcagca aggccaccag caggctccct   77640
gctccaccag ccccccagcca tggcatcctt cactcccta ctgttttcct cccagggcgg   77700
agcagcaaat ccatgcagcg gctccatggc cgagcaccct gcccggtgct ccagccggcc   77760
tcctctgccc ctgccatttt ccataggagt cgagctccta cctgcagcag gcgcccctg    77820
ctctttcctg tccgcgacca gggagcttca gctggcgtga aacttcactt gcgcacggcg   77880
gccagcaccc tctccttggg ctccaacagc ttggatgcca aaccccttc ttccttcccc    77940
tggccgagct cgagcttccc atggagccat tcctccctct ctctgttgta catagtgcca   78000
agcagcaact ccattttccc tggccgcgcc caaggtcggt gaccagcctc cccttccctg   78060
ttcttgccgt ggccgagcca ccacttcccc agccgtagcc ctctcccct ccattgtttc    78120
agcgcctgaa acaaacacct ggccgccatc cacacttgtg ctgcatgaaa tgtgcagcag   78180
ccccgacggc tccgcgtgct gccggcttgc tgttttgcg cgtagtgagc agcacgccgt    78240
gatgccgccg tgtgctcgct gttttgtgcg agccccaaac gtcgtcgtcg ttcacccgg    78300
tgagaccgcg acgctccttg tttgattccg catcgatgtt attttcctat gattaattat   78360
gtatgtgtgt tgcttttgttt tattttttgtg gaggagagaa cccgtgtttt tgcgaggaga   78420
aagcaggtcg cttaacgctc gttggatgtt tggagcgagt cacgaatcgg aatcaccgtc   78480
attcttgcaa acatcatttg ggtttgttta tggtgagccg atgcatgtcg ctctcgatcg   78540
actcgattaa tcattttgta tggatgtgtg taaaatgttc gattatgcgc attggtagga   78600
tcacgtttgc gattggagaa caagaggtta attgatgtgc acgattgta gttgtctaat    78660
tatgttttgg tcgatgatgt gcatgtggtt atatgtgtgt aactgtataa ttttataaat    78720
ggacgcgtgt agggaagaaa ttgaaataga aaagaactcg agtattttta ttttgatagg    78780
aaaatatgcg atgcgttgtt tgatgcgaaa actaagttac aaaatgtgga ttttgttttg    78840
ggaaatgcat cgatgtgttt atgtgaaaag tgtatttgtt ttaagcaatg tgatgggatt    78900
cataatttta gagggatat atttattgat gtgacgatta gttagagaa tgctagtttg    78960
cgtagaggat gtatcgttaa gacatgagtg tcagagtcca tttatactag tggtcgcgcc    79020
acatggattg aagtgtctcg agtgcacgcc ataatatggt tgtatgcgag acagggttat    79080
gcgtacgatg agtttagtaa aaattccatc ggtgtcagtt gtgttaagtt gaagtttatt    79140
tgtgcgtata aagtagtaag tgatttaatg cttacgactc ttaatcgatg gtagaaattg    79200
tcttgactta aatagagagg tggtgacatg ccagagtagt catcgctttc tctatattta    79260
taggtcaagt catgacgatg cgtattatgc gttcgttaaa attatgtttc gtatatagtg    79320
tatgattgtg ctcacgattt cgagtagaca cttcaaataa gtcaagtagc tttgtaatgc    79380
aagatgtgtg atgaagttag ttttgttttag gatatgtgtt gaaatgctcc attcctgtga    79440
tagacatgta gggttatttc aaaacggggtc gatgtgtgtg atgatgatat tcatgattta    79500
agtagatgtc ctgaaattat gtggcgaagc ttaagtaag ttgcaagcga tgtgaaatg     79560
ttttcgtaaa gatatatgtg gaatgtgaac gagtcattca atgtattcgg tatgtcatgt    79620
agtggtggta tgaaaaatgg gttaggaatc gatcggctaa atgccaagtt cggttagagt    79680
tattgtcggc gtttcgagac cgggggggtcc ctcaggtcga cgagtgagtg ccgcgtgcgc    79740
cagcccagat gggtcgagcg cgtgggcgag cgcgaagggg ggaaggagc gaggcggccg     79800
gagaccggcg tgagagaggt gggaatcccg cggccttcgt gttcgtcccg cgcccaggtc    79860
gggtgcgctt gcagtagggg gttacaagcg tccacacggg tgagggaagc gagcggcccc    79920
aagagagcgc ctgtcccgtc ctcgtcccgc gcggccaacc ctctctaaga ggaccctggt    79980
ccttcctttt atagacgcaa ggagaggatc caggtgtaca atggggggtgt agcagagtgc    80040
tacgtgtcta gcgagggaga gctagtgccc tgagtacatg ccaatgtggc agccgaagag    80100
atcttggaac ccagctagtg tgatgtcgtg gccgtcggag gagcggcgga gcctggcgga    80160
gggacagctg tcggagcggt tgtgtccttg ctgacgtcct cctgcttccg taagagagct    80220
gagagctgcc gtcgtcacag ggcatgcggg gcgccatcat tgcctatctg gtggagacag    80280
ccagatggga caccggtctt gttctctacg gcccgagtca gctcggggta gggtgatgat    80340
ggcgcttcct gttgacgtgg ctggcctgcg ccctaggttg ggcgacgtgg aggctcctcc    80400
gaagccgagg tcgagtctgt cttccatggc cgaggacgag tccgagcccc tgggtcgggc    80460
gaggcggagg tcgtcggcag aggccagggc ggtgtccgga ccctgggggtc gggcgaagcg    80520
gagttcgtcg tcttctgggg ctgagcccga gcccgaccc tggggtcggg gcaagcggag    80580
ttcgtcgtct tccgggtctt agcccgagtc cgagccctgg gtcggttgga cgggagttcg    80640
ccgtcttccg ggtcttagcc cgagtccgag ccctgggtcg gacggagcgg agttcgccgt    80700
cttccgggtc ttagcccgag tccgagccct gggtcgggcg agcggagtt cgccgtcttc    80760
cggggctgag cccgagtccg agccctgggt cgggcggagc ggagttcgcc gtcttccggg    80820
gctgagcccg agtccgagcc ctgggtcggg cggagcttcc tatggcgcct ttggcagggc    80880
```

```
ctggcttcct gtcagtatct ctctgtcaag tggcactgca gtcgaagtgg cgcaggcggc   80940
gctgtccttc tgtcagaccg gtcagtggag cggcgaagtg acggcggtca cttcggctct   81000
gccggagggc gcgcgtcagg ataaaggtgt caggtcacgt ttgcgttaaa tgctcctgcg   81060
acttggtcgg tcgtgcggc gatttagtca gggttgcttc ttagcgaagg cagggcctcg    81120
ggcgagccga agatgtgtcc gccgttagag gggggcctca ggcgagacgg aaatccctcg   81180
gggtcggctg cccttgtccg aggctaggct cgggcgaggc gtgatcgagt cgctcgaatg   81240
gactgatccc tgacttaatc gcacccatca ggcctttgca gctttatgct gatggggtt    81300
accagctgag aattaggagt cttgaggta cccctaatta tggtccccga cagtagcccc    81360
cgagcctcga aaggagtgtt agcactcgct tggaggcttt cgtcgcactt ttttgcaagg   81420
gaccagcctt tctcggttgc attttgttcc ggtgggtgcg cgcgagcgca cccgccgggt   81480
gtagcccccg aggcctcgga ggagtggttt cactccttcg aggtcttaat gccttgcgta   81540
atgcttcggc tggtctggtt gttccctcat gcgagctggc cgtagcccgg gtgtacggtc   81600
ggggcccaag ttctcgggct ggtatgttga cgctgtcaac ggtttggccg gagccgggtt   81660
tgcgagagca gcccctgagc ctctgcacag ggcaagaggg cgatcaggga cagactcggc   81720
tttttttacat atgcccctgc gtcgcctttc cgcaaggagg actaggggga gggcgccatg   81780
ttaccctcga tgggcgccga acatggtgtc tccggtgagc tgcaagcagg taatccgagt   81840
ggacgtccgt gccccgttcg ttaggggtcg gctaggggcc cagaggcacg cccaaaagta   81900
cctgcgggtg atctgccgga cccggtcccc tggcgacggg gtccgagggc tcgatgcctc   81960
cctccgatgg gattccatta caagatcgct cccgctggtc tcggaaatgt cctagggtac   82020
ctcaggagcg cagcccgagc cttggttatg tatcgaacgt accctggtc atccctcgct    82080
cggcgtctga ggcggctgtg aacccttcgg gggcagcct tcgaacccct gatcagtaat    82140
gggcacggag cccgagtagc gtggaaccc ttcggggggc cggccttcga ggcacggag    82200
acctctgacc agtagtgggt gtagggccca cgcgatctga ggcggctgtt gaacccttcg   82260
gggggccagc cttcgaacct ctgatcagta aggaggctcg gagcctggtt ccttcacggg   82320
gaaggatccc tttcggggta tccccctttc ccggtccctg tcgcaagaga tagagaaaga   82380
ggaaaaaggg aaaaggatac gaaaccgaac gacgcgagg acctttttg gcgcggttat    82440
ttcggcgaag gcgaagtgtc gcccgctgct cctgccagaa ggccgcctg tccagccgcg    82500
gagttaatgc gacgaggcga gtagttggcg gggcagccgt tgcgcgtgcg cgagccgttc   82560
gaggaacgga tcacgggcgc gttgtcttca cgccgtgaga gggggttctc ttgctgcccc   82620
cggatgggac gtgagcttgg ctgacgacgt gaccgctgct cccacgccgc tgccaccgtc   82680
attactgccg gcccactttt ggccgtgttg accgccgcgt caggctggcg ctgctgggtc   82740
gcacgctggg tcgcctcgag tcgcggtatt ggttccgcaa tcgaggaggc gcggtggtgg   82800
cgcaagtggc ggtgcagttg cttgcatgtc gtcgtagtca gagcgggcgg cggcgagccg   82860
ctcgtcagtc ttctgttgct ccgtaggccc accccctatcg agtggggctg ttcgtacctg   82920
cggaggggg aaccggagtt ccgtttgtaa tggcacttcg aatgccggtg tttttgttca    82980
ttgcggcttt cggggcctga acatgtatgt aattccggca cggagccgtg ttttttcctca   83040
tttttgagcg ctaagactcg tctgttgatt atctgaaccg cttcaccaag catgagtcgc   83100
cccgtgtcaa ggtgacgagt gaggtatccg tatcccggag gcgtaggagt ccctcggctc   83160
ggtcgccctt gctgtccgag gctcctctag cttagttaaa gggaccctc ggccgctctt    83220
cgacgagccg aggccagggg tagcgatatc agtgtgaaca gaggcggagt tggctcgaaa   83280
atgaaacctg gttggtcgga gcctagccgg gtttgtccgtt ggcgggaccg acgtcggggc   83340
tgatcagccg aggcctcagg tcgggctggc gcccttggga gatggtcggc cgaggcccca   83400
ggggtaaccg gccgagccgc ctgctcgggc cggattcccg gagaagtccc tggcagcgat   83460
tgcccgggcg tggtgatgac atcgtccttc ggagcggaga tcctcggacc gcgtcgccgt   83520
ccgaggctag gtcgggcctc gctgaaggtg tcatcgatgc cgagggtgtt gctgccccct   83580
tccagcgtca agacccgagc ctgtagggtc agattgtctt gtagcgtgtg ccttctgcag   83640
ccgccgaggc cagaatacac gccctgctg tgttgtaaag ctgcgtctcc tttcctcttg    83700
tttcgagtat cttgactttt ttgtcggtaa cagggatgtt tgtgtgagtg ggagttgctt   83760
ctcgcggaag gtgatgagtg aggtatccgt atccggagg cgtggaagtc cctcggctcg    83820
gtcggccttg ccgcttacac gtactttcac tcgtccatga ggcctgcca ccgactcagt    83880
cgagaaggct cgaaggttg cttcggcaga agaacttccg aacatgaaga cttgttcgt     83940
ccgcggaatc actttatccg aacgcgagtt acttatcgca gaaggtgatg agtgaggtat   84000
ccgtatcccg gagcgtagg agtccctcgg ctcggtccgc cttgactgct tacgtgtact    84060
ccgtcgtttt caggatccac ttttcgaagt agtcaaaaag cacgaaagat attctggcag   84120
aagagacctt ttttcgagga aaatttcgac gcagagggg ttcccccct tttagccccc     84180
gagggagggt cgggctttgc cgaggcgagg ccgacccttc cttgatgact aaactttgcg   84240
tgggtgcgag gtatatgaac gacctgaaaa catcttaagg gtagaagcga cgtagctgtt   84300
ggatgttcca agcgttgccg tagacctcgc cttgactgtt ggccagcttg tacgttccgg   84360
gcttcagaac tttggcgatg acgaatggcc cctcccaggg gggcgtgagc ttgtgcctcc   84420
ctcggcgtc ttgccgcagc cgaagcacca ggtcgcccac ctggaggtct cgggggtcgga   84480
cccctcgggc gtggtagcgc cgcagggact gctgataccg cgccgagtgt agtaaggcct   84540
tgtcccgagc ctcttccagc tggtccagcg agtcttctcg gctagcttgg ttgctttgat   84600
cgtcgtaggc cctcgtcctc ggggagccgt attctaggtc agtgggcaag acggcctcag   84660
ccccgtagac caggaagaac ggcgtgaaaa cccgtgcgc ggctcggcgt cgtcgtcagg    84720
ctccagacca ccgaggggag ttccttcatc catcgcttgc cgaacttgtt gaggtcgttg   84780
taaatccgag gcttgagccc ttgtagaatc atgccgctgg cacactctac ttgcccattc   84840
gacatgggat gagctacggc ggcccagtcc acccggatgt ggtgatcctc gcagaagtcc   84900
aagaattttc tgccggtgaa ctgggtgccg ttgtcggtga tgatggagtt caggacccg    84960
aagcgatgga tgatgttggt gaagaacgtc accgcctgct cggacctgat gctgttcaga   85020
ggtcggacct cgaccccactt ggagaattg tcgatgccga ccagcaggtg cgtctagccca    85080
ccgggcgcct tctgcaaagg gccgacgagg tccagacccc acacagcgaa gggcaggtg    85140
atgggtattg tctgcagagc ctgagcggc aggtgggtct actttgcata gaattgacac     85200
ccttcgcagg tgccgacaat tctagtgcg tcagccaccg ccgttggcca gtagaagcct    85260
tgccgaaag cattcccaac gagggctcga ggcgctggt gatggccgca agccccgag     85320
tgtatctctt gcaggagttc ctgaccttcg gcgatggaga tgcatcgctg gaggatgccc   85380
gagggattgc ggtggtagag ctcctgctca tcgcccagca agacgaacga cttggcgcgt   85440
cgcgctatcc gtcgagcctc ggctcggtcg aggggtagct ctccttggcg gagatattgc   85500
aggtacgggg tctgccaatt tcgatcaggc atggcccac ttcgctcctc ctcgatgcgc    85560
gatgcctcgc cctcggagac cgagggtacc tcgggttgag ctgagggtgc ctcgggccgt   85620
```

```
gccgagcgta cctcgggctg gtccgagggc gcctcgggct cgggagggtc atcgatcttg   85680
acggagggct aatgcagatc ccgggagaag acgtccgggg aaccgttgtt cgccccgagg   85740
ctattttgc cagctcgtct gcagtctcgt tgtagcgccg agcgatgtga ttaagctcga    85800
gcccgtagaa cttgtcttcc aggcgccgaa cctcatcgca ataggcctcc atcttcgagt   85860
cgcgatagtg ggagttcttc atgacttggt cgatgacgag ctgcgagtcg ccgcgagcgt   85920
cgaggcgtcg gaccccctagc tcgatgcga ttcgcaatcc gttggtcaga gcttcgtact    85980
cagccacatt gttcgacgcc gggaaatgga ggcgtagcac atagcgtagg tgtttcccga   86040
ggggtgagac gaagagtagg cccgcgccgg ctcctgtctt catcaatgac ccgtcgaaaa   86100
acatggtcca gagctccggt tggatcggag ccgtcggtag ctgggtgtcg acccattcgg   86160
ctacgaagtc cgccaagacc tgggacttga tggccttccg aggcgcgaac gagatggtct   86220
cgcccatgat ttccaccgcc cacttcgcaa tcctgcccga ggcctctcgg cactgatga    86280
tctcccccag ggggaaggat gacaccacag ttaccgggtg agactcaaag tagtgtcgca   86340
acttccgcct cgtcaggatc actgcataca gcagcttctg aacttgtggg tagcggatct   86400
tggtttcgga cagtacctca ctgacgaagt aaactagcct ctgaatgggc aatgcatgcc   86460
cctcttcttg cctctcgacc acaatcgcgg cgctaaccac ctgagtggtc gcggcgacgt   86520
agaccaagag ggcttttct ccatcagctg ggggcaccaa gataggcacc ttggtgagga    86580
gcgccttcag gtctacgaga gcttcctcgg cctcaggggt ccaagtgaag cactcggcct   86640
tccttaagag gcggtacaga ggcaggcctc tttcgccgag gcgtgagatg aagcggctca   86700
gggccgcgag acatcccatg accctctgta caccttttaa gtccttgatg ggccccatgc   86760
tggtgatggc tgcgatcttc tccaggttgg cttcgatgcc ccgctcggag acgatgaacc   86820
ccaagagcat gccccgggc accccgaaga cacacttctc gggattgagc ttgacgcctt    86880
ttgccttgag acaccggaat gtcacttcaa ggtcggagag gaggtcggaa gctttccttg   86940
tcttgactat gatgtcatcg acgtaggcct cgaccgtgcg accgatgtgt tcgccgaaca   87000
catggttcat gcaccgctgg tacgtcgcac ccgcattcct caaaccgaac ggcatggtga   87060
catagcagta catgccgaag ggcgtgatga aagaagtcgc gagctggtcg gactctttca   87120
tcctgatttg atgataccct gagtaggcat cgaggaaaga cagggttttcg caccccagcag  87180
tggaatccac gatttgatcg atgcgaggca gaggtaagg aaccttcgga catgctttgt    87240
tgagaccagt gtagtctaca cacatccgcc atttcccccc tttctttctc acaagcacag   87300
ggttggcgag ccattcggga tggaatacct ctttgatgaa cccggctgcc attagcttgt   87360
ggatctcctc gcctatcgct ctgcgcttct cctcgtcgaa tcggcgcaga ggctgcttga   87420
ccggtcgggc tccggcccga atatccagcg agtgctcggc gacatccctc ggtatgctag   87480
gcatgtctga gggactccac gcgaagacgt cggcgttcgc gcggagaaag tcgacgagca   87540
ctgcttccta tttgggctcg agcccggaac cgatccggat ctgcttggag gcgtcgccac   87600
tggggtcgag ggggacggcc ttagccgtct ccactggctc gaagttgccg gcatgacgct   87660
tcacgtctgg cacctctttg gagaggctct ccaggtcggc gatgagggcc tcggactcgg   87720
cgagggcctc ggcgtactcc acgcactcca cgtcgcattc gaacgcgtgt ttgtacgtgg   87780
ggccgacggt gatgaccccg ttgggccccg gcatcttgag cttcaggtag gtgtagttgg   87840
ggacggccat gaacttcgcg tagcatggcc tccccagcac cgcgtggtag gttcctcgga   87900
acccgaccac ctcgaacgtc agagtctccc ttccgaagtt ggagggtgtt ccgaaacaga   87960
cagggaggtc gagtcgtccg aggggctgga cgcgcttccc gggaatgatc ccgtggaagg   88020
gcgcagcgcc tgctcggacg gaggacagat cgacgcgcag gagcccgagg gtctcggcgt   88080
tgatgatgtt gaggctgctg ccccgtcca taaggacctt ggtgagcctg acgtcaccga    88140
tgacaggtc gacgacgagt gggtatttcc ccgggctgag cacgtggtcg gggtgatcag    88200
cttggtcgaa ggtgatgggc ttgtcggacc agtctaggta ggctggcgcc gccaccttca   88260
ccgagcagac ctcccggcgc tcttgcttgc gatgctgagc cgaggcattc gccacatgcc   88320
cgccgtagat catgaagcag tcgcggacct cgtggaactc tcctacttgg tgatcttcct   88380
tcttgtcgtc gtcgcgggcc ctgccaccct ccgcggggtg cccggccctg tggaagtggc   88440
gccgaagcat gacgcactcc tcaagggtgt gcttgacggg cccctgatga tagggggcacg  88500
gctccttgag catcttgtca aagaggttgg cacctccggg gggctttcga gggttcttgt   88560
actcggcggc ggcgacaagg tccgcgtcgg cggcgtcgcg tttcgcttac gacttcttct   88620
tgcctttctt cttggccgcg cacggagtag acgcctcggc agcatcttcc gacgggcggc   88680
cctgggctg cttgtccttt cggaagatag cctcgaccgc ctcctggcca gaggcgaact    88740
tggtggcgat gtccatcagc tcgctcgccc tggtgggggt cttgcgaccc aacttgctca   88800
ccaggtcgcg gcaggtggtg ccggcaagga acgcgccgat gacatctgag tcggtgatgt   88860
tgggcagctc ggtgcgctgc ttcgagaatc gccggatgta gtcccgaaga gactctcccg   88920
gctgctgtca gcagcttcgg aggtccagg aattccagg gcgcacatac gtgccctgga    88980
aatttccggc gaaggcttgg accaggtcat cccagttgga gatctgcccc ggaggcaggt   89040
gctccaacca ggcgcgagcg tgtcggaga ggaacagggg gaggttgcgg atgatgaggt    89100
tgtcgtcgtc tgttccacc agttggcagg ccaggcggta gtccgcgagc cacaaatccg    89160
gcctcgttc ccccgagtac tttgtgatag tagtcggagg tcggaaccgg gtcgggaacg    89220
gtgcccgccg gatggcccgg ctgaaggcct gcggaccggg tggttcgggc gagggactcc   89280
gatcctcccc gctgtcgtag cgtccccac gcctgggtg atagcctcag cgcacccct     89340
cgtcgaggtg ggctcgacgg tcgcagtgat ggcgctcgtt gccgaggtgg cccggggccg   89400
caggcggtc gttgcgcgtc cgcccggtgt agaccgaagg ttcccgcatg aatcgggaag    89460
tcgcggcatg aggttccgag gggtatccttg ccttcgggga ggcagtgctc tcggcccgtc   89520
ggaccgtggc gccttccagg agattttga gctctcccta gattcgccga ccctcggtgg    89580
tggatgctc cggcatcgcg cggaggagca tcgctgctgc gaccaggttc tgaccgaccc   89640
cactggatgc aagtggttggc ctgaccctga cgacatcgg gacgcggtgc tggagaccct   89700
ggggcaggtg acgtattct ccggccgggg gttggcccgc ccatgcctgc ccgacgtccc   89760
ggcggatcgg ctcaagcgct cctgctcct cgtcgatcct ggcctgcgcc cgcggactt    89820
gctcggagctg tgggtcgtaa cccccgccg gaacagggac cacaactagc tcccgcggga   89880
tgtcagcgcg aggcaccggc ccaggggag caccgtcctc cggcatgccg agatgattgc    89940
cttcggaggg accccctaga tcgacgtgga aacattcgcg gcttgggccg cagtcctcgt   90000
cgtcgagtac tcggaacagt cggagagcga gtagtcacat gcggtcatga              90060
agttccgctg gcactagggt tgccaaatcc agagaaatcc caacagatgt tggggtcgtc   90120
atcttcctcg gacccagagg gccgtaggc cgagacgtcc gtcagccggt ccaaggcga     90180
ccgcaagcga aacccagag ggtttgtact cgcctctaca agggcgcccg ccaaagcaag    90240
attgctagac gggttgaggc tgagtacaaa tgacgtagga tgggaatcgg ttggtacctt   90300
ttggtcgtcg agcggcgatg aagtcacgtc gaggactgac cgcatcgtcg cctcaggtac   90360
```

```
gagggcgatg tcctgcaagc ttttcgcaag cgcgctggcg tcgtccactt gctcggatt   90420
ggcgtgtcgc ggggagacgg cgctcgcctt tgtctcaaac gcgaggtcga cgcccaacgc   90480
gcccccgtt  ggggtgctag ggacgtcgac tcgctcgaca gccgacgagg cgcggcctcc   90540
tgcttggcct ttgttgcccc gcctcctcct ccgttggcgg gggagaggac ggggcgagct   90600
cgaatgttgt tcttccgcca cgcggggaag acgtcgtcga ttccgccgcc ggcgggcggg   90660
ctgtcggccg ccatcgtcgt tgtcgcgcgg cggtggaagg agtatcatgt cgtagctgcc   90720
gtcgagggac atgaactcaa gactcccgaa acggagcacc gtcccgggtt ggagaggttg   90780
ttggagactg cccatctgga gctcgacggg aagctgttcg tcaacacgca gcaggcccct   90840
acctggccg  ccaactgtag gcgtttcgag accgggggg  ccctcaggcc gacgagtgag   90900
tgccgcgtgc cccagcccag atgggtcgag cgcgtgggca agcgtgaagg ggggaaagga   90960
gcgaggcggc cggagaccgg cgtgagagag gtgggaatca cgcggccttc gtgttcgtcc   91020
cgcgcccagg tcgggtgcgc ttgcagtagg gggttacaag tgtccacgcg ggtgagggaa   91080
gcgagcggcc ccaagagagc gcctgtcccg tcctcgtccc gcgcggccaa ccctctctaa   91140
gagggccctg gtccttcctt ttatagacgc aaggagagga tccatgtgta caatggggt    91200
gtagcagagt gctacgtgtc tagcgaggga gagctagtgc cctgagtaca tgccaatgtg   91260
gcagccggag agatcttgga acccagctag tgtgatgtcg tggccgtcgg aggagcggcg   91320
gagcctggcg gagggacagc tgtcggagcg gttgtgtcct tgccgacgtc ctcctgcttc   91380
cgtaagagag ctgagagctg ccgtcgtcac agggcatgcg gggcgccatc attgcctatc   91440
tggtggagac agccagatgg gacaccggtc ttgttctcta cggtccgagt cagctcgggg   91500
tagggtaatg atggcgcttc ctgttgacgt ggctggcctg cgcctagtc tggggggtacg    91560
tggaggctcc tccgaagccg aggtggagtg gatcttccat ggccgagggt cgagtccgaa   91620
gcccactggg tcgggccaag gcggaaggtc gtcggcaaga ttccagggcg gtgtccgaac   91680
cctgggctcg ggtgaagcgg aattcgtcgt cttctggggc tgagctcgag cccgagccct   91740
ggggtcgggc gaagcggagt tcgtcgtctt ccgggtctta gcccgagtcc gagccctggg   91800
tcgggcgag cggagttcgc cgtcttccgg gtcttagccc gagtccgagc cctgggtcgg    91860
gcagagcgga gttcgccgtc ttccgggtct tagcccgagt ccgagccctg ggtcgggcgg   91920
agcggagttc gccgtcttcc ggggctgagc ccgagtccga gccctgggtc gggcggagcg   91980
gagttcgccg tcttccgggg ctgagcccga gtccgagccc tgggtcgggc ggagcttcct   92040
atggcgcctt tggcagggcc tggcttcctg tcaatatcac tctgtcaagt ggcactgcag   92100
tcgaagtggc gcaggcgggc ctgtccttct gtcagaccgg tcagtggagc ggcgaagtga   92160
cggcggtcac ttcggctctg ccggagggcg cgcgtcagga taaaggtgtc aggccacctt   92220
tgcgttaaat gctcctgcga cttggtcggt cggtgcggcg atttagtcag ggttgcttct   92280
tagcgaaggc agggcctcgg gcgagccgaa gatgtgtccg ccgttagagg ggggcctcgg   92340
gcgagacgga aatcctctgg ggtcggctgc ccttgtccga ggctaggctc gggcgaggcg   92400
tgatcgagtc gctcgaatgg actgatccct gacttaatcg cacctatcag gcctttgcag   92460
ctttatgctg gtgggggtta ccagctgaga attaggagtc ttgagggtac ccctaattat   92520
ggtctccgac agttattttg atagttggga ttgtggggtg aagtgatggc atgactacgt   92580
agccgtcacg tcatctattg cgtggctatg cttaagcgtg ccttgatata atttagaata   92640
agtcgatct  ctagaacgcg gcaattttta aaagtaaata gaagctgaat ttattgattg   92700
ctgtttggg  ctgcacgcac tgttttagtt gtgctgtttg tttgataaac caaatcatgt   92760
tttctataga aaagtcatat agaagagttg tagatgacat gattatcttg cttgtactaa   92820
aatttgacag ccataaacct gattgtttag gagttgtgct tttcacaagc ccagcacctg   92880
aatctgtcaa atttctgaac atatttcaga aattgcaata gttgcttaag ttaatgttga   92940
aattagttat tggtggtcac aaaaaagttg tagataactt tattatcgta cttgtgttaa   93000
aatttgacag gcataagtct gattgtttag gagttatgtt tttacaaat tcagtaactg     93060
aatctgtcca cttctctgtac agatttcaaa agctgcattg tttgcttaag ttaatgttag   93120
aatcagccct tgtcaattat aagaaagttg tagaggcttt tcttgtcttg cttgtgttaa   93180
aatttcataa ctataggcct gacggtttaa gagttatgaa ttttacaaac tggttgctgt   93240
gttctgtcca ccgtcagaac agatttcgaa aactgtaata tttgatttag ttaaacctgg   93300
aatcacttct tggtggattat aaaagttgtg tagtactttg gctaagcttt tcaaaaagtc    93360
ttagatcact cttttttggtg gtctgaagat taagttacat gtgtttgaag tgtgaagact    93420
gaatctgtcc agttttggac agcacagcct tcatagtata ttttaacctt gatacatgct   93480
aaaccagcct gggatgttta taataatttt gtagaacatt taattagctt tccagaaagt   93540
ctaggatcaa tttgtttgga tgtctgaatc ttcagttatg aattttttaaa atcacaagtc   93600
tgaatctgtc caaatctgga cagagctgct gtgattgcac ttttttgaccct tgctaagtgt   93660
ttaatcatgc tgtgatgaaa ataccaaaat tgtagagcac ttttctaaact ttccagaaag   93720
ttttagtttg ctatttttgg attaatattt taaaagttat gattaaaaca agtagctgct   93780
gtgctgctgt cctaaaaatc tgcacgtgct caaatgaata tttagttcac cattttggct   93840
aaaaacgctt tagtaagcac ttaacggaca tagacttgtg atggctaaac ttaggttaac   93900
atgtgttcca taattaatgt gtttgcttgc tgtagttgat tgtgatagag gagtccatcg   93960
acattgatgc atcggtcctt ttattaaact tgtgtttgtg atgttttttgt gtgatcaata   94020
taagaattaa tgaaaagccg tagcaactaa ataaatgctt gtacatatga tatcgtgttg   94080
cgttggttaa ttgtaggtag tgatcattgt cttttccagtg gtagtgttta cgtgtgccca   94140
atgacacata aataactagt gtttgcgtat agttgttgca gtgtcttact aattaatgtt   94200
tagttcgcca ctgtgtcttg gtatatctta tgttacttt  attatattca tacatatgca   94260
tcttgcacct catataggac cgagagatga tgatcgagcc agtgatgtgg tgccaaccac   94320
aagatgccgt tgatggacga cctgaagaat ggacttaacc agtggatgct caccaagcga   94380
gtacctcccc cagcaaacac tacctaagtg ttaaattaaa ggcaagcccc ggttcttatgc   94440
ataaccatta tatatatgct attttactgc acttaatgtt tgtaggcttg taccgtgcac    94500
ttaagtgtag gagttgaatg aaaccctagt tgcatgaact caggattccc tttgagatgg    94560
atactagtat gctaggtcga gtagctnnnn nnnnnnnnnn nnnnnnnnnn nnnnnnnnnn    94620
nnnnnnnnnn nnnnnnnnnn nnnnnnnnnn nnnnnnnnnn nnnnnnnnnn nnnnnnnnnn    94680
nnnnnacag  tgcacagtgc accggacttt ccggtgagcc taggcagagg tgattttgaa    94740
tccaaa ttttttgatc taaattttaa ccaaaccaaa tcccaactta taatcataca         94800
aaagaacacc tattgggata ggtattggcc ccctcatata ttttcccata attttcaaaa   94860
atattttgcc ataggctagt caattttag agaaaatagt caaatggtga gatttgcatt    94920
ttagctttga actaggggtt ttcatgaata atttgagttt tgaatactcc ccccctaagt   94980
gtagtactac atgcatatct caagaaccaa caatggcata gtaaataaga atttaagtac   95040
taaaagctta aagctaagac ttgtcaagtt tgagcccgag ttaagctttt ttcactcgct   95100
```

```
ttgttggcgg ttatcttaac taggttagac aagccctaga tgcaatacaa gaaatttaaa    95160
tatgcaatgc aggcttgaca acactatttt gagatcttta aataaaattt ctgagatcaa    95220
gtatgtttaa ttcatttctc aacatgcaaa agcgggtttt atcaagaggc ttagtgaaaa    95280
tatcctctaa ttgatcttcc gacctcactt cttctaaaat aatgtctcct ttagcaatat    95340
gatctctaag gaagtgatga cgaatatcaa tgtgcttggt gcgagagtgt tgtacaagat    95400
tattagcaat tttaacagca ctctcattgt cacacaacaa aggtaccttt tctagaacta    95460
caccatagtc tagaagagtt tgtttcatat ataaaatctg tgtgcaacaa gcaccagcgg    95520
caatgtattc cgcttcggcg gttgacaagg caacactatt tttcttttg gatgtccata     95580
atagtagtga tctcccaagc aaattacacc cctagaagta ctttttctat caatttttgca    95640
accggcataa tccgaatcgg aatagccaat taaatcaaaa gtagctcctt tgggatacca    95700
aaggccaaca cttggggtgt gcttgagata cctaagaatt cttttaagag cgcaaatatg    95760
agctttctta ggatttgatt gaatctagc acacatgcat acactaaaca tgatatcggg     95820
cctagatgca ataagataca ataaactacc aatcatagaa cggtagagag ttaccatcct    95880
ttcaacaagt gatctccatg ttgaacctt tcaacaagtc tttggtatac ttctcttgtg     95940
agaggaagtt accatctttc atttgcttca cttgaaagcc gaggaaatac atcagctcac    96000
caatcattga catctcgaac tccttcgaca tcaactcacc aaattccttg caatgatagc    96060
gatttatcga gccaaagatt atgtcatcaa catatacttg acaaatgaaa atatcaccgt    96120
tatgttttctt tgtgaataga gttgtgtcga cggtcttgat cttgaagcc tttttgatga    96180
ggaagtcgcg aagacgctca taccaagccc ttggagcttg cttaaccca tagcgcct      96240
tggacaacct ataagcatgg ttaggatatc tagggtcttc aaacccgggt ggttgctcaa    96300
catatacaag ttcatttatg aagccattta aaaatgcact ttttacatcc atttgataaa    96360
gcttttatc atagcatgat gcatatgcga gtaggataca gatgcttca agtcgagcaa     96420
ccggtgcaaa ggtctctcca aaatctaaac cttcaacttg agagaagccc tttgcaacaa    96480
gtcttgcctt gttcctcaca atcacgcctt gatcatcttg tttgtttctg aataaccact    96540
ttgttccaat gatccttgca tcttgtggag gcttctccag ggtccaaact tggttacggg    96600
tgaagttgtt tagttgttca tgcatggcat tcacccagtc cggatcctgt agcgcctcat    96660
ctatacagta ggctcaacac aagaaacaaa ggagtgatgt tcaataaaag aagcatgttt    96720
atgtgatcga gtaataaccc cttgtgaagg acttccaatg atttgatctt gtgggtgtgc    96780
ttgaagcagt gatgagtttc tcctatcaac cacttaggaa gaagatcctg gagcatcaac    96840
atcttcggct tgtatcctttg cttgttcatg agagacaaat gtatcttcat ttgcatgcct    96900
ctcatctttt tcatcatctt gtggtacact tgatgaagaa ggcctattaa tgttttgcac     96960
ctcttcttca tcttctttttg gtttgatagc tccaattggc atgttcttca tggcttcctt    97020
aagtggctca tcacctacat catcaagatt ttcaagtgct ccttgggagc cattagtctc    97080
atcaaactcc acatcatatg tttattctac cacgccagtg gcatgattga atactcgata    97140
tgctttggac tttaatgaat aacccagaag aaaaccaata tcacaacgtc tttgaaactt    97200
ccctaggtga tggcgtttct tgtaaatgta gcatttgcat ccaaacaccc aaaagaatga    97260
gacgtctggc ttttttccat ttagcagttc atagagagtc ttcgcaagta gccagtgagg    97320
aaatagcctg tttgatgcat aacatgcagt gttgatagct tcggcccaaa acctctccgg    97380
tgtgttatac tcatcaatca ttgtccttgc aagtgtgatc aaggtcctat tttcctttc    97440
aacaactcca ttttgttgag gtgtatatgt tgctgatcat tcatgcttga tcccaatctc    97500
atcacagtat tcatgaatgt tggtgttgtc aaattctttt ccattatcac ttctaatctt    97560
cttgatcttg taatcaaatt cattttgagc tttcttggca aacttcttga atatagatgc    97620
aacttcagat ttatcatgga gaaaaacacc caagtgattc ttgagaaatc atcaactatc    97680
accagacagt agaggttgcc accagcactt gcataagttg ttggtccaaa tagatccatg    97740
tgaagtagtt ccagtggcct tgatgttgac atgaaagctt ttgtaggatg tgtgttagca    97800
acttgctttc cagcttgata agcactacaa ggcttgtcct tttcaaatat aacatccttt    97860
agtcctctaa tcatgtcctt cttaaatact ttcttcattcc tgctcattcc aacatgtgca    97920
agccttctat gccatagtca tccaagagat gctttggtaa agaggcaagt tcttaagtct    97980
gcatcttcag aggtgaaatc cactaagtag agattgttgt atctaaatcc tttgagcacc    98040
atttattcat catccatttt tgatacaata acctctgttg gagtgaataa gcattgaagt    98100
ccaagaacac agagttgacc cactgataat aagttgaact ttaaaggtgc aaccaagaga    98160
acatttgaaa ttgatagatc atttgaaatt gccaccttgc caagtccttg aacttttccc    98220
tttgaattgt ccccaaatgt gattttgtct tgtccatcaa cattatcatc aagtgaggtg    98280
aacatccgtg ggttgccttat catatgttat gtgcatccac tatcaataac ccaatggctc    98340
ccaccggtct tgtagttcac ctacatccac agacaaatca agcttaagtt ttgagggccc    98400
tatattgcat aggaccagtg acttttctcaa tcaaggactt tgcaacccaa atttgtctag    98460
gtctactctt gcttggtgga cctaggaatg taacttcgac ttttccattt gctacttctt    98520
aaaacataat gagcattgaa ggcaaatggt cttgagtgct ttggcagggg agttggtggt    98580
ttggcttttgc agttgtggga aaaatgacct tctttttccac actcaaagca tttgatatgc    98640
ttatgagtct gatttggctt gtattgagtt gtagctttct tttgcacaaa ggagttatat    98700
ccaataccac tcttgttgtt tttcatgaca gtgttcatga gcaattcatt ttagaggtat    98760
tggcccttgt tgaacttttg cacacttgtt gcaagatgtt cattttcacg cttaagtttc    98820
ttgacctcat tttaagcctt tctttatcca ctgccaactc attgttgaag tcattgttct    98880
caatgcaac ctttcctcta gtagttgcat cagtcaagta tctcttcaat ttttggttgt    98940
ctaatgtcaa gacttcaact ttttcagtca attcatcatg tagactagtt tgatcacctt    99000
gactcaaatc atcacatgag gttgctacat caatattaac aacagggtta atagcctcat    99060
gtgtattgca agataaaagt tcattttcaa caagaagatt atcatgatca aatttaatct    99120
tagtatagtc ttccttattt tttactagtc tatctttcaa ctccctatta gcttcattta    99180
acttgtcaca tttatcctta gcatcttttta gggaggatgt aagctcatttt acagttggatg    99240
acatagtttt gttttcttct ttcatttcat tactagcttt cataactatg tcatatttag    99300
catttaaaaa ttcattttca tcttttcaact tatcacattt agcttttgac ttcctaatga    99360
gttgagtgta ttcattaagc aagtcaacta gttcatcata ggaaggtgaa gcaaattctt    99420
catcactatc actatcacta tcatcaataa tatcattatc attttgtact tttcgttcac    99480
ctctagccat gaggcatagg tgagaagtcg atgatggagg tggtggtggt gaagagaagt    99540
ccccagcgat ggcggtaact ttttcatcat ttcttcttc acttgaagaa gatccacttg    99600
acgactcaat gtcagtgagc caatcaccaa caatgtatgc ctttacattt ttctttttgt    99660
ggaacctctt atgctttcca tccttcctct tgaagaatct ttttcatttt ttctcatcat    99720
cactgtcatc ttctttcttg cccttgaact tgttcttctt ggcttgtta cattgatgag    99780
caagatgacc aagctctcca cagttgtagc aatccattta agaaatgggc tttctttgc     99840
```

```
tggaaaagaa tttcttcttt cttgagtcaa atttgatgcc ttctctgttg agcttcttta    99900
atatcttggt ggtcttcctc accatcaagg caatgttagc attaagatca tcgtcacttg    99960
aggattcctc ctcaacttgt actttagctt ttccttctct ttcttgattt tctttgagag   100020
ccaaatcctt tctcttgtaa gatgactcat ccttgtcatt gatgtgcatg tacatctcat   100080
gtgcattgat ctttcccaaa atttgtgtag gagtgacaac tgaaagatcc atctgatgca   100140
gcacagtgac aatgtgtcca tatttatcaa ttgggaggac actgagaatc ttcctcacaa   100200
catccggttg tgaaatttgt gtaagcccca agccatttac ttcctctaca agaatattga   100260
gacgtgagta catagcattg gcattttcat tagcaagcat ttcaaaagaa tttaattttc   100320
tcatagcaat gtgatatctc tcctcacgct caattctagt tccttcatgt agagcacata   100380
tgtccatcca caaatcatga caatttttat ggtttctaac tctattaaac acatctttgc   100440
aaaggcctct aaaaagggtg ttttttggcct tagcattcca tttctcatag ttcaactctt   100500
cacctacaag atttgtggga tctctaggtt cggggaatct ttgtgtggcg gctttgtaga   100560
caccaatgtc tatagcctct aaatatgctt ccatacgaat tttccaatat ggaaaatcgt   100620
caccataaaa aacgggagaa ggtccatccc caccggacat cgttactcta gcggttaagc   100680
taatctaaga gcaacaaggc tcttatacca attgaaagga tcacgatgcc caagaggggg   100740
ggttgaattg ggcttttcta aaaatcaaca ctaactaaaa tctaagcaag agcccaactt   100800
caccccgaca actagcacta agagaataat actagaaata caacaatgct aagataatac   100860
ttcaaatact tgctaaacaa atacacaatg taaaatactt gaattaagtg cggaatgtaa   100920
agcaaggttt agaagactcc tccaattttt ctagaggtat caaagagtcg gcactctccc   100980
ctagtcctcg ttggagcacc tgcgtaaggg tatcgctctc ccttggtcat cgcaagaacc   101040
aagtgctcac aacgagatga tcctttgcca ctccggcgcg gtggatccct cacgaccgct   101100
tacaaacttg agtcgggtca ccaacaagat ctccacggtg atcaccgagc tcccaacgcc   101160
accaagccgt ctaggtgatg ccgatcacca agagtaataa gccatagact ttcacttgac   101220
caagagaagc ctaatgcatg cggtgtgtgc tctaggtggc tctcgctagc gttaatgagg   101280
tccaaatgcg ggattaagat tctcaagtca cctcactagg ctttgtggtg cttgcaatgc   101340
tctaccaatg tgtaggagta aatgtgggca gcaagaccat caatatgtta ggtggatggg   101400
gtataaaatag ccctcaccca ccaactagcc attaccagga atctgctgcg catgggcgca   101460
ccggacagtc cggtgtgcca ccggtgcgcc aacggtcgac tcaaacggct agttctgaca   101520
gctagccgtt ggacagatgg catacccgac agtccgatac gctgtccggt gtgcctctaa   101580
aattcaactc acgaacagcg cgctctcggg tttctgcgcg cagggaaccc tcttccctgg   101640
gccaggctgg gcccactggc aaagggtgca ccggacagtc cggtgcccca aagccagaaa   101700
ccctagcttc tgtttttgtgc tgtttttttca atttggtttt tgttctaact tgtgagtatg   101760
ttctagagtt acacctagca ctatatgtga gtgtgaatat gcaccaacac tacactagaa   101820
ctcttttggt caaactactt atcgacaacc cctctttata gtacggctaa aacaaaataa   101880
aagacctaac tatatcacga gtgtccgcaa ctccttgaca ctcggaatac gaagaccttc   101940
acttttttgtt tcgtcgcttt agccgttgct tcaagttttt atctccggga ttgttttcac   102000
cattgtagta catctacctg taatgcgacc taacttacca tttgcctctg caaaacacat   102060
gttagtcaca tataaaatta cgttgtcatt aatcactaaa accaaccagg ggcctagatg   102120
ctttctagtt taaatcccca acaagtcaaa attctttcta tttttttttg caagttccaa   102180
ttgacatctg aaaggttgta aggtacacgt ttggctctca ttgataacgg gggaaagata   102240
cagtgcaaac caccatataa tgacccactt ctaatcgaat ggacctgtaa cgacgaaata   102300
ccctgtgaga actatggttc actcatgtta attcattgaa attgttgtag tgaattgaca   102360
tggttgggag cctgcttaga gagtatagat tgtcactttt ttttggaccg caacttattt   102420
ttaaaagata ttgcgatcgc ttgtttagta gctgtttcag gccccaatgc agtttctatc   102480
gtgatccatt taagtcactc aacattctca tacttctcat tttgcattaa ttcattccaa   102540
tctccactac tataaaatac tagcttcgat ggtcgtcata cgccatgcac gaagcatgta   102600
gatcaatccg cataccagtg ggcatctata gataggctgt gaaaaccacc caaatcccta   102660
ctagtggaca ttttatctat agatggaccg tgagaaacca cacaagtcta acacgacagg   102720
gaagccaaac gcagcgcagc gctcccacat agaaccacct cactacctaa aggaggacaa   102780
gccatcgagc aagctttaaa aaagtagtca ggcttcttc aactcatacc tttcctgata   102840
tttagctaa gataaaagcg taatatttgt ttttatcagt ttagtatctg atatatggac   102900
catatgttca ctttgatatt tgatattatt tttttattgg tatcaaatat gattgtatgt   102960
cgtcgcagcg cacatgtgtt gtactagtta tttttataaga taatcaagta tttcttaatc   103020
atttaagaca ttttgatgat tatttaaaac attctatttt tttctcagtc attcactcgt   103080
taggtcattc agtacatatt atgttaaatt aagtattct gttacaattc tagtcatcac   103140
atgtcattta gtcatttat gacttattta aaatatttca tattgtcaac agttgttaca   103200
agactttctt acaaatattt taagtcatcc aatagtttat tcatccagag actcataata   103260
tgttttaag tcattccttt ctattaaatt gatgtaatta tttttatcac gattggactt   103320
cttctttta tcacttagaa gccgtgcgag atgaaagtct catgcacggt tttgcatgag   103380
agaaagaagc gaggaattct ctttttgact ctgactcccc cactccaatc gttgcttttc   103440
tttctgttac ttcgaaagta gttgcttcag ctttagccac gcgaattctc gatattcctt   103500
tttatttctc atcaaacgaa tgacatcttc ttctggaaat cctagctatt cttagcatga   103560
tattggagaa tctccttgct attagtcaaa caagcatctg attggagcac aggcgtgtgg   103620
ggggagggat gtcaatggg ttattgaggt gtgatggata agcatccgg ttagagcgag   103680
gggcacgcag tggatactat ttggcaccac gctcagcgag tatgcgtgta tgcagtcatg   103740
caacccgcat atataggcat aaaaaaccaa aatccctttt tttgttatat tcgtgtttat   103800
gagatttcg aacaaaacta gacactcatg ctatatcttt ttcaattttt tatttaatcg   103860
caatgtccga ccctaataaa tacaatgatt ggtcctaata aatacgataa ctggctctaa   103920
taaaaatac aatgacttat cttgatagct ataatgagtg accctgataa aatacaatga   103980
ttgaacctaa taatacaata actaacctg ataaaaatat cctgctaaat acaatgactg   104040
accctaataa aaaaatacaa tgaccgacct tgataactat aatgagtgac tctgatataa   104100
atacaatgac tgatcctaat aatacaatga ttgaccttaa taaatacatt gactgacact   104160
gattaaaata taatgattga tcctgataac tacaataact gaccttgata aatgtgtagac   104220
cctaatagaa gaagtacaat gactgatcct gataaaatac aatgactgga taaaatacaa   104280
aataaaatga ccctaataat tacaatgaat gaccctgata aatacacgac tgatcctagt   104340
aactataatg attgaccttg ataaaagtac aagtgattca ccttgataac tacaaatgat   104400
tgatcctaat aacataaaga taaggagaa caaatgagag gttggttatg aaataattgg   104460
ggaaatttgg gctagccagt tgcatgggtc cgacctagtc acgaaccagc cagccaggcg   104520
cgtggaataa ccacacaaaa aataggacgt ggggattcaa accatgctct ttcgatacaa   104580
```

```
gcgagcgtct tctaccacta taacttatgt ctgtttatgt tatataaagg agagatattg   104640
tatgtgtgca cacatatata cacacataca ctataaaact gatgtcagcc attcacattt   104700
tgttcaacca tccattatct tttgttgagc catttctaat caataccact tgtcgggtat   104760
cataattagg ggtacccaga ttatgccoct aaaacacact taaccottag accaccttca   104820
agacacattc cccgagatca aaggatcata aaccgcgctt cgcccgaggc cccgctcagg   104880
ggtcaccata ggtccgcttc gctcaagcct gccctcggac atggtgtgct ctagggagaa   104940
ttctcgtccc ggccgaggct ccatctccca gaacaaaagt ctttgcctcg cccgagcaca   105000
tctcgggtaa ggaagacaac cccaatgcaa gactcaacca aagtctgcag ggggcaggag   105060
cattcaatat gcatacctac cccacgtaga gttgcaggtg aacaggagca acaagaccgc   105120
ggtcctgtca agcttcacca actacgatga cgcatgcgac cactattccc acatgccatc   105180
tgtcaacccc tgatgggacg tacaatacga caagagtgca ggatggctct cggacgtgaa   105240
ctctgcctcg ctgaaggcga cctcggcctc gggacaaact tcgcctcgcc tgagcccggc   105300
ctcgtttacc tgctccccgc gaatactgga gcgggctcgg tcgtgacctc gggcggactt   105360
ctgcctcgcc cgagcccgac tctagcctca atatccacaa cggaaaggcg cccaacgtca   105420
ccatatactg cagagctgac atattactta gggactttt gccatactca gtactgtgtc   105480
aaccactacg gcatgggcaa ccccccttgtc aggggggctc gggtacgtga ccaagcgctc   105540
agcccttgcc tcggctctca gcagaaatca agcgggcaca agtcaccaaa caagtacaag   105600
accatgcttc ttgaagatct ttgagtgatt tctgcagatt tgaacttttt tcaacttcag   105660
cttcgagttt tgtttcgaaa tctttcttct cttgctcaat gctttttgac ttcatggaaa   105720
gttcactatt cagtctggcg atctcggctt gagcttctgc cagtgaacct tccattgttt   105780
gaattatgaa gtctttcttt tctagggcag cttcatgatc tttaatcttg ttctctaagc   105840
cctcaattat aacttcgttt ttcttgtcct cgaggtcttg ttgcatcctc aaggttttgc   105900
ttagtagtag gctctgacaa aataaccttc atcagaaaat atcttcatat caaaacaata   105960
aaaagttaag ggaagaattt taccttaaag ttagaataaa ataggctacc gacgatatgc   106020
tgtcgtcggt atctgctgag atcggcttcg agtttcggaa aaccaacact tttcgataaa   106080
gtcctgacaa cttctccccc agtccggtct caaaggcaac ctaagctctc ttcgtctata   106140
ccaccgaaga gcagtgcccc tggctggtac ccgcaagata tagcaaagtc cctcagctct   106200
tcttttttag ccttagacaa ctcttgtcca attatgtttt gaaagttgat atttcttct   106260
tccgaagcat cttcggcaag ctccttctcc ttttcaggca ctgtagccgg ggtttcctca   106320
gcagctgcag cagttttctt ctcagccata ttcaaaatta tttcatcagt gtcagtaagc   106380
gtgttttcca aatttgtggc ttccgctgct gcaacttcgg aagtagaagc ttcggctgga   106440
gcagctttgg ctgctgctgt ttttagcact gaggccgacg atggtgtttc ttcaatagcc   106500
tcaatgatag taataatcct tcgctttttt ggttcagcgg gcttctcggc aaccgaaggt   106560
tccttcttct tcttctgtaa aagcttcatc agttccggtc ccagcgggct tagcttatta   106620
ggtagagatt cggtcattac ctttaaaatt tcttctgcgt cagtggcaga aggtgttgag   106680
ggaacttctt ctaaatcagc ttttggcttc ggagctgtag cttttctttt cttcgaaacg   106740
gccaccttcg gctcagggct ggattttttt tcttttttgc taaattttca tcttctttta   106800
tcattctggc agcttgtctt tgcataacac tgacagctct tttttgtttt ggcccttcgg   106860
caccttttact taaccgttca tagtctgggt attcaaattt cagagtgttc attactcggt   106920
ttagccttcg tttcggtcgg gtgccgaagg ctgccgtcat caattgatct tctttcttcg   106980
tataattgcc caatatttca ttgcacataa cttcgatcgt atccaaccat tcttggcagg   107040
gttctttgaa gtgtttcttg aacttaaaat gatagggcag tcgaacaagt tcattcttt   107100
tcttctctcc tttaagcttc ggcatactcc attccttaa cgttgggaat actctattgg   107160
ctaagtattc ctgaaccaaa tccctagttc cgatatgctc ggacacaact ctaaattcac   107220
ccacaacatc tgggcatgat gatcccagcg tcatgcgaca ctgggccta gttaacccga   107280
aggttaggcc cagtgggctc taaactagct tctccttctt ctcatcaacc ttaacataaa   107340
accattcagt tttccaaccg gttgtccatt tggtgcggta gctaaccaac ggtgtcttca   107400
tgtctttgcg gtaggcaaaa ttatagcagc cgaagttctc gtgcagtcca tcttctctag   107460
ccttcgtctg atagtgaagt tcgtgcaccc ggtagaaggc ttcggcaagc ggctccactc   107520
cttggcttgc aagagcccag ataaagacgc taagcctaac gatagcgtta ggagtcagct   107580
gatgaaaata aatttcgaaa ttttccaaaa catccacaat catcccatgc agaggaaacc   107640
tcagtcctgc tttaaagaaa cttctgaaaa ctaccacctc atcattttct agcttcggag   107700
tgatttattc tccgccaaaa cgaattagct tcttctcggc ttccccgaag tagcctagct   107760
tcgtcatcat gggcatatcg gcctcagaga cggtagactt tccaaattcc aagtggctgg   107820
gtttagatgg catgacgaaa taatctatct cctcttcatc agcctcacct tcttcaatgt   107880
cagcctgctc ggtttcggca gcacgtgcac cttcgtcaga aacaccctct agcacaacca   107940
agcctgattg tctcattact tcggagattg gggcggtctc ggcagcttcg gctcctcccc   108000
cgtcgcgtgt gactctagca gttgaacgca ccctggccat ttgatgctga atttctcgcg   108060
gttttgacaa agttgattac tttttgattt tgccgaagct ccctcttttg acgaagctaa   108120
agaacaagac gatgctctaa ttgagaatac gaagaataag cttcggctat ggtcaaattt   108180
ttcagcagca caacaatacg atagtaatga atgctgtggt aacttcacac ctacccgtct   108240
gtttatatag tgctacaggt gggaaggtga atcatcaagc cacctgcacc cgccgaacag   108300
tcgctcgcat tcactgaacg gtggaccgca tggcgcgaga aggagaatca ccagatcgtg   108360
cgtacccgtc ctatggtggg accacctcgc actaggaata cttaaatcgt ttctcgacaa   108420
cgagctcagg gaaggtgttt ttcggacctt cggcattccg aagcctaaaa gaattttca   108480
cgggtcgagc tcgttacaaa aaatgatctg gcaccgtgaa ggggctactg ttgggggtct   108540
gtttcgtcgc cgaaggtcct gtgagaaaaa acaccttcgg aaggccagaa caggaatgat   108600
gccgaagcta ccaatcagag agcttcgtag cgtatttcca gatgcaccga cttaaagatg   108660
aaatgacgaa ttgggcccat gataatctat gttatgattg taatcatttg tagaggacat   108720
gaatgtaaat ttcacaccgg ctgcgccctgt gcctataaat aggtgaacag taccctcgta   108780
ctgttcacgc tttcgcatct tacttttatc tttgccttct atcaagctca aggtataaat   108840
gtaatttgat attattctta tgttcttatg attatttaat aataaatatt tatgttaaga   108900
tgttatataa ttgtttatgt tgtcttccta tgttcataa gcttcatcct ttgtttatac   108960
atgtcatact tatgaaggta tgtccttcat aacccttcgtc cgaagatcgt tatctcctaa   109020
gggaaataat gcttcgaagg acgaaggaca ttaacatttta acattttgtg ttgccttgtt   109080
cttaactcat agcatttgag aacaagtccc caacaattat tatgatatcc tcgccactaa   109140
caagtgaatt tttgggagaa ggactaaaat gcagtcaacg ataatgtata agactttgga   109200
gcaaaaacaa agacaagaga cataaatatc caatacaaaa ggaaaccaga gaggtagtgg   109260
tattttttc ttcttggtg gctaagcatc gctcaccctg tgatgcaaaa atctaccaga   109320
```

```
gacaagtata gccaagacca tcaaataaag agacaattta gcaaacaatc caaatcaaga    109380
tcagtgtttt tatgtaaaat agagcatttt tatcatctcc aattgcattg acaattataa    109440
atatgatgaa attgagaaat agataggctg agtaccctag ctcagcctca tctttggcag    109500
aggcatcacc atcaacatct tcaaagtcac aatcttggaa gagtttcttt gcccttttt     109560
ggcaggggaa gggtgggtaa gtcctatcag tagattgcaa tcaacaatag gataagatct    109620
catatgtatt atgaaaacaa ataagtagat ttttgcgtta caaaggttac ctttttttata   109680
ccactcttct gtgtcccggt tatagaacca ccccaggttc acactagcat caaagatctg    109740
tagcaacccg cgatcaagca catagattac cattatattt tagacatggt gtctcatgtt    109800
attttatttt caagtactat gtaaattcaa tgaaatgcta agattaatat ggcaagaaca    109860
tttgacagaa attagcatca tactgctggt gacattggaa tgagagaatt tccatcatct    109920
cttagtatta gctaaaggaa tgagttccaa ggcgaaaaga ggcttcagtt agaagaaaaa    109980
tttaccttag gtaaagggc atcaccatca gttttctgtg tttctgttga cctcgcaaag     110040
caacttgcag aaactgcact catgatgtgc agattcatat catcttccac agatttaaga    110100
ataaaatatg agtgtacaaa aaatcaaatt ggtagtcaaa catgcgaact gtattctgtt    110160
gtttgagtga tttcacaaat tactgtcaaa tgtgagttag aatataccct agaagtggtc    110220
ctggcattcc tgctttgtgg tgtcactgtt ggttcagtga ttttcatcaa cattttgttg    110280
ttggtattct cgaagcatgg ctagcctctg aagctgtag ttaaggcatc actttttga      110340
agagtccctt gcatattgct tgttgtaact tgagagacca tgatcagtgt tgattgtgat    110400
cctgctggtg acatttccat aatctagctc aaccccctag ctgatataaa acagatcaac    110460
cataaatcaa atataacata ttgcaacaaa caattacaca atcatgattt ctatagcaga    110520
atattatatt gtgttcatga gttgtaactg ttagatgaag ttacgatatt ctagaagttt    110580
cttgtgcatg taatctttag ccaaccgaat caatctccta tagataaaa gggatatattc    110640
taggctgtgc atagatagaa actccaacaa tagattgatt cggttaccct attgtataag    110700
ttgttgcacc cagcctgtg cctatataaa catgcaatcc ttggccacct agtgtggtag      110760
aacgcttcaa ctgtgacacc ccagtgtcac gtagggtttt tcctagagtt gactccaacc    110820
attatcacat gtgaaccaaa aagaggaatg aacataaaaa aattaagaac aaggtttaag    110880
tgagtctttt tcatcttaag aaattctcct taatcatgcc atgcacctca aggtaagaag    110940
aactctcaaa ccctaattaa tcctaagtgg accatttaag cacataaagg gaatttggga    111000
aaagacttgg gaaaatacaa aattttggta agaaccaaat aacaaagttt tagtgcacta    111060
aataaccaac aaaatatagt aagaaagttt tgccatttga attttccaaa atcccaaatc    111120
agcccatgaa ccaatgccct atggggaaat tcagaaaattc agaaaactga atttcaaacc    111180
ctttcccaaa gttcagatgt gttccctgtt ttccaaaact cgaatccaca aagtccaaat    111240
atcaaagtgg cgccaaaata ccctaggaac actttggaga agtttgagat caaacccgaa    111300
tcgtttgaca cgacttgaca taagttttgt ctcggtttgg acagtgctaa cagagctatc    111360
ttcaggccat catatcttct cacctaggcc atatcttcac tcgggactca cacacgacag    111420
gaagaccttg gcacggtgaa gagacgctac acaggatcct tggcaagata tgcacgtttt    111480
ggtcggccaa caggcgtttg aactcgggca gaatcacact tccacgtgtt cgatcgcgtg    111540
ctcaagcgct tggccgcgca ctggctgccc tctgatcgcg cgccatgcac ggtcggcttc    111600
tgtccccgc gcctgcactc agccatgcct gagggcgcct ataagtaccc tggatgcaca    111660
atggtctgcc cttcactccg cctcacgcct cgagcaagaa ctccaactcc gcgagctctc    111720
ccccgcccgc catcaccgcc cgagcctcgg ccaccgcggc cagctccctc cagccacttc    111780
caagctgcac cagtcactcg gttagcttcg ccagtggccc gtgaagcttt ccaagtcctc    111840
ggacccaaca gagtttcacc agagacccaa gatcgacctc gctgaacttc cgctcacccgc   111900
agccgcgcgt agaccgagca atccggtgat tcattctcaa attcctcgcg cgcatgtctt    111960
ccttgacctc tggtgaagct ccctaacctg ttcaattgga ctatcgcgcc gtgagcaggc    112020
cggatccctc gccgccgacg agctcccgc ctgtgcacgt ggaccaacct actccgacca      112080
ccaccgccga cgatccgcac ctcgacgtga tcgccagaga ccccggacct caccccgaccc   112140
ctcaccggag caacctcgcc gccggtaagc ccctccgccc ttttcttcca ctgcggtcac    112200
tattccatta ggggaaggat cgcggggttcg atttcgcaaa accctagggg ttttctgcag   112260
agtcatagac tcagataaat agtgaaccaa ggacctgtct gtaatacact taaaaccttt    112320
cgccagggac cccagtgcaa aaccctttt ccttttatcca tttctgttta ttctttttaa    112380
attcagtaaa ggacttagga aatttgtatc ttgagaaata ttcaaccaaa tttagtcaaa    112440
ccaattttac tagattcaaa atattatgaa ctatcacata aaaatattga accctgtgct    112500
ttctgttta aattttggag tttagaatta attaaagaaa ctgaccaaac cttattaaaa     112560
tgaagaaaat tagttatgct tctgtgctga acttaagaaa atttgtagaa gttcaaaccc    112620
cacttagaca ctgtttaaaa atattgagca ccctagtatt gaagatttaa acagggttat    112680
ctattaaaag ccataattgt ccaaaactta ggaaaataag aaaggtacta gaaaataatg    112740
aacagtggat gcaaatattt ttcctagccc acttaagtaa tgaagaacct agaaaaaata    112800
aaaggaacac tagtccagag caaattcaag gtgaaatgtt ttattaggca ctaataaagc    112860
tagaagggca attattagaa atatgagaac aatttcaaaa ttggtaagaa aaattcagta    112920
gacttgtaac cactaggaca ccactacaaa aatgataaat acctagccca tcattttaag    112980
tgggttgaac aaataaaact tgatattgag ccatattcca attaaatcat aagcaagcca    113040
aaaagtgtgc aacaatgggc gaataaattt ttactagatt attaatgaaa tagatcacca    113100
gagcaaaatg caaaacctat tcaaactaca aagtaatcat cattgccct acttcatgaa     113160
aaaggccatt taattcaaga aattcctacc accctttccct taagaaaaag gttaccaaat    113220
tttagaatga ttgctcttgc gcaaagaaga agataggaaa aattgaaat ctgttgtttg     113280
atattttca agtatagtgg tagtagaaag cacccctttg gctagaaact ttagaaaatc     113340
ataataaaat aactaataaa tattagtggc tgaaaatttg tacaaaatca tgttataaca    113400
tctaaatgcc agcaaaaata agtcttaaag aataacccac tgttaaaaga gagttgtagt    113460
tcaaaacatc cccttttgcc caacacttgc taatttgta cagagagaac ccctcacttt      113520
ttaagcccca aattttgaga cagaaaatta tacaccagta agaagctact gtaatgtttg    113580
cagaatttct ggaatttat taagctatct tgtagttcaa acccaccta aaagcataaa       113640
aggaataaag aagggaggaa ttagaaagat taataagtat taccccaaca tggcagctaa    113700
gaatcttgtt aaaatatcca taagatataa agaagaaaat cagtagaaca ctaaaaatgg    113760
gttaaccatt cagtaatcaa cttgacccta agttggtgag tgtaccacca aaaatctcca    113820
gtagtgagaa tgaggtctac cctattaaat tgatcatcct ccatcaaatt ttaattgcta    113880
aattaaaatat catgccatgc atatatctta ctcattgcat tcattagatt gcaacctcgc   113940
tgatggagag tacgtgctca tccctgagca aggagctgtc cacgaggaag accaggagca    114000
agctcccgag actgccatcg aggatctccc cgcagcccca tcatttggag gcaagcccg     114060
```

```
gttttatgca taaccaattt atatatgcta ctttactaca cttagtgttt gtaggcttgt  114120
aatgtgcact taagtgtagg agttgcttga aacccttagt tgcatgaact caggattcct  114180
ttttgagatg gatactagta tgctaggtcg agtagctgct ttactaatta ggatctcggt  114240
agaagtcgag tgattttct agcaatcgcg cgaggtcagg aattgattgt attcatcttg  114300
ataatgggat ctatgatggt ctatggtctt ggatccaagg tggatgcctt gtccatgaga  114360
caggaaaatg aattaaggat taatgtgtgg ataccgagt caagcgtttg aacgtactaa  114420
acacatgtcg ggaaatatgg taaccggtaa acctagtacc tgattgaagc tgggcgcgga  114480
ctttctcct cactcgtcct gagactgggt ctcctatgct agctttggtg ggtacaagtg  114540
cggtcactgc acggcggcag cccgggtcag tggagcattg tatgccaagg cggtgagccc  114600
tggccgcgaa aggggaatcg atggggacgg agtgccctga catgtcgtgt gtttaggttt  114660
accttgcaag gttaatactc gatttgaatc gtctgcttct cgcagctaat gagactgctt  114720
gaccccttgt actacattga gtaagaagtg aaatgaggat tacatgagat aacttgttga  114780
ttgtattaaa tgattgttac catgtatgct tagaaagagc aaacttagct acaataatga  114840
tactagaaat ggaaaagata aagttgacct tagatacaac tagtgctttt ggcaaaccaa  114900
accccctcaac caaacagcta catggtctag aggtagaaga gtagattcct cacaccgggt  114960
aagtctagct gagtattagt atacttagcc ttgcttgtgg cataattttt gcaggtacgc  115020
tctaggatat ggttgacggt gtaacttggc ctacaaccct gtcaccgggt tggacggtcg  115080
agtgggatgc tgctccggca ggagaggagc aggagaagta gtgggccagg ccttgcccta  115140
ttcctcgctt ttgacgacat cgattatccg ctgcagttta ttttgtgaac ttttctcagc  115200
tacttcgaaaa actctgattt atgtaataac tccagtactt taatttgagg ttttcctgtt  115260
ttattgtatt tcttctgtga ctcaccttcg agtgagcttg tggtatttga tcctggataa  115320
gtggctttat tagactagat ctgagggact gatggcttat tccgatttaa gtgcattgcg  115380
gcctttaagg cgtgacttgg gcacttaaac tggaataatc cggcggttc tgccacatca  115440
accattccaa tctacatggt accatagcca ggtcctctac aacacatcca tcatggcgag  115500
tagattctca aattccacca ccatcccctc ctccttctcg atcccggtca ccgaaaaact  115560
caccaaaacc aactaccgcc tatggagtgc ccaaatccta ccgcccatcc aatctgcaca  115620
gctctacggt ctgctcatcg gcaaagaaaa gatgctggtt aagactgtct ctgtgatgac  115680
taacgacgcc tatatggaga cgcccaatcc cgagtacatc aactgggtga ctcacgatca  115740
agcgctgctg ggatatatcc tctcctctct gatgcgtgag gtcttgatgg gtgtcacgac  115800
agccacgacc tcggccgacg tctggagctc cctcgcgact atgtacggat cttgcacacg  115860
tgcgcgttct gtcaaacacg gcattgcgct cgccaccacg aagaaaggca cgaccacaat  115920
ggccggattc taatccaaga tgaagagtta tgccgatgag atgtcggcgt ccggccaacc  115980
tctgggcgat gaggagttcg tcgcctatgt cctcaccgac cttgatgaag aaatctacaa  116040
cccgcttgtg tcgtccatcg tcacttgcgt cgagccaatc tcctctgcca agttatactc  116100
gcagatgctc agctatgagc ttcggcttgc gaagcagtcc ggcggcaggt acgctgctca  116160
tggatcagcc aatacggcta ctcgtggccg tggtggctcc tggcatgatg gttctccaaa  116220
atcacggtcg cggacgctcg cgcggaaatg gccatggcta tccttcgtcg tcttcgcgcg  116280
gcaactcag caacaacaac tacttcaggc gcagttccgg tccaccgaca gatcaatccg  116340
gtggccagtc ttgtccacgc tgctaggtct accttaaagt cggtcacaga gctaatatct  116400
gttggtaccg ctttatgaa gaattcactc ctgatgatcg ggttgcgcc atggcatcat  116460
cctccactgc tgctgatcca aactggtacc ttgacttcgg tgtgactgat cacatcaccg  116520
acgagctgga aaagctaaca gcatgatcgt tacaatggca atgatcagat cgggcggct  116580
aatggtgcag gtatggagat tactcacatt ggttattctg ttttgcccac ttccttccgc  116640
cctctgcacc taaatcatgt ccttcgtgtc cctcatccc ataaaaatct tgtttccatt  116700
catcgtttca atcttgataa taacaccttt attgagttcc atccgttctt tttcttgatt  116760
aaggatcagg ccacgaggca agtgctggtg cgcggaccat gtaggggtgg cctctaccca  116820
ttgacatctc ttgcacacct acccagaagc acgaccttgc cgcaataaag ccatcctatg  116880
agcgttggca ttgcagatta ggtcatccat cgcgtgatat tgtcgctcgt gtcattagaa  116940
ataataattt agtgtgttca ggcttagatt cctcggagta tgtttgtgat gcctgccttc  117000
gtgctaaggc ccatcagttg ccttatccta agtcgaccag tcagtctgct gctccttag  117060
atctggttt tttcgatgtc tggggacccg ccattgattc ttttttgtaat aaaaggtatt  117120
atgtcagctt cattgatgat tatagtaaat ttacttggat ctatcttctt cgccataagt  117180
ctgaggtgtt tcagttcttc aaagaatttc aaagccttgt tgagcgcttg ctcaatagaa  117240
aaatcattgc tatgcaaacc gattggggtg gcgaatttga gcggcttatc tcctttttc  117300
ttatcactcg gcgtccctca tcgtgtctac tgccccccatg ctctgcaaca aatgaggact  117360
cctatcgtga attaatcgcg cttgtttata tgatccttc tttatttctg aacatagtca  117420
taaactttat tctctttgga cgaccggtcc taccgctctt ggcaatattg ctcagcnnnn  117480
nnnnnnnnnn nnnnnnnnnn nnnnnnnnnn nnnnnnnnnn nnnnnnnnnn nnnnnnnnnn  117540
nnnnnnnnnn nnnnnnnnnn nnnnnnnnnn nnnnngaaa tctagagtaa tcgttctcat  117600
cgcctaattt atgttttaaa aaattaggca tgtgagtttt aacaaatgca tgtgtcatcc  117660
tctctatatc ctccgtgata ctttaatcc gattatcaaa agaaatttta atagatggaa  117720
tatcatcggc tgacctggca tcacctattg tggggagctg ttgcagcacg gctaacatat  117780
actcggcgtt tatctccctc tcttggacgg tcttctggtg gcagtctacc ttgaagtgcg  117840
agaggtacca cttgtccgcc accttgagca cctgatcctt ttgtcggtgg gcctcctcgt  117900
ctattttctt catgtcatct tctaattttt tatgctcagc ggccgataaa ttagtcagcc  117960
ttgtgttgct gtttggagaa gcactgttga gatctttaga atcggccatg taagcctgat  118020
tttgtagatc tgcaacttct tccccagcgg agtcgccaaa aagtatgttg acgcttttt  118080
ggagcgccaa acactcaaca agaaccgtgg cggtgccctc tggtcaggcg cggacggtct  118140
gcagccttgg gccggacgat ccgcagcctt gggccgcgcc tggcgcagg  118200
agtggtgtct tccctgcgtc acaccggacg gtccgcagct ctgggccgga cggtccgcga  118260
cctggcgaca gggtcgtctt cctactcctt gctggaatct agatctgtc ccctgggggg  118320
aaagatctta aggtgctccg ggtcgacagg tcacccgggg cgtccccaga cgacgtggag  118380
tcgcctagga attaagagat caaatcgagg aagaagtctt ggatggacaa ctagatcttg  118440
aggggccaca ccccgtggc cctaggggtc tcttgggatc gccaggccac ccaagacgga  118500
tctagacgac gtagagtcga ataggggtgg aggtggagat gtggaagact acaactagaa  118560
ctatgctaca tctactccta gggcaggaaa agtaaataag gtaattggtt cgattggaat  118620
gtgttcgggg gttctcaatc ggccgtaccc ctttatattt ataggggagg aggtctggac  118680
cttttcctaa gagatagcca acaaactccc acgtgattag atggataacc acgcacgaga  118740
taaggataaa catccgagtt aatctaatct cgggacacgc ggaccgtccg ggccaatggg  118800
```

```
ccggaccgtc cgctcatttt ggtgtccaac agctacgtag tcatgccatc acttcacccc  118860
acaatcccaa ctatcaaaat aactctaacc gaacttggca tttagccgat cgattcctaa  118920
ctcattttc ataccaccac tacacgacat accgaataca ttgaatgact cgttcacatt   118980
ccacatatat ctttacgaaa acatttccac atcgcttgca acttaaccta agcttcgcca  119040
cataattca ggacatctac ttaaatcatg aatatcatca tcacacacat cgacccgttt   119100
tgaaataacc ctacatgtct atcacaggaa tggagcattt caacacatat cctaaaacaa  119160
actaacttca tcacacatct tgcattacaa agctacttga cttatttgaa gtgtctactc  119220
gaaatcgtga gcacaatcat acactatata cgaaacataa ttttaacgaa cgcataatac  119280
gcatcgtcat gacttgacct ataaatatag agaaagcgat gactactctg gcatgtcacc  119340
acctctctat ttaagtcaag acaatttcta ccatcgatta agagtcgtaa gcattaaata  119400
ccttactact ttatacgcac aaataaactt caacttaaca caactgacac cgatggaatt  119460
tttactaaac tcatcgtacg cataaccctg tctcgcatac aaccatatta tggcgtgcac  119520
tcgagacact tcaatccatg tggcgcgacc actagtataa atggactccg acactcatgt  119580
cttaacgata catcctctac gcaaactagc attctctaca ctactcgtca catcaataaa  119640
tatatcccct ctaaaattac gaatcccatc acattgctta aaacaaatac acttttcaca  119700
taaacacatc gatgcatttt ccaaaacaaa atccacattt tgtaacttag ttttcgcatc  119760
aaacaacgca tcgcatattt tcctatcaaa ataaaaatac tcgagttctt ttgtatttca  119820
ttttcttccc tacacgcgtc catttataaa attatacttt tacacacata taaccacatg  119880
cacatcatcg accaaaacat aattagacaa ctacaaatcg cgcacatcaa ttaacctctt  119940
gttctccaat cgcaaacatg atcctaccaa tgcgcataat cgaacatttt acacacatcc  120000
atacaaaatg attaatcgag tcgatcgaga gcgacatgca tcggctcacc ataaacaaac  120060
ccaaacgatg tttgcaagaa tgacggtgat tccgattcgt gcatcgctcc aaacatccga  120120
cgagcgttaa gcgacttgct ttctcctcgc aaaacacggg gttctctcct ccacaaaaat  120180
aaaacaaagc aacacacata cataattaat cataggaaaa taacatcgat gcggaatcga  120240
acaaggagcg tcgcggtctc accggggtga acgacgacga cgtttgggc tgcgcaaaaa   120300
cagcgaacac acggcggcat cacggcgtgc tgctcactgc gcaacaaaac agcaagcgt   120360
cagcgcgcgg agccgtcggg gctgctgcac atttcatcga gcacaagtgt ggatggcgga  120420
caggtgttg tttcaggcgc tgaaacaatg gagggggaga gggctacggc tggggaagtg   120480
gtggctcggc cacagcaaga acaggaaagg ggaggctggt cgccgacctt gggcgcgggc  120540
agggaaaatg gagttgctgc ttggcgctat gtacaacaga gagaggagg aatggcgcca   120600
tgggaagctc gagctcggcc aggggaagga agaaagggt tcggcatcca agctgttgga   120660
gcccaaggag agggtgctgg ccgccgtgcg caagtgaagt ttcacgccag ctgaagctcc  120720
ctggtcgcgc ataggaaaga gcagggggcg cctgctgcag gtaggagctc ggctcctgtg  120780
gaaaatggca ggggcagagg aggccggctg gagcaccggg cagggcgctc ggccatggag  120840
ccgctgcatg ggatttgctg ctgcgccctg ggagaaaaac agtaggggag tgaaggatgc  120900
catggctggg ggcgcgggga gcaggagcc tgctggtggc cttgctgctg tgaagcaggg   120960
aagaagaaag gcagaggacg ccacgggaag agcttcggcg cgctggaggg aaggaacgcc  121020
cggccatgga agccctgcg cgctgggaa ggagctccag ctctacgtgc ttgaaggagc    121080
ccacggctgg aaaatggtag aggaggaaga gaagggtgct ggcggctggg gtggaaatgg  121140
aaaatttca gaatgcaagg gagggaagcc catatttata gaggagaaat tagggtaggg   121200
tttcttatgg gccgaatggg ctggactgga tttggcccaa aacactaaat tgggtcgcgc  121260
taaatatttt ccggactaaa aatgttcctg cggaattcgt cgctactgag aaacagagcg  121320
aaaagagttc ggacgaacgg aaggttgcgc gattaactcg gccgagagtc tgtttagatt  121380
tcgcttgaaa ataattcct acgcgtaaat cgaaaataaa tcgtcctgag atttgatcgg   121440
ttttggattt ttagtcggag aaagcgaatc gtgatatata aaaatcgttg ccgatgttga  121500
ttttgaaatc ggattggata cagagatgct aagctgagtc gagtaagatt tgattagagg  121560
acgacatatt gattatttcg tttgtgagta tggactcaga ttaaaatagt tggacatcga  121620
tcgaacatcg agaaattgga ttcggacaca gatcaaataa cagtcgtcga gagtttgatt  121680
taatgagctt cagatgaggt ttataattcg agaatgattt ttgagttcgc atttgtgccg  121740
acgataaaag ttttaacagg ctccaaaatt ggccttctgt gagactgagt aactccgaat  121800
tcggtgaaac gtgaatgaat aatctggata atcagggaca tacgcgagcg agaaatagaa  121860
attttactg agcatccgag attaggataa atctcgcgac gtaacacgaa actgacacct   121920
ggggtgtcac agccttcccc ccttaaaaag aatctcgtcc cgagattcga atgaggatat  121980
ttatgggtgg agaagcatgt aactcccaga ctgaagatag atgcaaattc atgagagggt  122040
atctgacaag atactggaga cagatttggt tagaatatcg cgacatatcg agacaaaatg  122100
cagcgatcat tctgagagtg tccacaaaaa aatagcacat cagtatagtc tcgtaatgaa  122160
tcacgactat taaccgcgat actagcgcgt gccgagcagc tcaaccatgt gtgcaccata  122220
gtaggctctc ggtttcgtcg cggccaccatc agtcgttagt catgacatca ttaccaaacg  122280
caaccaataa gaaattcaca tagcactgat agttggagcc catgaagta tggctcagaa   122340
aataagaatg tgatcagagt tgaagcagag attattggca aaagatcatc acatgagaat  122400
tttcttcaac tcatagagtt attttatgat catcacgggg attagcaggc cagcgattag  122460
tacgagattt gatatgagaa ggaagcactc cagagatcat gttgatgaac ttgtagagac  122520
atgagagaac cacaagatga caacaacatc ccttgaacca aatggataca ctgtttagag  122580
ataagttga taaacatcgt catgatcctc agagaacgag tatgagaatt accagaattg   122640
agagacttag gtagatcaac attcgatact tgagaacggg ttatagtaga taacaagata  122700
ataggcaga atcatgaaag atcagagatt cggatgataa ggtcacaaca tgattcacaa  122760
ggaaaaagat cactagatcc atgcgaaagg agaggtaggc aacaagatca gctggatgat  122820
caacaggaa gctatgaagt tttaggggca aggaatttat ggaaagaaac atggccttga  122880
tagggtttgc gcaactagac accaaacaac aaatttttt tgacgtaacc agtgcacaag   122940
gaagctttgg tcgatctagg agtcaagcta tgggaatcta caagctgtgc aggtgtaact  123000
tcaagggtaa aacccacaag ggctagaaaa cgccaacaca agcattttt taaaagcggg   123060
ttcacttgct aaactcaagg ttgtttggag gagtcttttt atgaacagaa caagcaacaa  123120
aatgttttgc aaaaagggtt gaacaattac aatactacct agatagcaag acaagagaag  123180
cacataacat aacctagtaa agactatcat gacacaagat aagacatt tttttgcag    123240
ttcctagcaa tacagcacat tattcacaat tttttttatt atttgaataa aggtgagaga  123300
agcatgttgg tgcacaaaag acaattataa tgcgacaatc atgatgcatg ctcattctag  123360
tcgtcttctc agacctaact acttttttcgg ttgcttctac agcatcctta ttaatagtag  123420
tagtagcctt tatggcctat ataaaatagcc acctagctac ccatctattt cctaaggctt  123480
cacgtcctaa gtctatcctt atcgtcctga catctatcca acattggttt ctagcaagtt  123540
```

```
ttacttttag aaaaggttgg taatcatgac ttattgactt ctctgtgatg gtattcgctc 123600
cgataccagc tgtggcggaa ccgcccgaat tattcaaact taagtgccca agtcccgcct 123660
tagaggctag accacactta aataggaata aaccgtcagt ccctcggatc tagtccgata 123720
aagccactta tccaggatcg aataccacta gctcactcga aggtgagaca cagagaaata 123780
caataaaaca taataccaca aatttaataa gtatcattag tgattacatt atcggagttt 123840
cagaaataat aaccataaat tttaatgcag cagaaataaa taacggagaa gaaccgagta 123900
acatggcgaa gcctggccac tctactcctc ctggtcctct cttgcggaag cagtaaccca 123960
ctcgaccatc tatcccggtg gtagggatgg aggccaagtc acaccatcaa ccaatcatcc 124020
taatgaatat ctgcaaaaat tatgccacaa gcaaggctga gtatacatta ctcaactaga 124080
cttaccggt gtgaggagtc tacttctcta cctctagaca tgcagctgtt tggctgaggg 124140
gtttggtttg ccaaaagcac tagctgagtc taaaatcaag ttttagcttt tcaagtttta 124200
gtatgatcct ttttgactag atgtgtacct agctaatcat acatgatatc aagaattttt 124260
atcaaacaac atcttttgcc aatcacctca tttccactta ttactcaatg cagtacaatg 124320
gatcaagaag tctcattagc tgcgagaagc agacgattcg aatcaagttt ttaaaccttg 124380
caaggtaaac ctaaacacac gacatgtagg ggcactccgt ccccacacac atcaaccgtc 124440
cccatcgatt ccctggcaac agaaagggc tcaccgcctt ggcgtacaat gcctcactga 124500
ccccgactgc cgtcgtgcag tgaccgcact tgtacccacc ataaccggaa tgggagacca 124560
cgtctcaggt cgcctgagga gggcaatctg cgggcaggtt cactcaggta ctaggcttac 124620
cgatttacca tatttctcgg catgtgttta gtacgttcaa acgcttgaca caggtatccg 124680
cacgttaatc cttattccaa tttcatctcg tagaccacgc gtccccatgg acccgtgtcc 124740
acagaccatc accattatgt tatcaaagtg gatacaacca attcctgacc tcgcgcgagt 124800
gctagaaaaa tcactcgact tctaccgaga tccctaatta gcaaagcagc tactcaacct 124860
agcatactag tatccatctc aaagggaatc ctgagttcat gcaactaggg tttcattcaa 124920
ctcctacact taagtgcatg gtacaagcct acaaacatta agtgcagtaa aatagcatat 124980
atataacagt tatgcataaa accggggctt gcctttaatt taacacttag gtagtgtttg 125040
ctgggggagg tactcgcttg gcgagcatcc actggttaag tccattcttt aggtcgtcca 125100
tcaacggcat cttgtggttg gcaccacatc actggctcga tcatcatctc tcggtcctat 125160
atgaggtgca agatgcatat gtatgaatat aataaaagta acataagata taccaagca 125220
cagtggcgaa ctaaacatta attagtaaga cactgcaaca actatacgca aacactagtt 125280
atttatgtgt cattgggcac acgtaaacac taccactgga aagacaatga tcactaccta 125340
caattaacca acgcaacacg atatcatatg tacaagcatt tatttagttg ctacggcttt 125400
tcattagttc ttctattgat cacacaaaag catcacaaac acaagtttaa taaggaccg 125460
atgcatcaat gtcgatggac tcctctatca caatcaacta tagcaagcaa gcacattaat 125520
catggaacac atgttaacct aagtttagcc atcacaagtc tatgtccgtt aagtgctaac 125580
taagcgtttt tagccaaaat ggtgaactaa atattcattt gagcacgtgc agattttttg 125640
gacagcagca cagcagttac ttgttttaat aataacttt caaatattaa tccaaaaata 125700
gcaaactaaa actttctgga aagttagaa agtgctctac aattttggta ttttcatcac 125760
agcatgatta aacacttagc aaggtcaaaa agtgcaatca caacagctct gtccagattt 125820
ggacagattc agacttgtga ttttaaaaat tcataactga agattcagac atccaaacaa 125880
attgatccta gactttctgg aaagctaatt aaatgttcta caaattatt ataaacatcc 125940
caggctggtt tagcatgtat caaggttaaa atatactatg aaggctgtgc tgtccaaaac 126000
tggacagatt cagtcttcac acttcaaaca catgtaactt aatcttcaga ccaccaaaaa 126060
gagtgatca agactttttg aaaatcttag caaaagtact acacaacttt cataatcacc 126120
aagaagtgat tccaggttta actaaatcaa atattacagt tttcgaaatc tgttctgacg 126180
gtggacagaa cacagcaacc agtttgtaaa attcataact cttaaaccgt caggcctata 126240
gttatgaaat tttaacacaa gcaagataag aaaagcctct acaactttc ttataatcta 126300
caagggctga ttctaacatt aacttaagca aacaatgcag cttctgaaat ctgtacagaa 126360
agtggacaga ttcagttact gaatttgtaa aaaacataac tcctaaacaa ttagacttat 126420
gcctgtcaaa ttttaacaca agtacgataa taaagttatc tacaactttc ttgtgaccac 126480
caataactaa tttcaacatt aacttaagca accattgcaa tttctgaaat atgttcagaa 126540
atttgacaga ttcaggtgct gggcttgtga aaagcacaac tcctaaacaa tcaggtttat 126600
ggctgtcaaa ttttagtaca agcaagataa tcatgtcatc tacaactctt ctatatgact 126660
tttctacaga aaacatgatt tggtttatca aacaaacagc acaactaaaa cagtgcgtgc 126720
agcccaaaac agcaatcaat aaattcagct tctgttact tttaaaaatt gccgcgttct 126780
agagactga cttattctaa attatatcaa ggcacactta agcatagcca cacaatagat 126840
gatgtgacgg ctactgttga cgccttttg gagcgccaaa cactcaacaa gaaccgtggc 126900
ggtgccctct ggtcaggcgc ggacggtccg cagccttggg ccggacggtc cgcagccttg 126960
ggtcggacgg tccgcgacct gggcgcagga gcggtgtctt cctgcgtca caccggacgg 127020
tccgcagctc tgggccggac ggtccgcgac ctggcgacag ggtcgtcttc ctactccttg 127080
ctggaatcta gatctcgtcc cctgggggga aagatcttaa ggtgctccgg gtcgacaggt 127140
cacccggggc gtcccagac gacgtggagt cgcctaggaa ttaagagatc aaatcgagga 127200
agaagtcttg gatggacaac tagatcttgc cccccgggag gggtgagatc ctagggtcgt 127260
cttgggatcg gcaggccacc caagacggat ctagacgacg tagagtcgaa taggggtgga 127320
ggtggatatg tggaagacta caactagaac tatgctacat ctactcctag ggcaggaaaa 127380
gtaaataagg taattggttc gattgacaag ttttcggggt ttctctcact gccgacccctt 127440
tttatcataa ctgagcacca ggtctgaaac tcaaacctct ccgaaaggga agcgtatcac 127500
ctgatccgag ctgataagc tccgactatc gacggatgac atagcatcac aactgatctc 127560
gggacagcag gtgctgccgg ttccctggac caagcaagcc catatcattt gatgtccacc 127620
agatgccccc tgccgcaagc gcgcaaaaag ctgcacccgg gagcctgaat tacactccga 127680
aaagcgtgag cccgtgattg ccttttcatg tcaaaggatc gatacggatc gatgggagat 127740
cacgcccgat gggcctggat tgctctgtt accttggcga gcgtttggtg cagaggccat 127800
cctctgaac ggattccact gcaccatggc tgatggaata tcctgcgtca tgcagaccat 127860
tgatggaggt gggtccccag cccagatagt gaagcgcgaa ctcgcatggt gtccacatgg 127920
attgaccgca ccgtcccgca gcttgaaata aagccccggt cccgaaggag acatgtcggg 127980
gagctcggcg gctgtcccta ctggacggct gctagctgca aaatggggg ttggccgctc 128040
ctacgggacg ttccgcacgc gtctctcgtg cgaccggacg caatgccat cggatagtgt 128100
tgctctggac tggttcatga ttagcacccn nnnnnnnnn nnnnnnnnnn nnnnnnnnnn 128160
nnnnnnnnnn nnnnnnnnnn nnnnnnnnnn nnnnnnnnnn nnnnnnnnnn nnnnnnnnnn 128220
nnnnnnnnng aattctttat tcctaagtta atttgatcct catgcttact ttggttcaca 128280
```

```
taaaataatg gttcttggtt tggcattttt aagagaaacc gtaggtgaca ctagggtgtc  128340
acagccttcc cccctaaaag gaatctcgtc ccgagattcg ggccagagtc ctcccagggt  128400
gaagcgaagg gtgagactta taggaaaagg gtggggattg ttatgcttca aatcatggta  128460
catcttggtg cttcccggat gcatagagaa tttggagaga tgagcctcat ccaaaatttt  128520
cttcttgaga tcctggtcct taggaattac caatctgctt ttgaaccata acacacccct  128580
ctcatcctgg cggaaacaat tatacttctc aaccttctga tggagattct tcttgataat  128640
ttgcactccc ttgtcactga gctgggccat gataatctgg tcttgcaagg ctggctcaac  128700
agcaatgtga gacaaagaac cagaaggaat cacttcaatt tgcatcttgc tcaactcatc  128760
acacaaggtg ttaacacgag aatccatcag aatacagttg cactgcaact tccgactcaa  128820
ggcatctgct accacattag ctttccctgg gtgataatgt acctccaggt cataatcctt  128880
gatcagctct agccatcttc tctgcctcat gttgagatca gcctgagtaa aaatgtactt  128940
aaggctctta tgatcagtga agatgttgca gtgggttccc attagatagt gcctccacat  129000
cttcaatgca tgaaccactg ctgctaactc aaggtcatga gtaggataat tttgctcatg  129060
aggcctgagt gctcttgagg cataagcaat gactcggttg tcttgcatca agacacaacc  129120
tagcccggtg ccagaggcat cacaatatac atcaaaaggc ttgctgctgt cgggttgcgc  129180
caatactggt gctgtggtca gatgctgcct taatgcatgg aaggcatctt cgcacttctg  129240
actccacaca aatttgactt cttcttcag caactcagta ataggcttcg caattcgaga  129300
gaagtccgga ataaatcttc ggtaataacc agccaatccc agaaaactcc gaatctggcg  129360
aacagtcgtt ggtggcctcc agttcatcac ctcttgcact ttatcaggat caacagctat  129420
tccagcctga gagatagtgt gacccaagaa tttgatttcc tttagccaaa aatcacattt  129480
ggataacttg gcataaaggt ggtgatctcg cagacgttga agtactacat gcaaatgccc  129540
ggcatgttct tcttcgttcc ttgagtacac cagaatatca tcgatgaaaa ccaccacgaa  129600
cttgtccaat tctggcatga aaacagaatt catcagatac atgaaatatg ctggtgcatt  129660
cgtcagcccg aatgacatca ccaagaattc atatagccca tatctggttg agaatgccgt  129720
cttcggaata tcacttgctc gtatttgat ctgatggtag ccagagcgaa ggtctatctt  129780
ggaaaacacc ttggcccccga ccaactggtc aaagagaaca tcaatacgag gcaaaggata  129840
cttgttcttg atagttaccg cattaagagg gcgtaatct atacacaacc tcaagctttc  129900
atccttcttc ttcacaaaca gtgctggaca gccccaaggc gaagtgcttg ggcgaataaa  129960
tcccttatcc agcaactctt gcaactgctt cttcaactct gccaactcag cgggtggcat  130020
tcggtagggc ctcttggaaa ttggggccgt tcccggttgc aactcgatgg cgaactcaat  130080
atcccggtcc agtggcattc ttggcaattc atcaggaaag acatctgcat actcacagac  130140
cactgggatc ttcttcaggg gtaattccgt catagagaaa gcacatgact gagaagaacc  130200
ctgactaggc agaatcaaag tgaaattccc gcagaaggga gaattaactt ccacggtacg  130260
actggctacg tcgagcacaa cttggtgcaa ggtcatccaa tttgctccta gaataatgtc  130320
cacattttcc aatcccaaca caagaagagt ggttttgata atgtggcttc ccagttgaat  130380
aggcacactt tggtttaatt gattagttgc aattttaccc ccaggtgtga ctatcatgaa  130440
tgacccttt gagtgagaga atggaagttt gcaattagca ctgaactttt ggctaatgaa  130500
actatgagat gcaccagaat caaacagaat taaagcaggt tgattataaa ctgaaaaggt  130560
accggtcatg atgggagctc cttctggcac ttcctctgga gcagtgaagt tgagcttccc  130620
ttgcctgact tgtaccttct gctttcttcc cttgtcttga tttggtgctg gcatctgcct  130680
ctgctggttc ctgggacaat tcttggcata gtgcccaca ttgccacaag tgaaacactt  130740
gttcccattg ccctggcgga actgctgctg ctgcggaggc tgattgtttc ttggggcggg  130800
agctggatag cggttgggtg ccggctgctg ctgctgcctga ggtggcctga tcacccatct  130860
gcctgcctgc tgctgaaaac ccctgctctg attgtgagaa acaatccgga acctctgagc  130920
ctgagcggat ggtgctgcca ttggtgcctt tctcttcttc tctgcccggt gagcaacaat  130980
gcaatcctcc tgagagatgg ccatgttgac caactcattg aagctatcgg cccggacagt  131040
gttgagtcgt tcccgcagct tggtattgag acccctgcgg aagcgatccc tcttctttcc  131100
atcagaatca gcatgatacc ctgcatactg gcataagtcg ttgaaggctt cgcgcatactg  131160
cagtaccgtg cgggttcctt gattgagggc caggaattcg ttcaacttcc gatcaagaat  131220
gccagctgga atgtggtgcc ctctgaaggc agtcttgaat tcctcccaag atacttcacg  131280
atcaccgggg agcatagcac ggaagtgatc ccaccaagtc cgagcaggc cgcgaagctg  131340
ctgtgcggcg aagcgagcct tggcctcatc agggcagtct cctgtgagga ggggaaactt  131400
ggactcgacg acgcgaagcc acacgtcggc gtccaatgga tcctctgcct tggtgaacaa  131460
gggcggctgc gtgctcagaa actcctggta tgttgccata gccggaggtc gctgatgctg  131520
gcctccacca ggatgctgag ggtggggctg gcgctgcaga agctgtcgca gaatctcatt  131580
ctgctgggcc atcagctcct gcactgtggg agctggagga ggtggcgggg gagcttgctc  131640
attttgcccg cgacgctgcc tcgctgccat ctgaaaacag agattgtcgc cattgttatc  131700
ccaattcaca tttccgaacg acaagatatc atctcatatg gaaggaaaat gccataatca  131760
taatattagg ttcgaatgaa gataacatgg tgacaaggat cccacagata tcaaaagttt  131820
acagggttac attaatcagg ggaaggtacc cacaagccta gtccaaaatg tgataccact  131880
aagctcgcat aggtttctat ccgcctaaaa atgtcaaagc gactgcttaa ccctgagcgg  131940
tggaagcgac actggatacg ggtgaaggag gtatcgcgga ggtagtccca ttggcaccag  132000
gggctggtcc tagcctcctcg ggagcctctt ctccctcgct tcctgcttca ttggcctcca  132060
tctccaggtg gtgcatgtcc aagtggtcat ttgcttccctc gagttccctc tgcacgtcgt  132120
gaagctggtt ctccaagaca tcaatagtgt tatctcggat ctccacttgc tgctccaggg  132180
tggtaatacg ctggttcagc ctctccacct gcagatcctt ttccaccaac tctgtggata  132240
ggtcgaccac aaaatcttcc cgactgtcga gggtgagctt ggctgcctga gcggtattgg  132300
caagaagtgt catagcatcg ctctgaaggg cctgaaggcg gtacacgcca ctcatgcact  132360
gaacagtgac cctcccaacc aagtcaggat acattgccca cacatcctc acatggctca  132420
cgcggttaca ccacatggga tcatccttct tctcagcggg gaagagtccc aaggggtgca  132480
tcaccatctc caggggatgg tagccacaaa aagtcgtcag agtcttcatg gctgctgcct  132540
caacggtgtc gtccgtcctg agtccaatcg tctcagagtc aagagaacgc caacccggct  132600
gaaggggatg agcctccaaa gttagccaga cccgacaacg aggtacccga tgctcctcat  132660
acaactgcac cgtgtacaaa gggggcgtag ggtaaccgac ggaattaagc acttcccaca  132720
aaatggaagg gaagccatcg cgagaaagga agtcagaact gaaacgagag tctcctccac  132780
tggcgggggt gggtgaattc atctgcggaa gggaatcaaa gataaagatt atggtggaag  132840
gaaaagaaa aagagagccc ggatgatttc gaagaaaagg gggttagctc aattttaatt  132900
cctctttatg tttttataatg catgcatgcg gaaagaaacg ttgcctctca aaaggaaaat  132960
agggtgcctt tttagggcat cctaaaatat aagtattggc ccacagggcc taattagtta  133020
```

```
gccacctatt tctccctcta tgcctaaggc ctttcgtcct aggtctagcg gtctagtcct    133080
gacgatccgt agtagcttct aggcaggttt tagattttga aaattggtat tcatggttta    133140
ttgcccttct ctgtggtgga atttgctctg ataccagctg tggcagaacc gcccgaatta    133200
ttccagctta agtgcctaag tcacgcctca ggggccgtaa cacacttaaa tcggaataac    133260
ccgtcagtcc ctcagatcta gtctgatgaa gccacttaac aggatcaaa tcccacaatc     133320
tcactcgaag gtgagtcaca gaagaaatac aataaaacag gaaacctcaa attaagtact    133380
gagttattac ataaatcgga gttttttgagt agcgaataaa gttcataaat taaagtgcag   133440
cggataatcg atgtcgtcgg taatgaggaa atgggcaagg cctagcccac tactcctcat    133500
gctcctctcc tgccggagca acatcccact cgaccgtcca acccggtggc agggtggtag    133560
gccaagtcac accatcaact acatcctgca tggtacctgc aaaaatggtg ccacaagcaa    133620
ggctgagtat actaatactc agctagactt aaccggtgtg aggagtctac tcctctacct    133680
ctagactatg cagctgtttg gctgaggggt ttggtttgcc aaaagcacta gctgtttcta    133740
aaatcaactt ttagcttttc aaattctacc atcattaact tagctagatt tgctcctct    133800
aagcatacat ggtaacaatc aattagttca gtcaacaagt tatctcatat aatccacatt    133860
tcacttctta ctcgatgcag tacaaggaat caagcagtct cattagctgc gagaagcaga    133920
cgattcgaat cgagttttta aaccttgcaa ggtaaaccta aacacacggc atgtcagggt    133980
actccgaccc cacacatgac aaccgtcccc atcgattccc cgttcgcgtc caggcctcac    134040
cgccttggca tacaatgctc cactgacccc gactgccgtc atgcagtggc cgcacttgta    134100
cccaccatag ctagcatggg agaccctgtc tcaggtcgca tgagggataa agtccgcgcc    134160
cggcttcact caggtactag gtttaccggt taccattttt cccggcatgt gcttagtacg    134220
ttcaaaagct tgactcaggt atccacacat taatccttaa ttcattttc ccgtctcatg     134280
gacatggcat cctccctgga cccaagtcca cggactaaca tataccccat tatcaagatg    134340
aatacaatca attcctgacc tcgcgcgagt gctagaaaaa tcactcgact tctaccgaga    134400
tcctgattag caagcagcta ctcgacctag catactagta ttcatctcaa aaaggaatcc    134460
taagttcatg caactagagg tttcaagcaa ctcctacact taagtgcaca ttgcaatcct    134520
acaagcatta agtgtagtaa agtagcatat aataacatg ttatgcataa aaccggggct     134580
tgccttcaat tgctggggct gcggggagat cctcaatagc agcctctgaa gcctgctcct    134640
ggtcctcctc ttggataggt ccttgctcag ggatgagcac gtactctccg tcggcaagat    134700
tacaatctaa tgaatgcaat gcgtaagata tatgcatgat atgatatgtg ctttagaatt    134760
tataacttta aagatgtatg atctttttgat ttaaaaccag ttaactttac ttatgtaaaa   134820
cccctttagtg gtatacttgg taaattgggt tagtctttatt gggatgaggt ttatttcttc   134880
ttctctttc ttttattctc tttaatgttt tggagtaggt ttgaactaca agttgctttt     134940
ataaaattcc aaaaattctg caaaaattac agtggcttgt tactggtgta tggttctctg    135000
tctcaaaatt tggggttcag aaagtgaatg gttttctctg gacaaaatta ccaaatttta    135060
gggcagaagg ggtactttga actacaacta ttatttaata gtgggtaatt ctcaaaaact    135120
tattttgct ggcttttagg tgttataaca tgacttgata caaatttcta gtcattaata    135180
cccttaatt ctttccctaa gattttctta aggtttctag ccaaggggg gctttctact    135240
accactatac ttgaaaaaca tcaaacaaca gagttcttat ttttcttagc tagtatttttg    135300
tgcaagagca atcattctgg agtttggctt ccttttgcct aagggaaggg gtggtttgca   135360
ttatttgagc taaatggcct tcctcacaaa ttactagcaa aaggcatggg ttcacttctt    135420
tttcatgggt ttgtattttt ctctggtggt ttatctcatc atggacttag caaaattttg    135480
gttgcccatt atcacattat ttggggttgc tcatgattta gtgggaaaat gccttattat    135540
cattctgtat ttatttttccc tacttaaaaa gttaggctgg ggtgctctgt attttttgtag  135600
tggggctctg gtggttataa gttcactgga ttttttgttaa ccactttggt tatagttttg    135660
caattctaat aattgatttt cagtctcact aatgctaatt aaagcatctt aattagaaac    135720
tggtccaaat taatggtctc tgcatttttc ctaggttctc tgctgcataa gtaatctagg    135780
aaaaatatta ctaatcactg ttcattaatc tctaaggcct ttctgatttt ctctaagttt    135840
tggacaaaat ggctttaaat gaataactac atcataatct ctaatgctag ggctcctact    135900
atttttaaac agtgtctaat taaggtataa gcatctacaa attttcttaa gctcagcaca    135960
aaagaaaaac taattttcct taattaaaca aggtttaggg ggtttctgtt tttaattta     136020
aactctaaaa tttagaacag aaagcatatg gttcactatt tttaaatgat aggtcataaa    136080
attccagagc tagcaaaatt ggtttgacag cttttcatta agattcatc aagttatgga     136140
ttttctaagt tctctggtca tttttaaaag aaataacaaa attgattaaa tggaaatcca    136200
ctttgcactg gggtccctgg cggttttcta agttttcctc gcaattcagt ccttaggtta    136260
ctattctcat gagtcgctga cattacgaaa aaccctcgg gttctacaga acctaaccg     136320
aggtccttct tctaccttaa acagtagccg cggcgaagaa aagggcggag gggcttaccg    136380
gcggcgagac tgttccggtg aagtggccga gggtgaaggg gaggtcgcgg ggatcacaac    136440
ggtgtgcgga acaccgtcgg agatggccgg agtcggtcgg tccacgcgcg caggcgggga    136500
tgctcgtcgg cggcgaggag accggcctgg tcgcggcgag atagttcaat caaataggtc    136560
atggaggtcc acgggatgcc agagaagaca tgagcgaagaa gaatcgggcg ggagactcac    136620
tggatagctt ggtccacgcg cggcggcgga agaccgaagt ccgtgaggt tgattcttcg     136680
ggcctcccgg tgaagttccg gtcgggtccg agggcttggc aagcttcacg ggctactggc    136740
ggagctagcc gagcactggt tgggctggag ggtggctgga gtgggctggc cacggcggcc    136800
gtagttctgg cggcaatggc gggcggaaat gagctcgcgg gagctaagga acagtggcgtg   136860
gccggtgagg gtgagtgcgg ggcgaagaga ggtgcgcccg gggaggcttt ataggcgcgg    136920
gcgggcacgg ccgagggcgt gggcgcgcgg cggacttgac cggacgccgg ggcgagcgcg    136980
cgcgcggggtt gggcgagctc tggcgtgccg accaggtgtcg aacacgtgtg cccgtgcgtt    137040
ctgcccaagc tctggcgcgt gtggtcgctc atccgagcct gctctcgctc tggtcagtgc    137100
acaaaccctc ttctcctccc tacaagctac cattcttgtg tggaggtcat aggatttga    137160
ctactggttg cagagatatg gagccaggaa atctggtctg tctccctgcc caaacccgag    137220
gcaaatccca agttttgtcg tgtctagggc tcgcgtccca atgccatctt ctggcacaag    137280
acagaggggt tagttagaca caattttgtc aatgggggcca ttaggattcg agttaggat     137340
caaggtgaac atccctgatc tttggctcaa ggtctgaatt tcagaattct gaaattcaga    137400
attcccaatg agtcccaaca aaagaagctt gatttggggg ttttcttgaa ttattttgaa    137460
taagcttttct caatctatct tgttgcttat caaatatact ttaacttata taattggctc    137520
aactcaaaat tttaaacttt tcattccctt tgcttatttt tctgaattt tgttcatggg     137580
gttcacttag ggttcttaat tagggttgca cattcttatc ctttaagaga ctcaattgtc    137640
ttgatcatga cactttttaag catatacttg gtgaattctt tcttacttaa gttatttttga   137700
tgctcatgct tactttggtt cacataaaat aatggtcctt ggtttggctt tttaagagaa    137760
```

```
accctaggtg acactggggt gtcacaggag gcatacaa  ggatgctgag cctcgacatg 137820
cgggcctagg agcataatgg aagaaataga ttatgtaaat aactaatgct gacagagtaa 137880
cgcatgacca aacttggagg cctgaccgt  atatacaggg gtctggcatg ggttcggcac 137940
tctcctatgg gggtccggac tcactattga tgccttggag tacatcactt tctctgaca  138000
catggcggcc ccggaccgc  ccatgtggtg gggtcaggtg ctgttgctgg cctagagtag 138060
tcgcccgagg ctagggcgag tcatggtttg gtcccacata cagctctttt accacgcgac 138120
taaagatagt cgccgtgggta ctgcgtattt atacagtagt aaggggtacc cttgtttcag 138180
ggtgccgaaa gtgccccccg gacccacctt agggggaggat gcgagcctgc atgtggggcc 138240
aaagcttgta ctttgcttca acgtgacctg atcggtgatt ggcatgccgt tttagccgcgt 138300
ctgcagacac gcccgctgtc aatccgcctt cagtcacgtc aactgccata tctgtctctg 138360
cagctgactg acccatggcc ccatgcctgg tggtttcgtc gggccacgcg tgggacgcct 138420
cgttgccgct gcataaccctt ttgtcttctg cagcggcccc gaggaggtgc gctatcgtgc 138480
gcggcagttc gcatggcgat tcgctctttc cgcactcgaa atccagcaca caatctgtat 138540
gacttgtgga ccccgggccac cgtgtcatag agtgggctgc ctggggtccta tgtgcgcatc 138600
gggcgagatt tcctgtggca attcaagggc gcacggaagg gtttccctga caaggactc  138660
aggtttcctt gaaaaaggat tcaccccgcg tgcagcagtt acctttttcgc attctctccc 138720
aatcgcctgc acccctttgc cttcgtgctc ctctgttcca cgctcgcgcc gccgcacacg 138780
ccatggcctc gcttggtcat cctgactgct ttcagtctaa ggaggcgctc aacctggtgc 138840
gcggcctgct tggatggagc gcgccagggc tcgccggaag ttccgcgccg cgccgtccc  138900
tcatggcgat ctcaccgccg gggagttcgt gctgttcacc tcctacatct tctacgggtt 138960
ggcgttgccg attctcgccc ttcttcttgc tgctgctgga ggagtttggg cttcagcttc 139020
aacacctcac accccactcc gtcctccagg cagccatctt cgtccacctc tgtgagatgt 139080
tcgtaggtgt ggccccctgt acttccctct tccgctgctt cttcgtgctg gtcaagttcg 139140
ggaagactag ggaccacatc ggtgcctact acttccagac gaggccagat ccagccgtcg 139200
tatacatccc caccttttggc ggtgcgaggt gggaaaactg gcgcaacgat tgggtgattg 139260
ccagccgcga ggcaacgac  cgcctcgtcc tgccgacgga tgggcagcg  ctcgaccgca 139320
agcagtggag gactaagccg tccctcttgc tagagttcct gcctgtattg gacagaatca 139380
agggcttggc tacgggcggc ctgccatcaa tgcacgtggt cggcgatctc ctgaagcacc 139440
ggatcgcgcc gctgcagagg agaccgcgta tgtgctgttg gttcaccggc ccaaacgaca 139500
tcgataggat ccaacgcagg ccgggcaccg ttctgtccgg ggacgagcta gcagtcctga 139560
tgggagggat tattgggaa  acttttgtcc ctgagtccct gatactccc  cagaacatcc 139620
ctgcgctctg cgacgatcca ggcctgagga tggtgatctt ggccacgttg ccgaccctcg 139680
acgagagcgg catggcggtt cgctagaccg gtggccggga ccccctccgt gggatccaga 139740
tttctaatgc accgattgga ggttcccagc ccactggtgc ggctccccag ccaaccccg  139800
ccgtggcccc tagcccctttg gacaaaggca aagggggctgc gagcagtgcc tccgcccag  139860
gtagctccga ggggggtcgga ggaggagagg caacgcaggc catgtcgcgc tgatgggtcg 139920
ctcatttcgg agccccccccc agaagcgtca gagggctgca ggtggggccg aggaagctag 139980
ctcccaggcc cacggcgcgc agaggcgcgt cagtcctcac ccccagggggc accagcagca 140040
gcaacagcaa cagcaacagc gatacaaca  gcaggagcgg tgatcgcccc gcttccaggg 140100
tcactagaaa gtctagggcc ccaagtaagc gtagcccctt ttccatgagt ctaatcatca 140160
tgccgaccag ttttaaccca tcatctgttc gctagggctt cttccttcgc cgctcccaag 140220
gtcatgcctc ctccaccaga taccaggccc accgacgggt ctggctctca acagcaggaa 140280
cctgctgaga gtggtgccgg cggcccaccc ccagctgctg ccaagacagc accagccggt 140340
tctcatgccc cagccggggg tccggtggca gcgtcaggcg gcgtcgcagt ggcgaaggag 140400
gtcccagctg ggggatccgc gcccgctctc gacactgggg gtgacgcagt aggcatgtcc 140460
agctccaacc cccccgcctgc tccggaggag atggaggtgg tgtttgggcg gcgactccgg 140520
tcgggtgccg agcaagaagc ggcgccagtc cccctccctc gcataatgtc tcgtgcccac 140580
taggtcctta gtgacactgg ggcagcaatc ttgcgggagt gggaggcgct tgaggctgag 140640
caccagcgcc taagtgactg gcgcacccaa ctggaggagc gcaccagaac ggcgtcccaa 140700
caattcatct ccgagcggtc ccaactcgag caggaccata aggagtacaa gagggacctc 140760
cagagggtgt gcgccaggga gctgaggcg  tcccggaagg agaagaaggt gaccaggaag 140820
gaggaggtcg tgacccagcg ggagaccctc acaacagagt accaggccaa gctgagtgcc 140880
ctggaccaga ctctgaaagc ccagcgggcc cagcaggtca gggtcgtgga gaggctgcaa 140940
aagtggtagc aggagctcga gggcaaggct agcaatgcca ccctcgccga ggaaaatctt 141000
aaggcgaagg agcagtggg  ggaccggtgg gagacgacc  tcgccaggca agagacggat 141060
ctcagcttca gggaagaaat gctcaccccgg cgaggcgagt tgctggccaa gcacaagctc 141120
gaggcagagg agaaagagag gaagctggag gagcagatcc gctagttcaa tgcagcgcag 141180
gcggcaccgg gtcccaagc  gatggaggcc accaggaagg cccttgaaga tctccaagcg 141240
gagcaccgcg tcgaggtcca gtgtattgtc gcgtgggccg gcgaggcaga cacggcacta 141300
gtgccactag ggatgagccc catcccaatg tcggagctac cgcgtcgat  ctctgatgcg 141360
ctccggtgc  tggactctac cgccgatcgc ctccgtcgcc tggatcagat cctcggggcc 141420
cgcctagagg cagagggcag caagctctgt cgggcagtgg ttgaataagt cctaacatgc 141480
ttccggagtc acgaccccac catatccttg gcgctagtga tcgctggtcc ggtagccgcc 141540
atagaagacg ccgcctggga gagtgtacaa gacgccgtgg agctggtggc cgagcgcttg 141600
cagcacgatc ctgctgacga cctatagaga caaagcaagg gttccactgg gaagcggttg 141660
taataaccttt tgattttgta agatattata agaaccgcta atgaggtagc attgggaactt 141720
aaactttattg gtatgttatt tgtccttgtt atgtgtagtg tcatcaactt ccccttggta 141780
cttggccccc tgggaggtag gctcgacgtg tcgaggctgg ataccagtat accaaagata 141840
aaattggtgg tccggcccct aggaggtagt ctctacagtt tgagactacc tactactgga 141900
ctgggacctg gacttgtaca cagcttcggc tttaaagtgt taggagcaca ccataggatc 141960
catcgtctgt tatctgccat cctttgattt atgcaacagg acctgcagga tttagcctgg 142020
gaagccaagc cgtatgcctg gacccatagg atcacagttc caaatactag ggcacccgtt 142080
atagagtggt gggagcatgca ggcttaggggt acggaaccat gctaagcggc tacacaactc 142140
cggaccccctc caggaggcta gcgccccattc tctagaactg gtccagcagtt tgccggaccc 142200
cctgtagcag taaaggggtc ttgaactgca agcctgtcta ctcaattcgg atgtcatcat 142260
accaacaagg gtgggaaact atatggggggg gttagataaa aaataatgca tgtaaaccga 142320
agtagaataa aaccatcaca aaatcacatc taggggggtaa atccttttcct tataactcga 142380
tatacatggg tgtagaccaa cagatgggct tacgagggcg ggcctcaccg aattgacata 142440
cacatatgcg taacctagtt acaaaggaag aaaaactcaac ccccccagttt tgctattatg 142500
```

```
gatagaactt acagagatgc tctatattcc agggattggg aagaggcact ccttctgttg   142560
tggcaaggcg gacacaccat ggtcggcata tttctgtcac cttgaagggt ccttcccaac   142620
tgggggagag tttgtggagc ccttctcggt tcagtactcg ccttaggact aggtccccga   142680
ccctgagctc cctactatgc acaaaccgtt ggtggtagcg cctgagcgct tggttgtacc   142740
gtgcatttcg gatcaccgct tgccatctgc gttcgtcgat gaagtccatg tcctcacgtc   142800
gtagctattc ctgcatagac tcatcgaaag actggactca tggggagccc ataatgattt   142860
ccgggagaag gcaggcttcg gccccgtaga ccaagaagaa cggggtctcc ccggtagctc   142920
ggctgggtgt ggtccggttc ccccatagta cggacggaag ctcattggcc caattggcac   142980
catgcttttt taagcagtcg taggtgtgtg ccttgagtcc cctaaggatt tctgtgtttg   143040
ccctctcagc ctggtcgttg ctcctgggat gagacacaga tgtaaagcag agctgggtgc   143100
caatgccctc gcaatactct tggaagagtc gactttgaa ctgggtccca ttgtccgtaa   143160
tgatatggct tgggacccca aatctgcata caatcgaatt gaggaaggca acagcagcac   143220
cttgggtgat actgaccata ggggtggcct ccgaccactt tatgaatttg tagatggcga   143280
caaagagaaa acggtacccg ccgacagccc taggaaatgg tcccaggata tccaccccc    143340
atacggcgaa tggccaagag ggtggaatca tttgcagagc ctgagctggt gtgtgtgtgt   143400
gtctgctttg catgaaactg acatgcttcg caggacttca ccaactcggc tccctcctag   143460
agagcagttg gccagtagaa gccatgccag aagaacgaat caagctgatt ctcagagttg   143520
aaaannnnnn nnnnnnnnnn nnnnnnnnnn nnnnnnnnnn nnnnnnnnnn nnnnnnnnnn   143580
nnnnnnnnnn nnnnnnnnnn nnnnnnnnnn nnnnnnnnnn nnnnaattct tagaaaattc   143640
gtcctcaaac ccaagagaca ttaaagggat tcttgagacg ggctcaaaat gagttcggct   143700
taagggtcaa gaaaataaga agcgacaacg gaacggagtt caagaactct caaattgaaa   143760
gctttcttga ggaagagggga atcaagcatg agttctcttc tccctacacc cctcaacaaa   143820
atggtgtagt ggagaggaag aatcgaactc tattggacat ggcaaggacc atgctcgatg   143880
agtacaaaac ttcggatcgg ttttgggccg aggcggtcaa caccgcctgc tacgccatca   143940
accgattgta tctacaccga atcctcaaga agacatcata tgaactccta accggtaaaa   144000
agcccaacat ttcatacttt agagtttttg gtagcaaatg ctttattctt gttaaaagag   144060
gtagaaaatc taaatttgct cctaaaactg tagaaggttt tttacttggt tatgactcaa   144120
acacaagggc atatagggtc tttaacaagt ccactggact agttgaagtc tcatgtgacg   144180
ttgtgtttga tgaaactaac ggctctcaag tagagcaagt tgatcttgat gagataggtg   144240
atgaagaggc tccatgcatc gcattaagga acatgtccat tggggatgtg tgtcctaagg   144300
aatccgaaga gcctccaaat gcacaagatc aaccatcctc ctccatgcaa gcatctccac   144360
caactcaaga tgaggaagaa gctcaagtcg atgaagaaga agatcaatca aatgagccac   144420
ctcaagatga tggcaatgat caaggggag atgcaaataa tcaagaaaag gaggatgagc   144480
aagaaccaag ggcgccacac ccaagagcc accaagcaat caacgagat caccccgtcg   144540
acaccatcct cggcgacatt cataagggg taacaactag atctcgtatt gcacattttt   144600
gtgaacatta ctcgtttgtt tcctctattg agccacacag ggtagaggaa gcactacaag   144660
attcggattg ggtggtggca atgcaagagg agctcaacaa cttcacaagg aatgaggtat   144720
ggcatttggt tccacgtcct aaccaaaatg ttgtaggaac caaatgggtc ttccgcaaca   144780
agcaagatga gcatggtgtg gtgacaagga acttgtggcc aagggatact   144840
cccaagtcga aggtttggat ttcggtgaaa cctatgcacc cgtagctagg cttgagtcaa   144900
ttcgcatttt attggcatat gctacttacc atggctttaa gctttatcaa atggacgtga   144960
aaagtgcctt cctcaatgga ccaatcaagg aagaggtcta tgttgagcaa cctccccggct   145020
ttgaagacag tgagtaccct aaccatgtct ataggctctc taaggcgctt catgggctca   145080
agcaagcccc aagagcatgg tatgaatgcc taagagattt ccttatttct aatagcttca   145140
aagtcggcaa ggccgatcct acactcttta ctaaaactct tgaaaatgac ttgtttgtat   145200
gccaaattta tgttgatgat attatatttg ggtctactaa cgagtctaca tgtgaagagt   145260
ttagtaggat tatgacacag aaattcgaga tgtctatgat gggggagttg aagtatttct   145320
taagatttca agtaaagcaa ctccaagagg gcactttcat tagccaaaca aagtacactc   145380
aagacatcct aagcaagttt ggaatgaagg atgccaagcc catcaaaaca cccatgggaa   145440
ccaatgggca tctcgacctc gacacgggag gtaagtccgt ggatcaaaag gtataccggt   145500
cgatgattgg ttcattgctt tatttatgtg catctcgacc ggacattatg ctctccgttt   145560
gcatgtgtgc aagattccaa tccgacccta aggaatccca ccttacggcc gtaaaacgaa   145620
tcttgagata tttggcttat acacctaagt ttgggctttg gtaccctcgg ggatccacgt   145680
ttgatttgat tggttattcg gatgccgatt gggcggggtg caaattaat aggaagagca   145740
catcggggac ttgccagttc ttgggaagat ccttggtgtc ttgggcttca aagaagcaaa   145800
actcggtcgc tctttccacc gccgaagccg agtacattgc cgcaggacat tgttgcgcgc   145860
aattgctctg gatgaggcaa accctgcggg actatggtta caaattaacc aaagtccctt   145920
tgctatgtga taatgagagt gcaatcaaaa tggccgacaa tcccgtcgag catagccgca   145980
ctaagcacat agccattcgg tatcattttc ttagggatca ccaacaaaag gggatatcg    146040
agatttctta cattaatact aaagatcaat tagccgatat cttaccaag ccacttgatg    146100
aacaatcttt taccagactt aggcatgagc tcaatattct tgattctaga aatttctttt   146160
gctagcttgc acacatagct catttgaata cccttgatca tatctctttt atatgctatg   146220
actaatgtgt tttcaagtct atttcaaacc aagtcatagg tatattggaa gggaattgga   146280
gtcttcggcg aagacaaagg cttccactcc gtaactcatc cttcgccatc actccaacca   146340
tctctctatt ctttgggggga gaatgagca tcaaagaaaa ggacttcgtc tttggtataa   146400
tcttaactca tttacttatg accaaggag aagaaattac ttcgagggct ctaatgattc    146460
cgttttggc gattcatgcc aaaaagggg agaaggagc ccaaagcaaa aggaccgcac      146520
caccaccaat ttcaaaaact tagtgttttc caagaaatat ttatcaattg gcatcctatc   146580
gtgttcaaaa gggggagaaa gtagtatttc aaaaatgata tatcaaaacc ctcttgaaca   146640
ctaagaggag gatttaattt aggggagtt ttgtttagtc aaaggaaaag catttgaaac    146700
aggggggagaa aacttcaaaa tcttgaaaat gctttgcaaa aatcttattc attcacctttt 146760
gactatttgc aaaagatctt tgaaatggac ttacaaaga atttgcaaaa acaaaacatg    146820
tggtgcaaac gtggtccaaa atgctaaata aagaaagaaa cattccatgc atatcttgta   146880
agtagttata ttggctcaat tccaagcaac ctttacactt acattatgca aactagttca   146940
attatgcact tctatatttg ctttggtttg tgttggcatc aatcaccaaa aaggggagga   147000
ttgaagggga attaggctta cacctagttc ctaaataatt ttggtggttg aattgcccaa   147060
cacaaatctt ttgactaac ttgtttgccc aagtgtatag tgtatacagg agtaaaaggt    147120
tcacactcag ccaataaaaa gaccaagttt tggattcaac aaaagagcaa aggggcaacc   147180
gaaggcaccc ctggtctggc gcaccggact gtccggtgtg ccaccggaca gtgaacagta   147240
```

```
cctgtccggt gcaccagggg actcagactc aaactcgcca ccttcgggaa tttctaaggc  147300
gactcggcta taattcaccg gactgtccgg tgtacaccgg acagtgtccg gtgcgccaag  147360
ggaggtcggc ctcaggaact cgctagcctc gggttcgcgc ggcagccgct ccgctaaaat  147420
tcaccggact gtccggtgtg caccggactg tccggtgtgc cagcggagca acggctccct  147480
gcggcgccaa cggctccctg cggtgcattt aatgcgcgcg cagcgcgcgc agacgccagg  147540
cacgcccata ccggtgcacc ggacatcaaa cagtacatgt ccggtgtgca ccggacaccc  147600
aggcgggccc acaagtcgga agcttcaacg gctagaatcc aacggcagtg atgacgtggc  147660
aggggcaccg gactgtccgg tgtgcaccgg actgtccggt gcgccatcga gcagacgcct  147720
ccagccaacg gtcaagtttg gtggttgggg ctataaatac cccaaccacc ccaccattca  147780
tagcatccaa gtttttccact tcccaactac tacaagagct aggcattcaa ttctagacac  147840
atacaaagag atcaaatcct ctccaattca tcacaaagcc ctagtgacta gtgagagtga  147900
tttgtcgtgt tcatttgagc tcttgcgctt ggattgcttc ttttctttct cacttgttct  147960
tgagatcaaa actccattgt aatcaaggca agaggcacca attgtgtggt ggcccttgcg  148020
gggaagtttt gttcccggct ttgatttgag aagagaagct cactcgatcc gtggatcgtt  148080
tgagagaggg aagggttgaa agagacccgg cctttgtggc ctcctcaacg gggagtaggt  148140
ttgcaagaac cgaacctcgg taaaacaaat ctccgtgtct cacttgctca ttcgcttggg  148200
atttgttttg cgccctctct tgcggactca ttccttatta ctaacgctaa ccccggcttg  148260
tagttgtgtt tatatttgca aatttcagtt tcgccctatt caccccctc taggcgacta  148320
tcaattggta tcggagcccg gtgcttcatt agagcctaac cgctcgaagt gatgtcggga  148380
gatcacgcca agaaggagat ggagaccggc gaaaggccca ctacaagcca cgggagcact  148440
tcatcggaag agtctcgcac caaaggagg gagaagaaga agagctcctc caacaaaggg  148500
aaggagaaga aatcttcttc tcaccacaaa gagaagaagt aaaaatcttc ttcccacaag  148560
ccgcatcgga aaggcgacaa gcacaaaagg atgaggaagt tggtctacta cgagaccgac  148620
acttcatcaa catcgacctc cgactccgat gcgccctccg tcacttctaa gcgccaagag  148680
cgcaagaagt atagtaagat ccccctacg taccctcgca tttccaaaca tacacccttta  148740
ctttccgtcc cattaggcaa accaccaact tttgatggtg aagattacgc taggtggagc  148800
gatttaatgc gatttcatct aacctcgctc cacaaaagca tatgggatgt tgttgagttt  148860
ggcgcgcagg taccatccgt aggggatgag gactatgatg aggatgaggt ggcccaaatc  148920
gagcacttca actctcaagc aacaacaata ctcctcgcct ctctaagtag agaggagtat  148980
aacaaagtac aagggttgaa gagcgccaag gagatttggg atgtactcaa aaccgcgcac  149040
gagggagacg agctcaccaa gatcaccaag cgggaaacga tcgagggga gctcggtcgg  149100
ttccggcttc acaaaggaga ggagccacaa cacatgtaca accggctcaa gactttggtg  149160
aaccaagtgc gcaacctcgg gagcaagaag tgggacgatc acgaagtggt aaatgttatt  149220
ttaagatctc tcatttttct taatcccact caagttcaat tgattcgtgg taatcctaga  149280
tatactaaaa tgaccccga ggaagttatc gggcattttg taagttttga gtgcatgata  149340
gaaggctcga ggaaaatcaa cgagcttggc gactcatccg aagcccaacc cgttgcattc  149400
aaggcaacgg aggagaagaa ggaggagtct acaccaagtc gacaaccaat agacgcctcc  149460
aagcttgaca atgaggagat ggcgctcgt attaagagct tccgccaaat cctcaaacaa  149520
aggaggggga aagactacaa gtcccgctcc aagaaggttt gctacaaatg tggtaagccc  149580
ggtcattttta ttgctaaatg tccaatatct agtgacagtg accgaggcga cgacaagaag  149640
gggagaagaa aggagaagaa gaggtattac aagaagaagg gcggcgatgc ccatgtttgt  149700
cgcaaatggg actccgacga gagctcaagc gactcctccg acgacgagga tgccgccaac  149760
atcgccgtca ccaagggact tctcttcccc aacgtcggcc acaagtgcct catggcaaag  149820
gacggcaaaa agaagaaggt taaatccaac tcctccacta aatatgaatc gtctagtgat  149880
gataatgcta gtgatgagga ggaaaatttg cgtatcctct tgccaacct taacatagct  149940
caaaaggaaa aattaaatga attagtcagt gctattcatg aaaaggatga ccttttggat  150000
tcccaagagg attgtctaat taaagaaaac aagaaacatg ttaaggttag aaaggcttat  150060
gctctagaag ttgagaaatg tgaaaaattg tctagtgagc taagcacttg ccgtgagatg  150120
attgacaacc ttagaaatga aaatgctagt ttaaatgcta aggttgattc tcatatttgt  150180
aatgtttcaa ttcccaatcc tagagataat aatgatgagt tgcttgctag gattgaagaa  150240
ttaaacattt ctcttgctag ccttagatta gagaatgaaa atttgattgc taaggctaaa  150300
gattttgatg tttgcaaagt tacaaatttcc gatcttagag ataagaatga tattcttcat  150360
gctaagatt ttgaacttaa ttccttgcaaa ccctctacat ctattgatga gcatgtatct  150420
atttgtacta gatgtagaga tgttgatgtt aatgctattc ttgatcatat ggctttaatt  150480
aaacaacaaa atgatcatat agcaaaatta gatgctaaaa ttgccgagca caacctagag  150540
aatgagaaat ttaaatttgc tcgtagcatg cttttataatg ggagacgccc tgacattaag  150600
gatggcattg gcttccaaag gggagacaat gtcaaactta atgcccctct aaaaaacttg  150660
tctaactttg ttaagggcaa ggctcccatg cctcaggata acgagggtta catttttgtac  150720
cctgccggtt atcccgagag caaaattagg aaaattcatt ctaggaagtc tcactctggc  150780
cctaatcatg ctttttatgta taagggtgag acatctagct ctaggcaacc aacccgtgcc  150840
aagttgccta gaaagaaaac tcctattgca tcaaatgatc atgctatttc atttaaaact  150900
tttgatgctt cttatgtgct tacaaacaaa tccggcaaag tagttgccaa atatgttggg  150960
ggcaagcaca aggggtcaaa gacttgtgtt tgggtaccca aagttattgt gtctaatgcc  151020
aaaggaccca aaaccatttg ggtacctaaa gtcaagaact aaatttgttt ttgtaggttt  151080
atgcatccgg gggctcaagt tggatactcg acagcgggtg cacaaaccca catgaccggg  151140
gagaaaagga tgttctcctc atatgagaaa aaccaagatc cccaacgagc tatcacattc  151200
ggggatggaa atcgaggttt ggtcaaagga ttgggtaaaa ttgctatatc acctgaccat  151260
actatttcca atgttttcct tgttgattca ttagattaca acttgcttt tgtttcccaa  151320
ttgtgtcaaa tgggctacaa ctgtctttt actgatgtag gtgtcactgt ctttagaaga  151380
agtgacgatt caatagcatt taaggggtgtg ttagagggtc agctatactt agtgagatttt  151440
gatagagctg aactcgacac atgcttaatt gccaagacta acatgggttg gctctggcac  151500
cgccgactag cccatgttgg gatgaagaat cttcataagc ttctaagggg agaacacatt  151560
ttaggattaa caaatgttca ttttgagaaa gacaggattt gtagcgcatg ccaagccggg  151620
aagcagttg gcactcatca tccacacaag aacataatga caagtgacag gccactggag  151680
ctcctccaca tggatttatt cggcccgatc gcttacataa gtatcggcgg gagtaagtac  151740
tgtctagtta ttgtggatga ttattctcgc ttcacttggg tattcttttt acaggaaaaa  151800
tctctaaccc aagagacatt aaagggattc ttgagacggg ctcaaaatga gacgaatctc  151860
agatcgtctg tatagattan nnnnnnnnnn nnnnnnnnnn nnnnnnnnnn nnnnnnnnnn  151920
nnnnnnnnnn nnnnnnnnnn nnnnnnnnnn nnnnnnnnnn nnnnnnnnnn nnnnnnnnng  151980
```

```
catcttgcaa cctcacagac cgtggcgtgc tctggtcagg cgcggacggt cccagccttg   152040
ggcggacgtc cgagccttgg gtcggacggt ccgcgacctg ggcgaggagc ggtgtcttcc   152100
ctgcgtcaca ccggacgtcc gcagctctgg gccggacgtc cgcgacctgg cgacagggtc   152160
gtcttcctac tccttgctgg aatctagatc tcgtcccctg ggggaaagat cttaaggtgc   152220
tccgggtcga caggtcaccc ggggcgtccc cagacgacgt ggagtcgcct aggaattaag   152280
agatcaaatc gaggaagaag tcttggatgg acaactagat cttgccccccc ggaggggtga   152340
gatcctaggg tcgtcttggg atcggcaggc cacccaagac ggatctagac gacgtagagt   152400
tgaatagggg tggaggtgga tatgtggaag actacaacta gaactatgct acatctactc   152460
ctagggcagg aaaagtaaat aaggtaattg gttcgattgg aatgtgttcg ggggttctca   152520
atcggccgta cccctttata tttataggg gaggaggtctg gacctttcc taagagatag   152580
ccaacaaact cccacgtgat tagatggata accacgcacg agataaggat aaacatccga   152640
gttaatctaa tctcgggaca cgcggaccgt ccgggcccat gggccggacc gtccgctcat   152700
tttggtgtcc aacatatgcc cccctgcctt ttggtggagc atggcgaacc aaaagcatta   152760
gcgaaaactt cggaaacaat tgacctcatg aggttttttt ttccgaagta aggactcagc   152820
tcgatgcaag tcatcggctc ttgcgatcag ataatataaa tacttgatgg gactttaatg   152880
cacagaggcc gtttcggatc gcatcctctt cagccatgtc tatctgatca acctgtcaat   152940
aggcaaaaac ttgtggtgcc ccccagccca aataagcaaa cggattgggc cagtaataca   153000
aattcatcgc cgtaccaccc cacacatgag taggacaaca catcggcgat ggatagaatg   153060
ggacgcacca tgctatccct ggaggaggat gataaggcga tattggttgt gctaccctt   153120
gggtccgttt agtcggcttt tgctttcgca cagatcgccc tattgacttt gtttgtttta   153180
ttggccggtt gtgtggaacg gccttcttca tatatttggc aagcaactga ccaaaagtag   153240
ggccgactct actgagtcgt ccagacgtct tagtagtgtt ttgtttccta acacttgtgt   153300
tggaacgttg tggtccgatg gtctgaggtt gctgcttctg accatctgcg gaccgtccgg   153360
ccatcatagc cggactgtcc gcgcctgtct cggactgttc ggccttagta cccggatcgt   153420
ccggcgtacg catgacaggc gaccgtgatc gggtgtccga tcgtgcttgc ccccggtgc   153480
ctccggtctt tcttttgtcc ggagccttca gagtaaccat tctgcgtgac atattggtg   153540
tgcgaggatc accaatgacg atattttat ttttactttt atcggccgca caaggccgaa   153600
ttatggcctt tttgctcatg ggctctaatg tggtgacagg aacaggtggc ctgtcaattt   153660
tcacctcttt ttgaaacctc aaccggcctt cgtttatagc cgattgtatt tgccgacgga   153720
agacggcaca atcattggtg ttatggagaa aggagccatg ccatttgcaa taaacacgcc   153780
ctttttaattg ttcaaccgga ggaattacat gtgacaattt aatattacca tgtttaagca   153840
actcatcaaa tattttatca catttagtaa tattaaatgt gaacttaacc ttttcctttt   153900
gtttcgagtg cgggtaagag cgaacagaag gtttggcctt agtgggccaa acaagctcag   153960
ggacatgtga cttttttagt tcttgggct tgggtggccg attatattta tgtcggcctt   154020
ccgcactagg tggatcacag gtgacttctg gtgccccgaa cggtccgact tgcacagtcg   154080
gacggtctgc gggtggatcg gacggtccgg tactatcctc ggacagtccg gtcacgtcag   154140
gcaacacctg tgacccttgt ggtgggctct gtgtaactcc agactgtccg gcgtagggtg   154200
ccggacggtc cgacagaggg ccggacggtc cgcaattgtg tgcggacggt ccggctgtgc   154260
ccaggggtga ctcacccttt agcaaagatg gtgatgacgg tcgtcctaga tatgagtcca   154320
tcggcatacc agaatatggc tgggaaacc catttgccgc cgatgtgttt ggcgcaattg   154380
tttcatcgcc taatttatgt gataaaaaat taggcatgtg agtttttcct aatgcatgtg   154440
tcatcctctc tatatcctcc gtgatacttt taatccgatt atcaaaagaa attttaatag   154500
atggaatatc atcggctgac ctggcatcac ctattgtggg agctgttgc agcacggcta   154560
acatatactc ggcgtttatc tccctctctt ggacggtctt ctggtggcag tctaccttga   154620
agtgcgagag gtaccacttg tccgccacct tgagcacctg atccttttgt cggtgggcct   154680
cctcgtctat tttcttcatg tcatcttcta attttttatg ctcagcggcc gataaattag   154740
tcagccttgt gttgctgttt ggagaagcac tgttgagatc tttagaatcg gccatgtaag   154800
cctgattttg tagatctgca acttcttccc cagcggagtc gccaaaaagt atgttgacgc   154860
cttttttggag cgccaaacac tcaacaagaa ccgtggcggt gccctctggt caggcgcgga   154920
cggtccgcag ccttgggccg gacggtccgc agccttgggc cggacggtcc gcgacctggg   154980
cgcaggacgg gtgtcttccc tgcgtcacac cggacggtcc gcagctctgg gccggacgtc   155040
ccgcgacctg gcgacagggt cgtcttccta ctccttgctg gaatctagat ctcgtcccct   155100
gggggggaaag atcttaaggt gctccgggtc gacaggtcac ccggggcgtc cccagacgac   155160
gtggagtcgc ctaggaatta agagatcaaa tcgaggaaga agtcttggat ggacaactag   155220
atcttgcccc ccggaggggg tgagatcctta gggtcgtctt gggatcggcag ggccacccaa   155280
gacggatcta gacgacgtag agttgaatag gggtggaggt ggatatgtgg aagactacaa   155340
ctagaactat gctacatcta ctcctagggc aggaaaagta aataaggtaa ttggttcgat   155400
tggaatgtgt tcggggggttc tcaatcggcc gtacccctttt atatttatag gggaggaggt   155460
ctgaccttt tcctaagaga tagccaacaa actcccacgt gattagatgg ataaccacgc   155520
acgagataaa gaaaaacccc cnnnnnnnnn nnnnnnnnnn nnnnnnnnnn nnnnnnnnnn   155580
nnnnnnnnnn nnnnnnnnnn nnnnnnnnnn nnnnnnnnnn nnnnnnnnnn nnnnnnnnnn   155640
ngaattccaa gatttaaata gaagtctttt ataatgagag attaaataaa agaccctcat   155700
ataatttaaa ccaacccttg ttgaataaca tgattagaga tattctccaa aagaattaag   155760
cttaaaaaac cttaataaat actatacaca caaaaaaatc ctctatctta aaaattatga   155820
acataatttt aaatggacta tacattcaaa gaagtaattt ttactctatg tgtgtgcatt   155880
gcatacttaa aatatttgga taaaaataaac aaaactaaac agatatatgt aattattgca   155940
tatcatgccg gagttttgga ttgagcattt agattagagt ttaaaataag ggaaagaaat   156000
atgaaaggga agataaaaca gaaaatcatt aaagaataaa gaaaaagggg aagctttcgg   156060
gcgtatgggc cggatctctg gcttctcggc ccagtttctt tccttcgtta gcgggcccaa   156120
ctctatttcc ctgctccggc gcagcccgct cctgccacct ctcgcgcctg cagccgcgtc   156180
tggcatgtgg gccatggccg tcaagtctat cctcccatg gcgatcctgc tcgtccgctg   156240
caagctcgcc tcctgtaaac tgtgcaacga ccttcgtgcc atggtgcacc cgcccactgc   156300
tagccgtacc cctggccata taacgggac gctccaacct cggccatggg tgcagctcta   156360
gtttcctctc cttcagcatc gtgggctacg ctcggctcgc cgatcgggag agaaggcgcc   156420
atcaccatcg tcgtaaggga gaaggagaac acagggggtg aattgccacc gacgggggtt   156480
cccgggcacg ccggtattgc ggtctcgcg tcgggttggg tcatccgtgg gacgcgtgca   156540
ggattctaga aggcacctcg tgcgagaaca acgaccagtg catgcttcgc tggtgacccg   156600
cggcgccacg gagcaactgc gtggtggggt caacacttga aacaccgtga tccttggtaa   156660
gaacagccct agcatacttg gagcctcctc ctctccgtga ttcacgtacc cacgctcgat   156720
```

```
actaggaaat ggggagccgg gcgggatatc actggtggtg tggtgggggca tggccgcggc  156780
gtgcccgcac cagtgctctg ctttccgtcg tgaggtggaa ggaaatgcag cagccgttag  156840
atcatgggtg agcgatcacg atcagggcat ggctgggcct cgcgtgaacc gtggatctgg  156900
gaggtatcgg ctgtgattag atcacacgta acgtttcatc cgaatcgatc cgggtcgtct  156960
gatctggatc ttgcatatga ggatcgatct ctattatttt aagcgtgtgc gtttatcgt   157020
agatccgacg atctaggatg cgtaccggtt cggcgggcaa atcttctact ctgggcgctt  157080
ggctgatgat ccaaggaatt agtcacgtgt accccttcac cgtgactaac ttataaaaga  157140
gaccccagac ttcttgcaaa tcagcccgca gtccgggtat aggtagaaat cattgcggat  157200
aagtcctaaa tattatatgg agcccccctga tcttttatgg aatagtgtcc ccaatccaga  157260
aatatttaat aattatagaa ttaaatccta aaacttaata aatacatatc tctttcattt  157320
taactctgat ttaatgtatt catgttgcgt tagcttcgta ataattttgc ctacgcttct  157380
gtaaaattat tttagcaaat agcatgtttc caaaaaataa atattcattt aatatatgct  157440
tagtagatta ttcctactaa tcaaagttag tttgtctatg attataaggt aactaaaata  157500
ttatgtctac tctagtatga tgtagattaa agttatttct ttaatatctt tatcacataa  157560
ttttataaaat caacataaag acctagtctc atatttaatc acataggtct tccgaaaacc  157620
acatcttgtt aaccgtaact ccgaatttag tggttctcga acctaggatc tcgttgtggt  157680
gcgtagatca ttattatgca gttttgttctt tatgtttggt gtgatgttaa ttttgcctat  157740
accatgtttg tttgtattgc tatgattagc agcgaggtta cgagaatctt gaagaccaag  157800
ctggtaccta ggaatcttga gtctcagcca agttgtgccc ttgatcactt ttctttacct  157860
aataatgttc ctattaatca ctgtgacatg ctcaggttaa tttgatggga cccaataggt  157920
tttcctagta ttgtttatcc cctaccttgc aaacaaaagc actattgggt agtattgcta  157980
ttgctctacc tggttttggg aaattaatgt tacattatga tcatgttaca attcttttgt  158040
tattttaatt attgttcatg ataagattgc tatgttaatt ggaacatgga gcaaccaccc  158100
aggaaaacag tgctaccaca agggtggtat gggacgccct tggctgacta attaagaaag  158160
ctagtggaag actaccttac ccgaaagggg caagggcggt agaggagcat gcgtataggg  158220
aggttctcga gtcgatcata ctgcgatggc tttttggacg agggattcct atatttttcct 158280
tcttagaaac cgtagcgggt tttcggaagc tagtggaagt ttgtaaaggc ctcgtagtgg  158340
taacctacct tgtcttctcg gtagagatga atgagaagtc gcgatccctt ggcaaatagg  158400
taacatgact tgtgggtaaa gatgtgcaac ctgtgcagac tgtaaaactg ttatatcagc  158460
cgtgctcacg gtcatgagca gctcggaccc tcacatgagt aaattatgga actaaactta  158520
aattgtcata tgcattgcat tgtgggtgtt gttattaatt taatctctta tttatttggg  158580
tcggtatcta cttatactta gtaactgcta ataaaatttt gaccaacttt aaaagtcatg  158640
ctcatcttta cccatctcct ttggtaagcc ttacacttca catgagctcc caccctttggt 158700
gagttcatac acattattcc ccacaacttg ttgagcgatg aacgtatgtg agctcaccct  158760
tgctgtactc aaatccccct ggtcaagaac aggtaccgca agatgaggag catgaaggat  158820
gtcgcgatga gttcatgaga ggtctaggcc gtcgtctcac agtaaacttt gggttgatgg  158880
atcgtcgtca tcgtatgatg taattatttta gttatttttgt gcagaacttc tattatatag  158940
taaagatgtg acatttgttt ctataccatg agtcatcata tgtgtgagac tcgatcccag  159000
cacttggtga atttcgcgcc tgggttttgg accccctaaaa cccgggtgtg acatgctgct  159060
gttgagggaa ctgcctctgg aattgctact ggtgcgaaca ttggttctgg tgttggtatc  159120
cctgagggtg gatctacttg aactgctagg gtggattgcc agaaacggga gacgactgct  159180
gctcctggcc tagggtccac caatcttgcg cttttggtct tccatctcct ggcgcttcct  159240
ctcagtcatt attgccctat caatcagatg ttggaaggta gggaatgtgt ggttcatcaa  159300
ctagtagtgc aggggtcaac caaccctctc ggaaacctgt agtacctctt agcatcaatg  159360
ttgacatcct cgggtgcatt gtgagatagt tgcaggaatt tgtccatgta ctcactgaca  159420
gacagggggcc cttgcttcag tgccagaaat tcttccttcc tcactatcat caaaccttgt  159480
agaacgtggt accccgcagnn nnnnnnnnnn nnnnnnnnnn nnnnnnnnnn nnnnnnnnnn  159540
nnnnnnnnnn nnnnnnnnnn nnnnnnnnnn nnnnnnnnnn nnnnnnnnnn nnnnnnnncg  159600
cgcggaggcc ggtttgtcgg tgccggtttc tttcacgcaa cacgcccgct cctttttgcc  159660
tcggtgggtc ggcctgtcag cgcagaaccg ctcgttcgcg tattcaccct cgctggcaag  159720
cggacccccac ctgtcagcca cctcccctt ccctaaccac ccgctcgcgc accccgccgg  159780
ggatgcacac atgtcgcgtg ttttttcggcc actcccccca cgcgcctgac ttttttggag  159840
cccacactca ctcgctcact cccctcgctc agtagcgtcc cacagccgac cccctcgcac  159900
ctctctctcg caccgagcgc acagccgtgg agcactgccg tagtccaccg tccgttccgt  159960
ggccgtcgtc gagttcctgt cgcgtccatt gccctactga tcttcgcctc ctcgccagca  160020
acacgagaca ccctctgtt ttccccagcc cctctatttc ccttggttcg ctcaccggac  160080
ctatcaccat gcagccgagt ctccgccacc gtccaccagg gccctcgcgg tgtcctcgcc  160140
gttgctcaag cgctctagag tcatctctcg acgtaaccaa cccacccatg cccttaattt  160200
cccatttact gccctgttgt ccatgcaatc gctcgccaga gttaagctgc gccgccgtgg  160260
ggctgctttg cctcggaccg tgctctctgg tgcctctacg ccggttcgt gcccatgcct  160320
gagcccgccg tgtcaccctg agctcgcctg agccttttcc cagcgcccag accctcacca  160380
tggccgcgcc acgccgcgaa attgggcggc ggcgccatga gcagcctagc aaccccgccc  160440
gagcttgcca tcagatttca ggcatccatc tgagatctaa cgacctggct tcaattaaac  160500
tcgatctgat cccagctgtc cgatgggagat ctggccaatg cgatccgcca cctcaccgg   160560
gccctgcagc taggccccggc cagacagtcc gcctcgcccc taggtcgctg actatcctgg  160620
cccacctgtt agctcgtgct cgtgctgcg ctcaaatcta atcctggccg ttgatctgtg   160680
atcatgcagt cgagatcagc tgataccct ttgcgtggta gttttgttaa aaaggccctc    160740
ggcttttctga gaatcaaccc catcgtccctg gtttcgcac gcatgccct gtactttgc    160800
agaaggccc ctaatctttt caggttatcac ataattagac ctagttttgt atttttgaatt  160860
ccaaaacttg tttatttcat atcttttgca tatgaactcc aaattgagtg attcaaattg  160920
caaaatgttt gtaaggttat tctctacctg tttaaattat aaccttttac tgtctgcatg  160980
tgctaatttt atgcctagac tataggttag tgtaactgat ggcttattta ttaataagaa  161040
ggataaaagg aaaccataa tggtagttag atgtttaact ttgtgggtta ataatatgta   161100
atatatgaac ctatccctgg tataattctt ttgtctcatt aagtaaaatg aaattaagtt   161160
atgtaatcta ttgagataag taatacttag agaaccacaa acctatatgt gtattggtcc  161220
accctagacc ctaggcttcg cttgagtttg ttactttctt ttgaattagt gttcacttga   161280
ttgtatattt ttggtgtatt gttcttcttat cattatcgaa atgtgttgaa tgcatgatcg  161340
cttttgcgtag acaacaagca gtctatggtt cctgagtgtg ttgccgaaga tcttcctggg  161400
caacaaccctg gtgaaggcaa gtgtcctctg acctattatg tcctacttac ttcataattc  161460
```

-continued

```
actgtccccc tttacttaat tgaaacctaa ggtttgacta gtctgtattt atcttgtcct   161520
tgtttacctt ttgggttatt atggtaagct tcaagctatt gctccacttt aatcaacaaa   161580
catgatgcga atatttatga tatgatgttg ttattatgat tacgatgatg ttcttatggc   161640
actttaggag actcaggcta ttttcctgag tacctttcct ttggacctgc tcgttgagtg   161700
accacccgtg ataacagaac gaatcaagct gattcatcag cggccggg                161748

SEQ ID NO: 111            moltype = DNA   length = 1348
FEATURE                   Location/Qualifiers
source                    1..1348
                          mol_type = genomic DNA
                          organism = Zea mays
SEQUENCE: 111
tacaagaata ttgagacgtg agtacatagc attggcattt tcattagcaa gcatttcaaa     60
agaatttaat tttctcatag caatgtgata tctctcctca cgctcaattc tagttccttc    120
atgtagagca catatgtcca tccacaaatc atgacaattt ttatggtttc taactctatt    180
aaacacatct ttgcaaaggc ctctaaaaag ggtgtttttg gccttagcat tccatttctc    240
atagttcaac tcttcaccta caagatttgt gggatctcta ggttcgggga atctttgtgt    300
ggcggctttg tagacaccaa tgtctatagc ctctaaatat gcttccatac gaattttcca    360
atatggaaaa tcgtcaccat aaaaaacggg agaaggtcca tccccaccgg acatcgttac    420
tctagccggtt aagctaatct aagagcaaca aggctcttat accaattgaa aggatcacga    480
tgcccaagag ggggggttga attgggcttt tctaaaaatc aacactaact aaaatctaag    540
caagagccca acttcacccc gacaactagc actaagagaa taatactaga aatacaacaa    600
tgctaagata atacttcaaa tacttgctaa acaaatacac aatgtaaaat acttgaatta    660
agtgcggaat gtaaagcaag gtttagaaga ctcctccaat ttttctagag gtatcaaaga    720
gtcggcactc tcccctagtc ctcgttggag cacctgcgta agggtatcgc tctcccttgg    780
tcatcgcaag aaccaagtgc tcacaacgag atgatccttt gccactccgg cgcggtggat    840
ccctcacgac cgcttacaaa cttgagtcgg gtcaccaaca agatctccac ggtgatcacc    900
gagctcccaa cgccaccaag ccgtctaggt gatgccgatc accaagagta ataagccata    960
gactttcact tgaccaagag aagcctaatg catgcggtgt gtgctctagg tggctctcgc   1020
tagcgttaat gaggtccaaa tgcgggatta agattctcaa gtcacctcac taggcttttgt  1080
ggtgcttgca atgctctacc aatgtgtagg agtaaatgtg ggcagcaaga ccatcaatat   1140
ggtaggtgga tggggtataa atagccctca cccaccaact agccattacc aggaatctgc   1200
tgcgcatggg cgcaccggac agtccggtgt gccaccggtg cgccaacggt cgactcaaac   1260
ggctagttct gacagctagc cgttggacag atggcatacc ggacagtccg atacgctgtc   1320
cggtgtgcct ctaaaattca actcacga                                      1348
```

CORN EVENT 5307

RELATED APPLICATION INFORMATION

This application is a continuation of U.S. patent application Ser. No. 16/988,681 filed Aug. 9, 2020, (now abandoned), which is a divisional of U.S. patent application Ser. No. 16/126,171 filed Sep. 10, 2018 (now U.S. Pat. No. 10,844,400 B2) which is a divisional of Ser. No. 14/815,345 filed Jul. 31, 2015 (now U.S. Pat. No. 10,100,371 B2), which is a divisional of U.S. patent application Ser. No. 13/140,429 (now U.S. Pat. No. 9,133,474 B2), which is a national stage filing under 35 U.S.C. § 371 of International Application No. PCT/US2009/067873, filed Dec. 14, 2009 and published Jul. 8, 2010 as WO 2010/077816, which claims the benefit of U.S. Provisional Application Ser. No. 61/122,885, filed Dec. 16, 2008, the contents of each of which are incorporated herein by reference in their entireties.

STATEMENT REGARDING ELECTRONIC SUBMISSION OF A SEQUENCE LISTING

A sequence listing in XML format, submitted under 37 C.F.R. § 1.831 (a), entitled "71922 Sequence Listing.xml", 471 KB in size, generated on Feb. 24, 2023, and filed via EFS-Web is provided in lieu of a paper copy. This sequence listing is hereby incorporated by reference into the specification for its disclosures.

FIELD OF THE INVENTION

The invention relates generally to the field of plant molecular biology, plant transformation, and plant breeding. More specifically, the invention relates to insect resistant transgenic corn plants comprising a novel transgenic genotype and to methods of detecting the presence of the corn plant DNA in a sample and compositions thereof.

BACKGROUND

Plant pests are a major factor in the loss of the world's important agricultural crops. About $8 billion are lost every year in the U.S. alone due to infestations of non-mammalian pests including insects. Species of corn rootworm are considered the most destructive corn pests. Important rootworm pest species include *Diabrotica virgifera virgifera*, the western corn rootworm; *D. longicornis barberi*, the northern corn rootworm, *D. undecimpunctata howardi*, the southern corn rootworm, and *D. virgifera zeae*, the Mexican corn rootworm.

Corn rootworm is mainly controlled by intensive applications of chemical pesticides. Good corn rootworm control can thus be reached, but these chemicals can sometimes also affect beneficial organisms. Another problem resulting from the wide use of chemical pesticides is the appearance of resistant insect varieties. This has been partially alleviated by various resistance management practices, but there is an increasing need for alternative pest control strategies. One such alternative includes the expression of foreign genes encoding insecticidal proteins in transgenic plants. This approach has provided an efficient means of protection against selected insect pests, and transgenic plants expressing insecticidal toxins have been commercialized, allowing farmers to reduce applications of chemical insecticides.

The expression of foreign genes in plants can to be influenced by their chromosomal position, perhaps due to chromatin structure or the proximity of transcriptional regulation elements close to the integration site (See for example, Weising et al., 1988, "Foreign Genes in Plants," Ann. Rev. Genet. 22:421-477). Therefore, it is common to produce hundreds of different events and screen those events for a single event that has desired transgene expression levels and patterns for commercial purposes. An event that has desired levels or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

It would be advantageous to be able to detect the presence of a particular event in order to determine whether progeny of a sexual cross contain a transgene of interest. In addition, a method for detecting a particular event would be helpful for complying with regulations requiring the pre-market approval and labeling of foods derived from recombinant crop plants, for example. It is possible to detect the presence of a transgene by any well-known nucleic acid detection method including but not limited to thermal amplification (polymerase chain reaction (PCR)) using polynucleotide primers or DNA hybridization using nucleic acid probes. Typically, for the sake of simplicity and uniformity of reagents and methodologies for use in detecting a particular DNA construct that has been used for transforming various plant varieties, these detection methods generally focus on frequently used genetic elements, for example, promoters, terminators, and marker genes, because for many DNA constructs, the coding sequence region is interchangeable. As a result, such methods may not be useful for discriminating between constructs that differ only with reference to the coding sequence. In addition, such methods may not be useful for discriminating between different events, particularly those produced using the same DNA construct unless the sequence of chromosomal DNA adjacent to the inserted heterologous DNA ("flanking DNA") is known.

The invention includes an insect resistant transgenic corn event that has incorporated into its genome a FR8a gene, disclosed in International Publication No. WO 08/121633, published Oct. 9, 2008, which is herein incorporated by reference, encoding a FR8a insecticidal toxin, useful in controlling *Diabrotica* spp. insect pests. The transgenic corn event also has incorporated in its genome a PMI gene, encoding a phosphomannose isomerase enzyme (PMI), disclosed in U.S. Pat. No. 5,767,378, which is herein incorporated by reference, useful as a selectable marker, which allows the plant to utilize mannose as a carbon source. The invention further includes novel isolated nucleic acid sequences which are unique to the transgenic corn event, useful for identifying the transgenic corn event and for detecting nucleic acids from the transgenic corn event in a biological sample, as well as kits comprising the reagents necessary for use in detecting these nucleic acids in a biological sample.

SUMMARY

The invention is drawn to a transgenic corn event, designated 5307, comprising a novel transgenic genotype that comprises a FR8a gene and a PMI gene which confers insect resistance and the ability to utilize mannose as a carbon source, respectively, to the 5307 corn event and progeny thereof. The invention also provides transgenic corn plants comprising the genotype of the invention, seed from transgenic corn plants comprising the genotype of the invention, and to methods for producing a transgenic corn plant comprising the genotype of the invention by crossing a corn inbred comprising the genotype of the invention with itself or another corn line of a different genotype. The transgenic corn plants of the invention may have essentially all of the morphological and physiological characteristics of the corresponding isogenic non-transgenic corn plant in addition to those conferred upon the corn plant by the novel genotype of the invention. The invention also provides compositions and methods for detecting the presence of nucleic acids from event 5307 based on the DNA sequence of the recombinant expression cassettes inserted into the corn genome that resulted in the 5307 event and of genomic sequences flanking the insertion site. The 5307 event can be further characterized by analyzing expression levels of FR8a and PMI proteins as well as by testing efficacy against corn rootworm.

According to one aspect, the invention provides a preferably isolated nucleic acid molecule comprising at least 10 contiguous nucleotides of a heterologous DNA sequence inserted into the corn plant genome of corn event 5307 and at least 10 contiguous nucleotides of a corn plant genome DNA flanking the point of insertion of a heterologous DNA sequence inserted into the corn plant genome of corn event 5307. The preferably isolated nucleic acid molecule according to this aspect may comprise at least 20 or at least 50 contiguous nucleotides of a heterologous DNA sequence inserted into the corn plant genome of corn event 5307 and at least 20 or at least 50 contiguous nucleotides of a corn plant genome DNA flanking the point of insertion of a heterologous DNA sequence inserted into the corn plant genome of corn event 5307.

According to another aspect, the invention provides a preferably isolated nucleic acid molecule comprising at least one junction sequence of event 5307 selected from the group consisting of SEQ ID NO: 1 and SEQ ID NO: 2, and complements thereof. A junction sequence spans the junction between the heterologous DNA comprising the expression cassettes inserted into the corn genome and DNA from the corn genome flanking the insertion site and is diagnostic for the 5307 event.

According to another aspect, the invention provides a preferably isolated nucleic acid linking a heterologous DNA molecule to the corn plant genome in corn event 5307 comprising a sequence of from about 11 to about 20 contiguous nucleotides selected from the group consisting of SEQ ID NO: 1, SEQ ID NO: 2, and complements thereof.

According to another aspect, the invention provides a preferably isolated nucleic acid molecule comprising a nucleotide sequence selected from the group consisting of SEQ ID NO: 1, SEQ ID NO: 2, SEQ ID NO: 3, SEQ ID NO: 4, and complements thereof.

According to another aspect of the invention, an amplicon comprising a nucleic acid molecule of the invention is provided.

According to still another aspect of the invention, flanking sequence primers for detecting event 5307 are provided. Such flanking sequence primers comprise a preferably isolated nucleic acid sequence comprising at least 10-15 contiguous nucleotides from nucleotides 1-1348 as set forth in SEQ ID NO: 5 (arbitrarily designated herein as the 5' flanking sequence), or the complements thereof, also disclosed as SEQ ID NO: 111. In one embodiment of this aspect the flanking sequence primers are selected from the group consisting of SEQ ID NO: 9 through SEQ ID NO: 14, and complements thereof.

In another aspect of the invention, the flanking sequences primers comprise a preferably isolated nucleic acid sequence comprising at least 10-15 contiguous nucleotides from nucleotides 1-1093 as set forth in SEQ ID NO: 6 (arbitrarily designated herein as the 3' flanking sequence), or the complements thereof. In one embodiment of this aspect the flanking sequence primers are selected from the group consisting of SEQ ID NO: 69 through SEQ ID NO: 72, and complements thereof.

According to another aspect of the invention, primer pairs that are useful for nucleic acid amplification, for example, are provided. Such primer pairs comprise a first primer comprising a nucleotide sequence of at least 10-15 contiguous nucleotides in length which is or is complementary to one of the above-described genomic flanking sequences (SEQ ID NO: 5, or SEQ ID NO: 6) and a second primer comprising a nucleotide sequence of at least 10-15 contiguous nucleotides of heterologous DNA inserted into the event 5307 genome. The second primer preferably comprises a nucleotide sequence which is or is complementary to the insert sequence adjacent to the plant genomic flanking DNA sequence as set forth in SEQ ID NO: 7. In one embodiment of this aspect the insert sequence primers are selected from the group consisting of SEQ ID NO: 15 through SEQ ID NO: 68, and complements thereof.

According to another aspect of the invention, methods of detecting the presence of DNA corresponding to event 5307 in a biological sample are provided. Such methods comprise: (a) contacting the sample comprising DNA with a pair of primers that, when used in a nucleic acid amplification reaction with genomic DNA from corn event 5307; produces an amplicon that is diagnostic for corn event 5307; (b) performing a nucleic acid amplification reaction, thereby producing the amplicon; and (c) detecting the amplicon. In one embodiment of this aspect, the amplicon comprises a nucleotide sequence selected from the group consisting of SEQ ID NO: 1, SEQ ID NO: 2, SEQ ID NO: 3, SEQ ID NO: 4, SEQ ID NO: 5, SEQ ID NO: 6, and complements thereof.

According to another aspect, the invention provides methods of detecting the presence of a DNA corresponding to the 5307 event in a biological sample. Such methods comprise: (a) contacting the sample comprising DNA with a probe that hybridizes under high stringency conditions with genomic DNA from corn event 5307 and does not hybridize under high stringency conditions with DNA of a control corn plant; (b) subjecting the sample and probe to high stringency hybridization conditions; and (c) detecting hybridization of the probe to the DNA. The detected hybridized DNA sequence includes at least one polynucleotide sequence comprising SEQ ID NO: 1, SEQ ID NO: 2, SEQ ID NO: 3, SEQ ID NO: 4, SEQ ID NO: 5, SEQ ID NO: 6, and complements thereof.

According to another aspect of the invention, a kit is provided for the detection of event 5307 nucleic acids in a biological sample. The kit includes at least one DNA sequence comprising a sufficient length of polynucleotides which is or is complementary to SEQ ID NO: 1, SEQ ID NO: 2, SEQ ID NO: 3, SEQ ID NO: 4, SEQ ID NO: 5 or SEQ ID NO: 6, wherein the DNA sequences are useful as primers or probes that hybridize to isolated DNA from event 5307, and which, upon amplification of or hybridization to a nucleic acid sequence in a sample followed by detection of the amplicon or hybridization to the target sequence, are diagnostic for the presence of nucleic acid sequences from event 5307 in the sample. The kit further includes other materials necessary to enable nucleic acid hybridization or amplification methods.

In another aspect, the invention provides a method of detecting corn event 5307 protein in a biological sample comprising: (a) extracting protein from a sample of corn event 5307 tissue; (b) assaying the extracted protein using an immunological method comprising antibody specific for the insecticidal or selectable marker protein produced by the 5307 event; and (c) detecting the binding of said antibody to the insecticidal or selectable marker protein.

In another aspect, the invention provides a biological sample derived from a event 5307 corn plant, tissue, or seed, wherein the sample comprises a nucleic acid comprising a nucleotide sequence which is or is complementary to a sequence selected from the group consisting of SEQ ID NO: 1 and SEQ ID NO: 2, and wherein the sequence is detectable in the sample using a nucleic acid amplification or nucleic acid hybridization method. In one embodiment of this aspect, the sample is selected from the group consisting of corn flour, corn meal, corn syrup, corn oil, cornstarch, and cereals manufactured in whole or in part to contain corn by-products.

In another aspect, the invention provides an extract derived from a event 5307 corn plant, tissue, or seed comprising a nucleotide sequence which is or is complementary to a nucleotide sequence selected from the group consisting of SEQ ID NO: 1 and SEQ ID NO: 2. In one embodiment of this aspect, the sequence is detectable in the extract using a nucleic acid amplification or nucleic acid hybridization method. In another embodiment of this aspect, the sample is selected from the group consisting of corn flour, corn meal, corn syrup, corn oil, cornstarch, and cereals manufactured in whole or in part to contain corn by-products.

According to another aspect of the invention, corn plants and seeds comprising the nucleic acid molecules of the invention are provided. In one embodiment of the invention, a deposit of event 5307 corn seed was made to the American Type Culture Collection (ATCC) in accordance with the Budapest Treaty on 15 Oct. 2008. An example of said seed being deposited as ATCC Accession No: PTA-9561.

According to another aspect, the invention provides a method for producing a corn plant resistant to at least corn rootworm infestation comprising: (a) sexually crossing a first parent corn plant with a second parent corn plant, wherein first or second parent corn plant comprises corn event 5307 DNA, thereby producing a plurality of first generation progeny plants; (b) selecting a first generation progeny plant that is resistant to at least corn rootworm infestation; (c) selfing the first generation progeny plant, thereby producing a plurality of second generation progeny plants; (d) selecting from the second generation progeny plants, a plant that is at least resistant to corn rootworm infestation; wherein the second generation progeny plants comprise a nucleotide sequence selected from the group consisting of SEQ ID NO: 1, SEQ ID NO: 2, SEQ ID NO: 3 and SEQ ID NO: 4.

According to yet another aspect, the invention provides a method for producing corn seed comprising crossing a first parent corn plant with a second parent corn plant and harvesting the resultant first generation corn seed, wherein the first or second parent corn plant is an inbred corn plant of the invention.

According to another aspect, the invention provides a method of producing hybrid corn seeds comprising the steps of: (a) planting seeds of a first inbred corn line according to the invention and seeds of a second inbred corn line having a different genotype; (b) cultivating corn plants resulting from said planting until time of flowering; (c) emasculating flowers of corn plants of one of the corn inbred lines; (d) allowing pollination of the other inbred line to occur, and (e) harvesting the hybrid seed produced thereby.

According to another aspect of the invention, the invention provides a method of selecting corn plants and seeds comprising the nucleic acid molecules of event 5307 on chromosome 5. In one embodiment of the invention, polymorphic markers are used to select or track the sequences specific to the 5307 corn event. The invention provides a method of selecting sequences specific to the 5307 corn event comprising the steps of: (a) detecting a polymorphic marker sequence; (b) designing an assay for the purposes of detecting the marker; (c) running the assay on corn nucleic acid sequences from many corn lines, and (d) selecting corn lines based upon the sequences with nucleotides specific to corn event 5307.

According to another aspect of the invention, the invention provides a site on chromosome 5 for targeted integration of a heterologous nucleic acid. The invention provides a method of selecting sequences specific to the 5307 corn event for targeted integration comprising the steps of: (a) designing homologous sequences based on the insertion site or vector sequence; (b) using these homologous sequences at a target locus; (c) using zinc finger nucleases to create a break in the target locus, and (d) inserting a heterologous donor molecule within nucleotides specific to corn event 5307 or the vector sequence of pSYN12274. An example of this technique is demonstrated in Shukla et al. (Nature vol. 459, 21 May 2009).

The foregoing and other aspects of the invention will become more apparent from the following detailed description.

DESCRIPTION OF THE SEQUENCES IN THE SEQUENCE LISTING

SEQ ID NO: 1 is the 5' genome-insert junction.
SEQ ID NO: 2 is the 3' insert-genome junction.
SEQ ID NO: 3 is the 5' genome+insert sequence.
SEQ ID NO: 4 is the 3' insert+genome sequence.
SEQ ID NO: 5 is the 5' genome+insert sequence.
SEQ ID NO: 6 is the 3' corn genome flanking sequence.
SEQ ID NO: 7 is the event 5307 full length insert.
SEQ ID Nos: 8-14 are 5' flanking sequence primers useful in the invention.
SEQ ID Nos: 15-68 are 5307 transgene insert primers useful in the invention.
SEQ ID Nos: 69-72 are 3' flanking sequence primers useful in the invention.
SEQ ID Nos: 73-75 are FR8a TAQMAN primers and probe.
SEQ ID Nos: 76-78 are PMI TAQMAN primers and probe.
SEQ ID Nos: 79-81 are ZmAdh TAQMAN primers and probe.
SEQ ID Nos: 82-90 are 5307 event specific primers and probes useful in the invention.
SEQ ID Nos: 91-102 are corn genomic primers and probes useful in the invention.
SEQ ID NO: 103 is the AC202955 Chromosome 5 Sequence, where N is any base "A", "T", "G" or "C".
SEQ ID NO: 104 is the umc 1475 marker region.
SEQ ID Nos: 105-106 are umc1475 primers.
SEQ ID NO: 107 is the uaz 190 marker region.
SEQ ID NOs: 108-109 are uaz 190 primers
SEQ ID NO: 110 is the reverse complement of SEQ ID NO: 103, AC202955 Chromosome 5 Sequence, where N is any base "A", "T", "G" or "C".
SEQ ID NO: 111 is the 5' corn genome flanking sequence.

DEFINITIONS

Figure 1:
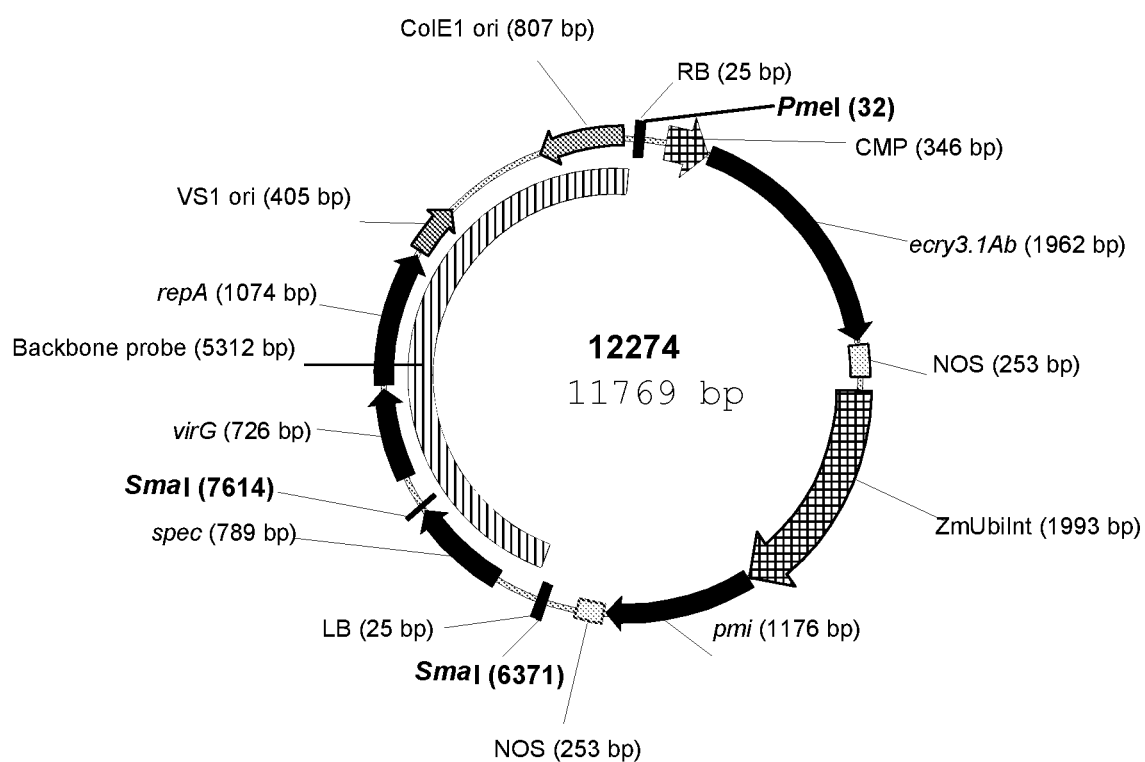
FIG. 1 illustrates a plant expression vector designated pSYN12274. The plasmid map identifies the SmaI and PmeI restriction sites used for Southern analysis.
Figure 2:
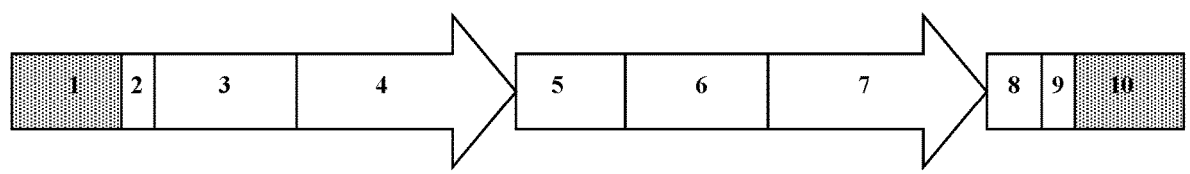
FIG. 2 is a graphical map illustrating the organization of the elements comprising the heterologous nucleic acid sequences inserted into the genome of corn to create event 5307 and sets forth the relative positions at which the inserted nucleic acid sequences are linked to corn genomic DNA sequences which flank the ends of the inserted heterologous DNA sequences. 1=5'flanking plant genome (SEQ ID NO: 5); 2=right border region; 3=CMP promoter; 4=FR8a gene; 5=NOS terminator; 6=ZmUbINT promoter; 7=PMI gene; 8=NOS terminator; 9=left border region (sections 2 through 9 are contained within SEQ ID NO: 7); and 10=3' flanking plant genome (SEQ ID NO: 6).

The following definitions and methods are provided to better define the invention and to guide those of ordinary skill in the art in the practice of the invention. Unless otherwise noted, terms used herein are to be understood according to conventional usage by those of ordinary skill in the relevant art. Definitions of common terms in molecular biology may also be found in Rieger et al., Glossary of Genetics: Classical and Molecular, 5$^{th}$ edition, Springer-Verlag: New York, 1994.

As used herein, the term "amplified" means the construction of multiple copies of a nucleic acid molecule or multiple copies complementary to the nucleic acid molecule using at least one of the nucleic acid molecules as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., Diagnostic Molecular Microbiology: Principles and Applications, D. H. Persing et al., Ed., American Society for Microbiology, Washington, D.C. (1993). The product of amplification is termed an amplicon.

A "biological sample" is a plant, plant material or products comprising plant material. The term "plant" is intended to encompass corn (Zea mays) plant tissues, at any stage of maturity, as well as cells, tissues, organs taken from or derived from any such plant, including without limitation, any seeds, leaves, stems, flowers, roots, single cells, gametes, cell cultures, tissue cultures or protoplasts. "Plant material", as used herein refers to material which is obtained or derived from a plant. Products comprising plant material relate to food, feed or other products which are produced using plant material or can be contaminated by plant material. It is understood that, in the context of the invention, such biological sample are tested for the presence of nucleic acids specific to corn event 5307, implying the presence of nucleic acids in the samples. Thus, the methods referred to herein for identifying corn event 5307 in biological samples, relate to the identification in biological samples of nucleic acids which from an event 5307 corn plant and are diagnostic for event 5307.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

"Detection kit" as used herein refers to a kit used to detect the presence or absence of DNA from event 5307 corn plants in a sample comprising nucleic acid probes and primers of the invention, which hybridize specifically under high stringency conditions to a target DNA sequence, and other materials necessary to enable nucleic acid hybridization or amplification methods.

As used herein the term transgenic "event" refers to a recombinant plant produced by transformation and regeneration of a single plant cell with heterologous DNA, for example, an expression cassette that includes a gene of interest. The term "event" refers to the original transformant and/or progeny of the transformant that include the heterologous DNA. The term "event" also refers to progeny produced by a sexual outcross between the transformant and another corn line. Even after repeated backcrossing to a recurrent parent, the inserted DNA and the flanking DNA from the transformed parent is present in the progeny of the cross at the same chromosomal location. Normally, transformation of plant tissue produces multiple events, each of which represent insertion of a DNA construct into a different location in the genome of a plant cell. Based on the expression of the transgene or other desirable characteristics, a particular event is selected. Thus, "event 5307", "5307 event" or "5307" as used herein, means the original 5307 transformant and/or progeny of the 5307 transformant, including any plant derived therefrom.

"Expression cassette" as used herein means a nucleic acid molecule capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The expression cassette may also comprise sequences not necessary in the direct expression of a nucleotide sequence of interest but which are present due to convenient restriction sites for removal of the cassette from an expression vector. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation process known in the art. The expression of the nucleotide sequence in the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue, or organ, or stage of development. An expression cassette, or fragment thereof, can also be referred to as "inserted sequence" or "insertion sequence" when transformed into a plant.

A "gene" is a defined region that is located within a genome and that, besides the aforementioned coding nucleic acid sequence, comprises other, primarily regulatory, nucleic acid sequences responsible for the control of the expression, that is to say the transcription and translation, of the coding portion. A gene may also comprise other 5' and 3' untranslated sequences and termination sequences. Further elements that may be present are, for example, introns.

"Gene of interest" refers to any gene which, when transferred to a plant, confers upon the plant a desired characteristic such as antibiotic resistance, virus resistance, insect resistance, disease resistance, or resistance to other pests, herbicide tolerance, improved nutritional value, improved performance in an industrial process or altered reproductive capability. The "gene of interest" may also be one that is transferred to plants for the production of commercially valuable enzymes or metabolites in the plant.

"Genotype" as used herein is the genetic material inherited from parent corn plants not all of which is necessarily expressed in the descendant corn plants. The 5307 genotype refers to the heterologous genetic material transformed into the genome of a plant as well as the genetic material flanking the inserted sequence.

A "heterologous" nucleic acid sequence is a nucleic acid sequence not naturally associated with a host cell into which it is introduced, including non-naturally occurring multiple copies of a naturally occurring nucleic acid sequence.

A "homologous" nucleic acid sequence is a nucleic acid sequence naturally associated with a host cell into which it is introduced.

The term "isolated" when used in relation to a nucleic acid refers to a nucleic acid sequence that is identified and separated from at least one contaminant nucleic acid with which it is ordinarily associated in its natural source. An isolated nucleic acid is present in a form or setting that is different from that in which it is found in nature. In contrast, a non-isolated nucleic acids such as DNA and RNA found in the state they exist in nature. An isolated nucleic acid may be in a transgenic plant and still be considered "isolated".

"Operably-linked" refers to the association of nucleic acid sequences on a single nucleic acid fragment so that the function of one affects the function of the other. For example, a promoter is operably-linked with a coding sequence or functional RNA when it is capable of affecting the expression of that coding sequence or functional RNA (i.e., that the coding sequence or functional RNA is under the transcriptional control of the promoter). Coding sequences in sense or antisense orientation can be operably-linked to regulatory sequences.

"Primers" as used herein are isolated nucleic acids that are annealed to a complimentary target DNA strand by nucleic acid hybridization to form a hybrid between the primer and the target DNA strand, then extended along the target DNA strand by a polymerase, such as DNA polymerase. Primer pairs or sets can be used for amplification of a nucleic acid molecule, for example, by the polymerase chain reaction (PCR) or other conventional nucleic-acid amplification methods.

A "probe" is an isolated nucleic acid to which is attached a conventional detectable label or reporter molecule, such as a radioactive isotope, ligand, chemiluminescent agent, or enzyme. Such a probe is complimentary to a strand of a target nucleic acid, in the case of the invention, to a strand of genomic DNA from corn event, M5307. The genomic DNA of event 5307 can be from a corn plant or from a sample that includes DNA from the event. Probes according to the invention include not only deoxyribonucleic or ribonucleic acids but also polyamides and other probe materials that bind specifically to a target DNA sequence and can be used to detect the presence of that target DNA sequence.

Primers and probes are generally between 10 and 15 nucleotides or more in length, Primers and probes can also be at least 20 nucleotides or more in length, or at least 25 nucleotides or more, or at least 30 nucleotides or more in length. Such primers and probes hybridize specifically to a target sequence under high stringency hybridization conditions. Primers and probes according to the invention may have complete sequence complementarity with the target sequence, although probes differing from the target sequence and which retain the ability to hybridize to target sequences may be designed by conventional methods.

"Stringent conditions" or "stringent hybridization conditions" include reference to conditions under which a probe will hybridize to its target sequence, to a detectably greater degree than to other sequences. Stringent conditions are target-sequence-dependent and will differ depending on the structure of the polynucleotide. By controlling the stringency of the hybridization and/or wash conditions, target sequences can be identified which are 100% complementary to the probe (homologous probing). Alternatively, stringency conditions can be adjusted to allow some mismatching in sequences so that lower degrees of similarity are detected (heterologous probing). Longer sequences hybridize specifically at higher temperatures. An extensive guide to the hybridization of nucleic acids is found in Tijssen (1993) *Laboratory Techniques in Biochemistry and Molecular Biology-Hybridization with Nucleic* Acid Probes, Part I, Chapter 2 "Overview of principles of hybridization and the strategy of nucleic acid probe assays", Elsevier: New York; and *Current Protocols in Molecular Biology*, Chapter 2, Ausubel et al., Eds., Greene Publishing and Wiley-Interscience: New York (1995), and also Sambrook et al. (2001) *Molecular Cloning: A Laboratory Manual* (5th Ed. Cols Spring Harbor Laboratory, Cold Spring Harbor, NY).

Specificity is typically the function of post-hybridization washes, the critical factors being the ionic strength and temperature of the final wash solution. Generally, high stringency hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typically, under high stringency conditions a probe will hybridize to its target subsequence, but to no other sequences.

An example of high stringency hybridization conditions for hybridization of complementary nucleic acids which have more than 100 complementary residues on a filter in a Southern or northern blot is 50% formamide with 1 mg of heparin at 42° C., with the hybridization being carried out overnight. An example of very high stringency wash conditions is 0.15M NaCl at 72° C. for about 15 minutes. An example of high stringency wash conditions is a 0.2×SSC wash at 65° C. for 15 minutes (see, Sambrook, infra, for a description of SSC buffer).

Exemplary hybridization conditions for the invention include hybridization in 7% SDS, 0.25 M $NaPO_4$ pH 7.2 at 67° C. overnight, followed by two washings in 5% SDS, 0.20 M $NaPO_4$ pH7.2 at 65° C. for 30 minutes each wash, and two washings in 1% SDS, 0.20 M $NaPO_4$ pH7.2 at 65° C. for 30 minutes each wash. An exemplary medium stringency wash for a duplex of, e.g., more than 100 nucleotides, is 1×SSC at 45° C. for 15 minutes. An exemplary low stringency wash for a duplex of, e.g., more than 100 nucleotides, is 4-6×SSC at 40° C. for 15 minutes.

For probes of about 10 to 50 nucleotides, high stringency conditions typically involve salt concentrations of less than about 1.0 M Na ion, typically about 0.01 to 1.0 M Na ion concentration (or other salts) at pH 7.0 to 8.3, and the temperature is typically at least about 30° C. High stringency conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under high stringency conditions are still substantially identical if the proteins that they encode are substantially identical. This occurs, e.g., when a copy of a nucleic acid is created using the maximum codon degeneracy permitted by the genetic code.

The following are exemplary sets of hybridization/wash conditions that may be used to hybridize nucleotide sequences that are substantially identical to reference nucleotide sequences of the invention: a reference nucleotide sequence preferably hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C. The sequences of the invention may be detected using all the above conditions. For the purposes of defining the invention, the high stringency conditions are used.

"Transformation" is a process for introducing heterologous nucleic acid into a host cell or organism. In particular, "transformation" means the stable integration of a DNA molecule into the genome of an organism of interest.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule. As used herein, "transgenic" refers to a plant, plant cell, or multitude of structured or unstructured plant cells having integrated, via well known techniques of genetic manipulation and gene insertion, a nucleic acid representing a gene of interest into the plant genome, and typically into a chromosome of a cell nucleus, mitochondria or other organelle containing chromosomes, at a locus different to, or in a number of copies greater than, that normally present in the native plant or plant cell. Transgenic plants result from the manipulation and insertion of such nucleic acid sequences, as opposed to naturally occurring mutations, to produce a non-naturally occurring plant or a plant with a non-naturally occurring genotype. Techniques for transformation of plants and plant cells are well known in the art and may comprise for example electroporation, microinjection, *Agrobacterium*-mediated transformation, and ballistic transformation.

The nomenclature for DNA bases and amino acids as set forth in 37 C.F.R. § 1.822 is used herein.

DETAILED DESCRIPTION

This invention relates to a genetically improved line of corn that produces the insect control protein, FR8a, and a phosphomannose isomerase enzyme (PMI) that allows the plant to utilize mannose as a carbon source. The invention is particularly drawn to a transgenic corn event designated event 5307 comprising a novel genotype, as well as to compositions and methods for detecting nucleic acids from this event in a biological sample. The invention is further drawn to corn plants comprising the event 5307 genotype, to transgenic seed from the corn plants, and to methods for producing a corn plant comprising the event 5307 genotype by crossing a corn inbred comprising the event 5307 genotype with itself or another corn line. Corn plants comprising the event 5307 genotype of the invention are useful in controlling coleopteran insect pests including *Diabrotica virgifera virgifera*, the western corn rootworm, *D. virgifera zeae*, the Mexican corn rootworm, and *D. longicornis barberi*, the northern corn rootworm. Corn plants comprising the event 5307 genotype of the invention are also able to utilize mannose as a carbon source.

In one embodiment, the invention encompasses a transgenic corn seed of an event 5307 corn plant. An example of said seed being deposited as ATCC Accession No: PTA-9561. The transgenic seed of event 5307 comprises SEQ ID NO: 1, SEQ ID NO: 2, SEQ ID NO: 3, SEQ ID NO: 4, SEQ ID NO: 5, or SEQ ID NO: 6, and complements thereof. These sequences define a point of insertion of a heterologous DNA sequence inserted into the corn plant genome of corn event 5307. In another embodiment, the invention encompasses a preferably isolated nucleic acid molecule comprising SEQ ID NO: 1, SEQ ID NO: 2, SEQ ID NO: 3 or SEQ ID NO: 4. In another embodiment, the invention encompasses a preferably isolated nucleic acid molecule, wherein the nucleic acid molecule is comprised in a corn seed deposited as ATCC Accession No. PTA-9561

In one embodiment, the invention encompasses a nucleic acid molecule, preferably isolated, comprising at least 10 or more (for example 15, 20, 25, or 50) contiguous nucleotides of a heterologous DNA sequence inserted into the corn plant genome of corn event 5307 and at least 10 or more (for example 15, 20, 25, or 50) contiguous nucleotides of a corn plant genome DNA flanking the point of insertion of a heterologous DNA sequence inserted into the corn plant genome of corn event 5307. Also included are nucleotide sequences that comprise 10 or more nucleotides of contiguous insert sequence from event 5307 and at lease one nucleotide of flanking DNA from event 5307 adjacent to the insert sequence. Such nucleotide sequences are diagnostic for event 5307. Nucleic acid amplification of genomic DNA from the 5307 event produces an amplicon comprising such diagnostic nucleotide sequences.

In another embodiment, the invention encompasses a nucleic acid molecule, preferably isolated, comprising a nucleotide sequence which comprises at least one junction sequence of event 5307 selected from the group consisting of SEQ ID NO: 1, SEQ ID NO: 2, SEQ ID NO: 3, SEQ ID NO: 4, and complements thereof, wherein a junction sequence spans the junction between a heterologous expression cassette inserted into the corn genome and DNA from the corn genome flanking the insertion site and is diagnostic for the event.

In another embodiment, the invention encompasses a preferably isolated nucleic acid linking a heterologous DNA molecule to the corn plant genome in corn event 5307 comprising a sequence of from about 11 to about 20 contiguous nucleotides selected from the group consisting of SEQ ID NO: 1, SEQ ID NO: 2, and the complements thereof.

In another embodiment, the invention encompasses an nucleic acid molecule, preferably isolated, comprising a nucleotide sequence selected from the group consisting of SEQ ID NO: 1, SEQ ID NO: 2, SEQ ID NO: 3, SEQ ID NO: 4, and complements thereof.

In one embodiment of the invention, an amplicon comprising a nucleotide sequence selected from the group consisting of SEQ ID NO: 1, SEQ ID NO: 2, SEQ ID NO: 3, SEQ ID NO: 4, and the complements thereof is provided.

In another embodiment, the invention encompasses flanking sequence primers for detecting event 5307. Such flanking sequence primers comprise an isolated nucleic acid sequence comprising at least 10-15 contiguous nucleotides from nucleotides 1-1348 of SEQ ID NO: 5 (arbitrarily designated herein as the 5' flanking sequence), or the complements thereof, also disclosed as SEQ ID NO: 111. In one aspect of this embodiment the flanking sequence primers are selected from the group consisting of SEQ ID NO: 8 through SEQ ID NO: 14, and complements thereof. The flanking sequences can be extended to include chromosome 5 sequences, with specific emphasis on nucleotide comprised with SEQ ID NO: 103, useful in detecting sequences associated with the 5307 corn event. In the context of SEQ ID NO: 103, an "N" is defined as any base "A", "T", "G", or "C". SEQ ID NO: 110 is the reverse complement of this sequence. In the context of SEQ ID NO: 110, an "N" is defined as any base "A", "T", "G", or "C".

In another embodiment, the invention encompasses flanking sequence primers that comprise at least 10-15 contiguous nucleotides from nucleotides 1-1093 of SEQ ID NO: 6 (arbitrarily designated herein as the 3' flanking sequence), or the complements thereof. In one aspect of this embodiment the flanking sequence primers are selected from the group consisting of SEQ ID NO: 69 through SEQ ID NO: 72, and complements thereof.

In still another embodiment, the invention encompasses a pair of polynucleotide primers comprising a first polynucleotide primer and a second polynucleotide primer which function together in the presence of a corn event 5307 DNA template in a sample to produce an amplicon diagnostic for the corn event 5307, wherein the first primer sequence is or is complementary to a corn plant genome flanking the point of insertion of a heterologous DNA sequence inserted into the corn plant genome of corn event 5307, and the second polynucleotide primer sequence is or is complementary to the heterologous DNA sequence inserted into the corn plant genome of the corn event 5307.

In one aspect of this embodiment the first polynucleotide primer comprises at least 10 contiguous nucleotides from position 1-1348 of SEQ ID NO: 5 or complements thereof. In a further aspect of this embodiment, the first polynucleotide primer comprises the nucleotide sequence set forth in SEQ ID NO: 8 through SEQ ID NO: 14, or the complements thereof. In another aspect of this embodiment the first polynucleotide primer least 10 contiguous nucleotides from position 1-1093 of SEQ ID NO: 6 or complements thereof. In another aspect of this embodiment, the first polynucleotide primer comprises the nucleotide sequence set forth in SEQ ID NO: 69 through SEQ ID NO: 72, or the complements thereof. In yet another aspect of this embodiment, the second polynucleotide primer comprises at least 10 contiguous nucleotides of SEQ ID NO: 7, or the complements thereof. In still a further aspect of this embodiment, the second polynucleotide primer comprises the nucleotide sequence set forth in SEQ ID NO: 15 to SEQ ID NO: 68, or the complements thereof.

In another aspect of this embodiment, the first polynucleotide primer, which is set forth in SEQ ID NO: 8, and the second polynucleotide primer which is set forth in SEQ ID NO: 41, function together in the presence of a corn event 5307 DNA template in a sample to produce an amplicon diagnostic for the corn event 5307 as described in Example 4. In another aspect of this embodiment, the first polynucleotide primer, which is set forth in SEQ ID NO: 69, and the second polynucleotide primer which is set forth in SEQ ID NO: 72, function together in the presence of a corn event 5307 DNA template in a sample to produce an amplicon diagnostic for the corn event 5307 as described in Example 4.

It is well within the skill in the art to obtain additional sequence further out into the genome sequence flanking either end of the inserted heterologous DNA sequences for use as a primer sequence that can be used in such primer pairs for amplifying the sequences that are diagnostic for the 5307 event. For the purposes of this disclosure, the phrase "further out into the genome sequence flanking either end of the inserted heterologous DNA sequences" refers specifically to a sequential movement away from the ends of the inserted heterologous DNA sequences, the points at which the inserted DNA sequences are adjacent to native genomic DNA sequence, and out into the genomic DNA of the particular chromosome into which the heterologous DNA sequences were inserted. Preferably, a primer sequence corresponding to or complementary to a part of the insert sequence should prime the transcriptional extension of a nascent strand of DNA or RNA toward the nearest flanking sequence junction. Consequently, a primer sequence corresponding to or complementary to a part of the genomic flanking sequence should prime the transcriptional extension of a nascent strand of DNA or RNA toward the nearest flanking sequence junction. A primer sequence can be, or can be complementary to, a heterologous DNA sequence inserted into the chromosome of the plant, or a genomic flanking sequence. One skilled in the art would readily recognize the benefit of whether a primer sequence would need to be, or would need to be complementary to, the sequence as set forth within the inserted heterologous DNA sequence or as set forth in SEQ ID NO: 3 or SEQ ID NO: 4 depending upon the nature of the product desired to be obtained through the use of the nested set of primers intended for use in amplifying a particular flanking sequence containing the junction between the genomic DNA sequence and the inserted heterologous DNA sequence. Further more, one skilled in the art would be able to design primers for a multitude of native corn genes for the purposes of designing a positive control. One such example is the corn Adh1 gene, where examples of suitable primers for producing an amplicon by nucleic acid amplification are set forth as SEQ ID NO: 79 and SEQ ID NO: 80.

In another embodiment, the invention encompasses a method of detecting the presence of DNA corresponding to the event 5307 in a biological sample, wherein the method comprises: (a) contacting the sample comprising DNA with a probe that hybridizes under high stringency conditions with genomic DNA from corn event 5307 and does not hybridize under high stringency conditions with DNA of a control corn plant; (b) subjecting the sample and probe to high stringency hybridization conditions; and (c) detecting hybridization of the probe to the DNA. In one aspect of this embodiment the amplicon comprises a nucleotide sequence selected from the group consisting of SEQ ID NO: 1, SEQ ID NO: 2, SEQ ID NO: 3, SEQ ID NO: 4, and complements thereof.

In another embodiment, the invention encompasses a method of detecting the presence of a DNA corresponding to the 5307 event in a biological sample, wherein the method comprises: (a) contacting the sample comprising DNA with a probe that hybridizes under high stringency conditions with genomic DNA from corn event 5307 and does not hybridize under high stringency conditions with DNA of a control corn plant; (b) subjecting the sample and probe to high stringency hybridization conditions; and (c) detecting hybridization of the probe to the DNA. Detection can be by any means well known in the art including but not limited to fluorescent, chemiluminescent, radiological, immunological, or otherwise. In the case in which hybridization is intended to be used as a means for amplification of a particular sequence to produce an amplicon which is diagnostic for the 5307 corn event, the production and detection by any means well known in the art of the amplicon is intended to be indicative of the intended hybridization to the target sequence where one probe or primer is utilized, or sequences where two or more probes or primers are utilized. The term "biological sample" is intended to comprise a sample that contains or is suspected of containing a nucleic acid comprising from between five and ten nucleotides either side of the point at which one or the other of the two terminal ends of the inserted heterologous DNA sequence contacts the genomic DNA sequence within the chromosome into which the heterologous DNA sequence was inserted, herein also known as the junction sequences. In addition, the junction sequence comprises as little as two nucleotides: those being the first nucleotide within the flanking genomic DNA adjacent to and covalently linked to the first nucleotide within the inserted heterologous DNA sequence.

In yet another embodiment, the invention encompasses a kit for detecting the presence of event 5307 nucleic acids in a biological sample, wherein the kit comprises at least one nucleic acid molecule of sufficient length of contiguous nucleotides homologous or complementary to a nucleotide sequence selected from the group consisting of SEQ ID NO: 1, SEQ ID NO: 2, SEQ ID NO: 3, and SEQ ID NO: 4, that functions as a DNA primer or probe specific for event 5307, and other materials necessary to enable nucleic acid hybridization or amplification. A variety of detection methods can be used including TAQMAN (Perkin Elmer), thermal amplification, ligase chain reaction, southern hybridization, ELISA methods, and colorimetric and fluorescent detection methods. In particular the invention provides for kits for detecting the presence of the target sequence, i.e., at least one of the junctions of the insert DNA with the genomic DNA of the corn plant in event 5307, in a sample containing genomic nucleic acid from event 5307. The kit is comprised of at least one polynucleotide capable of binding to the target site or substantially adjacent to the target site and at least one means for detecting the binding of the polynucleotide to the target site. The detecting means can be fluorescent, chemiluminescent, colorimetric, or isotopic and can be coupled at least with immunological methods for detecting the binding. A kit is also envisioned which can detect the presence of the target site in a sample, i.e., at least one of the junctions of the insert DNA with the genomic DNA of the corn plant in event 5307, taking advantage of two or more polynucleotide sequences which together are capable of binding to nucleotide sequences adjacent to or within about 100 base pairs, or within about 200 base pairs, or within about 500 base pairs or within about 1000 base pairs of the target sequence and which can be extended toward each other to form an amplicon which contains at least the target site In another embodiment, the invention encompasses a method for detecting event 5307 protein in a biological sample, the method comprising: (a) extracting protein from a sample of corn event 5307 tissue; (b) assaying the extracted protein using an immunological method comprising antibody specific for the insecticidal or selectable marker protein produced by the 5307 event; and (c) detecting the binding of said antibody to the insecticidal or selectable marker protein.

Another embodiment of the invention encompasses a corn plant, or parts thereof, comprising the genotype of the transgenic event 5307, wherein the genotype comprises the nucleotide sequence set forth in SEQ ID NO: 1, SEQ ID NO: 2, SEQ ID NO: 3, SEQ ID NO: 4, or the complements thereof. In one aspect of this embodiment, the corn plant is from the inbred corn lines CG5NA58, CG5NA58A, CG3ND97, CG5NA01, CG5NF22, CG4NU15, CG00685, CG00526, CG00716, NP904, NP948, NP934, NP982, NP991, NP993, NP2010, NP2013, NP2015, NP2017, NP2029, NP2031, NP2034, NP2045, NP2052, NP2138, NP2151, NP2166, NP2161, NP2171, NP2174, NP2208, NP2213, NP2222, NP2275, NP2276, NP2316, BCTT609, AF031, H8431, 894, BUTT201, R327H, 2044BT, and 2070BT. One skilled in the art will recognize however, that the event 5307 genotype can be introgressed into any plant variety that can be bred with corn, including wild maize species, and thus the preferred inbred lines of this embodiment are not meant to be limiting.

In another embodiment, the invention encompasses a corn plant comprising at least a first and a second DNA sequence linked together to form a contiguous nucleotide sequence, wherein the first DNA sequence is within a junction sequence and comprises at least about 10-15 contiguous nucleotides selected from the group consisting of nucleotides SEQ ID NO: 5, SEQ ID NO: 6, and complements thereof, wherein the second DNA sequence is within the heterologous insert DNA sequence selected from the group consisting of SEQ ID NO: 15 through SEQ ID NO: 68, and complements thereof; and wherein the first and the second DNA sequences are useful as nucleotide primers or probes for detecting the presence of corn event 5307 nucleic acid sequences in a biological sample. In one aspect of this embodiment, the nucleotide primers are used in a DNA amplification method to amplify a target DNA sequence from template DNA extracted from the corn plant and the corn plant is identifiable from other corn plants by the production of an amplicon corresponding to a DNA sequence comprising SEQ ID NO: 1 or SEQ ID NO: 2

Corn plants of the invention can be further characterized in that digesting the plant's genomic DNA with the restriction endonucleases SmaI and PmeI results in a single hybridizing band using a full length probe under high stringency conditions. Exemplified herein is a full length probe comprising a nucleotide sequence set forth in SEQ ID NO: 7.

In one embodiment, the invention provides a corn plant, wherein the event 5307 genotype confers upon the corn plant resistance to insects or the ability to utilize mannose. In one aspect of this embodiment, the genotype conferring resistance to insects upon the corn plant comprises a FR8a gene. In another aspect of this embodiment, the genotype conferring upon the corn plant the ability to utilize mannose comprises a PMI gene.

In one embodiment, the invention provides a biological sample derived from a event 5307 corn plant, tissue, or seed, wherein the sample comprises a nucleotide sequence which is or is complementary to a sequence selected from the group consisting of SEQ ID NO: 1, SEQ ID NO: 2, SEQ ID NO: 3 and SEQ ID NO: 4, and wherein the sequence is detectable in the sample using a nucleic acid amplification or nucleic acid hybridization method. Thus, the genetic sequence functions a means of detection. In one aspect of this embodiment, the sample is selected from corn flour, corn meal, corn syrup, corn oil, corn starch, and cereals manufactured in whole or in part to contain corn products.

In another embodiment, the invention provides an extract derived from a event 5307 corn plant, tissue, or seed comprising a nucleotide sequence which is or is complementary to a nucleotide sequence selected from the group consisting of SEQ ID NO: 1, SEQ ID NO: 2, SEQ ID NO: 3 and SEQ ID NO: 4. An example of such seed is deposited at the ATCC under Accession No. PTA-9561. In one aspect of this embodiment, the sequence is detected in the extract using a nucleic acid amplification or nucleic acid hybridization method. In another aspect of this embodiment, the sample is selected from corn flour, corn syrup, corn oil, cornstarch, and cereals manufactured in whole or in part to contain corn products.

In yet another embodiment, the invention provides a method for producing a corn plant resistant to at least corn rootworm infestation comprising: (a) sexually crossing a first parent corn plant with a second parent corn plant, wherein said first or second parent corn plant comprises corn event 5307 DNA, thereby producing a plurality of first generation progeny plants; (b) selecting a first generation progeny plant that is resistant to at least corn rootworm infestation; (c) selfing the first generation progeny plant, thereby producing a plurality of second generation progeny plants; and (d) selecting from the second generation progeny plants, a plant that is at least resistant to corn rootworm infestation; wherein the second generation progeny plants comprise a nucleotide sequence selected from the group consisting of SEQ ID NO: 1, SEQ ID NO: 2, SEQ ID NO:3 and SEQ ID NO: 4.

In another embodiment, the invention provides a method of producing hybrid corn seeds comprising: (a) planting seeds of a first inbred corn line comprising a nucleotide sequence selected from the group consisting of SEQ ID NO: 1, SEQ ID NO: 2, SEQ ID NO: 3, and SEQ ID NO: 4, and seeds of a second inbred line having a different genotype; (b) cultivating corn plants resulting from said planting until time of flowering; (c) emasculating said flowers of plants of one of the corn inbred lines; (d) sexually crossing the two different inbred lines with each other; and (e) harvesting the hybrid seed produced thereby. In one aspect of this embodiment, the first inbred corn line provides the female parents. In another aspect of this embodiment, the first inbred corn line provides the male parents. The invention also encompasses the hybrid seed produced by the embodied method and hybrid plants grown from the seed.

In another embodiment, the invention provides a method of selecting markers associated with corn event 5307 comprising: (a) screening corn event 5307 chromosome 5 sequences, (b) comparing these with a non-transgenic NP2222 sequences, (c) comparing the sequences for the purpose of detecting sequence variations, (d) using these sequence variations as a means to develop markers associated with corn event 5307, (e) using the markers to screen lines, and (f) detecting marker confirming the presence of corn event 5307 sequences on chromosome 5.

One skilled in the art will recognize that the transgenic genotype of the invention can be introgressed by breeding into other corn lines comprising different transgenic genotypes. For example, a corn inbred comprising the transgenic genotype of the invention can be crossed with a corn inbred comprising the transgenic genotype of the lepidopteran resistant Bt11 event, which is known in the art, thus producing corn seed that comprises both the transgenic genotype of the invention and the Bt11 transgenic genotype. Examples of other transgenic events which can be crossed with an inbred of the invention include, the glyphosate herbicide tolerant events GA21 and NK603, the glyphosate tolerant/lepidopteran insect resistant MON802 event, the lepidopteran insect resistant event DBT418, the lepidopteran insect resistant event DAS-06275-8, the lepidopteran insect resistant event MIR162, the male sterile event MS3, the phosphinothricin tolerant event B16, the lepidopteran insect resistant event MON 80100, the phosphinothricin herbicide tolerant events T14 and T25, the lepidopteran insect resistant event 176, the coleopteran insect resistant event MIR604 and the coleopteran insect resistant event MON863, all of which are known in the art. It will be further recognized that other combinations can be made with the transgenic genotype of the invention and thus these examples should not be viewed as limiting.

One skilled in the art will also recognize that transgenic corn seed comprising the transgenic genotype of the invention can be treated with various seed-treatment chemicals, including insecticides, to augment or syngergize the insecticidal activity of the FR8a protein. For example, the transgenic corn seed of the invention can be treated with the commercial insecticide Cruiser®. Such a combination may be used to increase the spectrum of activity and to increase the efficacy of the expressed protein and chemical.

Breeding

The transgenic genotype of the invention can be introgressed in any corn inbred or hybrid using art recognized breeding techniques. The goal of plant breeding is to combine in a single variety or hybrid various desirable traits. For field crops, these traits may include resistance to insects and diseases, tolerance to herbicides, tolerance to heat and drought, reducing the time to crop maturity, greater yield, and better agronomic quality. With mechanical harvesting of many crops, uniformity of plant characteristics such as germination and stand establishment, growth rate, maturity, and plant and ear height, is important.

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two different homozygous lines produces a uniform population of hybrid plants that may be heterozygous for many gene loci. A cross of two plants each heterozygous at a number of gene loci will produce a population of hybrid plants that differ genetically and will not be uniform.

Corn can be bred by both self-pollination and cross-pollination techniques. Corn has separate male and female flowers on the same plant, located on the tassel and the ear, respectively. Natural pollination occurs in corn when wind blows pollen from the tassels to the silks that protrude from the tops of the ears.

A reliable method of controlling male fertility in plants offers the opportunity for improved plant breeding. This is especially true for development of corn hybrids, which relies upon some sort of male sterility system. There are several options for controlling male fertility available to breeders, such as: manual or mechanical emasculation (or detasseling), cytoplasmic male sterility, genetic male sterility, gametocides and the like.

Hybrid corn seed is typically produced by a male sterility system incorporating manual or mechanical detasseling. Alternate strips of two corn inbreds are planted in a field, and the pollen-bearing tassels are removed from one of the inbreds (female). Providing that there is sufficient isolation from sources of foreign corn pollen, the ears of the detasseled inbred will be fertilized only from the other inbred (male), and the resulting seed is therefore hybrid and will form hybrid plants.

The laborious, and occasionally unreliable, detasseling process can be avoided by using one of many methods of conferring genetic male sterility in the art, each with its own benefits and drawbacks. These methods use a variety of approaches such as delivering into the plant a gene encoding a cytotoxic substance associated with a male tissue specific promoter or an antisense system in which a gene critical to fertility is identified and an antisense to that gene is inserted in the plant (see: Fabinjanski, et al. EPO 89/3010153.8 publication no. 329,308 and PCT application PCT/CA90/00037 published as WO 90/08828).

Development of Corn Inbred Lines

The use of male sterile inbreds is but one factor in the production of corn hybrids. Plant breeding techniques known in the art and used in a corn plant breeding program include, but are not limited to, recurrent selection, backcrossing, pedigree breeding, restriction length polymorphism enhanced selection, marker assisted selection and transformation. The development of corn hybrids in a corn plant breeding program requires, in general, the development of homozygous inbred lines, the crossing of these lines, and the evaluation of the crosses. Pedigree breeding and recurrent selection breeding methods are used to develop inbred lines from breeding populations. Corn plant breeding programs combine the genetic backgrounds from two or more inbred lines or various other germplasm sources into breeding pools from which new inbred lines are developed by selfing and selection of desired phenotypes. The new inbreds are crossed with other inbred lines and the hybrids from these crosses are evaluated to determine which of those have commercial potential. Plant breeding and hybrid development, as practiced in a corn plant-breeding program, are expensive and time-consuming processes.

Pedigree breeding starts with the crossing of two genotypes, each of which may have one or more desirable characteristics that is lacking in the other or which complements the other. If the two original parents do not provide all the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: $F_1 \rightarrow F_2$; $F_2 \rightarrow F_3$; $F_3 \rightarrow F_4$; $F_4 \rightarrow F_5$; etc.

Recurrent selection breeding, backcrossing for example, can be used to improve an inbred line and a hybrid that is made using those inbreds. Backcrossing can be used to transfer a specific desirable trait from one inbred or source to an inbred that lacks that trait. This can be accomplished, for example, by first crossing a superior inbred (recurrent parent) to a donor inbred (non-recurrent parent), that carries the appropriate gene(s) for the trait in question. The progeny of this cross is then mated back to the superior recurrent parent followed by selection in the resultant progeny for the desired trait to be transferred from the non-recurrent parent. After five or more backcross generations with selection for the desired trait, the progeny will be homozygous for loci controlling the characteristic being transferred, but will be like the superior parent for essentially all other genes. The last backcross generation is then selfed to give pure breeding progeny for the gene(s) being transferred. A hybrid developed from inbreds containing the transferred gene(s) is essentially the same as a hybrid developed from the same inbreds without the transferred gene(s).

Elite inbred lines, that is, pure breeding, homozygous inbred lines, can also be used as starting materials for breeding or source populations from which to develop other inbred lines. These inbred lines derived from elite inbred lines can be developed using the pedigree breeding and recurrent selection breeding methods described earlier. As an example, when backcross breeding is used to create these derived lines in a corn plant-breeding program, elite inbreds can be used as a parental line or starting material or source population and can serve as either the donor or recurrent parent.

Development of Corn Hybrids

A single cross corn hybrid results from the cross of two inbred lines, each of which has a genotype that complements the genotype of the other. The hybrid progeny of the first generation is designated F1. In the development of commercial hybrids in a corn plant-breeding program, only the F1 hybrid plants are sought. Preferred F1 hybrids are more vigorous than their inbred parents. This hybrid vigor, or heterosis, can be manifested in many polygenic traits, including increased vegetative growth and increased yield.

The development of a corn hybrid in a corn plant breeding program involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with different inbred lines to produce the hybrid progeny (F1). During the inbreeding process in corn, the vigor of the lines decreases. Vigor is restored when two different inbred lines are crossed to produce the hybrid progeny (F1). An important consequence of the homozygosity and homogeneity of the inbred lines is that the hybrid between a defined pair of inbreds will always be the same. Once the inbreds that give a superior hybrid have been identified, the hybrid seed can be reproduced indefinitely as long as the homogeneity of the inbred parents is maintained. Much of the hybrid vigor exhibited by F1 hybrids is lost in the next generation (F2). Consequently, seed from hybrids is not used for planting stock.

Hybrid seed production requires elimination or inactivation of pollen produced by the female parent. Incomplete removal or inactivation of the pollen provides the potential for self-pollination. This inadvertently self-pollinated seed may be unintentionally harvested and packaged with hybrid seed.

Once the seed is planted, it is possible to identify and select these self-pollinated plants. These self-pollinated plants will be genetically equivalent to the female inbred line used to produce the hybrid.

As is readily apparent to one skilled in the art, the foregoing are only some of the various ways by which the inbred of the invention can be obtained by those looking to introgress the transgenic genotype of the invention into other corn lines. Other means are available, and the above examples are illustrative only.

EXAMPLES

The invention will be further described by reference to the following detailed examples. These examples are provided for purposes of illustration only, and are not intended to be limiting unless otherwise specified. Standard recombinant DNA and molecular cloning techniques used here are well known in the art and are described by Ausubel (ed.), Current Protocols in Molecular Biology, John Wiley and Sons, Inc. (1994); J. Sambrook, et al., Molecular Cloning: *A Laboratory Manual,* 3d Ed., Cold Spring Harbor, NY: Cold Spring Harbor Laboratory Press (2001); and by T. J. Silhavy, M. L. Berman, and L. W. Enquist, Experiments with Gene Fusions, Cold Spring Harbor Laboratory, Cold Spring Harbor, NY (1984).

Example 1. Transformation and Selection of the 5307 Event

The 5307 event was produced by *Agrobacterium*-mediated transformation of the inbred corn (*Zea mays*) line NP2222. Immature embyos were transformed essentially as described in Negrotto et al. (Plant Cell Reports 19:798-803, 2000), incorporated herein by reference, using a DNA fragment from plasmid pSYN12274 (FIG. 1). pSYN12274 contains a nucleotide sequence comprising tandem expression cassettes. The first expression cassette is comprised of a CMP promoter sequence (U.S. Pat. No. 7,166,770) operably linked to a FR8a coding sequence further operably linked to a nopaline synthase 3' end transcription termination and polyadenylation sequence. The second expression cassette is comprised of a maize ubiquitin promoter (ZmUbiInt) (Christensen et al. 1992 PMB 18:675) operably linked to a PMI coding sequence further operably linked to a nopaline synthase 3' end transcription termination and polyadenylation sequence.

Immature embryos were excised from 8-12 day old ears and rinsed with fresh medium in preparation for transformation. Embryos were mixed with the suspension of *Agrobacterium* cells harboring the transformation vector pSYN12274, vortexed for 30 seconds, and allowed to incubate for an additional 5 minutes. Excess *Agrobacterium* solution was aspirated and embryos were then moved to plates containing a non-selective culture medium. Embryos were co-cultured with the remaining *Agrobacterium* at 22° C. for 2-3 days in the dark. Embryos were transferred to culture medium supplemented with ticarcillin (100 mg/ml) and silver nitrate (1.6 mg/l) and incubated in the dark for 10 days. Embryos producing embryogenic callus were transferred to cell culture medium containing mannose.

Regenerated plantlets were tested by TAQMAN® PCR analysis (see Example 2) for the presence of both the PMI and FR8a genes, as well as for the absence of the antibiotic resistance spectinomycin (spec) gene. Plants positive for both transgenes, and negative for the spec gene, were transferred to the greenhouse for further propagation. Positive events were identified and screened using insect bioassays against corn rootworm. Insecticidal events were characterized for copy number by TAQMAN analysis. Event 5307 was chosen for further analysis based on having a single copy of the transgenes, good protein expression as identified by ELISA, and better insecticidal activity against corn rootworm when compared to other events made with the same construct.

The $T_0$ 5307 event was backcrossed to inbred corn line NP2460, creating the $T_1$ population. The $T_1$ plants were self-pollinated to create the $T_2$ generation, and this process was repeated to create a $T_3$ generation. Progeny testing of the $T_3$ plants was employed to identify homozygous (converted) families. The event 5307-converted NP2460 inbred was crossed to other elite inbred lines to create hybrids used in further studies.

Example 2. Event 5307 Detection by TAQMAN PCR

TAQMAN analysis was essentially carried out as described in Ingham et al. (Biotechniques, 31:132-140, 2001) herein incorporated by reference. Briefly, genomic DNA was isolated from leaves of transgenic and non-transgenic corn plants using the Puregene® Genomic DNA Extraction kit (Gentra Systems, Minneapolis, MN) essentially according to the manufacturer's instruction, except all steps were conducted in 1.2 ml 96-well plates. The dried DNA pellet was resuspended in TE buffer (10 Mm Tris-HCl, pH 8.0, 1 mM EDTA).

TAQMAN PCR reactions were carried out in 96-well plates. For the endogenous corn gene control, primers and probes were designed specific to the *Zea mays* alcohol dehydrogenase (Adh) gene (Genbank accession no. AF044295). It will be recognized by the skilled person that other corn genes can be used as endogenous controls. Reactions were multiplexed to simultaneously amplify FR8a and Adh or PMI and Adh. For each sample, a master mixture was generated by combining 20 uL extracted genomic DNA with 35 uL 2×TAQMAN Universal PCR Master Mix (Applied Biosystems) supplemented with primers to a final concentration of 900 nM each, probes to a final concentration of 100 nM each, and water to a 70 uL final volume. This mixture was distributed into three replicates of 20 uL each in 96-well amplification plates and sealed with optically clear heat seal film (Marsh Bio Products). PCR was run in the ABI Prism 7700 instrument using the following amplification parameters: 2 min at 50° C. and 10 min at 95° C., followed by 35 cycles of 15 s at 95° C. and 1 min at 60° C.

Results of the TAQMAN analysis demonstrated that event 5307 had one copy of the FR8a gene and one copy of the PMI gene.

Examples of suitable primer/probe sequence combinations which were used are:

| Primer Name | Primer Sequence | SEQ ID NO: |
|---|---|---|
| FR8a-forward | 5'-TACGAGAGCTGGGTGAACTTCA-3' | SEQ ID NO: 73 |
| FR8a-reverse | 5'-CGATCAGGTCCAGCACGG-3' | SEQ ID NO: 74 |
| FR8a-probe | 5'-CCGCTACCGCCGCGAGATGA-3' (5' label = FAM, 3' label = TAMRA) | SEQ ID NO: 75 |
| PMI-forward | 5'-CCGGGTGAATCAGCGTTT-3' | SEQ ID NO: 76 |
| PMI-reverse | 5'-GCCGTGGCCTTTGACAGT-3' | SEQ ID NO: 77 |

-continued

| Primer Name | Primer Sequence | SEQ ID NO: |
|---|---|---|
| PMI-probe | 5'-TGCCGCCAACGAATCACCGG-3'<br>(5' label = FAM, 3' label = TAMRA) | SEQ ID NO: 78 |
| ZmADH-267 forward | 5'-GAACGTGTGTTGGGTTTGCAT-3' | SEQ ID NO: 79 |
| ZmADH-337 reverse | 5'-TCCAGCAATCCTTGCACCTT-3' | SEQ ID NO: 80 |
| ZmADH-316 probe | 5'-TGCAGCCTAACCATGCGCAGGGTA-3'<br>(5' label = TET, 3' label = TAMRA) | SEQ ID NO: 81 |

The PM1271, MIC5307a and MIC5307b TAQMAN assays are designed as an event specific assay, which covers the 3' junction sequence.

Examples of suitable primer/probe sequence combinations which were used are:

| Primer Name | Primer Sequence | SEQ ID NO: |
|---|---|---|
| PM1277-forward | 5'-GCCGTATCCGCAATGTGTTA-3' | SEQ ID NO: 82 |
| PM1277-reverse | 5'-GGCCCAGGGAAGAGGGTATAT-3' | SEQ ID NO: 83 |
| PM1277-probe | 5'-AAGTTGTCTAAGCGTCAAT-3'<br>(5' label = TET, 3' label = TAMRA) | SEQ ID NO: 84 |
| MIC5307a-forward | 5'-TGTCTAAGCGTCAATTTGTTTACACC-3' | SEQ ID NO: 82 |
| MIC5307a-reverse | 5'-TTTGCCAGTGGGCCCA-3' | SEQ ID NO: 83 |
| MIC5307a-probe | 5'-ACAATATACCCTCTTCCCTGGGCCAGG-3'<br>(5' label = TET, 3' label = TAMRA) | SEQ ID NO: 84 |
| MIC5307b-forward | 5'-GCCGTATCCGCAATGTGTTA-3' | SEQ ID NO: 82 |
| MIC5307b-reverse | 5'-AAGTTGTCTAAGCGTCAAT-3' | SEQ ID NO: 83 |
| MIC5307b-probe | 5'-GGCCCAGGGAAGAGGGTATAT-3'<br>(5' label = TET, 3' label = TAMRA) | SEQ ID NO: 84 |

Example 3. Event 5307 Detection by Southern Blot

Genomic DNA used for southern analysis was isolated from pooled leaf tissue of ten plants representing the backcross six (BC6) generation of event 5307 using essentially the method of Thomas et al. (Theor. Appl. Genet. 86:173-180, 1993), incorporated herein by reference. All plants used for DNA isolation were individually analyzed using TAQMAN PCR (as described in Example 2) to confirm the presence of a single copy of the FR8a gene and the PMI gene. For the negative segregant controls, DNA was isolated from pooled leaf tissue of five plants representing the BC4 generation of event 5307. These negative segregant plants were individually analyzed using TAQMAN PCR and the assays were negative for the presence of the FR8a gene and the PMI gene, but were, as expected, positive for the assay internal control, the endogenous maize Adh gene.

Southern analysis was carried out using conventional molecular biology techniques. Genomic DNA (7.5 ug) was doubly digested with SmaI and PmeI restriction enzymes, which have single recognition sites within the event 5307 T-DNA insert from plasmid pSYN12274 (FIG. 1). This approach allows for determination of the number of copies of the elements, corresponding to the specific probe used for each Southern, which have been incorporated into event 5307. This results in one hybridization band per copy of the element present in event 5307. This results in one hybridization band per copy of the element present in event 5307. Following agarose gel electrophoresis and alkaline transfer to a Nytran® membrane, hybridizations were carried out using element-specific full-length PCR-generated probes. The full length probe used in the Southern blots comprises the nucleotide sequences set forth in SEQ ID NO: 7. The probe was labeled with 32P via random priming using the Rediprime™ II system (Amersham Biosciences, Cat. No. RPN1633).

The following high stringency hybridization conditions were used: 1-2 million cpm/ml are added to PerfectHyb (Sigma) supplemented with 100 μg/ml Calf Thymus DNA (Invitrogen) pre-warmed to 65° C. Pre-hybridization takes place in the same solution as above, at the same temp overnight or for at least one hour. Hybridization was carried out at 65° C. for 3 hours followed by washing 2× in 2×SSC, 0.1% SDS for 20 minutes at 65° C. and 2× in 0.1×SSC, 0.1% SDS for 20 minutes at 65° C.

Included on each Southern were three control samples: (1) DNA from a negative (non-transformed) segregant used to identify any endogenous Zea mays sequences that may cross-hybridize with the element-specific probe; (2) DNA from a negative segregant into which is introduced an amount of SmaI-PmeI digested pSYN12274 that is equal to one copy number based on probe length, to demonstrate the sensitivity of the experiment in detecting a single gene copy within the Zea mays genome; and (3) SmaI-PmeI digested pSYN12274 plasmid that is equal to one copy number based on probe length, as a positive control for hybridization as well as to demonstrate the sensitivity of the experiment.

The hybridization data provide confirmatory evidence to support the TAQMAN PCR analysis that event 5307 contains a single copy of the FR8a and PMI genes, and that 5307 event does not contain any of the vector backbone sequences present in pSYN12274. As expected for both the FR8a and PMI probes, the SmaI-PmeI digest resulted in a single hybridization band of the correct size, demonstrating that a single copy of each gene is present in the 5307 event. Additionally, for the backbone probe lack of hybridization demonstrates the absence of any pSYN12274 vector backbone sequences being incorporated into event 5307 during the transformation process.

Example 4. T-DNA Insert Sequencing

The nucleotide sequence of the entire transgene DNA insert present in event 5307 was determined to demonstrate overall integrity of the insert, contiguousness of the functional elements and to detect any individual basepair changes. The event 5307 insert was PCR amplified from DNA derived from the BC5 generation as two individual overlapping fragments. Each fragment was amplified using one polynucleotide primer homologous to plant genomic sequences flanking the event 5307 insert and one polynucleotide primer homologous to the FR8a gene. To generate the 5' fragment, a first polynucleotide primer homologous to the 5' flanking sequence, SEQ ID NO: 8 through SEQ ID NO: 15, was combined with a second polynucleotide primer homologous to the inserted DNA the FR8a gene, SEQ ID NO: 33 through SEQ ID NO: 41, the Ubiquitin promoter, SEQ ID NO: 42 through SEQ ID NO: 53 or the PMI gene, SEQ ID NO: 54 through SEQ ID NO: 60. To generate the 3' fragment, a first polynucleotide primer homologous to the 3' flanking sequence, SEQ ID NO: 69 through SEQ ID NO: 72, was combined with a second polynucleotide primer homologous to the inserted DNA within the FR8a gene, SEQ ID NO: 9 through SEQ ID NO: 17, the Ubiquitin promoter, SEQ ID NO: 18 through SEQ ID NO: 26 or the PMI gene, SEQ ID NO: 27 through SEQ ID NO: 32.

PCR amplification was carried out using the Expand High Fidelity PCR system (Roche, Cat. No. 1732650) and the following amplification parameters: 2 min at 94° C. for 1 cycle, followed by 10 cycles of 15 s at 94° C., 30 s at 55-65° C. and 5 min at 68° C., followed by 20 cycles of 15 s 94° C., 30 s at 55-65° C., and 5 min+5 s/cyc of 72° C., followed by 1 cycle of 7 min at 72° C.

The amplicon resulting from the PCR amplification using SEQ ID NO: 8 and SEQ ID NO: 41 comprised the 5' junction sequence (SEQ ID NO: 1). The amplicon resulting from the PCR amplification using SEQ ID NO: 69 and SEQ ID NO: 72 comprised the 3' junction sequence (SEQ ID NO: 2). Each sequencing fragment was individually cloned into the pCR R-XL-TOPO vector (Invitrogen, Cat. No. K4700-20) and three separate clones for each fragment were identified and sequenced. Sequencing was carried out using the ABI3730XL analyzer using ABI BigDye® 1.1 or Big Dye 3.1 dGTP (for GC rich templates) chemistry. The sequence analysis was done using the Phred, Phrap, and Consed package from the University of Washington and was carried out to an error rate of less than 1 in 10,000 bases (Ewing and Green, 1998). The final consensus sequence was determined by combining the sequence data from the six individual clones (three for each sequencing fragment) to generate one consensus sequence of the event 5307 insert. To further validate any individual basepair discrepancies between the event 5307 insert and the pSYN12274 plasmid, small (approximately 300-500 bp) PCR products specific to any regions where a basepair discrepancy was seen in the initial consensus sequence were amplified using the same methodology above. For all putative basepair discrepancies in the event 5307 insert, direct PCR product sequencing resulted in single clear peaks at all basepairs in question, indicating these discrepancies are likely present in the event 5307 insert. Alignment was performed using the ClustalW program with the following parameters: scoring matrix blosum55, gap opening penalty 15, gap extension penalty 6.66 (Thompson et al, 1994, Nucleic Acids Research, 22, 4673-4680).

The consensus sequence data for the event 5307 T-DNA insert demonstrates that the overall integrity of the insert and contiguousness of the functional elements within the insert as intended in pSYN12274 have been maintained.

Example 5. Analysis of Flanking DNA Sequence

Corn genome DNA sequence flanking the heterologous DNA inserted into the corn plant genome of event 5307 was obtained using OmniPlex™ Technology essentially as described in Kamberov et al (Proceedings of SPIE, Tools for Molecular Analysis and High-Throughput Screening, 4626: 1-12, 2002), incorporated herein by reference.

The 5' and 3' flanking sequences and junction sequences were confirmed using standard PCR procedures. The 5' flanking and junction sequences were confirmed using a first polynucleotide primer set forth in SEQ ID NO: 8 through SEQ ID NO: 14 combined with a second polynucleotide primer set forth in SEQ ID NO: 33 through SEQ ID NO: 41. The 3' flanking and junction sequences were confirmed using a first polynucleotide primer set forth in SEQ ID NO: 69 through SEQ ID NO: 72 combined with a second polynucleotide primer set forth in SEQ ID NO: 27 through SEQ ID NO: 32. It will be recognized by the skilled person that other primer sequences can be used to confirm the flanking and junction sequences.

The event 5307 insert was found to be flanked on the right border (5' flanking sequence) by the corn genomic sequence shown in SEQ ID NO: 5 and flanked on the left border (3' flanking sequence) by the corn genomic sequence shown in SEQ ID NO: 6. The 5' junction sequence is set forth in SEQ ID NO: 1. The 3' junction sequence is set forth in SEQ ID NO: 2. The integration site of the pSYN12274 vector insertion is comprised within SEQ ID NO: 103 or its reverse complement SEQ ID NO: 110, depending on the orientation of the nucleic acid used.

Example 6. Detection of Event 5307 Protein Via ELISA

To characterize the range of expression of FR8a (the active insecticidal principle) and phosphomannose isomerase (PMI) (the selectable marker) proteins in event 5307 plants, the concentrations of FR8a protein and PMI were determined by ELISA in several plant tissues. The hybrids were hemizygous for the transgenes in event 5307, whereas the inbred was homozygous for the transgenes.

Whole plants and individual parts (except pollen) were reduced to a fine powder by processing using either a coffee grinder, blender, Grindomix™ grinder (Brinkmann Instruments; Westbury, NY, USA), mortar with a pestle or mill, or a combination of these devices. All processing was done in the presence of either dry ice or liquid nitrogen. Samples were mixed well to ensure homogeneity. The entire plant tissue sample, or a representative sub-sample, was retained for analysis, allowing sufficient sample size for archival storage of reserve plant tissue samples. The percent dry weight of each sample was determined and the processed samples were stored at ca. −80° C. until lyophilization.

Fresh tissue (except pollen and silage) and whole-plant samples were extracted. For each sample analyzed, a 1.0 g aliquot of the powdered fresh material was weighed into a 15-ml polypropylene tube, suspended in 3 ml extraction buffer [50 mM CAPS, 0.1 M NaCl, 2 mM EDTA, 1 mM dithiothreitol, 1 mM 4-(1-aminoethyl)benzenesulfonyl fluoride HCl, 1 mM leupeptin, pH 10], and extracted using an Autogizer® homogenizer (Tomtek; Hamden, CT, USA). After centrifugation for 15 min at 10,000×g at 4° C., the supernatant was used for FR8a and PMI analysis by ELISA.

After treatment with iodoacetamide as described by Hill and Straka (1988), total protein in the extracts was quantitated using the BCA™ Protein Assay Reagent (Pierce; Rockford, IL, USA).

Pollen extracts were prepared by suspending pollen 1:30 (w/v) in extraction buffer. After 30 min on ice, the pollen suspensions were disrupted by three passages through a French pressure cell at ca. 15,000 psi, followed by centrifugation at 14,000×g for 5 min at 4° C. Cry3A055 and PMI analyses by ELISA were performed on the supernatants as described below. Total protein was quantitated as described above.

Silage extracts were prepared by suspending silage 1:25 (w/v) in 2× extraction buffer. After 30 min on ice, the silage suspensions were extracted using a Brinkmann Polytron® Homogenizer (Brinkmann; Westbury, NY, USA). After centrifugation for 15 min at 10,000×g at 4° C., the supernatant was used for FR8a and PMI analysis by ELISA. Total protein was quantitated as described above.

FR8a Quantification

The extracts prepared as described above were quantitatively analyzed for FR8a by ELISA (Tijssen, 1985) using immuno-affinity purified monoclonal, anti-mCry3A antibody and immuno-affinity purified polyclonal anti-Cry1Ab antibody. The lower limit of quantification of the double-sandwich ELISA was estimated based on the lowest concentration of pure reference protein lying on the linear portion of the standard curve, the maximum volume of a control extract that could be analyzed without background interference, and the corresponding weight of the sample that the aliquot represented.

Quantifiable levels of FR8a protein were detected in all event 5307-derived plant tissues. In most cases, results are presented as means of the five replicate tissue samples. Control sample levels were below the limit of quantification for all tissues.

Across all growth stages, mean FR8a levels measured in leaves, roots and pollen ranged from ca. 18-29 µg/g fresh wt. (77-113 µg/g dry wt.), ca. 1.8-4.1 µg/g fresh wt. (22-41 µg/g dry wt.) and ca. <LOD-0.15 µg/g fresh wt. (<LOD-0.15 µg/g dry wt.) respectively. [limit of detection (LOD)=0.08 µg/g fresh wt., 0.08 µg/g dry wt.].

The levels of FR8a were generally similar among the inbred and hybrid genotypes for each tissue type at each time point PMI Quantification The extracts prepared as described above were quantitatively analyzed for PMI by ELISA (Tjissen, 1985) using Protein A-purified polyclonal rabbit and immunoaffinity-purified polyclonal goat antibodies specific for PMI. The lower limit of quantification of the double-sandwich ELISA was estimated based on the lowest concentration of pure reference protein lying on the linear portion of the standard curve, the maximum volume of a control extract that could be analyzed without background interference, and the corresponding weight of the sample that the aliquot represented.

PMI protein was detected in most of the event 5307-derived plant tissues analyzed. In most cases, results are presented as means of the five replicate tissue samples. Control sample levels were below the limit of quantification for all stages and tissues.

Across all plant stages, mean PMI levels measured in leaves, roots and pollen ranged from ca. 0.4 to ca. 0.6 µg/g fresh wt. (1.5-2.3 µg/g dry wt.), ca. 0.1-0.2 µg/g fresh wt. (0.9-1.5 µg/g dry wt.) and ca. 16.7-30.6 µg/g fresh wt. (17.1-31.1 µg/g dry wt.) respectively. [limit of detection (LOD)=0.08 µg/g fresh wt., 0.08 µg/g dry wt.].

The levels of PMI were generally similar among the inbred and hybrid genotypes for each tissue type at each time point.

Example 7. Field Efficacy of Event 5307

Western and Northern Corn Rootworm

Event 5307 plants were tested for efficacy against western and northern corn rootworm at 12 locations in the United States. Event 5307 was tested with and without the addition of the insecticidal seed treatment Crusier®. Control groups consisted of seed treated with two different rates of Cruiser® and an untreated check. Treatments consisted of four replications of two 17.5-20 foot rows spaced 30" on center designed in a randomized complete block. Ten plants per treatment were chosen at random and evaluated for efficacy using a 0-3 scale wherein 0=No feeding damage (lowest rating that can be given); 1=One node (circle of roots), or the equivalent of an entire node, eaten back within approximately two inches of the stalk (soil line on the 7th node); 2=Two complete nodes eaten; 3=Three or more nodes eaten (highest rating that can be given). Damage in between complete nodes eaten was noted as the percentage of the node missing, i.e. 1.50=1½ nodes eaten, 0.25=¼ of one node eaten.

Event 5307 efficacy was compared with commercial granular insecticide standards applied in-furrow. The experimental design was as described above. Results in Table 2 demonstrate that the efficacy of event 5307 was comparable to the commercial standards in protecting plants against corn rootworm feeding damage.

TABLE 2

Comparison of efficacy of event 5307 with commercial insecticides applied in-furrow.

| Treatment | Root Damage Rating (0-3 CRW Scale) |
|---|---|
| 5307 | 0.06 |
| Force® 3G | 0.23 |
| MIR604 | 0.13 |
| Untreated Check | 2.05 |

Mexican Corn Rootworm

Event 5307 plants were evaluated for resistance to the Mexican corn rootworm at two locations in Texas. Experimental design was essentially the same as described above.

A clear rate response was evident. Results shown in Table 3 demonstrate that the efficacy of event 5307 was comparable to the commercial standards in protecting plants against Mexican corn rootworm feeding damage.

TABLE 3

Efficacy of event 5307 compared with commercial insecticides applied in-furrow against Mexican corn rootworm.

| Treatment | Root Damage Rating (0-3 CRW Scale) |
|---|---|
| Event 5307 | 0.025 |
| Force® 3G | 0.084 |
| MIR604 with Cruiser® | 0.104 |
| Untreated Check | 0.710 |

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the invention.

Example 8. Use of Event 5307 Insertion Site for Targeted Integration in Maize The event 5307 flanking sequences disclosed in SEQ ID NO: 5 and SEQ ID NO: 6 were used to search maize genome databases. Identical matches to both flanking sequences where found on a BAC clone, ZMMBBc0077H14, of chromosome 5 (NCBI Accession No. AC202955). More specifically, the event 5307 insert lies between a 5' marker, designated herein as the public molecular marker umc 1475 (SEQ ID No: 104), and a 3' marker, designated herein as the public molecular marker uaz190 (SEQ ID No: 107). Using this information, it was determined that the heterologous DNA inserted into event 5307 displaced 38 nucleotides of maize genomic DNA, which lies between the 5' flanking sequence (upstream of the deleted sequence) and the 3' flanking sequence (down stream of the deleted sequence). Primers useful for identifying molecular marker uaz 190 are set forth as SEQ ID NO: 108 and 109. Primers useful for identifying molecular marker umc 1475 are set forth as SEQ ID NO: 105 and 106. Further markers were developed for the purposes of fine mapping the insertion site. These markers are designated as SM1108C, SM0584B, SM0377D and SM0501D. Primers and probes useful for detecting these markers are as follows: SM1108C, SEQ ID NO: 91 through SEQ ID NO: 93; SM0584B, SEQ ID NO: 94 through SEQ ID: 96; SM0377D, SEQ ID NO: 97 through SEQ ID NO: 99; and SM0501D, SEQ ID NO: 100 through SEQ ID NO: 102.

Consistent agronomic performance of the transgene of event 5307 over several generations under field conditions suggests that these identified regions around the event 5307 insertion site provide good genomic locations for the targeted integration of other transgenic genes of interest. Such targeted integration overcomes the problems with so-called "positions effects," and the risk of creating a mutation in the genome upon integration of the transgene into the host. Further advantages of such targeted integration include, but are not limited to, reducing the large number of transformation events that must be screened and tested before obtaining a transgenic plant that exhibits the desired level of transgene expression without also exhibiting abnormalities resulting from the inadvertent insertion of the transgene into an important locus in the host genome. Moreover, such targeted integration allows for stacking transgenes rendering the breeding of elite plant lines with both genes more efficient.

Using the above disclosed teaching, the skilled person is able to use methods know in the art to target transgenes to the same insertion site as that in event 5307 or to a site in close proximity to the insertion site in 5307. One such method is disclosed in US Patent Application Publication No. 20060253918, herein incorporated by reference in its entirety. Briefly, up to 20 Kb of the genomic sequence flanking 5' to the insertion site (SEQ ID NO: 5) and up to 20 Kb of the genomic sequence flanking 3' to the insertion site (SEQ ID NO: 6) are used to flank the gene or genes of interest that are intended to be inserted into a genomic location on Chromosome 5 via homologous recombination. These sequences can be further flanked by T-DNA border repeats such as the left border (LB) and right border (RB) repeat sequences and other booster sequences for enhancing T-DNA delivery efficiency. The gene or genes of interest can be placed exactly as in the event 5307 insertion site or can be placed anywhere within the 20 Kb regions around the event 5307 insertion sites to confer consistent level of transgene expression without detrimental effects on the plant. The DNA vectors containing the gene or genes of interest and flanking sequences can be delivered into plant cells via one of the several methods known to those skilled in the art, including but not limited to *Agrobacterium*-mediated transformation. The insertion of the DNA vector into the event 5307 target site can be further enhanced by one of the several methods, including but not limited to the co-expression or up-regulation of recombination enhancing genes or down-regulation of endogenous recombination suppression genes. Furthermore, it is known in the art that cleavage of specific sequences in the genome can be used to increase homologous recombination frequency, therefore insertion into the event 5307 insertion site and its flanking regions can be enhanced by expression of natural or designed sequence-specific endonucleases for cleaving these sequences.

An example of this technique is demonstrated in Shukla et al. (Nature vol. 459, 21 May 2009). This method uses zinc finger nucleases for the purposes of targeting heterologous sequences to a specific locus based upon the use of homologous sequences within the target plant. One skilled in the art could use the event 5307 insert between a 5' marker, designated herein as the public molecular marker umc1475 (SEQ ID No: 104), and a 3' marker, designated herein as the public molecular marker uaz190 (SEQ ID No: 107) to create a locus for targeted insertion.

Example 9. Use of Event 5307 Insertion Site and Flanking Sequences for Stabilization of Gene Expression The genomic sequences flanking the event 5307 insertion site may also be used to stabilize expression of other gene(s) of interest when inserted as a transgene in other genomic locations in maize and other crops. Specifically, up to 20 Kb of the genomic sequence flanking 5' to the insertion site (SEQ ID NO: 5) and up to 20 Kb of the genomic sequence flanking 3' to the insertion site (SEQ OD NO: 6) are used to flank the gene or genes of interest that are intended to be inserted into the genome of plants. These sequences can be further flanked by T-DNA border repeats such as the left border (LB) and right border (RB) repeat sequences and other booster sequences for enhancing T-DNA delivery efficiency. The gene or genes of interest can be placed exactly as in the event 5307 insertion site or can be placed anywhere within the 20 Kb regions around the event 5307 insertion sites to confer consistent level of transgene expression. The DNA vectors containing the gene or genes of interest and event 5307 insertion site flanking sequence can be delivered into plant cells via one of the several methods known to those skilled in the art, including but not limited to protoplast transformation, biolistic bombardment and *Agrobacterium*-mediated transformation. The delivered DNA can be integrated randomly into a plant genome or can also be present as part of the independently segregating genetic units such as artificial chromosome or mini-chromosome. The DNA vectors containing the gene(s) of interest and the event 5307 insertion site flanking sequences can be delivered into plant cells. Thus, by surrounding a gene or genes of interest with the genomic sequence flanking the event 5307 insertion site, the expression of such genes are stabilized in a transgenic host plant such as a dicot plant or a monocot plant like corn.

DEPOSIT

Applicants have made a deposit of corn seed of event 5307 disclosed above on 15 Oct. 2008 in accordance with the Budapest Treaty at the American Type Culture Collection (ATCC), 10801 University Boulevard, Manassas, VA 20110-2209 under ATCC Accession No. PTA-9561. The deposit will be maintained in the depositary for a period of 30 years, or 5 years after the last request, or the effective life of the patent, whichever is longer, and will be replaced as necessary during that period. Applicants impose no restrictions on the availability of the deposited material from the ATCC; however, applicants have no authority to waive any restrictions imposed by law on the transfer of biological material or its transportation in commerce.

All publications and published patent documents cited in this specification are incorporated herein by reference to the same extent as if each individual publication or patent document was specifically and individually indicated to be incorporated by reference.

What is claimed is:

1. A transgenic corn plant comprising SEQ ID NO: 1 and SEQ ID NO: 2.

2. The transgenic corn plant of claim 1 comprising SEQ ID NO: 1, 2, and 7.

3. A transgenic corn plant cell comprising SEQ ID NO: 1 and SEQ ID NO: 2.

4. The transgenic corn plant cell of claim 3 comprising SEQ ID NO: 1, 2, and 7.

* * * * *